United States Patent
Garcez Lopes et al.

(10) Patent No.: US 9,518,273 B2
(45) Date of Patent: Dec. 13, 2016

(54) MODIFIED MICROORGANISMS AND METHODS OF MAKING BUTADIENE USING SAME

(71) Applicant: Braskem S/A, São Paulo-SP (BR)

(72) Inventors: Mateus Schreiner Garcez Lopes, São Paulo (BR); Avram Michael Slovic, São Paulo (BR); Iuri Estrada Gouvea, São Paulo (BR); Johana Rincones Perez, São Paulo (BR); Lucas Pedersen Parizzi, São Paulo (BR)

( * ) Notice: Subject to any disclaimer, the term of this patent is extended or adjusted under 35 U.S.C. 154(b) by 0 days.

(21) Appl. No.: 14/365,441

(22) PCT Filed: Dec. 17, 2012

(86) PCT No.: PCT/US2012/070161
§ 371 (c)(1),
(2) Date: Jun. 13, 2014

(87) PCT Pub. No.: WO2013/090915
PCT Pub. Date: Jun. 20, 2013

(65) Prior Publication Data
US 2014/0370564 A1    Dec. 18, 2014
US 2015/0152439 A2    Jun. 4, 2015

Related U.S. Application Data

(60) Provisional application No. 61/576,788, filed on Dec. 16, 2011, provisional application No. 61/606,035, filed on Mar. 2, 2012.

(51) Int. Cl.
*C12P 5/02* (2006.01)
*C12N 15/52* (2006.01)
*C12N 9/88* (2006.01)

(52) U.S. Cl.
CPC .............. *C12P 5/026* (2013.01); *C12N 9/88* (2013.01); *C12N 15/52* (2013.01); *C12P 5/02* (2013.01); *C12Y 402/01127* (2013.01)

(58) Field of Classification Search
None
See application file for complete search history.

(56) References Cited

U.S. PATENT DOCUMENTS

| | | |
|---|---|---|
| 2009/0155869 A1 | 6/2009 | Buelter et al. |
| 2011/0165644 A1 | 7/2011 | Marliere |
| 2011/0172476 A1 | 7/2011 | Dumesic et al. |
| 2011/0262975 A1 | 10/2011 | Berry et al. |
| 2011/0300597 A1 | 12/2011 | Burk et al. |
| 2012/0021478 A1 | 1/2012 | Osterhout et al. |

OTHER PUBLICATIONS

Slater et al., "Multiple beta-Ketothiolases Mediate Poly(beta-Hydroxyalkanoate) Copolymer Synthesis in Ralstonia eutropha," Journal of Bacteriology, American Society for Microbiology, US, vol. 180, No. 8, Apr. 1, 1998, pp. 1979-1987.
Tseng et al., "Controlled biosynthesis of odd-chain fuels and chemicals via engineered modular metabolic pathways," Proceedings of the National Academy of Sciences, vol. 109, No. 44, Oct. 30, 2012, pp. 17925-17930.
Patent Examination Report issued in related Australian Patent Application No. 2012353654 on May 2, 2016. 3 pages.

*Primary Examiner* — Suzanne M Noakes
*Assistant Examiner* — Jae W Lee
(74) *Attorney, Agent, or Firm* — K&L Gates LLP

(57) ABSTRACT

The present disclosure generally relates to microorganisms that comprise one or more polynucleotides coding for enzymes in one or more pathways that catalyze a conversion of a fermentable carbon source to butadiene. Also provided are methods of using the microorganisms in industrial processes including, for use in the production of butadiene and products derived therefrom.

18 Claims, 3 Drawing Sheets

SEQUENCE LISTING

<160> NUMBER OF SEQ ID NOS: 139

<210> SEQ ID NO 1
<211> LENGTH: 651
<212> TYPE: DNA
<213> ORGANISM: Escherichia coli K12

<400> SEQUENCE: 1

```
atggatgcga aacaacgtat tgcgcgccgt gtggcgcaag agcttcgtga tggtgacatc      60
gttaacttag ggatcggttt acccacaatg gtcgccaatt atttaccgga gggtattcat     120
atcactctgc aatcggaaaa cggcttcctc ggtttaggcc cggtcacgac agcgcatcca     180
gatctggtga acgctggcgg gcaaccgtgc ggtgttttac ccggtgcagc catgtttgat     240
agcgccatgt catttgcgct aatccgtggc ggtcatattg atgcctgcgt gctcggcggt     300
ttgcaagtag acgaagaagc aaacctcgcg aactgggtag tgcctgggaa aatggtgccc     360
ggtatgggtg gcgcgatgga tctggtgacc gggtcgcgca aagtgatcat cgccatggaa     420
cattgcgcca aagatggttc agcaaaaatt ttgcgccgct gcaccatgcc actcactgcg     480
caacatgcgg tgcatatgct ggttactgaa ctggctgtct ttcgttttat tgacggcaaa     540
atgtggctca ccgaaattgc cgacgggtgt gatttagcca ccgtgcgtgc caaaacagaa     600
gctcggtttg aagtcgccgc cgatctgaat acgcaacggg gtgatttatg a              651
```

<210> SEQ ID NO 2
<211> LENGTH: 663
<212> TYPE: DNA
<213> ORGANISM: Escherichia coli K12

<400> SEQUENCE: 2

```
atgaaaacaa aattgatgac attacaagac gccaccggct tctttcgtga cggcatgacc    60
atcatggtgg gcggatttat ggggattggc actccatccc gcctggttga agcattactg   120
gaatctggtg ttcgcgacct gacattgata gccaatgata ccgcgtttgt tgataccggc   180
atcggtccgc tcatcgtcaa tggtcgagtc cgcaaagtga ttgcttcaca tatcggcacc   240
aacccggaaa caggtcggcg catgatatct ggtgagatgg acgtcgttct ggtgccgcaa   300
ggtacgctaa tcgagcaaat cgctgtggt ggagctggac ttggtggttt tctcaccca   360
acgggtgtcg gcaccgtcgt agaggaaggc aaacagacac tgacactcga cggtaaaacc   420
tggctgctcg aacgcccact gcgcgccgac ctggcgctaa ttcgcgctca tcgttgcgac   480
acacttggca acctgaccta tcaacttagc gcccgcaact ttaaccccct gatagccctt   540
gcggctgata tcacgctggt agagccagat gaactggtcg aaaccggcga gctgcaacct   600
gaccatattg tcaccctgg tgccgttatc gaccacatca tcgtttcaca ggagagcaaa   660
taa                                                                663
```

```
<210> SEQ ID NO 3
<211> LENGTH: 1509
<212> TYPE: DNA
<213> ORGANISM: Corynebacterium glutamicum ATCC 13032

<400> SEQUENCE: 3
```

```
atgtctgatc gcattgcttc agaaaagctg cgctccaagc tcatgtccgc cgacgaggcg    60
gcacagtttg ttaaccacgg tgacaaggtt ggtttctccg gcttcaccgg cgctggctac   120
ccaaaggcac tgcctacggc aatcgctaac cgggctaaag aagcacacgg tgcaggcaac   180
gactacgcaa tcgacctgtt cactggcgca tcgaccgccc ctgactgcga tggcgtactt   240
gcagaagctg acgctatccg ctggcgcatg ccatacgcat ctgatccaat catgcgtaac   300
aagatcaact ccggctccat gggatactcc gatatccacc tgtcccactc cggccagcag   360
gttgaagagg gcttcttcgg ccagctcaac gtagctgtca ttgaaatcac ccgcatcact   420
gaagagggct acatcatccc ttcttcctcc gtgggtaaca acgttgagtg gctcaacgct   480
gcagagaagg tcatcctcga ggttaactct tggcagtctg aagacctcga aggtatgcac   540
gacatctggt ctgttcctgc cctgccaaac cgcattgccg tgccaatcaa caagccaggc   600
gaccgcatcg gtaagaccta tcgagttc gacaccgaca aggttgttgc tgttgttgag   660
accaacaccg cagaccgcaa cgcaccattc aagcctgtcg acgacatctc taagaagatc   720
gctggcaact tcctcgactt cctggaaagc gaagttgctg caggtcgcct gtcctacgac   780
ggctacatca tgcagtccgg cgtgggcaac gtgccaaacg cggtgatggc aggcctgctg   840
gaatccaagt ttgagaacat ccaggcctac accgaagtta tccaggacgg catggtggac   900
ctcatcgacg ccggcaagat gaccgttgca tccgcaactt ccttctccct gtctcctgag   960
tacgcagaga agatgaacaa cgaggctaag cgttaccgcg agtccattat cctgcgccca  1020
cagcagatct ctaaccaccc agaggtcatc cgccgcgttg gcctgatcgc caccaacggt  1080
ctcatcgagg ctgacattta cggcaacgtc aactccacca cgtttctgg ctcccgcgtc  1140
atgaacggca tcgcggctc cggcgacttc acccgtaacg gctacatctc cagcttcatc  1200
accccttcag aggcaaaggg cggcgcaatc tctgcgatcg ttcctttcgc atcccacatc  1260
gaccacaccg agcacgatgt catggttgtt atctctgagt acggttacgc agaccttcgt  1320
ggtctggctc cacgtgagcg cgttgccaag atgatcggcc tggctcaccc tgattaccgc  1380
ccactgctcg aggagtacta cgctcgcgca acctccggtg acaacaagta catgcagacc  1440
```

```
cctcatgatc ttgcaaccgc gtttgatttc cacatcaacc tggctaagaa cggctccatg    1500
aaggcataa                                                            1509

<210> SEQ ID NO 4
<211> LENGTH: 378
<212> TYPE: DNA
<213> ORGANISM: Corynebacterium glutamicum ATCC 13032

<400> SEQUENCE: 4
atgaatggta tcggcggctc gggcgatttc acgcgtaacg cctttgcttc cacatttatc      60
tctccctcgg cagccaaagt tgatgcgatt tccgcgattg tgcctttcgc gtcccatatc     120
gatcacacgg aacatgatgc gatggttgtc attactgaat atggctacgc agacctgcgc     180
gggctatcgc caaacaacg agtccccaaa atgattgcca tcgccacccc ggactatcga     240
ccactgctgg aagcatactt tgaccgggcg ctgaacagtg ctgattccta tcagcacacc     300
ctgcatgatc tgcgcaccgc cttcgatttc cataatcgct gaactcaca aggaaccatg     360 aaaatcgaaa agcatag                                                    378

<210> SEQ ID NO 5
<211> LENGTH: 657
<212> TYPE: DNA
<213> ORGANISM: Clostridium acetobutylicum

<400> SEQUENCE: 5
atgaactcta aataattag atttgaaaat ttaaggtcat tctttaaaga tgggatgaca      60
attatgattg gaggtttttt aaactgtggc actccaacca aattaattga tttttttagtt    120 aatttaaata taaagaattt aacgattata agtaatgata catgttatcc taatacaggt    180
attggtaagt taatatcaaa taatcaagta aaaaagctta ttgcttcata taggcagc      240 aacccagata ctggcaaaaa actttttaat aatgaacttg aagtagagct ctctccccaa    300
ggaactctag tggaaagaat acgtgcaggc ggatctggct taggtggtgt actaactaaa    360
acaggtttag gaactttgat tgaaaaagga agaaaaaaa tatctataaa tggaacggaa    420
tatttgttag agctacctct tacagccgat gtagcattaa ttaaaggtag tattgtagat    480
gaggccggaa acaccttcta taaggtact actaaaaact ttaatcccta tatggcaatg    540
gcagctaaaa ccgtaatagt tgaagctgaa aatttagtta gctgtgaaaa actagaaaag    600
gaaaaagcaa tgaccccgg agttcttata aattatatag taaggagcc tgcataa       657

<210> SEQ ID NO 6
<211> LENGTH: 666
<212> TYPE: DNA
<213> ORGANISM: Clostridium acetobutylicum

<400> SEQUENCE: 6
atgattaatg ataaaaacct agcgaaagaa ataatagcca aaagagttgc aagagaatta      60
aaaaatggtc aacttgtaaa cttaggtgta ggtcttccta ccatggttgc agattatata    120
ccaaaaaatt tcaaaattac tttccaatca gaaacggaa tagttggaat gggcgctagt    180
cctaaaataa atgaggcaga taagatgta gtaaatgcag gaggagacta tacaacagta    240
cttcctgacg gcacattttt cgatagctca gtttcgtttt cactaatccg tggtggtcac    300
gtagatgtta ctgttttagg ggctctccag gtagatgaaa agggtaatat agccaattgg    360
attgttcctg gaaaaatgct ctctggtatg ggtggagcta tggatttagt aaatggagct    420
```

```
aagaaagtaa taattgcaat gagacataca aataaaggtc aacctaaaat tttaaaaaaa      480
tgtacacttc ccctcacggc aaagtctcaa gcaaatctaa ttgtaacaga acttggagta      540
attgaggtta ttaatgatgg tttacttctc actgaaatta ataaaaacac aaccattgat      600
gaaataaggt ctttaactgc tgcagattta ctcatatcca atgaacttag acccatggct      660
gtttag                                                                 666
```

<210> SEQ ID NO 7
<211> LENGTH: 1753
<212> TYPE: DNA
<213> ORGANISM: Roseburia sp. A2-183

<400> SEQUENCE: 7

```
agaaatctgc tacgaactgg gaacctattt tgtgggacag cgcgactacg cggaagcggt       60
tctctggttc tacaatgccg cctatgagac ggaaagcatc ctggacgttc acacaagcgg      120
ggatcttccg ctgctcggtc ttgtcgaatg ttacgagacg ctcctcgccg gggaggaagc      180
caaaattcct tccgacacag cgcttaccat ccagtacgaa atgatgctcg acaaataccg      240
ggaggcttcc agagactggc ggatgccgga ggagacctga tcttacaaat ctccggaaat      300
acgctccggc agggcttgta aaatacgaca taaagtgata ggatgaaact atggtaaaat      360
tttaacaatc ttttgtgtgg gaggtatttg agatggattt tcgtgaagaa tacaaacaga      420
agcttgtctc cgcagatgag gcggtaaagc tcatcaaatc cggagactgg gtagattacg      480
gctggtgcac caacaccgtt gacgcactgg atcaggctct cgcaaagcgc accgacgaac      540
tgacagacgt caagctgcgc ggcggtatcc tgatgaagcc gctggctgtt tttgcacgtg      600
aggatgcagg tgagcatttc tgctggaact cctggcatat gtccggtatc gagcgcaaga      660
tgataaacag aggcgtggct tactactgtc cgatccgcta ctccgagctg ccgcgctact      720
accgcgagct tgactgcccg gatgacgttg ccatgttcca ggttgctccg atggatgcgc      780
acggctactt taacttcggt ccgagtgcct cacatctggg tgcaatgtgc gagcgcgcaa      840
agcacatcat cgtagaagtc aatgaaaata tgccacgctg cctcggcggt accgagtgtg      900
gcatccacat ttccgatgtc acctacatcg tggaaggctc caacccgcca atcggtgaac      960
tgggtgcagg cggtcctgct acagatgtgg ataaggctgt cgcaaagctg atcgtcgatg     1020
agattccgaa cggtgcctgc ttacagctcg gtatcggcgg catgccaaac gctgtcggtt     1080
ccctgattgc agagtccgac ttgaaggatc tcggcgttca cactgagatg tacgtggatg     1140
catttgtcga tattgcaaag gcaggtaaga tcaacggttc caaaaagaat atcgaccgtt     1200
accgccagac ctacgctttc ggcgccggca ccaagaaaat gtacgattat ctggacgaca     1260
acccggaact gatgagcgct ccggtcgact cacgaacga catccgctcg atctccgcac     1320
tggataactt tatttccatc aacaatgccg tggatattga tctctatggt caggtaaatg     1380
cagagtctgc aggcatcaag cagatcagcg gcgcaggcgg acagcttgac ttcgtgctcg     1440
gagcttatct gtccaaggge ggcaagagct ttatctgctt atcctctacc ttcaagacca     1500
aggacggtca ggtgcagtcc cgtatccgcc cgacgctggc aaacggttcc atcgttaccg     1560
acgcaagacc gaatacacac tatgttgtaa ccgaatacgg caaggtgaac ttaaagggtc     1620
tgtctacctg gcagagagcc gaggctctga tctcgatcgc gcatcccgat ttccgcgacg     1680
acctcatcaa agaggcggag cagatgcaca tctggagaag aagcaaccgc tagtaccgga     1740
ggacgactga cgg                                                        1753
```

<210> SEQ ID NO 8
<211> LENGTH: 1000
<212> TYPE: DNA
<213> ORGANISM: Clostridium propionicum

<400> SEQUENCE: 8

```
gaattcaaaa ttgctatcgt tgatgacgat ttggctcagg aatccagaca gattcgtgtt      60
gacgttctgg atggcgaagg tggccctctt tatagaatgg caaaagcttg gcagcaaatg     120
tacggttgct ctcttgcaac tgatacaaag aaaggccgcg gcagaatgct gatcaacaag     180
acaattcaga caggtgcaga tgctatcgtt gttgcgatga tgaaattctg tgatcctgaa     240
gaatgggatt accctgtaat gtacagagaa tttgaagaaa aaggcgttaa gagtctgatg     300
atcgaagttg atcaggaagt ttcttccttc gaacagatca agacaagact gcagtctttc     360
gtagaaatgc tgtaatttga acaatcgttt gctgaaaaac tgtacactgg ggtgggtgac     420
tgctccagtg tattgtaata agcaaataag caaaaatcga taagatttag gaggattttc     480
gacaatgaga aaggttccca ttattaccgc agatgaggct gcaaagctta ttaaagacgg     540
tgatacagtt acaacaagtg gtttcgttgg aaatgcaatc cctgaggctc ttgatagagc     600
tgtagaaaaa agattcttag aaacaggcga acccaaaaac attacatatg tttattgtgg     660
ttctcaaggt aacagagacg gaagaggtgc tgagcacttt gctcatgaag gccttttaaa     720
acgttcatcg ctggtcact gggctacagt tcctgctttg ggtaaaatgg ctatggaaaa     780
taaaatggaa gcatataatg tatctcaggg tgcattgtgt catttgttcc gtgatatagc     840
ttctcataag ccaggcgtat ttacaaaggt aggtatcggt actttcattg accccagaaa     900
tggcggcggt aaagtaaatg atattaccaa agaagatatt gttgaattgg tagagattaa     960
gggtcaggaa tatttattct accctgcttt tcctattcat                          1000
```

<210> SEQ ID NO 9
<211> LENGTH: 1554
<212> TYPE: DNA
<213> ORGANISM: Clostridium beijerinchii

<400> SEQUENCE: 9

```
gtgagaaaag taaaagtttt aacaagtcgc gaagcagtac aaatagtgaa ggatggagat      60
gtgttagtaa ctggcggatt tgttggtagt tgtgcacctg aaactcttag ttgtgcttta     120
gaaaaacgtt tcattgaaac aaatcatccg caaaatataa cttttatttca tgcagcagga     180
caaggcgata gtaaggggaa aggttcagat cattatgccc acgaaggctt acttaagaga     240
gtggttgcag gtcattataa tttagcaccg aaaattggaa agttaattaa tgaaaataaa     300
atagaagctt ataatctacc acaagggaca atttctcaat tatttagaga tattgcggga     360
aaaagaattg ggacaataac tcacgttgga ttgaatacat ttgtggatcc aagaattagt     420
ggtggaaaat taaatgaaaa aacaaaagaa gatctagtaa agctaataaa tatagaaggt     480
gaagaaaaat tattatacaa atcaattcca gttaatgtct gcttcttaag aggatctttt     540
gcagatgaat acggtaatgt atcattagaa aaagaaatag ctacacttga ggatacgtca     600
atagcccaag cttgtaagaa taatggcgga aaagtaatag ttcaagtaga aaaagtagtt     660
gaagcaggat ctttagaccc acgtcttata aaaattccag gtatatatgt agatgcggtt     720
gtaatctcaa ctccccgaaga gcatgaacaa tccttcgaat gcccatttaa tccagcagta     780
acaggtgaaa tgagaattcc attaaacagt gtagaaaaag ctccattaaa tgagagaaag     840
ataattgcga gaagagcagc tatggaatta agaaagata cggtagtaaa tttaggtata     900
```

```
gggataccag aagttatttc tttagttgcg aatgaagaag gaattggtga atatatgaca    960
ttaactgtag aagccggtcc aataggaggt ataccacaag gatgcacagc ttttggagcg   1020
agtataaatc cagaagctat tatagatcag ccatatcaat ttgattttta tgatggtgga   1080
ggcgtcgata tagcatttt aggactagct caggttgatg aacatggaaa tttgaatgta   1140
agtaagtttg ggcctagaat tgctggatgt ggtggattca taaatataac tcaaaatgct   1200
aagaaagtgt tattttgtgg aacattcact gcaggaggct aaaagtagt aacaggagat   1260 ggcaaattag aaattaaaca agaaggaaaa gctaaaaaat tcattaagga tgtagagcaa   1320
attacattta gtggagatta tgcaagaagg atggatcaac aagttatgta tataactgag   1380
agagcagtat ttgagttaag gaaagatgga ttatacctta cagaaatagc gcctgggata   1440
gatctaaaaa aggatgtatt ggatttaatg gatttcaaac ctaaaatgga tggagtacct   1500
agactaatga atggaagaat attttatgat aagttgatgg gattaaggga gtaa          1554

<210> SEQ ID NO 10
<211> LENGTH: 687
<212> TYPE: DNA
<213> ORGANISM: Acinetobacter sp. ADP1

<400> SEQUENCE: 10
atgatagata aaagtgcagc gaccctaacg gaagcgctct cccagatcca cgacggtgcc     60
accatcctga ttggtggttt tggaacagcc ggccaacccg ccgagctgat tgacggactg    120
attgaactag gtcgcaagaa cctaaccatc gtcagcaaca acgccggcaa tggagactat    180
ggactggcca agctgctaaa aactggcgcc gtcaaaaaga tcatctgttc cttcccacgt    240
caggccgact cctacgtatt tgacgagcta taccgtgcgg gcaaaattga acttgaaatc    300
gtgccgcagg gcaatctggc ctgtcgtata caggccgccg catgggggct ggggccgatc    360
tacaccccaa ccggttttgg cactttactc gcagaaggta aacctaccct gaactttgat    420
ggcaaagact acgtactgga aaacccgatc aaggccgact ttgccctgat caaagcctac    480
aagggcgacc gctggggcaa tctggtctat cgcaaatcag cacgaaactt cggcccgatc    540
atggccatgg ccgccaacgt gaccatcgca caagtgagcg aagtggtggc actaggagaa    600
ctcgacccgg aaaacgtggt gaccccaggc atctttgttc aacacgttgt accagtccaa    660
tctaccccag caagcgctgc accataa                                          687

<210> SEQ ID NO 11
<211> LENGTH: 654
<212> TYPE: DNA
<213> ORGANISM: Acinetobacter sp. ADP1

<400> SEQUENCE: 11
atgagttatc acaaactgac ccgtgaccag atcgcccagc gcgttgccca agacattccg     60
gaaggctcct atgtcaatct tggcattggc ctgccgacca agattgccag ctatctgcct    120
gccgacaaag acgtatttct acattcagaa aacggactgc tggcctttgg cccaccacca    180
gcggccggcg aagaagatcc ggaactgatc aacgcaggca agaatacgt aaccatgctc    240 gaaggcggtt gcttctttca ccatggcgac tccttcgcca tgatgcgcgg tggacatctg    300
gatatctgcg tattaggcgc attccagatc gccgccaatg gagacctggc caactggcac    360
accggtgcac cggatgccat accgtcggtc ggtggagcca tggatcttgc ggttggggca    420
aaaaagtttt tgtaaccac cgatcatgtc accaaaaaag gtgagccgaa gattgtagct    480
gaactgacgt atccagccac gggtcagaaa tgtgtcgacc ggatctacac cgacctgtgc    540
```

```
atcatcgatg tggtgccaga aggactgaaa gtgatcgaga agtcgaagg cttaagcttt      600 gaagaactac aacgcctgac cggtgcaaca ctgatcgatg cgacacaagg ctaa           654

<210> SEQ ID NO 12
<211> LENGTH: 696
<212> TYPE: DNA
<213> ORGANISM: Pseudomonas putida

<400> SEQUENCE: 12
ttgatcaata aaacgtacga gtccatcgcc agcgcggtgg aagggattac cgacggttcg      60
accatcatgg tcggtggctt cggcacggct ggcatgccgt ccgagctgat cgatggcctc     120
attgccaccg gtgcccgcga cctgaccatc atcagcaaca cgccggcaa cggcgagatc      180 ggcctggccg ccctgctcat ggcaggcagc gtgcgcaagg tggtctgctc gttcccgcgc     240
cagtccgact cctacgtgtt cgacgaactg taccgcgccg gcaagatcga gctggaagtg     300
gtcccgcagg gcaacctggc cgagcgtatc cgcgccgcag gctccggcat ggtgcgttc     360 ttctcgccaa ccggctacgg caccctgctg gccgagggca aggaaacccg tgagatcgat     420
ggccgcatgt acgtgctgga aatgccgctg cacgccgact cgcactgat caaggcgcac     480 aagggtgacc gttggggcaa cctgacctac cgcaaggccg cccgcaactt cggcccgatc     540
atggccatgg ctgccaagac cgccatcgcc caggtcgacc aggtcgtcga actcggtgaa     600 ctggaccogg aacacatcat caccccgggt atcttcgtcc agcgcgtggt cgccgtcacc     660
ggtgctgccg cttcttcgat tgccaaagct gtctga                              696

<210> SEQ ID NO 13
<211> LENGTH: 642
<212> TYPE: DNA
<213> ORGANISM: Pseudomonas putida

<400> SEQUENCE: 13
atgaccatca ccaaaaagct ctcccgcacc gagatggccc aacgcgtggc cgcagacatc      60
caggaaggcg cgtatgtaaa cctgggtatc ggcgcaccaa ccctggtggc caactacctg     120
ggcgacaagg aagtgttcct gcacagcgaa acggcctgc tgggcatggg cccaagccct      180
gcgccgggcg aggaagacga tgacctgatc aacgccggca gcagcacgt caccctgctg     240 accggtggtg ccttcttcca ccatgccgat tcgttctcga tgatgcgtgg cggccacctg     300
gacatcgccg tactgggtgc cttccaggtg tcggtcaagg cgacctggc caactggcac     360 acgggtgccg aaggttcgat cccggccgta ggcggcgcaa tggacctggc caccggcgcc     420
cgccaggtgt tcgtgatgat ggaccacctg accaagaccg gcgaaagcaa gctggtgccc     480
gagtgcacct acccgctgac cggtatcgcg tgcgtcagcc gcatctacac cgacctggcc     540
gtgctggaag tgacaccgga agggctgaaa gtggtcgaaa tctgcgcgga catcgacttt     600
gacgaactgc agaaactcag tggcgtgccg ctgatcaagt aa                        642

<210> SEQ ID NO 14
<211> LENGTH: 717
<212> TYPE: DNA
<213> ORGANISM: Bacillus subtilis

<400> SEQUENCE: 14
atgggaaaag tgctgtcatc aagcaaggaa gctgcgaaac tgattcatga tggggatacg      60
ctgatcgcgg gagggtttgg gctgtgcggc atccctgaac agctcatttt gtctataaga     120
```

```
gatcaggag taaaggattt aaccgttgtc agcaataact gcggagtcga tgactggggg      180
cttggtttgc ttctggctaa caagcaaatc aagaaaatga tcgcttccta tgtcggtgaa      240
aataaaattt ttgagcggca gttttaagc ggagagcttg aggtagagct tgttccccaa       300
ggaacgctcg ctgagagaat tcgtgcaggc ggtgcaggca taccgggatt ttatacggcg      360
acaggcgtcg gcacctccat agccgaggga aaagaacata aacattcgg cggccggact      420 tatgtgctgg agcgaggcat taccggcgat gtggcgatcg tcaaagcgtg gaaagcggac     480
accatgggca atttgatttt taggaaaacg gcgagaaatt tcaatcccat tgccgccatg     540
gcaggcaaga tcacgattgc cgaggcggaa gaaatcgtgg aagcaggaga gctcgatcca     600
gatcacatcc atacgccggg aatttacgta cagcatgtcg tgcttggcgc gagccaagaa    660
aaacggattg aaaacgaac agttcagcaa gcatcgggaa agggtgaggc caagtga       717

<210> SEQ ID NO 15
<211> LENGTH: 651
<212> TYPE: DNA
<213> ORGANISM: Bacillus subtilis

<400> SEQUENCE: 15
gtgaaggaag cgagaaaacg aatggtcaaa cgggctgtac aagaaatcaa ggacggcatg     60
aatgtgaatc tcgggattgg aatgccgacg cttgtcgcaa atgagatacc cgatggcgtt    120
cacgtcatgc ttcagtcgga aaacggcttg ctcggaattg ccccctatcc tctgaagga    180 acggaagacg cggatttgat caatgcggga aaggaaacga tcactgaagt gacaggcgcc    240 tcttatttg acagcgctga gtcattcgcg atgataagag gcgggcatat cgatttagct    300
attctcggcg gaatggaggt ttcggagcag ggggatttgg ccaattggat gatcccgggc   360
aaaatggtaa aagggatggg cggcgccatg gatctcgtca acggggcgaa acgaatcgtt   420
gtcatcatgg agcacgtcaa taagcatggt gaatcaaagg tgaaaaaac atgctcccctt   480 ccgctgacag gccagaaagt cgtacacagg ctgattacgg attggctgt atttgatttt   540 gtgaacggcc gcatgacact gacggagctt caggatggtg tcacaattga agaggtttat   600 gaaaaacag aagctgattt cgctgtaagc cagtctgtac tcaattctta a             651

<210> SEQ ID NO 16
<211> LENGTH: 1617
<212> TYPE: DNA
<213> ORGANISM: Clostridium kluyveri

<400> SEQUENCE: 16
atgagtaaag ggataaagaa ttcacaattg aaaaaaaga atgtaaaggc tagtaatgtg      60
gcagaaaaga ttgaagagaa agttgaaaaa acagataagg ttgttgaaaa ggcagctgag    120
gttacagaaa acgaattag aaacttgaag cttcaggaaa agttgtaac agcagatgtg     180 gcagctgata tgtagaaaa cggtatgatt gttgcaatta gcggatttac tccttccggg    240
tatcctaaag aagtacctaa agcattgact aaaaaagtta atgccttaga ggaagaattc    300
aaggtaacac tttatacagg ttcatctaca ggagccgata tagacggaga atgggcaaaa    360
gcaggaataa tagaagaag aattccatat cagacaaatt ctgatatgag gaaaaaata    420 aatgatggtt ctattaagta tgctgatatg catttaagcc atatggctca atatattaat    480
tattctgtaa ttcctaaagt agatatagct ataatagagg cagtagctat tacagaagaa    540
ggggatatta ttccttcaac aggaattgga aatacagcta cttttgtgga aaatgcagat    600 aagtaatag tggaaattaa tgaggctcaa ccgcttgaat tggaaggtat ggcagatata    660
```

```
tatacattaa aaaaccctcc aagaagagag cccatacccta tagttaatgc aggcaatagg    720 ataggggacca catatgtgac ctgtggttct gaaaaaatat gcgctatagt gatgacaaat    780
acccaggata aaacaagacc tcttacagaa gtgtctcctg tatctcaggc tatatccgat    840
aatcttatag gattttttaaa taagagggtt gaagagggaa aattacctaa gaacctgctt    900
cctatacagt caggagttgg aagtgtagca aatgcagttt tggccggact ttgtgaatca    960
aattttaaaa atttgagttg ttatacagaa gttatacagg attctatgct gaagcttata   1020
aaatgtggta agcagatgt ggtgtcaggc acttccataa gtccttcacc ggagatgttg   1080
cctgagttca taaggacat aaattctct agagaaaaga tagtattaag accacaggaa    1140
ataagtaata atccagagat agcaagaaga ataggagtta tatccataaa cactgctttg   1200
gaagtagata tatatggtaa tgtaaactcc actcatgtta tgggaagcaa aatgatgaat   1260
ggtataggcg ttctggaga ctttgccaga aatgcatatt tgactatatt cactacagag    1320
tctatcgcca aaaaggaga tatatcatct atagttccta tggtatccca tgtggatcat    1380
acagaacatg atgtaatggt aattgttaca gaacagggag tagcagattt aagaggtctt   1440
tctcctaggg aaaaggccgt ggctataata gaaaattgtg ttcatcctga ttacaaggat   1500
atgcttatgg aatattttga agaggcttgt aagtcatcag gtggaaatac accacataat   1560
cttgaaaaag ctctttcctg gcatacaaaa tttataaaaa ctggtagtat gaaataa     1617

<210> SEQ ID NO 17
<211> LENGTH: 1290
<212> TYPE: DNA
<213> ORGANISM: Clostridium kluyveri

<400> SEQUENCE: 17
atggagtggg aagagatata taagagaaaa ctggtaactg cagaaaaagc tgtttcaaaa     60
atagaaaacc atagcagggt agtttttgca catgcagtag gagaacccgt agatttagta    120
aatgcactag ttaaaaataa ggataattat ataggactag aaatagttca catggtagct    180
atgggcaaag gtgaatatac aaaagaggt atgcaaagac attttagaca taatgcttta    240
tttgtaggcg gatgtactag agatgcagta aattcaggaa gagcagatta tacaccttgt    300
tttttctatg aagtgccaag tttgtttaaa gaaaaacgtt tgcctgtaga tgtagcactt    360
attcaggtaa gtgagccaga taaatatggc tactgcagtt ttggagtttc caatgactat    420
accaagccag cagcagaaag tgctaagctt gtaattgcag aagtgaataa aaacatgcca    480
agaactcttg gagattcttt tatacatgta tcagatattg attatatagt ggaagcttca    540
cacccattgt tagaattgca gcctcctaaa ttgggagatg tagaaaaagc cataggagaa    600
aactgtgcat ctttaattga agatggagct actcttcagc ttggaatagg tgctatacca    660
gatgcggtac ttttattctt aaagaacaaa aagaatttag aatacattc tgagatgata    720 tcagatggtg tgatggaact ggtgaaggca ggggttatca ataacaagaa aaagacccctc    780 catccaggca aaatagttgt aacatttta atgggaacaa aaaaattata tgattttgta    840
aacaataatc caatggtaga aacttattct gtagattatg taaataatcc actggtaatt    900
atgaaaaatg acaatatggt ttcaataaat tcttgtgttc aagtagactt aatgggacaa    960
gtatgttctg aaagtatagg attgaaacag ataagtggag tgggaggcca ggtagatttt   1020
attagaggag ctaatctatc aaagggtgga aaggctatta tagctatacc ttccacagct   1080
ggaaaaggaa aagtttcaag aataactcca cttctagata ctggtgctgc agttacaact   1140
```

```
tctagaaatg aagtagatta tgtagttact gaatatggtg ttgctcatct taagggcaaa    1200
actttaagaa ataggggcaag agctctaata aatatcgctc atccaaaatt cagagaatca    1260
ttaatgaatg aatttaaaaa gagattttag                                      1290

<210> SEQ ID NO 18
<211> LENGTH: 1314
<212> TYPE: DNA
<213> ORGANISM: Clostridium kluyveri

<400> SEQUENCE: 18
atggttttta aaaattggca ggatctttat aaaagtaaaa ttgttagtgc agacgaagct      60
gtatctaaag taagctgtgg agatagcata attttaggca atgcttgtgg agcatctctt     120
acacttttag atgccttggc tgcaaataag gaaaagtata agagtgtaaa gatacacaat     180
cttatactta attataaaaa tgatatatat actgatccgg aatcagaaaa gtatattcat     240
ggaaatactt tctttgtaag tggaggtaca aaggaagcag ttaattgtaa tagaacagat     300
tatactccat gctttttta tgaaatacca aaattattaa acaaaagta tataaatgca      360 gatgtagctt ttattcaagt aagtaagcct gatagccatg gatactgtag ctttggagta     420
tcaaccgatt attcacaggc aatggtacag tctgcaaagc ttataattgc agaagtaaac     480
gatcagatgc caagagttttt aggagacaat tttatacaca tttctgatat ggattacata     540
gtagaaagtt cacgtccaat tctagaattg actcctccta aaataggaga agtagagaag     600
acaataggaa aatactgtgc atctcttgta gaagatggtt ctacacttca gcttggaata     660
ggagctattc cagatgcagt actttttattc ttgaaggata aaaaggattt gggtatacat     720
tcagaaatga tatccgatgg tgttgttgaa ttagttgaag cagggggtaat tacaaataag     780 aaaaagtccc ttcatccagg aaaaataatt attacattct taatgggaac taagaaatta     840
tatgatttca taaatgataa tcctatggta gaaggatacc ctgtagatta tgtaaatgat     900
cctaaggtta ttatgcaaaa ttctaagatg gtatgtataa actcctgtgt agaagtggat     960
ttcacaggac aagtgtgtgc tgaaagtgta ggatttaaac aaataagcgg tgtaggtgga    1020
caagttgatt acatgagagg agctagcatg gctgatggag aaaatcaat tcttgctata    1080 ccatctactg cagctggcgg caaaatttca gaatagttc ctattttaac tgaaggagcg    1140
ggggttacta cttcaagata tgatgttcaa tatgttgtta cagaatatgg tattgcactt    1200
ctcaagggca aatccataag agaaagagct aaggagctta taaaaattgc acatcctaaa    1260
tttagggaag aattaacagc tcaatttgaa aaaagattca gttgtaagct ttaa           1314

<210> SEQ ID NO 19
<211> LENGTH: 963
<212> TYPE: DNA
<213> ORGANISM: Acidaminococcus fermentans

<400> SEQUENCE: 19
ttgagtaaag taatgacgtt aaaagacgca atcgccaagt atgtgcacag tggtgatcac     60
attgctctgg gtggttttac gacggaccgt aaaccctatg cggctgtgtt cgaaatcctg    120
agacagggta tcacggatct gaccggtctg ggcggcgctg ccggcggcga ctgggatatg    180
ctgatcggca acggccgtgt gaaagcctac atcaactgct acaccgccaa ctccggtgtg    240
accaacgttt ccagacggtt cagaaaatgg ttcgaagccg gcaaactgac catggaagac    300
tattcccagg atgttatcta catgatgtgg catgccgccg ctctgggcct gcccttcctg    360
cctgtaaccc tgatgcaggg ctccggcctg accgatgaat ggggcatcag caaggaagtc    420
```

```
cgtaaaaccc tggacaaagt tcctgatgac aaattcaaat acatcgacaa ccccttcaaa    480
ccgggtgaaa aagtcgtggc tgttcctgtt ccgcaggttg atgtggccat catccatgcc    540
cagcaggctt ctcccgatgg caccgttcgc atctggggcg gcaaattcca ggatgtggat    600
attgctgaag cagccaaata caccatcgtt acctgcgaag aaatcatttc tgatgaagaa    660
atcagaagag atcccaccaa gaacgatatc cccggcatgt gcgtagatgc tgttgtcctg    720
gctccttacg gtgcacatcc ttctcagtgc tatggcctgt acgactacga caatccgttc    780
ctgaaagtct atgacaaggt ctccaagacc caggaagact tcgatgcctt ctgcaaggaa    840
tgggtgttcg acctgaagga tcatgacgaa tacctgaaca aactgggtgc cactcgtctg    900
atcaacctga aggttgttcc tggtctgggc taccacatcg acatgacgaa ggaggacaaa    960
taa                                                                 963

<210> SEQ ID NO 20
<211> LENGTH: 963
<212> TYPE: DNA
<213> ORGANISM: Acidaminococcus fermentans

<400> SEQUENCE: 20
ttgagtaaag taatgacgtt aaaagacgca atcgccaagt atgtgcacag tggtgatcac     60
attgctctgg gtggttttac gacggaccgt aaaccctatg cggctgtgtt cgaaatcctg    120
agacagggta tcacggatct gaccggtctg ggcggcgctg ccggcggcga ctgggatatg    180
ctgatcggca acggccgtgt gaaagcctac atcaactgct acaccgccaa ctccggtgtg    240
accaacgttt ccagacggtt cagaaaatgg ttcgaagccg gcaaactgac catggaagac    300
tattcccagg atgttatcta catgatgtgg catgccgccg ctctgggcct gcccttcctg    360
cctgtaaccc tgatgcaggg ctccggcctg accgatgaat ggggcatcag caaggaagtc    420
cgtaaaaccc tggacaaagt tcctgatgac aaattcaaat acatcgacaa ccccttcaaa    480
ccgggtgaaa aagtcgtggc tgttcctgtt ccgcaggttg atgtggccat catccatgcc    540
cagcaggctt ctcccgatgg caccgttcgc atctggggcg gcaaattcca ggatgtggat    600
attgctgaag cagccaaata caccatcgtt acctgcgaag aaatcatttc tgatgaagaa    660
atcagaagag atcccaccaa gaacgatatc cccggcatgt gcgtagatgc tgttgtcctg    720
gctccttacg gtgcacatcc ttctcagtgc tatggcctgt acgactacga caatccgttc    780
ctgaaagtct atgacaaggt ctccaagacc caggaagact tcgatgcctt ctgcaaggaa    840
tgggtgttcg acctgaagga tcatgacgaa tacctgaaca aactgggtgc cactcgtctg    900
atcaacctga aggttgttcc tggtctgggc taccacatcg acatgacgaa ggaggacaaa    960
taa                                                                 963

<210> SEQ ID NO 21
<211> LENGTH: 1251
<212> TYPE: DNA
<213> ORGANISM: Escherichia coli

<400> SEQUENCE: 21
atgtcaactc cacttcaagg aattaaagtt ctcgatttca ccggtgtgca atctggccca     60
tcttgtactc aaatgctggc ctggtttggc gctgacgtta ttaaaattga acgtcccggc    120
gttggtgacg taacgcgtca ccagctgcga gatattcctg atatcgatgc gctttacttc    180
accatgctta acagtaacaa acgttctatt gagttaaata ccaaaacagc ggaaggcaaa    240
```

```
gaggtaatgg aaaagctgat ccgcgaagct gatatcttag tcgagaactt tcatccaggg      300
gccattgatc acatgggctt cacctgggag catattcaag aaatcaatcc acgtctgatt      360
tttggttcga tcaaagggtt tgatgagtgt tcgccttatg tgaatgtaaa agcctatgaa      420
aacgttgctc aggcagcggg tggcgcggca tccactacgg gttttggga tggtccgccg       480 ctggtaagcg ctgcagcgtt gggtgacagc aacaccggaa tgcatttgct gatcggttta      540
cttgctgctt tgctgcatcg cgaaaaaacg gggcgtgggc aacgagtcac catgtcaatg      600
caggatgccg tattgaacct tgccgcgtg aaattacgtg accagcagcg tctcgataaa       660
ttgggttatc tggaagaata cccgcagtat ccgaatggta catttggtga tgcagttccc      720
cgcggtggta atgcaggtgg tggcggtcag cctggctgga tcctgaaatg taaaggctgg      780
gaaaccgatc ctaacgccta tatttatttc actattcagg agcaaaactg ggaaaacacc      840
tgtaaagcca tcggcaaacc agaatggatt accgatccgg catacagtac agcccatgca      900
cgacagccac atattttcga tattttttgct gaaatcgaaa aatacactgt cactattgat     960
aaacatgaag cggtggccta tttgactcag tttgatattc cttgtgcacc ggttttaagt     1020
atgaaagaaa tttcacttga tccctctttg cgccaaagtg gcagtgttgt tgaagtggaa    1080
caaccgttgc gtggaaaata tctgaccgtt ggttgtccaa tgaaattctc tgcctttacg    1140
ccggatatta agctgcgcc gctattaggt gaacataccg ctgctgtatt gcaggagctg     1200
ggttatagcg acgatgaaat tgctgcaatg aagcaaaacc acgccatctg a             1251

<210> SEQ ID NO 22
<211> LENGTH: 1278
<212> TYPE: DNA
<213> ORGANISM: Bradyrhizobium sp.

<400> SEQUENCE: 22
atgaccaagg cgctcgaggg cgttcgcatt ctcgacttca cccacgtcca gtccggaccg       60
acctgcaccc agctgctggc ctggttcggc gccgacgtga tcaaggtcga gcggccgggc      120
gtgggtgaca tcacccgcgg ccagctgcag gacattccca acgtggacag cctgtatttc      180
acgatgctga ccacaacaa gcggtcgatc acgctcgaca ccaagaaccc caagggcaag      240
gaggttctga ccgagctgat caagaagtgc gacgtgctgg tcgagaattt cggccccggc     300
gtgcttgacc gcatgggctt cccctgggag aagatccagg ccatcaaccc gaagatgatc     360
gtcgcctcga tcaagggttt cggccctggc ccttacgagg actgcaaggt ctacgagaac     420
gtcgcgcagt gcaccggcgg cgccgcctcg accaccggct ccgtgacgg cctgccgctg      480 gtcaccggcg cgcagatcgg cgattccggc accggcctgc acctcgcgct cggcatcgtc     540
accgcgctct atcagcgcac ccataccggc aagggccagc gcgtcacggc tgcgatgcag     600
gacggcgtgc tcaacctctg ccgtgtcaag ctgcgcgacc agcagcgcct ggagcgcggc     660
ccgctcaagg aatacagcca gttcggtgag ggcgttccgt tcggcgacgc cgtgccgcgc     720
gccggcaacg attccggcgg tggccagccg ggccgcatcc tgaagtgcaa gggctgggag    780
accgacccga cgcctacat ctacttcatc acccaggccc cggtctggga agatctgc        840 gacgtgatcg cgagcccac ctggaagacc gatccgaact acgccaagcc ggccgcccgc     900
ctgccgcgcc tgaacgagat cttcggccgc atcgagcagt ggaccatgac caagaccaag    960
ttcgaggcca tggacatcct caacgagttc gacatcccct gcggcccgat cctgtcgatg   1020
aaggagatcg ccgaggacga gtcgctgcgc aagaccggca cctgtcga ggtcgaccac     1080 ccgacccgcg gcaaatatct ctcggtcggc aacccgatca agctgtcgga cagcccggcc   1140
```

```
gaggtgaccc gctcgccttt gctcggcgag cacaccgatg agatcctgcg ccaggtgctt    1200
ggcttcagcg accaccaggt cgccgagatc cacgactccg gcgcgctcga tccaccgcgt    1260
aaggaagctg cggagtaa                                                   1278
```

<210> SEQ ID NO 23
<211> LENGTH: 1326
<212> TYPE: DNA
<213> ORGANISM: Rhodopseudomonas palustris

<400> SEQUENCE: 23

```
atgggagaga tgccgcttcg gcgcgcaaga gacaacagga gcacgaccat gaccaaggcg     60
ctcgacggcg ttcgcgttct cgacttcacc cacgtccaat ccggcccgac ctgcacgcag    120
ctcttggcgt ggttcggtgc cgacgtgatc aaggtggagc gccccggcag cggcgacatc    180
acccgcggtc agctgcagga catcccgaag gtggacagcc tgtatttcac catgctgaac    240
cacaacaagc ggtcgatcac gctcgacacc aagaacccga agggcaagga ggtgctgacc    300
gcgctgatcc gcacctgcga cgtgctggta gagaatttcg gccccggtgt gctcgaccgg    360
atgggcttca cctgggagaa gatccaggag atcaacccgc ggatgatcgt cgcctcgatc    420
aagggcttcg gtcccggccc gtatgaagac tgcaaggtgt acgagaacgt tgcgcagtgc    480 accgcggcg ccgcctcgac caccggattc gcgcaaggcc tgccgctggt caccggcgcg    540
cagatcggcg atagcggcac cggcctgcat ctcgcgctcg gcatcgtcac cgcgctgtat    600
cagcgccacc acaccggccg cggccagcgc gtcaccgcgg cgatgcagga cggcgtgctg    660
aacctctgcc gcgtcaagct gcgcgatcag cagcgcctcg accatggtcc gctgaaggaa    720
tacagccagt tcggcgaagg catcccgttc ggcgatgcgg tgccgcgtgc cggcaacgat    780
tccggtggcg gccagcccgg ccgcatcctg aagtgcaagg gctgggagca ggatccgaac    840
gcctacatct acgtcatcac ccaggcgccg gtgtgggaga gatctgcga cgtgatcggc    900 gagaccggct ggaagacgca ccccgactac gccacgccgc cggcgcggct gtcgcggctc    960
aacgagatct tcgcgcgcat tgagcaatgg accatgacca agaccaagtt cgaggccatg   1020
gagatcctca cgccgacga catcccctgc ggccgatcc tgtcgatgaa ggaactcgcc   1080
gaagatcagt cgctgcgcgc caccggcacc atcgtcgagg tcgatcaccc gacccgcggc   1140
aagtatctgt cggtcggcaa cccgatcaag ctgtcggact ccccgaccga ggtgaagcgc   1200
tcgccgctac tcggtgaaca caccgacgaa atcctgcgcg acgtcctcgg ctacagcgac   1260
gcgcacgtcg cagagatcca cgactccggc gcgaccgctc cgccgcgcaa gcaagcggcg   1320
gagtaa                                                               1326
```

<210> SEQ ID NO 24
<211> LENGTH: 1251
<212> TYPE: DNA
<213> ORGANISM: Shigella dysenteriae

<400> SEQUENCE: 24

```
atgtcaactc cacttcaagg aattaaagtt ctcgatttca ccggtgtgca atctggccca     60
tcttgtactc aaatgctggc ctggtttggc gctgacgtca ttaaaattga acgccccggc    120
gttggtgacg taacgcgtca ccagctgcga gatattcctg atatcgatgc gctttacttc    180
accatgctta acgtaacaa acgttctatt gagttaaata ccaaaacagc ggaaggcaaa    240
gaggtaatgg aaaagctgat ccgcgaagct gatatcttag tcgagaactt tcatccaggg    300
```

```
gccattgatc acatgggctt cacctgggag catattcaag aaatcaatcc acgtctgatt    360
tttggttcga tcaaagggtt tgacgagtgt tcgccttatg tgaatgtaaa agcctatgaa    420
aacgttgctc aggcagcggg tggcgcggca tccactacgg gttttggga cggtccgccg    480 ctggtaagcg ctgcagcgtt aggagacagc aacaccggaa tgcatttgct gatcggttta    540
cttgctgctt tgctgcatcg cgaaaaaacg gggcgtgggc aacgagtcac catgtcaatg    600
caggatgccg tattgaacct tgccgcgtg aaattacgcg accagcagcg tctcgataaa    660
ttgggttatc tggaagaata cccgcagtat ccgaatggta catttggtga tgcagttccc    720
cgcggaggta atgcgggtgg tggcggtcaa cctggatgga tcctgaaatg taaaggctgg    780
gaaacagatc ctaacgccta tatttatttc actattcagg agcaaaactg ggaaaacacc    840
tgtaaagcca tcggcaaacc agattggatt accgatccgg catacagtac agcccatgcc    900
cgacagccac atattttcga tattttttgct gaaatcgaaa aatacactgt cactattgat    960
aaacatgaag cggtggccta tttgactcag tttgatattc cttgtgcacc ggttttaagt    1020
atgaaagaaa tttcacttga tccctcttta cgccaaagtg gcagtgttgt cgaagtggaa    1080
caaccgttgc gtggaaaata tctgacagtt ggttgtccaa tgaaattctc tgcctttacg    1140
ccagatatta agctgcgcc gctattaggt gaacataccc tgctgtatt acaggagctg    1200 ggttatagcg acgatgaaat tgctgcaatg aagcaaaacc acgccatctg a             1251

<210> SEQ ID NO 25
<211> LENGTH: 1278
<212> TYPE: DNA
<213> ORGANISM: Rhodopseudomonas palustris

<400> SEQUENCE: 25
atgaccaagg cgctcgacgg cgttcgcatt ctcgatttca cccacgtcca gtccggcccg     60
acctgcaccc agttgctggc gtggttcggc gccgacgtca tcaaggtcga gcgtcccggc    120
accggcgaca tcacccgcgg gcagttgcag gacatcccga aggtggacag cctgtatttc    180
accatgctga ccacaacaa gcgctcgatc acgctcgaca ccaagaaccc caagggcaag    240
gaggtgctga ccgcgctgat ccgctcctgc gacgtgctgg tggagaattt cggccccggc    300
gtgctcgatc gcatgggctt cacctgggac aagatccagg agatcaaccc gcggatgatc    360
gtcgcctcga tcaagggttt cggccccggt ccctatgaag actgcaaggt ctacgagaac    420
gtcgcgcaat gcaccggcgg cgccgcctcg accaccggct tccgcgacgg cccgccgctg    480
gtcaccggcg cacagatcgg cgactcgggc accgggctgc atctcgcgct cggcatcgtc    540
accgcgctgt atcagcgcca tcacaccggc cgcggccagc gcgtcaccgc cgcgatgcag    600
gacggcgtgc tcaatttgtc gcgcgtcaag ctgcgcgatc agcagcgcct cgcccacggc    660
ccgctcaagg aatacagcca gttcggcgaa ggcattccgt tcggcgacgc ggtgccgcgc    720
gccggcaatg attccggcgg cggccagccc ggccgcatcc tgaaatgcaa gggctgggag    780
accgatccca acgcctacat ctacttcatc gcgcaggccc cggtgtggga agatctgc      840 gacgtgatcg gcgagaccgg ctggaagacc catccggact acgcgacgcc gccggcgcgg    900
ctgaagcacc tcaacgacat cttcgcccgc atcgaacaat ggaccatgac caagaccaag    960
ttcgaggcga tggacatcct caacagggac gacattccct gcgggccgat cctgtcgatg   1020
aaggaactcg ccgaggacgc ctcgctgcgc gccaccggca cgatcgtcga ggtcgatcat   1080
ccgacccgcg gcaaatatct gtcggtcggc aacccgatca aactgtcgga ctcgccgacc   1140
catgtcgagc gctcgccgct tctcggcgag cacaccgacg aaattctgcg cgacgtcctc   1200
```

```
ggcttcaacg atcatcaggt cgctgaaatc cacgattccg gcgcactcgc tccgccgcgc   1260
aagcaggccg cagagtaa                                                 1278

<210> SEQ ID NO 26
<211> LENGTH: 1290
<212> TYPE: DNA
<213> ORGANISM: Methylobacterium extorquens

<400> SEQUENCE: 26
atgagcaagg caccgggcaa ggccctcgag ggcgttcgca tcctcgattt cacccatgtt     60
caatcggggc cgacctgcac gcaattgctc gcgtggttcg gggccgacgt catcaaggtc    120
gagcggccgg gtgcgggcga cgcgacgcgc cagcagcttc aggaccttcc cggcgtggac    180
agcctctatt tcacgatgct gaaccacaac aagcgttcga tcacgctcga cggcaagaac    240
cccaagggca acgcgatcct ctggcggctc attgccgagt gcgacgtgct ggtcgagaac    300 ttcgccccg gtgcgctcga ccgcatgggg ctgacctggg agaagctgca ggccgccaat    360
ccgggcctga tcctggcctc ggtgaagggc ttcgggcccg gccgctacca ggattgcaag    420
gtctacgaga acgtcgccca atgcgtcggc ggcgcgcct ccaccaccgg ctggcgcgac    480
ggcgtgccga tggtgtcggg ggcgcagatc ggcgattccg gcaccggcct gcatctggcg    540
ctcggcatcg tcacgccct ctaccagcgc acccagacgg gcagggcca cgcgtcgat     600 tgtgccatgc aggacggggt gctcaacctc tgccgggtga gctgcggga ccagcagcgc    660 ctcgcccacg gcccgctgat ggaatacagc cagtacggcg agggcgtccc cttcggcgag    720
gcggtgccgc gggccggcaa cgattccggc gggggcagc ccgccgcat cctcaagtgc    780 aagggctggg agcaggatcc caacgcttac atctacttca tcacgcaggg cgcggtctgg    840
gggccgatct gcgacatcat cggcgagccg gactggaaga ccgatccggc ctacgcgacg    900
ccgaaagccc gcctgccgca tctcaacgag atcttcacgc gcatcgaagc gtggacgatg    960
aagcacgaca agctcgaggc gatggagatc ctcaacgcct acgagatccc gtgcggaccg   1020
atcctgtcga tgcgggagat cgccgaggat ccgatgctgc gggcgaacgg cacggtggtc   1080
gaggtcgagc acccgacccg cggggcctat ctgacggtgg gcaacccgat caagctgtcg   1140
gcgagcccca ccgagatcac ccgcgcgccg ctgctcggcg agcataccga cgagatcctg   1200
cgcgaggtgc tgggctgcac cgatacggaa atcagcgaca tcctcggttc gggtgcggtg   1260
ggcggcgtcc accgcatcgc cgcggagtag                                   1290

<210> SEQ ID NO 27
<211> LENGTH: 1251
<212> TYPE: DNA
<213> ORGANISM: Ralstonia eutropha H16

<400> SEQUENCE: 27
gtgaacctcc cactcaacgg catcaagatc atcgacttca cgcacgtcca ggccggtccc     60
gcctgcacgc agcttctcgc gtggttcggt gcggacgtga tcaaggtcga gcgccccggt    120
tccggcgacg tgacgcgcac ccagctgcgc gacatcccgg atgtcgatgc cctgtacttc    180
accatgctca cagcaacaa gcgcagcctg acgctggata ccaagaagcc ggaaggcaag    240
aagatcctgg agcagctgat ccgcgagtcg gacgtgctgg tcgagaactt cggcccgggc    300
gcgctggacc gcatggggtt ctcgtgggaa cgcatcaacg aactgaaccc gaagatgatc    360
gtggcttcgg tcaagggctt cagcgacggc caccactatg aagacctgaa ggtctacgag    420
```

| | |
|---|---|
| aacgtggccc agtgcgccgg cggcgcggcc tcgaccaccg gcttctggga tggcccgccg | 480 |
| acggtgtccg ccgcggcgct gggcgattcc aacaccggca tgcacctggc catcggcatc | 540 |
| ctcaccgcgc tgatcggccg cgacaagacc ggcaagggcc agaaggtggc tgtgtcgatg | 600 |
| caggatgcgt tgctgaacct gtgccgggtc aagctgcgcg accagcagcg cctggaccgc | 660 |
| ctgggctacc tggaggagta cccgcagtat ccgcacggca gcttcagcga cgtggtgccg | 720 |
| cgcggcggca acgcgggcgg cggcggccag ccgggctggg tgctgaagtg caaggggtgg | 780 |
| gaaaccgacc ccaacgccta tatctacttc accatccagg ccatgcctg ggagccgatc | 840 |
| tgcaaggcgc tgggcaagcc ggaatggatt tccgatccca actacgccac cgccaaggct | 900 |
| cgccagccgc atatcttcga tatcttcaac accatcgagg aatggctggc cgacaagacc | 960 |
| aagtacgagg ccgtggacat cctgcgcaag ttcgacatcc cgtgctcgcc ggtgctgtcg | 1020 |
| atgaaggaaa tcgccgccga tccgtcgctg cgcgccagcg gcagcatcac cgaggtgccg | 1080 |
| cacaaggagc gcggtaccta cctgacggtg ggcagcccga tcaagttctc cgacctcaag | 1140 |
| ccggagatca ccgggtcgcc actgctgggc gagcatagcc aagaggtgct ggccggcctg | 1200 |
| ggctacggcg cggacgacat caagcgcctg cgcgagtccc aggtgatctg a | 1251 |

<210> SEQ ID NO 28
<211> LENGTH: 1251
<212> TYPE: DNA
<213> ORGANISM: Burkholderia xenovorans

<400> SEQUENCE: 28

| | |
|---|---|
| atgaccaaac tctctcgaagg catccggatc atcgacttca cccatgttca agccggccct | 60 |
| gcatgcaccc agttgctcgc ctggttcggc gcggacgtca tcaaggttga acggccgggt | 120 |
| tcgggcgacg tgacgcgcaa ccagttgcgc gatattcccg acgccgacgc gttgtacttc | 180 |
| acgatgctca acagcaacaa gaaatcgctg acgttggaca caaaaaaacc cgaaggcaag | 240 |
| gaagtactcg aaaagctgat tcgcgaatcc gacgtgctgg tggagaattt cggcccgggc | 300 |
| gcgttggacc gcatgggctt ttcgtgggaa cggctgaatg aactcaatcc gaagatgatc | 360 |
| gtcgcctcgg tgaaaggctt cagcgacggc caccactacg acgacctgaa ggtctacgaa | 420 |
| aacgtggcgc aatgcgcggg cggtgcggcc tccaccaccg gcttctggga cggtccgccc | 480 |
| accatcagcg ccgccgcgct cggcgacagc aataccggta tgcatctggc catcggcatt | 540 |
| ctgaccgcgc tgctcggtcg cgacaaaacc ggcaaaggcc agaaggtcgc agtgtccatg | 600 |
| caggacagcg tgctgaatct gtgccgcgtg aagcttcgtg accagcagcg gctggaacgc | 660 |
| gttggctatc tcgaggagta tccgcaatat ccgcacggcg aattcagcga cgtggtaccg | 720 |
| cgcggcggca atgcaggcgg cggcggccag ccgggttggg tgctcaaatg caaaggctgg | 780 |
| gaaacggatc cgaacgccta catctacttc acgattcagg ccatgcgtg ggagcccatc | 840 |
| tgcaaggcgc tcggcaagcc cgagtggatc gacgacccgg cctacaagac tgcggaagcg | 900 |
| cgtcaaccgc atatcttcga tatcttccag accatcgaaa cctggctcgc ggacaaaacc | 960 |
| aagttcgaag cggtcgacat cttgcgcaag ttcgacattc cgtgcgcacc ggtgctgacc | 1020 |
| atgaaggaac tggccaacga tccgtcgttg cgcgcgagcg gcacgatcgt cgaagtaccg | 1080 |
| cacaagaaac gcggcacgta tctgactgtc ggcagcccga tcaagttttc ggatctgaag | 1140 |
| ccggaagtca ccgcgtcgcc gctgctcggc gaacacaccg acgaggtgct ggcgagcctt | 1200 |
| ggctacagcc agcagcaaat cttcaacctg cgcgaagtca aggcagttta a | 1251 |

<210> SEQ ID NO 29
<211> LENGTH: 423
<212> TYPE: DNA
<213> ORGANISM: Azoarcus evansii

<400> SEQUENCE: 29

```
tcagtccttc ggcggttcca gatagcgccc gaagcgctcg cgccattcgt cgtcgatcaa      60
ggtcgcgcgc ggggcgccgc cgaggtcggc ccacacgacc gtctgcttcg cgcggaagcg     120
cacctgctcg cccatcgacg cggtcgtgac gatgtccatc gagctgccgc cgatgcgcgc     180
gacgtagagc gtgaaggtga gctcatcgcc gtgcatgctc ggtgcgaaaa agtcgacttc     240
gaggtggcgc atcggcacgc cgcggcggat ctccgcgtgc agcttgtaga agtccacgcc     300
gatgccgcgg tcgaaccagt cctcgaccac ctcattgcac agcaccaggc actgcgggta     360
gaagacgatg ccggccgggt cgcagtggtg gaaacggatg gatttcttgc attcgaagat     420
cat                                                                  423
```

<210> SEQ ID NO 30
<211> LENGTH: 432
<212> TYPE: DNA
<213> ORGANISM: Magnetospirillum magnetotacticum

<400> SEQUENCE: 30

```
tcattgggcc gcaacctcca ccagccgggt gcgataggct tccaggcgtt cgcgcatggg      60
accgggcatg ggaaccgcct tcaccttttc ctgatcggcg acgacacaga cgaaactggt     120
ctcgaaggcc accacgccgt caccccgcgc gccgatggtg cggaaatgaa tggaagagcc     180
ccccacccctg tccaccagga ccgagatatc caccccggtcg ccgggccgaa gcggcgattt     240
gatctccatg ccgatcttga cgaagggcgt gccgaagccg tgttccttgt tgatggtgta     300
ccagtcatag ccgatgacat cggccatgaa gacctccagc gcctccatgg cgtattccag     360
gaagcggggc gtatagacga tgcgcgccgc gtcggaatcg ccgaaatgga cccggcggcg     420
gtgaatgaac ac                                                        432
```

<210> SEQ ID NO 31
<211> LENGTH: 411
<212> TYPE: DNA
<213> ORGANISM: Jannaschia sp. CCS1

<400> SEQUENCE: 31

```
atgacccacc tctggcccct gcgcgtctac tatgaagacg tcgatctggc ggggatcgtc      60
tactacgcca actacctgaa atacctggag cgggggcgct ctgaaatggt gcgtgaggcc     120
ggcatttccc agctcgacat gaaagctgcg gggctggtct ttgccgtgcg gcgggtggag     180
gcggaatacc tcaaacccgc caaatacgat gatgagctgg tcgtggagac gcagctggac     240
cgcctgaaag gggccagttt cgacatgccc cagcgggtcc tgcgcggcga tgacgtgctg     300
ctggacgcgc ggatcaaggt tgtgatcctc aacgcggacg gccgggcggc gcgacttccg     360
gcggatattc gcgcaaaagt cacagccgtc gcggcaagtg atggcccgta a             411
```

<210> SEQ ID NO 32
<211> LENGTH: 432
<212> TYPE: DNA
<213> ORGANISM: Sagittula stellata

<400> SEQUENCE: 32

```
atgtcgcagg aggaagccgt ggggcagccg ttcgagcatg agatccgggt gacctggggg      60
```

```
gactgcgatc ccgcgcggat cgcctatacg gcgcgcatcc cctggttcgc gctggatgcg    120
atcaacgcct ggtgggagga gaagctgggc ggcggctggt tccagatgga gctggaccgc    180
ggtgtcggca cgccgttcgt caacatgacc atcgatttcc gcagtccggt cacgccgcgc    240
caccggctgc tctgcgccgt gcgcccggtg cggctgggcg agacctcggt cagtttcgaa    300
gtgctgggac ggcaggacgg tgtgctgtgt ttcgagggc ggttcacctg cgtgttcatc    360
gccgtgccgc gttttcgcaa ggcgccgccg ccggaggata tccgggcggt ggtggaggcg    420
catctgaact ag                                                        432

<210> SEQ ID NO 33
<211> LENGTH: 414
<212> TYPE: DNA
<213> ORGANISM: Escherichia coli

<400> SEQUENCE: 33
atgatctgga aacgccattt aacgctcgac gaactgaacg ccaccagcga taacacaatg     60
gtggcgcatc tgggaattgt gtatacccgt ctgggcgatg atgtgctgga agccgaaatg    120
ccggttgata cccgtactca tcagccgttc ggtttactac atggcggcgc gtcggcggcg    180
ctggcggaaa cgctgggatc gatggccgga tttatgatga cccgcgacgg acagtgtgtg    240
gtaggcacag aacttaatgc aacacaccat cgcccggtgt ctgagggaaa ggtacgcggc    300
gtctgccagc cgctgcatct tggtcggcaa aatcagagct gggaaatcgt cgttttcgat    360
gaacaggggc ggcgttgctg cacttgtcgg ctgggtacgg cagttttggg atga          414

<210> SEQ ID NO 34
<211> LENGTH: 1989
<212> TYPE: DNA
<213> ORGANISM: Acetobacter pasteurianus

<400> SEQUENCE: 34
atgtcggaaa acatcactat cctgcctaca cagtatgcag attacccggc tctgatgcca     60
cctgcggaac tggccgccat gcagcgctat gcacgccgag acccggatgg tttttggctg    120
caacaggccc ggcgtgtgca ctggcaccgc aagcctaggc gaggctttac gggcagcttt    180
acgggtgatg tgtccataag ctggtttgaa gatggcctta tcaacgcatc cgtatgctgt    240
attgataagc atctgacaga caaggctgat cagattgccc ttatcagcca ccgtgaaggc    300
cgggccgagg cagaaaaaat tacatatgcc atgctgcatg aacgggtttg ccgcctgtct    360
aacgcgctgg tgcatttggg ggtggaggaa gggcaccgcg ttgccatttg cctgcccatg    420
atttcagaag ccgtggtggc catgctggcc tgtgcgcgta ttggcgcggt gcatgtggtg    480
ctgtttggtg gttttcggc agaaggtatt gcagaacgta ttatagatag cggcgcagtt    540
gcggtaatta ccgccagcga aagcatgcgc ggcaacaaga tcgtgcccct taaagcgatt    600
atggatgaag ccctgtgcaa ggcaggtgca gaaagtggcg tgcgggctgt tctagttgtg    660
cgcacgtctg atgcacctgt tcccatgctg cctggtaggg attacgattt tcatgatttt    720
gtagattcgt ttgaggcaga ttttgtgccc gttgtcatgc gggcagaagc accattattt    780
atgctctaca catctggcag cacaggcaag cccaaagcag ttgtgcatgc cactggtggc    840
tatatggtgt gggcagctta cactatggac atggtgtacc atcatcaacc tggtgatgtg    900
ctgtggtgca cggcagatgt ggcatggata accgggcata catccgttgt gtatggcccg    960
ctggccaatg gcgaaccac catgatttcc gatagcctgc cttcataccc cgctccgggc   1020
agatggttgg atctgataga tgagcataag gtgaccatgc tgtttaccgc ccccacagcc   1080
```

```
gtgcgcgcca tgatggccga tggtgatgat gtggtgaacg cccgcaatct ggagtctctg    1140
cgtttgctgg gtgtggcggg ggagcccata agcccggatg cgtggctatg gtatcacgat    1200
gttgtgggta aaaagcgttg ccccgtggtg gatacatggt ggcagacaga aaccgccggc    1260
attgtgctgg ggccagtgcc gggtgtgcaa ccgcttaaac ccggctctgc cagcacgccg    1320
ctgccggggt tggaaatggt catagccgat acgcagggca ggccggtgca ggggcctgca    1380
gaaggtagcc tgtgcattgc gcgttcatgg ccggggcagg cccgcacaat ctggaaagat    1440
catgctcgct tctgccagac atattttggt atggttccgg gcattatttt cacgggtgat    1500
ggcgcacggc gagatgccga tggctattac tggattacgg ggcgcatgga cgatgttatc    1560
aatattgcag ggcaccgttt gggtacagca gaagtggaag atgcgttggc agcagatcat    1620
cgtattgtgg aatctgctgc agtgggcatc ccgcacccgg taaaggggca ggcgctggcg    1680
gtatttgtta ccagcgccga aacgtggct acggaactga cagaaaaagg cataagccgc    1740
cttatctccg gtatgttggg gcgttatgcc acgccagagg ccgtttatct ggtgccagat    1800
ctgcctcgca cgcgctctgg caagattgta cgccgcctgc tgcgcaaaat tgccagtggg    1860
gaaatggata atctgggaga tctttcatcg ctgaatgatc cttccatcgt gcgtatgctg    1920
tgtgacagag tatggagcca catggctttt gatgaggaat ctgcacctcg cacacaggca    1980
agggcctga                                                            1989

<210> SEQ ID NO 35
<211> LENGTH: 1890
<212> TYPE: DNA
<213> ORGANISM: Azotobacter vinelandii

<400> SEQUENCE: 35
atgaactatc agcactacca tgaacgctcc atcgccgatc ccgccggttt ctgggccgaa      60
caggcgcagg ccgtgcgctg gttccgccag ccgacggaaa ttctccgcgc cctggcggac     120
ggcacgcacc agtggttcgc cgacggccgg ttgaacagtt gctatctggc cctggatcat     180
cagatcgaac agggccgtgg cgagcagacg gccctgatcc acgactcgcc ggtcaccggc     240
ggcaaggccc gctacagcta ccgcgaactg cgcgacgaag tggcgcgcct ggccggcgcc     300
ctgcgcgagc tgggcgtgga aaagggcgac cgggtcatca tctacatgcc gatggtgccg     360
caagcggcca tggccatgct cgcctgcgcg cggatcggcg cggtgcactc ggtggtgttc     420
ggcggcttcg cccctcacga actggcgctg cgcatcgacg acgcccggcc caaactgctg     480
ctcaccgcgt cctgcggcct ggagttcgac cgggtcatcg aatacaaacc gctggtcgac     540
aaggccctgg aactggccag ccaccagccc gggcacgtac tggtgctgca acggccacaa     600
gcgagcgccg cgctgctccc agggcgcgac ctggactggc aggccagggt cccgctggcc     660
gcgccggtgg agcccgtgcc cctggacagc ggcgatccgc tgtacatcat gtacacctcc     720
ggcaccaccg gaaaacccaa gggcgtcgtg cgcgacaacg gcgcaacgc ggtggccctg     780 agcttcgcca tgcgccatgt ctacgccatg cgggccggcg acgtctggtg gggcatctcc     840
gacgtcggct gggtggtcgg ccattcgctg atcgtctacg gcccgctgat gaacggatgc     900
accagcatcc tctacgaagg caagccggtc cgcacgcccg acgccggcgc ctactggcgg     960
gtgatcgagg aatacggcgt caacggcctg ttctgcgcgc cgacggcgat ccgcgccatg    1020
cgcaaggaag atccttcggg cgaactgagc gggcgcacg acctgggctc gctgcggcac    1080
ctgttcctgg ccggcgagaa gctcgattcg agcacccacc ggtggctgga ggaactgacc    1140
```

| | |
|---|---|
| gggaagccgg tgcacgacca ctggtggcag accgagaccg gctggccggt caccgctccc | 1200 |
| tgcgccgggc tggagggcca caccgcacgc cacggttcga gcaaccgccc ggtgcccggc | 1260 |
| tatcgcgtcc aggtgatgga cgaacagggt cacctgctcg gagcgaaccg gcagggctcg | 1320 |
| atcgtcatcg ccctgcccct gccgccgggc tgcgcgcaga ccctgtggaa cgaccacgag | 1380 |
| cgctatctgc gctcttatct gagctcctat cccggctact accacaccgg cgacggcggc | 1440 |
| tacctggacg acgagggctt cgtctacatc atgggccgca ccgacgacgt gataaacgtg | 1500 |
| gccggccacc gcctctccac cggagaaatg gaagacctgg tggcccggca tccggcggtg | 1560 |
| gccgaatgcg cggtgatcgg catccccgac gcgatcaagg gacaggtgcc gctgggcctg | 1620 |
| atcgtcctca aggacggcag ccgaatccgc gaggagcaac tgcagcggga gttgaccgcc | 1680 |
| tcgatccgcg agcagatcgg cgcgctggcc tgcttccagc ggatagcgac ggtcaagcgc | 1740 |
| ctgccgaaga cccgttcggg caaaatcctc cgggcggtgc tgcgcaagat cgccaacggc | 1800 |
| gaggaggtgg ccacgcccat gaccatcgac gatccggcga tactcgggga aatcggcgcc | 1860 |
| gccctggcgt tgtacacgcg cgccagttga | 1890 |

<210> SEQ ID NO 36
<211> LENGTH: 1959
<212> TYPE: DNA
<213> ORGANISM: Dehalococcoides sp.

<400> SEQUENCE: 36

| | |
|---|---|
| atgagtaccg aagaaagaa gtttgacacg caaaacctgc ctaccaagac ttatttctgg | 60 |
| ccgctgaaaa gataccagga cctttataac agctcactgg ctgaccccga ggctttctgg | 120 |
| gccaaacact cagacgtgct ttcatgggaa aagccttggg aaaagtact ggactggaat | 180 |
| ccgccttatg cccgctggtt tgtaggcggc aagctgaata tgtcttacca atgcgtagac | 240 |
| cgccatgcca aaagctggcg taagagcaag gtagctatct attgggaagg cgaaaacggg | 300 |
| gatacccaga cccataagcta ttcagacctt tacgaaaatg taaaccgtta tgcatccgtc | 360 |
| ctgaaaaagc tgggcatatg caagggtgac agggtaactg tctacctgcc catgataacct | 420 |
| gaaatggtct atattctatt agcctgcaac cgggttggag ccgtccataa cgtaatattc | 480 |
| tcaggttttct cttcccagtc tatcgcagac agggtaaatg actccggttc aaaaatggtt | 540 |
| gttaccgcca gcggcggaca ccgccgcggt aagatactgc ctcttaaaga aatcgtagat | 600 |
| gaggctgtaa atccaccccc gactatagaa catgtactgg ttattaaata taccggccac | 660 |
| gaagtagcca tggaccccac cagagacgta tgggcacatg atctgctgaa agatgcagat | 720 |
| aaatacgtag cccctgaagc tatggaatcc accgacccgc ttttttatcct gtacacctca | 780 |
| ggcactaccg gtaaaccgaa gggtattctg catggtaccg gcggctacgg cgtctgggcg | 840 |
| tgcaataccc ttaagtgggc tttcaaaccc acggacgaat cagtcttctg gtgcacggca | 900 |
| gacgtaggct ggattaccgg gcacacatat gttgtatatg cccgctggc gctgggactt | 960 |
| acccaggtta tttacgaggg agctccggat tatccttcag tagaccgctg gtgggagatt | 1020 |
| attgataaat acggggtaag catattctat acctcgccta ccgccatacg catgtttatg | 1080 |
| cgccacggcg aggagttgcc tgccagacac gaccttggca ctctggaaat gctgggaagc | 1140 |
| gtgggcgaac ccattaaccc tgaagcctgg gaatggtatt acaagaatat aggccatgag | 1200 |
| aactgcccca tttccgatac ttggtggcag accgaaacag gcggttttat gattaccccc | 1260 |
| tgccccggca tacaatcctt cccgctcaaa ccgggctcag ccactttgcc tctaccggga | 1320 |
| gttgacccgg tagtggtaga tgctgaaggc aaggaactgc cggctaatga aaccgggttt | 1380 |

```
attgccatcc gcaaaccttg gccgggcata atgctgggta tatataacgg tgatgaactt    1440
tataaaaaga cctactggag ccgtttcccc ggctggtatt gtccgggaga cttttcaatg    1500
aaagattctg acggatatct gtggctgctg ggacgggctg acgaagttat caaggtagcc    1560
ggtcaccgca taagcaccgc cgaattggag catgctctgg taggccatag ttcagttgcc    1620
gaagcggcag tagcctcccg ccctgacgaa gtaaagggtg aagctattgt ggttttcgtc    1680
accctgaaaa aaggtgtaga agcctctgcg gaagtaaaga gagagcttac ccatcacctc    1740
cgctctgcta tcggcactat agccaccccg gaagagatca tttttcgtgga gaaactgccc    1800 aaaacccgtt cgggcaagat tatgcgccgc ctgctgaagg ccgttgccaa cgaagtaccc    1860
attggtgata ccactacact tgatgatgag acttcggtaa atgaggccag agcggctttt    1920
gatgaactgc tggcagcacg caaacaccac aaacactaa                          1959
```

<210> SEQ ID NO 37
<211> LENGTH: 810
<212> TYPE: DNA
<213> ORGANISM: Escherichia coli

<400> SEQUENCE: 37

```
atgacgaagc atactcttga caactggcg gcggatttac gccgcgccgc agagcagggc      60
gaagcgattg caccgctgcg cgatctgatt ggtatcgata cgctgaagc ggcttacgcc     120 attcagcaca taaatgtgca acatgacgtt gcgcaggggc gtcgcgtggt agggcgtaaa    180
gtgggcctga cacatccgaa agtgcaacaa caactgggcg ttgatcaacc ggattttggg    240
acgttatttg ccgacatgtg ttatggcgat aacgaaatca ttccttttc ccgtgttctg     300 caacccccgca ttgaagcgga gatcgcactg gtgttgaacc gcgatttgcc cgcaaccgat   360
atcaccttcg acgaattgta taacgccatt gaatgggtac ttccggcgct ggaagtggtg    420
gggagccgca ttcgcgactg gtcgattcag tttgtcgata ccgtggcaga taacgcctcc    480
tgtggggtgt atgtcatcgg cggtccggcg caacgtccgg cggggttaga cctgaaaaac    540
tgcgccatga agatgacgcg taataacgaa gaggtttcta gcgggcgcgg cagcgaatgc    600
ctgggacatc cgcttaatgc ggccgtctgg ctggcacgca aaatggccag tctgggtgaa    660
ccgctgcgca ccggagatat cattcttacc ggggcattag gtccgatggt ggcggtgaat    720
gcgggcgatc gttttgaagc ccatattgaa ggcataggtt cagttgctgc gacatttttca   780 agcgcagccc caaaaggaag tctgtcatga                                     810
```

<210> SEQ ID NO 38
<211> LENGTH: 789
<212> TYPE: DNA
<213> ORGANISM: Pseudomonas putida

<400> SEQUENCE: 38

```
atgaatgaag ccaacgtgat tgcgaacctg ttatgggatg cgcagcggca aaagctgccc      60
tgtgcaccgg tgcgggaata tttcgagggg aagagcgagg ttgaccaggc gctattggcc    120
tatgccgtac agcaggtgaa tgttcagcgc caggtggagg gcggccgacg tatcgtcggt    180
cgcaagatcg gccttacctc tccggcagtg cagaagcaat gggtgtaga tcggccggac    240 ttcggcacgt tgctggacga catggcgatc gtcgatggcg agccgatcaa cactgcgcgt    300
cttctgcagc ccaaggtcga agctgagatc gccctggtac tcgagcgtga cctcgatcgg    360
gagcgtcata cagtcgccga cctgatcgac gcgacagcgt atgcacttgc tgcaatcgag    420
```

```
gtggtggata gccgtatcac cggttggaac atccgctttg ttgacaccgt ggcagacaac    480
gcctcatcgg gcttgttcgt actcggtact cagcctgttg gcctgtcgaa gcttgatctg    540
gccggtatgt cgatgcgcat ggcgcgtggc gaagagcttg tatcgcaagg ggctggagct    600
gcctgccttg gcaacccgtt gaacgcagcg cgttggcttg ctgacacgtt ggtccaagtg    660
ggcacgccat tgcgtgccgg cgatgtggtt ctgaccggcg ctctggggcc aatggtcgcg    720
gtcgagtccg gtcacaccta tacggcatgg atcgatggct tcgccccggt acgagcaatt    780
ttctcctga                                                            789

<210> SEQ ID NO 39
<211> LENGTH: 807
<212> TYPE: DNA
<213> ORGANISM: Pseudomonas putida

<400> SEQUENCE: 39
atgagcgaac tagataccgc gcggacaggt gccgtgcgta aagctgccga cctgctgtac     60
gaagccaccc ggtccggtgt ggccgtggtg ccggtgcgca atctgatcgg cgagacggat    120
ttggaggcag cctatgcagt acaggaggtt aatacacaga gagcattggt tgccgggcgg    180
cgcctggttg acgcaagat tgggctgacc tctgtcgctg tacagaagca gctcggagtg    240
gaacagcccg actatggcat gttgttcgca gacatggcgc gtaccgaggg ggaggaaatc    300
gcccttgatg acgtgctcca acctaaagtc gaagccgaga tcgcctttgt cctgggacgt    360
gacctcgatg gcgatcaatt gacggtggcc gacctctttc gcgccatcga gttcgccgtt    420
ccggcgatcg agatcgtggg ttcgcggata accaattggg atatccgtat cacggacacc    480
attgctgaca atgcttcgtc tggcctgtat gtgctgggct ccacgccgaa gcgcttgtgc    540
gattttgact cgcgccaggc aggcatggtg atggagcggc aaggcatacc ggtgtcttcc    600
ggggtagggg ccgcctgcct tggagcgcct ctcaacgcag tcctttggtt ggccagggtc    660
atggctcgag cgggccgtcc gttgcgcact ggcgacacgg tgctttccgg tgcgctgggc    720
cccatggtgc cagtggcagg aggagatgta ttcgatgtgc ggatagccgg gcttggatcg    780
gtgaccgccg cttttgcaaa ggcataa                                        807

<210> SEQ ID NO 40
<211> LENGTH: 804
<212> TYPE: DNA
<213> ORGANISM: Klebsiella pneumoniae

<400> SEQUENCE: 40
atgctcgata aacagacccg taccctgatt gcccagcggc tgaaccaggc cgaaaagcag     60
cgtgaacaga tccgcgcgat ctcgctggat tatccgtcga tcaccattga ggacgcctac    120
gccgtccagc gcgagtgggt cgagatgaag atcgccgaag gccgcgtgct caaaggccac    180
aagatcggcc tgacctctaa agcgatgcag gccagttcgc agatcagcga gccggactac    240
ggcgcgctgc tcgacgatat gttcttccac gacggcagca atattccac cgaccgcttt    300
atcgttccgc gtatcgaagt cgagctggcc ttcgtgctgg ccaaaccgct gcgcggcccg    360
aactgtacgc tgtttgatgt ctacaacgcc accgactacg ttatcccggc gctggagctt    420
atcgacgcgc gctgccacaa catcgacccg gaaacccagc gtccgcgcaa agtgttcgac    480
accatctccg acaacgccgc caacgccggg gtgatcctcg gcggccggcc gattaaaccg    540
gacgagctcg acctgcgctg gatctccgcc ctgctgtatc gcaacggcgt aattgaagag    600
accggcgtcg ccgcgggcgt actcaatcat ccggccaacg gcgtggcctg gctggccaac    660
```

| | |
|---|---:|
| aagctggcgc cgtacgatgt ccagctcgaa gccgggcaga ttatcctcgg cggctccttc | 720 |
| acccgcccgg tcccggcgcg caagggcgat accttccacg tcgactacgg caacatgggc | 780 |
| gtcatcagct gccggtttgt ctag | 804 |

<210> SEQ ID NO 41
<211> LENGTH: 804
<212> TYPE: DNA
<213> ORGANISM: Escherichia coli

<400> SEQUENCE: 41

| | |
|---|---:|
| atgttcgaca acacaccca caccctgatc gcccagcgtc tggatcaggc agaaaaacag | 60 |
| cgcgaacaga tccgcgcgat ctcgctggat tacccggaga tcaccatcga agacgcttac | 120 |
| gcggtgcagc gtgaatgggt tcgactgaaa atcgccgaag tcgcacgct gaaaggccac | 180 |
| aaaatcggcc tgacttcgaa agcgatgcag gccagctcgc agatcagcga accggattac | 240 |
| ggtgcactgc tggacgacat gttcttccac gatggcagcg atatcccgac cgatcgcttt | 300 |
| atcgtgccgc gcattgaagt ggagctggct tttgtgctgg caaaaccgct gcgtggacca | 360 |
| aactgcacgc tgttcgacgt ttacaacgcc acggactatg tgatcccggc gctggagctg | 420 |
| atcgacgctc gctgccacaa catcgatccg gaaacccagc gcccgcgtaa agtgttcgac | 480 |
| accatttctg ataacgccgc caatgccggg gtgatcctcg gtggtcgtcc cattaagccc | 540 |
| gatgagttgg atctacgttg gatctccgcc ctgatgtatc gcaatggcgt gattgaagaa | 600 |
| accggcgtcg ccgctggcgt gctgaatcat ccggcaaacg cgtggcctg ctggcgaac | 660 |
| aaactcgccc cctatgacgt acaactggaa gccgggcaaa tcattctcgg cggttcgttc | 720 |
| acccgcccgg ttccggcgcg taagggcgac accttccacg tcgattacgg caacatgggc | 780 |
| tccattagct gccgctttgt ttaa | 804 |

<210> SEQ ID NO 42
<211> LENGTH: 840
<212> TYPE: DNA
<213> ORGANISM: Comamonas testosteroni

<400> SEQUENCE: 42

| | |
|---|---:|
| atgaaccgaa acaagccaa agtagtcgaa ggcaaatttc ccacacagaa caccatggac | 60 |
| aactccaaga tccagcacta cggcgacgag ctctaccagt cgctgctcga ccgccaaccc | 120 |
| gtcgctccgc tgaccgaccg cgaagcggac atcaccatcg aggacgccta ccagatccag | 180 |
| ctgcgcatga tccagcgccg gctggacgcg ggcgagcgcg tggtgggcaa gaaaataggc | 240 |
| gtgacgagca aggtcgtgat ggacatgctc aaggtcaacc agcccgactt cggccacctg | 300 |
| ctctcgggca tggtctacaa cgaaggccag cccatcccgg tgagcagcat gatcgcgccc | 360 |
| aaggccgagg cagaggtcgc cttcatcctg gcgcgcgacc tcgaaggccc cggcgtcacc | 420 |
| gcggccgacg tgctgcgcgc caccgactgc gtgatgccgt gcttcgagat cgtcgactcg | 480 |
| cgcatcaagg actggaagat caagatccag gacaccgtgg ccgacaacgc ctcctgcggc | 540 |
| gtgctcacgc tcggcggcct gcgcaagagc ccgcgcgacc tcgacctcgc gctggccggc | 600 |
| atggtgctgg aaaagaacgg cgaaatcatc agcacgtcct gcggcgcatc ggtgcagggc | 660 |
| tcgccggtca acgcggtggc ctggctggcc aacacgctcg gcgtctggg catcggcctc | 720 |
| aaggccggcg acatcatcct ctctggctcg cagtcgccgc tggtgccggt ggtcgcgggc | 780 |
| gacagcctgt attgcagcgt cggcggcctg ggcggcacgt cggtgcgttt cgtcgcctga | 840 |

<210> SEQ ID NO 43
<211> LENGTH: 507
<212> TYPE: DNA
<213> ORGANISM: Methanocaldococcus jannaschii

<400> SEQUENCE: 43

| | |
|---|---:|
| atgagaagta taataaaggg aagagtttgg aagtttggaa ataacgtaga tacagatgct | 60 |
| atattaccag caaggtattt agtttataca aaaccagagg aattagctca gtttgttatg | 120 |
| actggggcag acccagattt tccaaagaag gttaagccag agatataat agttggagga | 180 |
| aagaactttg gatgtggttc aagtagagag catgccccat taggattaaa aggagctgga | 240 |
| atcagctgtg ttattgctga gcttcgca agaatatttt atagaaatgc ataaatgtt | 300 |
| ggattaccat taattgaatg taagggcatt tcagagaaag tcaatgaagg ggatgagtta | 360 |
| gaggttaatt tagagactgg agagattaaa aacttaacca ctggagaggt tttaaaaggt | 420 |
| caaaaattac cagaattcat gatggaaatt ttagaggctg gaggattaat gccatactta | 480 |
| aagaaaaaga tggctgaaag ccaataa | 507 |

<210> SEQ ID NO 44
<211> LENGTH: 1263
<212> TYPE: DNA
<213> ORGANISM: Eubacterium limosum

<400> SEQUENCE: 44

| | |
|---|---:|
| ttgggtatga caatgactca gaaaatattg gcggcacatg ctggtctgga atccgtaaaa | 60 |
| ccgggtgatt tgatcatggc agacctggat ctggtgttgg ggaatgatat taccctcaccg | 120 |
| gtagccatca atgttttaa aaatattaat aaggaaaccg ttttttgacaa agacaaggtt | 180 |
| gcgctggtcc cagaccattt tgcgccgaac aaggatatta aggctgcgga gcagtgcaaa | 240 |
| caggtgcgct gttttgcctg tgagcaggat gtcaccaact attttgaaat cggcgaaatg | 300 |
| ggtgtagagc atgctctgct gccggaaaag ggactggtcg ttgccggcga tgtcgtgatt | 360 |
| ggggcagatt cgcacacctg tacctatggt gcgcttgggg ctttctcaac cggtgtgggt | 420 |
| tctaccgaca tggccgttgg tatggcaacc ggtaaagcct ggtttaaggt accgtctgcc | 480 |
| attaaattca atctgactgg cgcttttcaaa gaaggtgttt caggaaaaga cctgattctt | 540 |
| cacattatcg gaatgattgg tgtggatggt gcgctttata atcaatgga atttgccgga | 600 |
| gagggtgtgt caagcctgac gatggatgat cgcttcacca ttgcgaatat ggccattgaa | 660 |
| gctggcggta aaaatggtat cttccctgtc gacgataaga ccatcgaata tatgaaggag | 720 |
| cattctacca aggaatacaa ggcctttgaa gcagacgcag acgccgagta tgacgctgtg | 780 |
| tacgatatta atctggcaga tatcaagtct acggtagcat tcccgcactt gcctgaaaac | 840 |
| actaaaaccg ttgatgaaat tactgaaccg gttaagattg accaggttgt tatcggctca | 900 |
| tgcaccaatg gacgtttctc agactttaaa aaggccgcag atctgatgcg cggtaagcat | 960 |
| gttgccaaag gaatccgtgt tttgattatc ccagcaactc agcagattta cctggattgt | 1020 |
| atggaagcgg gatatttaaa agactttatt gaagcgggcg caacggtgag cacaccgacc | 1080 |
| tgcgggccat gcctgggcgg acatatgggg attctggcag cggagaacg ctgcgttcc | 1140 |
| acaacaaacc gtaactttgt cggacgcatg gccatgtgg actcggaagt ctatctggcg | 1200 |
| agccccgagg ttgcggcggc atctgctatc ctgggccgta ttgccggacc agaagaatta | 1260 |
| taa | 1263 |

<210> SEQ ID NO 45
<211> LENGTH: 492
<212> TYPE: DNA
<213> ORGANISM: Eubacterium limosum

<400> SEQUENCE: 45

```
atgaaagcaa aaggaaaagt atttagatat ggcaacaatg ttgatacaga cgttattatt      60
cccgcaagat acctgaacac cagcgatcct ctggaattag cggagcattg tatggaggat     120
attgacaagg attttataaa acgcgtggag gacggcgata tcatcgtcgc tgatgataat     180
tttggctgcg gctcttcaag agagcatgcg cccattgcca tcaaagcctc aggtgtctcc     240
tgtgtaatcg ccaatagctt tgcgcgtatt ttttatcgca attccatcaa tatcgggctg     300
ccgattctgg aatgtccgga agcggtggca gcgattgaag caggcgacga agtagaagtg     360
gattttgact ctggcgttat cactgacgtg accaagggac agagcttcca gggacaggca     420
ttccctgaat ttatgcagaa gctgatcgca gcaggcggcc tggtaaatta cgtcaacgag     480
aatctcattt ag                                                        492
```

<210> SEQ ID NO 46
<211> LENGTH: 1770
<212> TYPE: DNA
<213> ORGANISM: Macrococcus caseolyticus

<400> SEQUENCE: 46

```
atgtactata gtaatggaaa ctatgaagca tttgcaagac cgaagaagcc ggaaggggta      60
gataataagt ctgcatattt agttggttct ggtttagcgt cattagcagc ggcaagtttt     120
ttaatacgag atggtcaaat gaaaggtgaa aatattcata tattagaaga actcgatctc     180
cctggaggaa gcttggatgg aatattgaat cctgaacgtg ctatataat gcgtggcggt      240 cgtgagatgg agaatcattt tgaatgttta tgggatttat ttcgttcagt accatcattg     300
gaagtcgaag atgcttctgt tctggatgaa ttttactggt taaataaaga agatccaaac     360
tattcgaagt gccgcgtaat agaaaatcgt ggacaacgcc tagaatcaga tggaaaaatg     420
actctaacaa aaaaagcaaa taagaaaatt atccagctgt gcttaatgaa agaagaacag     480
ctgaatgatg tgaagatctc tgatgtcttc agtaaagact tcttagactc aaacttctgg     540
atctactgga aaacgatgtt tgcatttgaa ccttggcatt ctgctatgga gatgcgtcga     600
tatttaatgc gtttcatcca tcatattggt ggacttgcag acttttcagc tctaaaattt     660
acgaagttca atcagttcga atcacttgtt atgcctctga ttgagcatct taaagcgaag     720
aacgttacat ttgaatatgg tgtaactgtt aagaatatac aagttgaatg ttcaaaagag     780
tcaaaagttg caaaggcaat agacatcgtg cgcagaggta acgaggaatc aattccttta     840
actgaaaatg atttagtatt tgtaacaaat ggcagtatca ctgaaagtac tacttatgga     900
gataatgaca cacctgcacc gcctacatca aaacctggtg gcgcatggca actatgggaa     960
aacttaagta cgcaatgtga ggagtttggt aatccagcta aattctataa agatttacca    1020
gaaaaaagct ggttcgtgtc tgctacagca acaacaaata caaagaagt tatagattat    1080 attcaaaaaa tttgtaaacg cgatccatta tcaggtcgta cagtaactgg cggtatcgtt    1140
actgtagatg attcaaattg gcagttaagc tttacgctaa atcgacaaca gcagtttaaa    1200
aatcaacctg atgatcaagt gagtgtatgg atttacgcac tttattcaga tgaacgtgga    1260
gaacgtacaa ataaaacaat tgttgagtgt tctggtaaag aaatttgtga agaatggctt    1320
tatcatatgg gtgttcctga agagaagatt tcagcactag cagcagaatg taatacaatt    1380
```

| | |
|---|---|
| ccaagctata tgccgtacat taccgcttac tttatgccgc gtaaagaagg agatcgtcct | 1440 |
| ttagtagtac cacatggttc aaagaatatt gcatttatag gtaactttgc agaaacagaa | 1500 |
| agagataccg tatttacaac agaatattca gtaagaactg ctatggaagc ggtgtataaa | 1560 |
| cttctagaag tagaccgtgg agtgcctgaa gtattcgctt cagtatacga tgtgagaatt | 1620 |
| ttattacatg cgttatctgt actgaatgat ggcaagaaac tagatgaaat tgatatgcca | 1680 |
| ttctatgaaa gattggtaga aaaacgcttg ttgaagaaag catctggtac gttcattgaa | 1740 |
| gaactgttag aagaagcaaa tttgatataa | 1770 |

<210> SEQ ID NO 47
<211> LENGTH: 831
<212> TYPE: DNA
<213> ORGANISM: Pseudomonas putida

<400> SEQUENCE: 47

| | |
|---|---|
| atgagcaaat acgaaggccg ctggaccacc gtgaaggtcg aactggaagc gggcatcgcc | 60 |
| tgggtgaccc tcaatcgccc ggaaaaacgc aatgccatga gccccaccct gaaccgggaa | 120 |
| atggtcgacg tgctggaaac ccttgagcag gacgctgacg ctggcgtgct ggtattgacc | 180 |
| ggtgccggcg agtcctggac cgccggcatg gacctgaagg agtacttccg cgaggtggac | 240 |
| gccggcccgg aaatcctcca ggaaaagatt cgtcgcgaag cctcgcaatg caatggaag | 300 |
| ttgctgcgtc tgtatgccaa accgaccatc gccatggtca acggctggtg cttcggcggc | 360 |
| ggcttcagcc cactggtggc atgcgacctg gcgatctgcg ccaacgaagc gaccttcggc | 420 |
| ctgtcggaaa tcaactgggg catcccgcct ggtaacctgg tcagcaaggc catggccgat | 480 |
| accgttggcc atcgtcagtc gctgtactac atcatgaccg gcaagacctt cgatggtcgc | 540 |
| aaggctgccg agatgggcct ggtgaacgac agtgtgccgc tggccgagct gcgtgaaacc | 600 |
| acccgcgagt tggcgctgaa cctgctggaa aagaacccgg tggtgctgcg tgccgcgaag | 660 |
| aatggcttca gcgttgccg cgagctgacc tgggaacaga cgaggacta cctctacgcc | 720 |
| aagctcgacc agtcgcgcct gctggacact accggcggcc gcgagcaggg catgaagcag | 780 |
| ttcctcgacg acaagagcat caagccaggc ctgcaggcct acaagcgctg a | 831 |

<210> SEQ ID NO 48
<211> LENGTH: 786
<212> TYPE: DNA
<213> ORGANISM: Clostridium acetobutylicum

<400> SEQUENCE: 48

| | |
|---|---|
| atggaactaa acaatgtcat ccttgaaaag gaaggtaaag ttgctgtagt taccattaac | 60 |
| agacctaaag cattaaatgc gttaaatagt gatacactaa agaaatgga ttatgttata | 120 |
| ggtgaaattg aaaatgatag cgaagtactt gcagtaattt taactggagc aggagaaaaa | 180 |
| tcatttgtag caggagcaga tatttctgag atgaaggaaa tgaataccat gaaggtagaa | 240 |
| aaattcggga tacttggaaa taagtgtttt agaagattag aacttcttga aaagcctgta | 300 |
| atagcagctg ttaatggttt tgctttagga ggcggatgcg aaatagctat gtcttgtgat | 360 |
| ataagaatag cttcaagcaa cgcaagattt ggtcaaccag aagtaggtct cggaataaca | 420 |
| cctggttttg gtggtacaca aagactttca agattagttg aatgggcat ggcaaagcag | 480 |
| cttatatta ctgcacaaaa tataaaggca gatgaagcat taagaatcgg acttgtaaat | 540 |
| aaggtagtag aacctagtga attaatgaat acagcaaaag aaattgcaaa caaaattgtg | 600 |
| agcaatgctc cagtagctgt taagttaagc aaacaggcta ttaatagagg aatgcagtgt | 660 |

```
gatattgata ctgctttagc atttgaatca gaagcatttg gagaatgctt ttcaacagag      720
gatcaaaagg atgcaatgac agctttcata gagaaaagaa aaattgaagg cttcaaaaat      780
agatag                                                                 786
```

<210> SEQ ID NO 49
<211> LENGTH: 792
<212> TYPE: DNA
<213> ORGANISM: Pseudomonas putida

<400> SEQUENCE: 49

```
atgactttcc agcacatcct gttttccatc gaggacggcg ttgccttcct ttcattgaac       60
cgccccgagc agctgaacag cttcaatacg gccatgcacc tggaggtgcg cgaagcgctc      120
agacaagtgc gccagagcag tgacgcgcgg gtgctgctgc tgacggctga aggccgcggc      180
ttctgcgccg gccaggacct gtccgaccgc aacgttgccc aggcgccga  gatgccagac      240 ctgggccagt cgatcgacaa gttctacaac ccgctggtgc gcaccctgcg cgacctgcct      300
ttgccggtga tatgtgcggt caacggcgtg gcggccggtg ccggtgccaa cattcccttg      360
gcctgcgacc tggtgctggc cgcccgctcg gccagtttca tccaggcctt ctgcaagatc      420
ggcctggtgc cggactccgg cggtacttgg ctgctgccgc gcttggtcgg catggcccgg      480
gccaaggcgc tggccatgct gggcgagcgc cttggcgccg aacaggccga gcaatggggg      540
ctgatctacc gcgtggtgga tgatgcagcg ctgcgtgatg aagccctcac cctcgcccgc      600
cacctcgccg cccagcccac ctacggcctg acactgatca agcgcagcct caatgccagt      660
ttcgacaatg gttttgaggc gcagctggag ctggagcgcg acctgcagcg cctggcaggg      720
cgcagcgagg actaccgcga aggcgtgaac gccttcatga acaaacgcac gccagccttc      780 aagggggcgct ga                                                         792
```

<210> SEQ ID NO 50
<211> LENGTH: 1164
<212> TYPE: DNA
<213> ORGANISM: Escherechia coli

<400> SEQUENCE: 50

```
atggaacagg ttgtcattgt cgatgcaatt cgcaccccga tgggccgttc gaagggcggt       60
gcttttcgta acgtgcgtgc agaagatctc tccgctcatt taatgcgtag cctgctggcg      120
cgtaacccgg cgctggaagc ggcggccctc gacgatattt actggggttg tgtgcagcag      180
acgctggagc agggttttaa tatcgcccgt aacgcggcgc tgctggcaga agtaccacac      240
tctgtcccgg cggttaccgt taatcgcttg tgtggttcat ccatgcaggc actgcatgac      300
gcagcacgaa tgatcatgac tggcgatgcg caggcatgtc tggttggcgg cgtggagcat      360
atgggccatg tgccgatgag tcacggcgtc gattttcacc ccggcctgag ccgcaatgtc      420
gccaaagcgg cgggcatgat gggcttaacg gcagaaatgc tggcgcgtat gcacggtatc      480
agccgtgaaa tgcaggatgc ctttgccgcg cggtcacacg cccgcgcctg gccgccacg       540 cagtcggccg catttaaaaa tgaaatcatc ccgaccggtg gtcacgatgc cgacggcgtc      600
ctgaagcagt ttaattacga cgaagtgatt cgcccggaaa ccaccgtgga agccctcgcc      660
acgctgcgtc cggcgtttga tccagtaaac ggtatggtaa cggcgggcac atcttctgca      720
ctttccgatg gcgcagctgc catgctggta atgagtgaaa gccgcgccca tgaattaggt      780
cttaagccgc gcgctcgtgt gcgttcgatg gcggtcgttg gttgtgaccc atcgattatg      840
```

| | |
|---|---|
| ggttacggcc cggttccggc ctcgaaactg gcgctgaaaa aagcggggct ttctgccagc | 900 |
| gatatcggcg tgtttgaaat gaacgaagcc tttgccgcgc agatcctgcc atgtattaaa | 960 |
| gatctgggac taattgagca gattgacgag aagatcaacc tcaacggtgg cgcgatcgcg | 1020 |
| ctgggtcatc cgctgggttg ttccggtgcg cgtatcagca ccacgctgct gaatctgatg | 1080 |
| gaacgcaaag acgttcagtt tggtctggcg acgatgtgta tcggtctggg tcagggtatt | 1140 |
| gcgacggtgt tgagcgggt ttaa | 1164 |

<210> SEQ ID NO 51
<211> LENGTH: 2190
<212> TYPE: DNA
<213> ORGANISM: Escherechia coli

<400> SEQUENCE: 51

| | |
|---|---|
| atgctttaca aaggcgacac cctgtacctt gactggctgg aagatggcat tgccgaactg | 60 |
| gtatttgatg ccccaggttc agttaataaa ctcgacactg cgaccgtcgc cagcctcggc | 120 |
| gaggccatcg gcgtgctgga acagcaatca gatctaaaag gctgctgct gcgttcgaac | 180 |
| aaagcagcct ttatcgtcgg tgctgatatc accgaatttt tgtccctgtt cctcgttcct | 240 |
| gaagaacagt taagtcagtg gctgcacttt gccaatagcg tgtttaatcg cctggaagat | 300 |
| ctgccggtgc cgaccattgc tgccgtcaat ggctatgcgc tgggcggtgg ctgcgaatgc | 360 |
| gtgctggcga ccgattatcg tctggcgacg ccggatctgc gcatcggtct gccggaaacc | 420 |
| aaactgggca tcatgcctgg cttttggcggt tctgtacgta tgccacgtat gctgggcgct | 480 |
| gacagtgcgc tggaaatcat tgccgccggt aaagatgtcg gcgcggatca ggcgctgaaa | 540 |
| atcggtctgg tggatggcgt agtcaaagca gaaaaactgg ttgaaggcgc aaaggcggtt | 600 |
| ttacgccagg ccattaacgg cgacctcgac tggaaagcaa acgtcagcc gaagctggaa | 660 |
| ccactaaaac tgagcaagat tgaagccacc atgagcttca ccatcgctaa agggatggtc | 720 |
| gcacaaacag cggggaaaca ttatccggcc cccatcaccg cagtaaaaac cattgaagct | 780 |
| gcggcccgtt ttggtcgtga agaagcctta aacctggaaa acaaaagttt tgtcccgctg | 840 |
| gcgcatacca acgaagcccg cgcactggtc ggcattttcc ttaacgatca atatgtaaaa | 900 |
| ggcaaagcga agaaactcac caaagacgtt gaaaccccga acaggccgc ggtgctgggt | 960 |
| gcaggcatta tggcggcgg catcgcttac cagtctgcgt ggaaaggcgt gccggttgtc | 1020 |
| atgaaagata tcaacgacaa gtcgttaacc ctcggcatga ccgaagccgc gaaactgctg | 1080 |
| aacaagcagc ttgagcgcgg caagatcgat ggtctgaaac tggctggcgt gatctccaca | 1140 |
| atccacccaa cgctcgacta cgccggattt gaccgcgtgg atattgtggt agaagcggtt | 1200 |
| gttgaaaacc cgaaagtgaa aaaagccgta ctggcagaaa ccgaacaaaa agtacgccag | 1260 |
| gataccgtgc tggcgtctaa cacttcaacc attcctatca gcgaactggc caacgcgctg | 1320 |
| gaacgcccgg aaaacttctg cgggatgcac ttctttaacc cggtccaccg aatgccgttg | 1380 |
| gtagaaatta ttcgcggcga gaaaagctcc gacgaaacca tcgcgaaagt tgtcgcctgg | 1440 |
| gcgagcaaga tgggcaagac gccgattgtg gttaacgact gccccggctt ctttgttaac | 1500 |
| cgcgtgctgt tcccgtattt cgccggtttc agccagctgc tgcgcgacgg cgcggatttc | 1560 |
| cgcaagatcg acaaagtgat ggaaaaacag tttggctggc cgatgggccc ggcatatctg | 1620 |
| ctggacgttg tgggcattga taccgcgcat cacgctcagg ctgtcatggc agcaggcttc | 1680 |
| ccgcagcgga tgcagaaaga ttaccgcgat gccatcgacg cgctgtttga tgccaaccgc | 1740 |
| tttggtcaga gaacggcct cggtttctgg cgttataaag aagacagcaa aggtaagccg | 1800 |

```
aagaaagaag aagacgccgc cgttgaagac ctgctggcag aagtgagcca gccgaagcgc    1860
gatttcagcg aagaagagat tatcgcccgc atgatgatcc cgatggtcaa cgaagtggtg    1920
cgctgtctgg aggaaggcat tatcgccact ccggcggaag cggatatggc gctggtctac    1980
ggcctgggct tccctccgtt ccacggcggc gcgttccgct ggctggacac cctcggtagc    2040
gcaaaatacc tcgatatggc acagcaatat cagcacctcg gcccgctgta tgaagtgccg    2100
gaaggtctgc gtaataaagc gcgtcataac gaaccgtact atcctccggt tgagccagcc    2160
cgtccggttg gcgacctgaa aacggcttaa                                     2190
```

<210> SEQ ID NO 52
<211> LENGTH: 702
<212> TYPE: DNA
<213> ORGANISM: Escherechia coli

<400> SEQUENCE: 52

```
atgacaacct taagctgtaa agtgacctcg gtagaagcta tcacggatac cgtatatcgt     60
gtccgcatcg tgccagacgc ggccttttct tttcgtgctg gtcagtattt gatggtagtg    120
atggatgagc gcgacaaacg tccgttctca atggcttcga cgccggatga aaagggtt      180 atcgagctgc atattggcgc ttctgaaatc aacctttacg cgaaagcagt catggaccgc    240
atcctcaaag atcatcaaat cgtggtcgac attccccacg gagaagcgtg gctgcgcgat    300
gatgaagagc gtccgatgat tttgattgcg ggcggcaccg ggttctctta tgcccgctcg    360
attttgctga cagcgttggc gcgtaaccca aaccgtgata tcaccattta ctggggcggg    420
cgtgaagagc agcatctgta tgatctctgc gagcttgagg cgctttcgtt gaagcatcct    480
ggtctgcaag tggtgccggt ggttgaacaa ccggaagcgg gctggcgtgg gcgtactggc    540
accgtgttaa cggcggtatt gcaggatcac ggtacgctgg cagagcatga tatctatatt    600
gccggacgtt ttgagatggc gaaaattgcc cgcgatctgt tttgcagtga gcgtaatgcg    660
cgggaagatc gcctgtttgg cgatgcgttt gcatttatct ga                       702
```

<210> SEQ ID NO 53
<211> LENGTH: 2145
<212> TYPE: DNA
<213> ORGANISM: Escherechia coli

<400> SEQUENCE: 53

```
atggaaatga catcagcgtt taccctttaat gttcgtctgg acaacattgc cgttatcacc     60
atcgacgtac cgggtgagaa aatgaatacc ctgaaggcgg agtttgcctc gcaggtgcgc    120
gccattatta agcaactccg tgaaaacaaa gagttgcgag gcgtggtgtt tgtctccgct    180
aaaccggaca acttcattgc tggcgcagac atcaacatga tcggcaactg caaaacggcg    240
caagaagcgg aagctctggc gcggcagggc caacagttga tggcggagat tcatgctttg    300
cccattcagg ttatcgcggc tattcatggc gcttgcctgg tggtgggct ggagttggcg    360 ctggcgtgcc acgtcgcgt ttgtactgac gatcctaaaa cggtgctcgg tttgcctgaa    420
gtacaacttg gattgttacc cggttcaggc ggcacccagc gtttaccgcg tctgataggc    480
gtcagcacag cattagagat gatcctcacc ggaaaacaac ttcgggcgaa acaggcatta    540
aagctggggc tggtggatga cgttgttccg cactccattc tgctggaagc cgctgttgag    600
ctggcaaaga aggagcgccc atcttcccgc cctctacctg tacgcgagcg tattctggcg    660
gggccgttag gtcgtgcgct gctgttcaaa atggtcggca agaaaacaga acacaaaact    720
```

```
caaggcaatt atccggcgac agaacgcatc ctggaggttg ttgaaacggg attagcgcag    780
ggcaccagca gcggttatga cgccgaagct cgggcgtttg gcgaactggc gatgacgcca    840
caatcgcagg cgctgcgtag tatctttttt gccagtacgg acgtgaagaa agatcccggc    900
agtgatgcgc cgcctgcgcc attaaacagc gtggggattt taggtggtgg cttgatgggc    960
ggcggtattg cttatgtcac tgcttgtaaa gcggggattc cggtcagaat taaagatatc   1020
aacccgcagg gcataaatca tgcgctgaag tacagttggg atcagctgga gggcaaagtt   1080
cgccgtcgtc atctcaaagc cagcgaacgt gacaaacagc tggcattaat ctccggaacg   1140
acggactatc gcggctttgc ccatcgcgat ctgattattg aagcggtgtt tgaaaatctc   1200
gaattgaaac aacagatggt ggcggaagtt gagcaaaatt gcgccgctca taccatcttt   1260
gcttcgaata cgtcatcttt accgattggt gatatcgccg ctcacgccac gcgacctgag   1320
caagttatcg gcctgcattt cttcagtccg gtggaaaaaa tgccgctggt ggagattatt   1380
cctcatgcgg ggacatcggc gcaaaccatc gctaccacag taaaactggc gaaaaaacag   1440
ggtaaaacgc caattgtcgt gcgtgacaaa gccggttttt acgtcaatcg catcttagcg   1500
ccttacatta atgaagctat ccgcatgttg acccaaggtg aacgggtaga gcacattgat   1560
gccgcgctag tgaaatttgg ttttccggta ggcccaatcc aacttttgga tgaggtagga   1620
atcgacaccg ggactaaaat tattcctgta ctggaagccg cttatggaga acgttttagc   1680
gcgcctgcaa atgttgtttc ttcaattttg aacgacgatc gcaaaggcag aaaaaatggc   1740
cggggtttct atctttatgg tcagaaaggg cgtaaaagca aaaaacaggt cgatcccgcc   1800
atttacccgc tgattggcac acaagggcag ggcgaatct ccgcaccgca ggttgctgaa    1860
cggtgtgtga tgttgatgct gaatgaagca gtacgttgtg ttgatgagca ggttatccgt   1920
agcgtgcgtg acggggatat tggcgcggta tttggcattg gttttccgcc atttctcggt   1980
ggaccgttcc gctatatcga ttctctcggc gcgggcgaag tggttgcaat aatgcaacga   2040
cttgccacgc agtatggttc ccgttttacc ccttgcgagc gtttggtcga gatgggcgcg   2100
cgtggggaaa gtttttggaa acaactgca actgacctgc aataa                   2145

<210> SEQ ID NO 54
<211> LENGTH: 720
<212> TYPE: DNA
<213> ORGANISM: Escherechia coli

<400> SEQUENCE: 54
atggtcatta aggcgcaaag cccggcgggt ttcgcggaag agtacattat gaaagtatc     60 tggaataacc gcttccctcc cgggactatt tgcccgcag aacgtgaact ttcagaatta    120 attgcgtaa cgcgtactac gttacgtgaa gtgttacagc gtctggcacg agatggctgg    180
ttgaccattc aacatggcaa gccgacgaag gtgaataatt tctgggaaac ttccggttta    240
aatatccttg aaacactggc gcgactggat cacgaaagtg tgccgcagct tattgataat    300
ttgctgtcgg tgcgtaccaa tatttccact atttttattc gcaccgcgtt tcgtcagcat    360
cccgataaag cgcaggaagt gctggctacc gctaatgaag tggccgatca cgccgatgcc    420
tttgccgagc tggattacaa catattccgc ggcctggcgt ttgcttccgg caacccgatt    480
tacggtctga ttcttaacgg gatgaaaggg ctgtatacgc gtattggtcg tcactatttc    540
gccaatccgg aagcgcgcag tctggcgctg gcttctacc acaaactgtc ggcgttgtgc     600
agtgaaggcg cgcacgatca ggtgtacgaa acagtgcgtc gctatgggca tgagagtggc    660
gagatttggc accggatgca gaaaaatctg ccgggtgatt tagccattca ggggcgataa    720
```

<210> SEQ ID NO 55
<211> LENGTH: 1000
<212> TYPE: DNA
<213> ORGANISM: Castellaniella defragrans

<400> SEQUENCE: 55

```
atgcggttca cattgaagac gacggcgatt gtgtcggccg ccgccctgct ggccggtttc      60
gggccgccgc cccgcgcggc ggaactgccg ccggggcggc tcgccaccac cgaggactat     120
ttcgcgcagc aggcgaagca ggccgtcacc cccgacgtga tggcccagct ggcctacatg     180
aactacatcg atttcatctc gcccttctac agccggggct gctccttcga ggcctgggag     240
ctcaagcaca cgccgcagcg ggtcatcaag tattcgatcg ccttctatgc gtatggcctg     300
gccagcgtgg cgctcatcga cccgaagctg cgtgcgctcg ccggccatga cctggacatc     360
gcggtctcca agatgaagtg caagcgggtc tggggcgact gggaggaaga cgggttcggc     420
accgacccga tcgagaaaga gaacatcatg tacaagggcc acctgaacct gatgtacggc     480
ctctatcagc tggtgaccgg cagccgccgg tacgaagccg agcatgccca cctcacccgc     540
atcatccatg acgagatcgc ggccaacccc tttgccggca tcgtctgcga gccggacaat     600
tatttttgtcc agtgcaattc ggtcgcctac ctgagcctgt gggtctatga ccggctgcat     660
ggcaccgact accgggcggc caccagggcc tggctggatt tcatccagaa ggacctgatc     720
gatcccgagc ggggcgcctt ctacctgtcc tatcaccccg agtccggcgc ggtgaagccg     780
tggatctcgg cgtatacgac agcctggacg ctcgccatgg tgcacggcat ggaccccgcc     840
ttttccgagc gctactaccc ccggttcaag cagaccttcg tcgaggtcta cgacgagggc     900
cgcaaggccc gggtgcgcga cacggccggc acggacgacg cggatggcgg ggtgggcctg     960
gcttcggcgt tcaccctgct gctggcccgc gagatgggcg                          1000
```

<210> SEQ ID NO 56
<211> LENGTH: 1000
<212> TYPE: DNA
<213> ORGANISM: Castellaniella defragrans

<400> SEQUENCE: 56

```
atgcggttca cattgaagac gacggcgatt gtgtcggccg ccgccctgct ggccggtttc      60
gggccgccgc cccgcgcggc ggaactgccg ccggggcggc tcgccaccac cgaggactat     120
ttcgcgcagc aggcgaagca ggccgtcacc cccgacgtga tggcccagct ggcctacatg     180
aactacatcg atttcatctc gcccttctac agccggggct gctccttcga ggcctgggag     240
ctcaagcaca cgccgcagcg ggtcatcaag tattcgatcg ccttctatgc gtatggcctg     300
gccagcgtgg cgctcatcga cccgaagctg cgtgcgctcg ccggccatga cctggacatc     360
gcggtctcca agatgaagtg caagcgggtc tggggcgact gggaggaaga cgggttcggc     420
accgacccga tcgagaaaga gaacatcatg tacaagggcc acctgaacct gatgtacggc     480
ctctatcagc tggtgaccgg cagccgccgg tacgaagccg agcatgccca cctcacccgc     540
atcatccatg acgagatcgc ggccaacccc tttgccggca tcgtctgcga gccggacaat     600
tatttttgtcc agtgcaattc ggtcgcctac ctgagcctgt gggtctatga ccggctgcat     660
ggcaccgact accgggcggc caccagggcc tggctggatt tcatccagaa ggacctgatc     720
gatcccgagc ggggcgcctt ctacctgtcc tatcaccccg agtccggcgc ggtgaagccg     780
tggatctcgg cgtatacgac agcctggacg ctcgccatgg tgcacggcat ggaccccgcc     840
```

| | |
|---|---|
| ttttccgagc gctactaccc ccggttcaag cagaccttcg tcgaggtcta cgacgagggc | 900 |
| cgcaaggccc gggtgcgcga gacggccggc acggacgacg cggatggcgg ggtgggcctg | 960 |
| gcttcggcgt tcaccctgct gctggcccgc gagatgggcg | 1000 |

<210> SEQ ID NO 57
<211> LENGTH: 1392
<212> TYPE: DNA
<213> ORGANISM: Sulfolobus solfataricus

<400> SEQUENCE: 57

| | |
|---|---|
| atgagatcaa aagaagattt cctaaagtcc ttaaaagatg aagaaattt gtattatagg | 60 |
| gggaagttag tagaagatat aacaacacat cagatcttaa agacagccgc attgcacgca | 120 |
| gctaagttat atgaatacgc tgatagagtc tatgaggata taaaatggg aaaaatgagc | 180 |
| aagttctta aggtaccttg gacatctcaa gatttgctag atagacataa actaatttac | 240 |
| gatttaacga tgtattgtaa tggggtattt aacatttcac aagcaatagg aagtgatgcg | 300 |
| atctttgccc ttatgatcac ggcaaaacaa gttgatagaa atacggaac tgattactca | 360 |
| aaacgtgttg aaaatatttt tgagagagtt gctaaagaag atttaacgtt agccactgcc | 420 |
| cagactgacg ttaagggaga tcgaagtaag aggccttctg aacaagttga tccagatatg | 480 |
| tatgttagag tagttgatgt gaaaagcgat ggaatagttg ttagaggagc aaaggctcat | 540 |
| acaactcaat ctgcggtatc tgatgagatt attgtcatac caaccagagt aatgagggat | 600 |
| agcgataaag attacgcagt agcctttgcg gttccagcta atactaaagg tttgaagatg | 660 |
| tatattagac caattgatga aattgagggc aattcctcct cagtactcag tagaaaagat | 720 |
| tatgagctag aaacattaac cgtcttcaac gacgttttcg ttccttggga tagggtattt | 780 |
| ttatttaagg aatacgacta cgctggaaca ttggctatgc tatttgcaac cttccatagg | 840 |
| tttactgcat tatcgtatag gtcagcgacc atgaatctat atttgggagc atctaaagtg | 900 |
| gcatctcaag taaatggcat tgagaatgaa agcatgtga gagatgatat agttgatata | 960 |
| attctctaca aggaaattat gaggagtagc gcgatagctg cggctgtgta tccagtaaac | 1020 |
| atggagggta tagctgtgcc caacccgctt tttactaatg ttggtaaatt atactccaat | 1080 |
| atgcatttcc atgatgttgt aagagattta attgacattg ctgggggat aatagctact | 1140 |
| atgccctctc aagaagattt ggaaagtgat gaaggaaaga atattgttaa atatttaagg | 1200 |
| ggctcagttg atgagagga aagagcaaaa gtgttaaaac tagctaagga attaggggct | 1260 |
| agtacgttta ctggctattt gctaactggt atgatacatg cggaaggttc tatgaagct | 1320 |
| agcaaaatag agctattcag aagttataat tttaaggagg ccgagaactt agttaaaagg | 1380 |
| gtattaagct ag | 1392 |

<210> SEQ ID NO 58
<211> LENGTH: 1206
<212> TYPE: DNA
<213> ORGANISM: Escherichia coli

<400> SEQUENCE: 58

| | |
|---|---|
| atgcgtgaag cctttatttg tgacggaatt cgtacgccaa ttggtcgcta cggcggggca | 60 |
| ttatcaagtg ttcgggctga tgatctggct gctatccctt gcgggaact gctggtgcga | 120 |
| aacccgcgtc tcgatgcgga gtgtatcgat gatgtgatcc tcggctgtgc taatcaggcg | 180 |
| ggagaagata accgtaacgt agcccggatg gcgactttac tggcggggct gccgcagagt | 240 |
| gtttccggca caaccattaa ccgcttgtgt ggttccgggc tggacgcact ggggtttgcc | 300 |

```
gcacgggcga ttaaagcggg cgatggcgat tgctgatcg ccggtggcgt ggagtcaatg    360
tcacgggcac cgtttgttat gggcaaggca gccagtgcat tttctcgtca ggctgagatg    420
ttcgatacca ctattggctg gcgatttgtg aacccgctca tggctcagca atttggaact    480
gacagcatgc cggaaacggc agagaatgta gctgaactgt taaaaatctc acgagaagat    540
caagatagtt ttgcgctacg cagtcagcaa cgtacggcaa aagcgcaatc ctcaggcatt    600
ctggctgagg agattgttcc ggttgtgttg aaaaacaaga aggtgttgt aacagaaata     660 caacatgatg agcatctgcg cccggaaacg acgctggaac agttacgtgg gttaaaagca    720
ccatttcgtg ccaatggggt gattaccgca ggcaatgctt ccggggtgaa tgacggagcc    780
gctgcgttga ttattgccag tgaacagatg gcagcagcgc aaggactgac accgcgggcg    840
cgtatcgtag ccatggcaac cgccggggtg gaacccgcgcc tgatgggct tggtccggtg    900 cctgcaactc gccgggtgct ggaacgcgca gggctgagta ttcacgatat ggacgtgatt    960
gaactgaacg aagcgttcgc ggcccaggcg ttgggtgtac tacgcgaatt ggggctgcct   1020
gatgatgccc cacatgttaa ccccaacgga ggcgctatcg ccttaggcca tccgttggga   1080
atgagtggtg cccgcctggc actggctgcc agccatgagc tgcatcggcg taacggtcgt   1140
tacgcattgt gcaccatgtg catcggtgtc ggtcagggca tcgccatgat tctggagcgt   1200
gtttga                                                              1206

<210> SEQ ID NO 59
<211> LENGTH: 1221
<212> TYPE: DNA
<213> ORGANISM: Pseudomonas putida

<400> SEQUENCE: 59
atgaatgaac cgacccacgc cgatgccttg atcatcgacg ccgtgcgcac gcccattggc     60
cgctatgccg gggccctgag cagcgtgcgc gccgacgacc tggcggccat cccgctcaaa    120
gccttgatcc agcgtcaccc cgaactggac tggaaagcca ttgatgacgt tatcttcggc    180
tgtgccaacc aggctggcga agacaaccgc aacgtggccc acatggcgag cctgctggcc    240
gggctgccac tcgaagtacc agggaccacg atcaaccgcc tgtgcggttc cggtctggat    300
gccatcggta atgcggcacg tgccctgcgc tgcggtgaag cggggctcat gctggccggt    360
ggtgtggagt ccatgtcgcg tgcaccgttt gtgatgggta gtcggagca ggcattcggg     420 cgtgcggccg agctgttcga caccaccatc ggctggcgtt cgtcaacccc gctgatgaag    480
gccgcctacg gcatcgattc gatgccgaaa acggctgaaa acgtggccga acagttcggc    540
atctcgcgcg ccgaccagga tgcctttgcc ctgcgcagcc agcacaaagc cgcagcagct    600
caggcccgcg ccgcctggc gcgggaaatc gtgccggtca aatcccgca cgcaaaggc     660 ccagccaaag tggtcgagca tgacgagcac ccgcgcggcg acacgaccct ggagcagctg    720
gctcggctcg gacgccgtt tcgtgaaggc ggcagcgtaa cggcgggtaa tgcctccggc    780
gtgaatgacg gcgcttgcgc cctgctgctg gccagcagcg ccgcggcccg ccgccatggg    840
ttgaaggccc gcggccgcat cgtcggcatg gcggtggccg gggttgagcc caggctgatg    900
ggcattggtc cggtgcctgc gacccgcaag gtgctggcgc tcaccggcct ggcactggct    960
gacctggatg tcatcgaact caatgaggcc tttgccgccc aagggctggc cgtgttgcgc   1020
gagctgggcc tggccgacga cgacccgcga gtcaaccgca acggcggcgc catcgccctg   1080
ggccatcccc tgggcatgag cggtgcccgg ttggtgacca ctgccttgca cgagcttgaa   1140
```

| | |
|---|---:|
| gaaacggccg gccgctacgc cctgtgcacc atgtgcatcg gcgtaggcca aggcattgcc | 1200 |
| atgatcatcg agcgcctctg a | 1221 |

<210> SEQ ID NO 60
<211> LENGTH: 1203
<212> TYPE: DNA
<213> ORGANISM: Pseudomonas putida

<400> SEQUENCE: 60

| | |
|---|---:|
| atgcacgacg tattcatctg tgacgccatc cgtaccccga tcggccgctt cggcggcgcc | 60 |
| ctggccagcg tgcgggccga cgacctggcc gccgtgccgc tgaaggcgct gatcgagcgc | 120 |
| aaccctggcg tgcagtggga ccaggtagac gaagtgttct tcggctgcgc caaccaggcc | 180 |
| ggtgaagaca accgcaacgt ggcccgcatg gcactgctgc tggccggcct gccggaaagc | 240 |
| atcccgggcg tcaccctgaa ccgtctgtgc gcgtcgggca tggatgccgt cggcaccgcg | 300 |
| ttccgcgcca tcgccagcgg cgagatggag ctggtgattg ccggtggcgt cgagtcgatg | 360 |
| tcgcgcgccc cgttcgtcat gggcaaggct gaaagcgcct attcgcgcaa catgaagctg | 420 |
| gaagacacca ccattggctg gcgtttcatc aacccgctga tgaagagcca gtacggtgtg | 480 |
| gattccatgc cggaaaccgc cgacaacgtg gccgacgact atcaggtttc gcgtgctgat | 540 |
| caggacgctt cgccctgcg cagccagcag aaggctgccg ctgcgcaggc tgccggcttc | 600 |
| tttgccgaag aaatcgtgcc ggtgcgtatc gctcacaaga agggcgaaat catcgtcgaa | 660 |
| cgtgacgaac acctgcgccc ggaaaccacg ctggaggcgc tgaccaagct caaaccggtc | 720 |
| aacggcccgg acaagacggt caccgccggc aacgcctcgg gcgtgaacga cggtgctgcg | 780 |
| gcgatgatcc tggcctcggc cgcagcggtg aagaaacacg gcctgactcc gcgtgcccgc | 840 |
| gttctgggca tggccagcgg cggcgttgcg ccacgtgtca tgggcattgg cccggtgccg | 900 |
| gcggtgcgca aactgaccga gcgtctgggg atagcggtaa gtgatttcga cgtgatcgag | 960 |
| cttaacgaag cgtttgccag ccaaggcctg gcggtgctgc gtgagctggg tgtggctgac | 1020 |
| gatgcgcccc aggtaaaccc taatggcggt gccattgccc tgggccaccc cctgggcatg | 1080 |
| agcggtgcac gcctggtact gactgcgttg caccagctgg agaagagtgg cggtcgcaag | 1140 |
| ggcctggcga ccatgtgtgt gggtgtcggc caaggtctgg cgttggccat cgagcgggtt | 1200 |
| tga | 1203 |

<210> SEQ ID NO 61
<211> LENGTH: 1212
<212> TYPE: DNA
<213> ORGANISM: Acinetobacter calcoaceticus

<400> SEQUENCE: 61

| | |
|---|---:|
| atgacattaa aaacgctta tatcatcgat gccatccgta ctccattcgg tcgttatgcc | 60 |
| ggtggccttg cacctgtccg tgcagatgac cttggtgctg tgccgattaa agccctcatg | 120 |
| caacgtaacc caagtgtaga ttgggaacag gtcgatgatg tgatctatgg ctgtgccaac | 180 |
| caagccggtg aagataaccg taatgtcggt cgtatgtcag cacttcttgc aggtttacca | 240 |
| tatcaggtac cggcaaccac tattaaccgt ttatgcggtt cttcactcga tgccattgcc | 300 |
| attgcagccc gtgctattaa agcaggtgaa gcgaacttgg tgattgcagg tggtgtagaa | 360 |
| agcatgagcc gtgcgcctta tgtaatgggt aagtcagaca gtgcttttgg ccgtagccag | 420 |
| aagattgaag acaccaccat gggctggcgt tttattaacc caaaacttaa agaattgtat | 480 |
| ggtgtagaca ccatgcccca gactgccgaa aacgtggctg aacagtttaa cgtcaatcgt | 540 |

```
gcagatcagg accagtttgc cttggtgagc aacaacgca ccgcaagcgc gcaagccaaa      600 ggctttttt ctaaagaaat cgtggcagtt gaaatccctc agcgtaaggg tgatgctgtt      660
gtgattgata ctgatgaaca tccacgtgca tcaaccaccc ttgaaggttt aagcaaactt     720
aaatctgtgg ttaaagcaga tggcacagta acagcaggca atgcttcagg tattaatgat    780
ggtgcagcag ctctactgat tgcttctgat gaagcagttc aggcatacaa cctaaaaccc    840
cgcgccaaga ttattgcttc aacagcgtg ggtgtagaac cacgattat gggctttgct      900 ccagcaccag ccattaaaaa attacttaaa caagctaacc tgactttaga tcagatggat    960
gtaattgagc tcaatgaagc ttttgctgct caggctttgg cagtgacccg tgatttaggt    1020
ttgccagatg attctcacaa ggtaaaccca atggtggtg ccattgcttt gggtcatcca     1080
cttggtgctt caggtgcacg catcgtgact acagccttga accagcttga acaaacaggt    1140
ggtcgctacg ctttgtgttc aatgtgtatt ggggtgggcc aaggcatcgc attgattatt    1200
gagagagtct aa                                                        1212

<210> SEQ ID NO 62
<211> LENGTH: 1164
<212> TYPE: DNA
<213> ORGANISM: Aeromonas hydrophila

<400> SEQUENCE: 62
atgaaagacg tagtcattgt cgactgtatc cggaccccga tgggccggtc caagggcggc    60
gccttccgca acgtgcgtgc agaagacttg tccgcgcacc tgatgaaatc catcctgctg    120 cgcaaccca acctcgaccc gaacgagatc gaggatatct actggggctg cgtgcagcag    180
accctggagc agggcttcaa catcgcccgc aacgcagcct tgctggccgg cattcccaag    240 caggtgggg cggtcaccgt caaccgcctg tgcggctcca gcatgcaggc gctgcacgat    300
gcctcccgcg ccattcaggt aggtgatggg gatatcttca tcatcggcgg tgtcgagcac    360
atgggccacg tgccgatgag ccacggggtg gacttccacc ccggcatggc caagtcggtg    420
gcgaaagcct ccggcatgat ggggctgacc gccgagatgc tcggcaagct gcacggcatc    480
agtcgtcagc agcaggacga gttttgccgcc cgctcccatc gtcgcgctca cgccgccacc   540
gtggaaggac gtttcgccaa ggagatcgtc gggctggaag ccatgacgc cagcggcgcc    600 cgcttcttct acgactacga cgaggtgatc cgccccgaga ccacggtgga aaccctgagc    660
cagctgcgcc cggtgttcga cccggtcaac ggcaccgtca ccgccggcac ctcgtcggcc   720
ctgtccgatg gcgccgccgc catgctggta atgagtgcgg accgcgccaa ggcgctcggc   780
ctcaccccgc gcgccaagat acgtgccatg gccgtcgccg gctgcgatgc cgccatcatg   840
ggttacggcc cggtaccggc cacccagaag gcgctcaagc gggccggcct gaccatcggc   900
gacatcgacc tgttcgagct gaacgaggcg tttgccgccc agtccctgcc ttgcgtgaag    960
gatctgggtc tgcaagacgt ggtggatgag aaggtgaacc tgaacggcgg cgccatcgcc   1020
ctgggtcacc cgctcggctg ctccggcgcc cgcatctcca ccaccctgct caacctgatg   1080
gaagagaagg acgccaccct gggggttgcc accatgtgca tcggcctggg tcagggcatc   1140
gccaccgtgt cgaacgagt gtaa                                            1164

<210> SEQ ID NO 63
<211> LENGTH: 1005
<212> TYPE: DNA
<213> ORGANISM: Aeromonas salmonicida
```

<400> SEQUENCE: 63

```
atggatattg tgattgttgc ggccaagcgt accccatgg gggccttcca gggagccttg      60
gccaacctga ctgcccccga gcttggcgct tgcgccattg ctgccgccat agcacaagcc    120
gggctcaagg gggagcagat cgatgaagcc tacatgggca atgtgctcag tgccggggtg    180
gggcaggcac ccgcccgtca ggctgtgttg aaggcaggtt tgccggagag tgtgccatgc    240
accactgtca acaaggtgtg tggttccggc atgaaggcgg tgatgctggc ggcagacagc    300
ttgcgtctgg gtgacaccga catagtgatc gccggtggca tggagagcat gagccgggcg    360
ccttacctgc tcgacaaggc gcgcagcggt tttcgcatgg ggcatcagag cgtgctggat    420
catatgttcc tcgatggctt gcaggatgct tacgaaggcc agttgatggg cattatgcc     480
cagttgagtg cggatcgcgc cggtctggcc cgctccgaca tggacgcttt tgccatcgct    540
tccctgacgc gtgcgctggc tgcccagcag agcggtgctt tcaaggccga gctggcccag    600
gttactgtcg gtgacaccct gctgctcgcc gaggatgagc agcctgccaa ggccaggccc    660
gacaagatcc ctcatctgaa accggcattc agcaagcagg gcaccataac ggctgccaat    720
gccagctcca tctcggacgg agcggcggcg ctcatcctga tgcgagccga gacggcggcg    780
cagctgggcc tgcctgtgct ggccatggcg ggttgcaacc tgcctcatga caaggtgaac    840
gtgaacggcg gggcctgcgc actgggggcat ccactgggg cgagtggtgc ccgtattctg    900
gttacgctca ttcatgcact gcatgcgcgc agtctgaaac ggggtgtggc aagcctgtgt    960
atcggtggag gggaggcgac tgccgtcgcc atcgagttga gctaa                  1005
```

<210> SEQ ID NO 64
<211> LENGTH: 1206
<212> TYPE: DNA
<213> ORGANISM: Pseudomonas aeroginosa

<400> SEQUENCE: 64

```
atgagccgcg aggtattcat ctgcgatgcc gtgcgcacgc cgatcggccg tttcggcggc      60
agtctttccg cggtgcgcgc cgacgacctc gcggcggtgc cgctgaaggc cctggtcgag    120
cgcaaccccg gggtcgactg gtcggcgctg acgaggtgt cctcggctg cgccaaccag     180
gccggcgagg acaaccgtaa cgtggcgcgc atggcgctgc tgctggccgg tttgccggag    240
agcgtgcccg cgtcaccct caaccgcctc tgcgcctcgg ggatggacgc catcggcacg    300
gcgttccgcg ccatcgcctg cggcgagatg gagctggcca tcgccggcgg cgtcgagtcg    360
atgtcgcgcg cgccgtacgt gatgggcaag gccgatagcg ccttcgggcg cggccagaag    420
atcgaggaca ccaccatcgg ctggcgcttc gtcaacccgc tgatgaagga gcagtacggc    480
atcgacccga tgccgcagac cgccgacaac gtcgccgacg actatcgcgt gtcgcgtgcc    540
gaccaggatg ccttcgccct gcgcagccag cagcgcgccg gcagggcgca ggcggccggt    600
ttcttcgccg aggaaatcgt cccggtgacg attcgcgggc gcaagggcga caccctggtc    660
gagtacgacg agcatccgcg tcccgacacc acctggagg cgctggcccg gctcaagccg    720
gtcaacgggc cggagaagac cgtcaccgcc ggcaacgcgt ccggggtcaa cgacggcgcc    780
gccgcgctgg tcctggcctc cgccgaggca gtggagaagc acggcctgac tccgcgcgcg    840
cgggtgctgg gcatggccag cgccggcgtc gccccacgga tcatgggcat cggcccggtg    900
ccggcggtgc gcaagctgct gcggcgcctg gacctggcga tcgacgcctt cgacgtgatc    960
gaactcaacg aagccttcgc cagccagggc ctggcctgcc tgcgcgaact gggcgtggcc   1020
gacgacagtg agaaggtcaa cccgaacggc ggtgccatcg ccctcggcca ccgctgggg   1080
```

```
atgagcggtg cgcggctggt cctcaccgcg ctccatcaac ttgagaagag cggcggccgg    1140
cgcggcctgg cgaccatgtg cgtaggcgtc ggccaaggcc tggcgctggc catcgagcgg    1200
gtctga                                                               1206

<210> SEQ ID NO 65
<211> LENGTH: 1185
<212> TYPE: DNA
<213> ORGANISM: Ralstonia eutropha

<400> SEQUENCE: 65
atgacgcgtg aagtggtagt ggtaagcggt gtccgtaccg cgatcgggac ctttggcggc      60
agcctgaagg atgtggcacc ggcggagctg ggcgcactgg tggtgcgcga ggcgctggcg     120
cgcgcgcagg tgtcgggcga cgatgtcggc cacgtggtat tcggcaacgt gatccagacc     180
gagccgcgcg acatgtatct gggccgcgtc gcggccgtca acggcggggt gacgatcaac     240 gccccgcgc tgaccgtgaa ccgcctgtgc ggctcgggcc tgcaggccat tgtcagcgcc     300
gcgcagacca tcctgctggg cgataccgac gtcgccatcg gcggcggcgc ggaaagcatg     360
agccgcgcac cgtacctggc gccggcagcg cgctggggcg cacgcatggg cgacgccggc     420
ctggtcgaca tgatgctggg tgcgctgcac gatcccttcc atcgcatcca catgggcgtg     480
accgccgaga atgtcgccaa ggaatacgac atctcgcgcg cgcagcagga cgaggccgcg     540
ctggaatcgc accgccgcgc ttcggcagcg atcaaggccg gctacttcaa ggaccagatc     600
gtcccggtgg tgagcaaggg ccgcaagggc gacgtgacct tcgacaccga cgagcacgtg     660
cgccatgacg ccaccatcga cgacatgacc aagctcaggc cggtcttcgt caaggaaaac     720
ggcacggtca cggccggcaa tgcctcgggc ctgaacgacg ccgccgccgc ggtggtgatg     780
atggagcgcg ccgaagccga gcgccgcggc ctgaagccgc tggcccgcct ggtgtcgtac     840
ggccatgccg gcgtggaccc gaaggccatg ggcatcggcc cggtgccggc gacgaagatc     900
gcgctggagc gcgccggcct gcaggtgtcg gacctggacg tgatcgaagc caacgaagcc     960
tttgccgcac aggcgtgcgc cgtgaccaag gcgctcggtc tggacccggc caaggttaac    1020
ccgaacggct cgggcatctc gctgggccac ccgatcggcc caccggtgc cctgatcacg    1080 gtgaaggcgc tgcatgagct gaaccgcgtg cagggccgct acgcgctggt gacgatgtgc    1140
atcggcggcg gcagggcat tgccgccatc ttcgagcgta tctga                     1185

<210> SEQ ID NO 66
<211> LENGTH: 1188
<212> TYPE: DNA
<213> ORGANISM: Rhodopseudomonas palustris

<400> SEQUENCE: 66
atgaccgagg ccgttatcgt ttcaaccgcg cgcacgccga tcggcaaggc gtatcgcggc      60
gccctcaacg ccaccgaggg tgccacactg ctcggcacg ccatcgagca cgcggtgaag     120
cgcgccggta tcgacccgaa ggaggtcgag gacgtggtga tgggcgcggc gatgcagcag     180
ggcgccaccg cggcaacat cgcccgcaag gcgctgctgc gcgccggcct gccggtgact     240
accgccggca ccaccatcga tcggcagtgc gcctccggcc tgcaggcgat cgcgctcgcc     300
gctcgctcgg tgctgttcga cggcgtcgag atcgcggtcg gcgtggcgg cgagtcgatc     360 tcgctcgtcc agaacgacaa gatgaacacc ttccacgccg tcgatccggc gctcgaggcg     420
atcaagggcg acgtctacat ggcgatgctc gacaccgccg aaaccgtggc gaagcgctac     480
```

```
ggcatctcgc gcgagcgcca ggacgagtat tcgctggaaa gccagcgccg caccgcggct      540
gcgcagcagg gcggcaagtt caacgacgag atcgcgccga tctcgaccaa gatgggcgtc      600
gtcgacaagg ccaccggcgc ggtgtcgttc aaggatatca cgctgtcgca ggacgaaggc      660
ccgcggccga aaaccaccgc tgaaggtctc gccggtctta aggccgtgcg tggtgaaggc      720
ttcaccatca ctgccggcaa tgccagccag ctgtcggacg gcgcctcggc cacggtgatc      780
atgagcgaca agacggcggc cgcgaagggc ctcaagccgc tcggcatctt ccgcggcatg      840
gtctcctacg gctgcgagcc ggacgagatg ggcatcggcc cggtgttcgc ggtgccgcgc      900
ctgttgaagc gccatggtct cagcgtcgac gacatcggtc tgtgggagct gaacgaagcc      960
ttcgccgtgc aggtgctgta ctgccgcgac aagctcggca tcgatccgga gaagctcaat     1020
gtcaacggcg gcgcgatctc ggtcggccac ccctacggca tgtcgggtgc acgcctcgcc     1080
ggccacgcgc tgatcgaagg ccgtcgccgc aaggcgaagt acgcggtggt cacgatgtgc     1140
gtcggcggcg gcatgggctc cgccggcctg ttcgagatcg tgcactga                  1188

<210> SEQ ID NO 67
<211> LENGTH: 1293
<212> TYPE: DNA
<213> ORGANISM: Syntrophus aciditrophicus

<400> SEQUENCE: 67
atgaaagatg tcgtcatcgt aagcggcgcc agaaccgccg tgggtgcttt tggcggatcg       60
ctgaaaggcg tgagagttac ggatttggga gcgctggtca tcaaagaggc catcaagaga      120
gcggggctgc ggccggccat cagtgaagaa gtgaaaggct gccgttgcga taccttcgga      180
gaattcgaca agaccgaaat caacaagaaa tattatgatt acgatgaatc cctgaccccc      240
gtttatttcg acgagtgcat catggggaac tgcctgatcg ccggcctggg acagaatccc      300
ggccgtcagt ccagcatcta tgccggtctg cccgaagaaa cgaacaccat cacagtgaac      360
aaggtctgcg catccggcat gaaagccatc accctggccg cccagatcat caaagccggc      420
gatgccgaca tcatggtggc cggcggcatg gaaaacatga gcaatgtacc ctacgccctg      480
cccgacgccc gctggggata ccggatgaac atgcctacgg gttccatcat cgacctcatg      540
gttcatgatg gtctctggga aatcttcaac ggctatcaca tgggattcac ggcggaaaat      600
atcgcctccc gttatggaat cagccgtcag gcccaggacg agctggccct catgagccat      660
cagcgcgccc gtgcggccat cgccagcggc gccgtcgccg atgaaatcat ccccgttccg      720
ctgcccgtga gaaaggcgc ggctccgcag tttttctccg tcgacgagcg tcccatggac      780
accagcctgg aaaagatggc gaagctggcc ccagtcttca agaaggacgg aaccgtcacg      840
gcggccaacg cctcgggtat caatgacggt gcggcggctg tcgtcgtgat gagcgccgac      900
aaggcaaagg aactgggcct caaaccgctg gcgaagatcc tcggctatgc ctccggcggc      960
gtcgatccgg catacatggg tctgggtccg attccggcaa cccgcaaggt cttcaagaaa     1020
ctcggcctga ccatgaagga catggacatc gtggaactga acgaggcctt tgcatcccag     1080
gccctgggct gcgtccagga aatgggtgtg atctggaca aaaccaatct caacggcagc     1140
gggatctcca tcggtcaccc cgtcggctgc accggcgccc ggatcaccta cagcttggcc     1200
atgcagctgc agaagaagaa cgcgcacctc ggactcgcca cgctgtgtat cggtggcgga     1260 cagggggatgg ccattgtcct ggaaagagtg taa                                 1293

<210> SEQ ID NO 68
<211> LENGTH: 1209
```

```
<212> TYPE: DNA
<213> ORGANISM: Cupriavidus necator

<400> SEQUENCE: 68
atgcgcagag ctgcaatcgt cactccctc cgcacgcccg tcggcacctt cggcggcagc      60
ctgcgcccgg tgcccgtgga ggagctggcc gccaccgccg tgcgcgccgt ggtggaacgc     120
agcggcatcg atcccgcgcg tatcgatgac gtggtctttg cccagtccta cgccaacagc     180
gaagtgccct gcgtcggccg ctgggccgcg ctgcaggccg gctgccggt cgaagtgccg      240
ggcatgcagc tggaccgccg ctgcggcggc ggcctgcagg ccatcgtcac ggcctcgatg     300
atggtgcaaa gcgcgccgc cgacgtggtg atcgcgggcg cgtcgagag catgagcaat      360
atcgagtact acaccaccga catgcgctgg ggcgcgcgct cgggcaatgt gcgcttcttc     420
gaccgcctcg accgcggccg tgaacgctcc cagccggtcg agcgcttcgg caagatctcc     480
gggatgatcg agacggccga gaacctggcg cgcgactacg gcatcagccg cgaagcggcc     540
gatgtcttcg ccgcccgcag ccacgcacgc gccgcggcag cctgggaggc cggccgcttc     600
gatgccgagg tcgtccccgt gcaggtgccc cagcgcaagg gcgatccggt gcggttcgcg     660
cgcgacgaag gtttccgccc ggaaaccacg cgtgaaagcc tgggcaagct cgcacgctg      720
atgccgaacg gtaccgtcac cgccggcaac gccagccagc agaacgacgc ctcggccgcg     780
tgcctgatcg tggccgaaga caagctggcc gaattgggcc tcacccccat ggcctcgctg     840
gtgggctggg cggcggctgg ctgcgagccc tcgcacatgg gcatcggccc ggtgcccgcg     900
gtgaagaagc tgctggcgcg cctgaacctg acgctggacc ggatggacct ggtcgagctg     960
aacgaagcct tcgcctgcca ggtgctggcc gtgctcaagg gctgggaatg gcatgaccag    1020
gacgcgatcg agcagaagct caacgtgaac ggctcgggca tctcgcttgg ccatccgatc    1080
ggcgccaccg gcgtgcgcat cctggccacg ctgctgcacg aactgcagcg ccgcggcggc    1140
cgctatggcc tggaaaccat gtgcatcggc ggcggccagg gtattgccgc ggtcttcgaa    1200
cgctactga                                                            1209

<210> SEQ ID NO 69
<211> LENGTH: 1185
<212> TYPE: DNA
<213> ORGANISM: Escherichia coli

<400> SEQUENCE: 69
atgaaaaatt gtgtcatcgt cagtgcggta cgtactgcta tcggtagttt taacggttca     60
ctcgcttcca ccagcgccat cgacctgggg gcgacagtaa ttaaagccgc cattgaacgt     120
gcaaaaatcg attcacaaca cgttgatgaa gtgattatgg gtaacgtgtt acaagccggg     180
ctggggcaaa atccggcgcg tcaggcactg ttaaaaagcg gctggcaga acggtgtgc      240
ggattcacgg tcaataaagt atgtggttcg ggtcttaaaa gtgtggcgct tgccgcccag     300
gccattcagg caggtcaggc gcagagcatt gtggcggggg gtatggaaaa tatgagttta     360
gccccctact tactcgatgc aaaagcacgc tctggttatc gtcttggaga cggacaggtt     420
atgacgtaa tcctgcgcga tggcctgatg tgcgccaccc atggttatca tatgggggatt    480
accgccgaaa acgtggctaa agagtacgga attacccgtg aaatgcagga tgaactggcg     540
ctacattcac agcgtaaagc ggcagccgca attgagtccg tgcttttac agccgaaatc     600
gtcccggtaa atgttgtcac tcgaaagaaa accttcgtct tcagtcaaga cgaattcccg     660
aaagcgaatt caacggctga agcgttaggt gcattgcgcc cggccttcga taagcagga     720
```

-continued

```
acagtcaccg ctgggaacgc gtctggtatt aacgacggtg ctgccgctct ggtgattatg    780
gaagaatctg cggcgctggc agcaggcctt acccccctgg ctcgcattaa aagttatgcc    840
agcggtggcg tgccccccgc attgatgggt atggggccag tacctgccac gcaaaaagcg    900
ttacaactgg cggggctgca actggcggat attgatctca ttgaggctaa tgaagcattt    960
gctgcacagt tccttgccgt tgggaaaaac ctgggctttg attctgagaa agtgaatgtc   1020
aacggcgggg ccatcgcgct cggcatcct atcggtgcca gtggtgctcg tattctggtc   1080
acactattac atgccatgca ggcacgcgat aaaacgctgg ggctggcaac actgtgcatt   1140
ggcggcggtc agggaattgc gatggtgatt gaacggttga attaa                   1185
```

<210> SEQ ID NO 70
<211> LENGTH: 1179
<212> TYPE: DNA
<213> ORGANISM: Clostridium acetobutylicum

<400> SEQUENCE: 70

```
atgaaagaag ttgtaatagc tagtgcagta agaacagcga ttggatctta tggaaagtct     60
cttaaggatg taccagcagt agatttagga gctacagcta taaaggaagc agttaaaaaa    120
gcaggaataa aaccagagga tgttaatgaa gtcattttag gaaatgttct tcaagcaggt    180
ttaggacaga atccagcaag acaggcatct tttaaagcag gattaccagt tgaaattcca    240
gctatgacta ttaataaggt ttgtggttca ggacttagaa cagttagctt agcagcacaa    300
attataaaag caggagatgc tgacgtaata atagcaggtg gtatggaaaa tatgtctaga    360
gctccttact tagcgaataa cgctagatgg ggatatagaa tgggaaacgc taaatttgtt    420
gatgaaatga tcactgacgg attgtgggat gcatttaatg attaccacat gggaataaca    480
gcagaaaaca tagctgagag atggaacatt tcaagagaag aacaagatga gtttgctctt    540
gcatcacaaa aaaaagctga agaagctata aaatcaggtc aatttaaaga tgaaatagtt    600
cctgtagtaa ttaaaggcag aaagggagaa actgtagttg atacagatga gcaccctaga    660
tttggatcaa ctatagaagg acttgcaaaa ttaaaacctg ccttcaaaaa agatggaaca    720
gttacagctg gtaatgcatc aggattaaat gactgtgcag cagtacttgt aatcatgagt    780
gcagaaaaag ctaaagagct tggagtaaaa ccacttgcta agatagtttc ttatggttca    840
gcaggagttg acccagcaat aatgggatat ggacctttct atgcaacaaa agcagctatt    900
gaaaaagcag gttggacagt tgatgaatta gatttaatag aatcaaatga agcttttgca    960
gctcaaagtt tagcagtagc aaaagattta aaatttgata tgaataaagt aaatgtaaat   1020
ggaggagcta ttgcccttgg tcatccaatt ggagcatcag gtgcaagaat actcgttact   1080
cttgtacacg caatgcaaaa aagagatgca aaaaaaggct tagcaacttt atgtataggt   1140
ggcggacaag gaacagcaat attgctagaa aagtgctag                          1179
```

<210> SEQ ID NO 71
<211> LENGTH: 1179
<212> TYPE: DNA
<213> ORGANISM: Clostridium acetobutylicum

<400> SEQUENCE: 71

```
atgagagatg tagtaatagt aagtgctgta agaactgcaa taggagcata tggaaaaaca     60
ttaaaggatg tacctgcaac agagttagga gctatagtaa taaaggaagc tgtaagaaga    120
gctaatataa atccaaatga gattaatgaa gttatttttg gaaatgtact tcaagctgga    180
ttaggccaaa acccagcaag acaagcagca gtaaaagcag gattaccttt agaaacacct    240

```
gcgtttacaa tcaataaggt ttgtggttca ggtttaagat ctataagttt agcagctcaa      300
attataaaag ctggagatgc tgataccatt gtagtaggtg gtatgaaaaa tatgtctaga      360
tcaccatatt tgattaacaa tcagagatgg ggtcaaagaa tgggagatag tgaattagtt      420
gatgaaatga taaaggatgg tttgtgggat gcatttaatg gatatcatat gggagtaact      480
gcagaaaata ttgcagaaca atggaatata acaagagaag agcaagatga attttcactt      540
atgtcacaac aaaaagctga aaaagccatt aaaaatggag aatttaagga tgaaatagtt      600
cctgtattaa taaagactaa aaaaggtgaa atagtctttg atcaagatga atttcctaga      660
ttcggaaaca ctattgaagc attaagaaaa cttaaaccta ttttcaagga aaatggtact      720
gttacagcag gtaatgcatc cggattaaat gatggagctg cagcactagt aataatgagc      780
gctgataaag ctaacgctct cggaataaaa ccacttgcta agattacttc ttacggatca      840
tatggggtag atccatcaat aatgggatat ggagcttttt atgcaactaa agctgcctta      900
gataaaatta atttaaaacc tgaagactta gatttaattg aagctaacga ggcatatgct      960
tctcaaagta tagcagtaac tagagattta aatttagata tgagtaaagt taatgttaat     1020
ggtggagcta tagcacttgg acatccaata ggtgcatctg gtgcacgtat tttagtaaca     1080
ttactatacg ctatgcaaaa aagagattca aaaaaaggtc ttgctactct atgtattggt     1140
ggaggtcagg gaacagctct cgtagttgaa agagactaa                            1179

<210> SEQ ID NO 72
<211> LENGTH: 1197
<212> TYPE: DNA
<213> ORGANISM: Saccahromyces cerevisiae

<400> SEQUENCE: 72
atgtctcaga acgtttacat tgtatcgact gccagaaccc caattggttc attccagggt       60
tctctatcct ccaagacagc agtggaattg ggtgctgttg ctttaaaagg cgccttggct      120
aaggttccag aattggatgc atccaaggat tttgacgaaa ttatttttgg taacgttctt      180
tctgccaatt gggccaagc tccggccaga caagttgctt tggctgccgg tttgagtaat       240
catatcgttg caagcacagt taacaaggtc tgtgcatccg ctatgaaggc aatcattttg      300
ggtgctcaat ccatcaaatg tggtaatgct gatgttgtcg tagctggtgg ttgtgaatct      360
atgactaacg caccatacta catgccagca gcccgtgcgg gtgccaaatt tggccaaact      420
gttcttgttg atggtgtcga aagagatggg ttgaacgatg cgtacgatgg tctagccatg      480
ggtgtacacg cagaaaagtg tgcccgtgat tgggatatta ctagagaaca acaagacaat      540
tttgccatcg aatcctacca aaaatctcaa aaatctcaaa aggaaggtaa attcgacaat      600
gaaattgtac ctgttaccat taagggattt agaggtaagc ctgatactca agtcacgaag      660
gacgaggaac ctgctagatt acacgttgaa aaattgagat ctgcaaggac tgttttccaa      720
aaagaaaacg gtactgttac tgccgctaac gcttctccaa tcaacgatgg tgctgcagcc      780
gtcatcttgg tttccgaaaa agtttttgaag gaaaagaatt tgaagccttt ggctattatc      840
aaaggttggg gtgaggccgc tcatcaacca gctgatttta catgggctcc atctcttgca      900
gttccaaagg ctttgaaaca tgctggcatc gaagacatca attctgttga ttactttgaa      960
ttcaatgaag cctttccggt tgtcggtttg gtgaacacta gattttgaa gctagaccca     1020 tctaaggtta atgtatatgg tggtgctgtt gctctaggtc acccattggg ttgttctggt     1080
gctagagtgg ttgttacact gctatccatc ttacagcaag aaggaggtaa gatcggtgtt     1140
```

```
gccgccattt gtaatggtgg tggtggtgct tcctctattg tcattgaaaa gatatga       1197
```

<210> SEQ ID NO 73
<211> LENGTH: 2283
<212> TYPE: DNA
<213> ORGANISM: Escherichia coli

<400> SEQUENCE: 73

```
atgtccgagc ttaatgaaaa gttagccaca gcctgggaag gttttaccaa aggtgactgg       60
cagaatgaag taaacgtccg tgacttcatt cagaaaaact acactccgta cgagggtgac      120
gagtccttcc tggctggcgc tactgaagcg accaccaccc tgtgggacaa agtaatggaa      180
ggcgttaaac tggaaaaccg cactcacgcg ccagttgact ttgacaccgc tgttgcttcc      240
accatcacct ctcacgacgc tggctacatc aacaagcagc ttgagaaaat cgttggtctg      300
cagactgaag ctccgctgaa acgtgctctt atcccgttcg gtggtatcaa aatgatcgaa      360
ggttcctgca aagcgtacaa ccgcgaactg gatccgatga tcaaaaaaat cttcactgaa      420
taccgtaaaa ctcacaacca gggcgtgttc gacgtttaca ctccggacat cctgcgttgc      480
cgtaaatctg gtgttctgac cggtctgcca gatgcatatg gccgtggccg tatcatcggt      540
gactaccgtc gcgttgcgct gtacggtatc gactacctga tgaaagacaa actggcacag      600
ttcacttctc tgcaggctga tctgaaaaac ggcgtaaacc tggaacagac tatccgtctg      660
cgcgaagaaa tcgctgaaca gcaccgcgct ctgggtcaga tgaaagaaat ggctgcgaaa      720
tacggctacg acatctctgg tccggctacc aacgctcagg aagctatcca gtggacttac      780
ttcggctacc tggctgctgt taagtctcag aacggtgctg caatgtcctt cggtcgtacc      840
tccaccttcc tggatgtgta catcgaacgt gacctgaaag ctggcaagat caccgaacaa      900
gaagcgcagg aaatggttga ccacctggtc atgaaactgc gtatggttcg cttcctgcgt      960
actccggaat acgatgaact gttctctggc gacccgatct gggcaaccga atctatcggt     1020
ggtatgggcc tcgacggtcg taccctggtt accaaaaaca gcttccgttt cctgaacacc     1080
ctgtacacca tgggtccgtc tccggaaccg aacatgacca ttctgtggtc tgaaaaactg     1140
ccgctgaact tcaagaaatt cgccgctaaa gtgtccatcg acacctcttc tctgcagtat     1200
gagaacgatg acctgatgcg tccggacttc aacaacgatg actacgctat gcttgctgc      1260
gtaagcccga tgatcgttgg taaacaaatg cagttcttcg gtgcgcgtgc aaacctggcg     1320
aaaaccatgc tgtacgcaat caacggcggc gttgacgaaa aactgaaaat gcaggttggt     1380
ccgaagtctg aaccgatcaa aggcgatgtc ctgaactatg atgaagtgat ggagcgcatg     1440
gatcacttca tggactggct ggctaaacag tacatcactg cactgaacat catccactac     1500
atgcacgaca gtacagctac gaagcctctc tgatggcgc tgcacgaccg tgacgttatc     1560
cgcaccatgg cgtgtggtat cgctggtctg tccgttgctg ctgactccct gtctgcaatc     1620
aaatatgcga agttaaaccg gattcgtgac gaagacggtc tggctatcga cttcgaaatc     1680
gaaggcgaat acccgcagtt tggtaacaat gatccgcgtg tagatgacct ggctgttgac     1740
ctggtagaac gtttcatgaa gaaaattcag aaactgcaca cctaccgtga cgctatcccg     1800
actcagtctg ttctgaccat cacttctaac gttgtgtatg gtaagaaaac gggtaacacc     1860
ccagacggtc gtcgtgctgg cgcgccgttc ggaccgggtg ctaacccgat gcacggtcgt     1920
gaccagaaag gtgcagtagc ctctctgact tccgttgcta aactgccgtt tgcttacgct     1980
aaagatggta tctcctacac cttctctatc gttccgaacg cactgggtaa agacgacgaa     2040
gttcgtaaga ccaacctggc tggtctgatg gatggttact ccaccacga agcatccatc     2100
```

```
gaaggtggtc agcacctgaa cgttaacgtg atgaaccgtg aaatgctgct cgacgcgatg    2160
gaaaacccgg aaaatatatcc gcagctgacc atccgtgtat ctggctacgc agtacgtttc    2220
```
(Note: reading again)

```
gaaggtggtc agcacctgaa cgttaacgtg atgaaccgtg aaatgctgct cgacgcgatg    2160
gaaaacccgg aaaatatcc  gcagctgacc atccgtgtat ctggctacgc agtacgtttc    2220
aactcgctga ctaaagaaca gcagcaggac gttattactc gtaccttcac tcaatctatg    2280
taa                                                                  2283

<210> SEQ ID NO 74
<211> LENGTH: 741
<212> TYPE: DNA
<213> ORGANISM: Escherichia coli

<400> SEQUENCE: 74
atgtcagtta ttggtcgcat tcactccttt gaatcctgtg aaccgtaga cggcccaggt      60 attcgcttta tcacctttt ccagggctgc ctgatgcgct gcctgtattg tcataaccgc     120
gacacctggg acacgcatgg cggtaaagaa gttaccgttg aagatttgat gaaggaagtg    180
gtgacctatc gccactttat gaacgcttcc ggcggcggcg ttaccgcatc cggcggtgaa    240
gcaatcctgc aagctgagtt tgttcgtgac tggttccgcg cctgcaaaaa agaaggcatt    300
catacctgtc tggacaccaa cggttttgtt cgtcgttacg atccggtgat tgatgaactg    360
ctggaagtaa ccgacctggt aatgctcgat ctcaaacaga tgaacgacga gatccaccaa    420
aatctggttg gagtttccaa ccaccgcacg ctggagttcg ctaaatatct ggcgaacaaa    480
aatgtgaagg tgtggatccg ctacgttgtt gtcccaggct ggtctgacga tgacgattca    540
gcgcatcgcc tcggtgaatt tacccgtgat atgggcaacg ttgagaaaat cgagcttctc    600
ccctaccacg agctgggcaa acacaaatgg gtggcaatgg gtgaagagta caaactcgac    660
ggtgttaaac caccgaagaa agagaccatg aacgcgtga aaggcattct tgagcagtac    720
ggtcataagg taatgttcta a                                              741

<210> SEQ ID NO 75
<211> LENGTH: 2364
<212> TYPE: DNA
<213> ORGANISM: Lactococcus lactis

<400> SEQUENCE: 75
atgaaaaccg aagttacgga aaatatcttt gaacaagctt gggatggttt taaaggaacc     60
aactggcgcg ataaagcaag cgttactcgc tttgtacaag aaaactacaa accatatgat    120
ggtgatgaaa gctttcttgc tgggccaaca gaacgtacac ttaaagtaaa gaaaattatt    180
gaagatacaa aaaatcacta cgaagaagta ggatttccct tcgatactga ccgcgtaacc    240
tctattgata aaatccctgc tggatatatc gatgctaatg ataagaact gaactcatc     300 tatgggatgc aaaatagcga acttttccgc ttgaatttca tgccaagagg tggacttcgt    360
gttgctgaaa agattttgac agaacacggt ctctcagttg acccaggctt gcatgatgtt    420
ttgtcacaaa caatgacttc tgtaaatgat ggaatctttc gtgcttatac ttcagcaatt    480
cgtaaagcac gtcatgctca tactgtaaca ggtttgccag atgcttactc tcgtggacgt    540
atcattggtg tctatgcacg tcttgcccct tacggtgctg attacctat gaaggaaaaa    600 gcaaaagaat gggatgcaat cactgaaatt aacgaagaaa acattcgtct taagaagaa    660 attaatatgc ataccaagc tttgcaagaa gttgtaaact tggtgctttt atatggtctt    720
gatgtttcac gtccagctat gaacgtaaaa gaagcaatcc aatgggttaa catcgcttat    780
atggcagtat gtcgtgtcat taatggagct gcaacttcac ttgacgtgt tccaatcgtt    840
```

| | |
|---|---|
| cttgatatct tgcagaacg tgaccttgct cgtggaacat ttactgaaca agaaattcaa | 900 |
| gaatttgttg atgatttcgt tttgaagctt cgtacaatga aatttgcgcg tgcagctgct | 960 |
| tatgatgaac tttattctgg tgacccaaca ttcatcacaa catctatggc tggtatgggt | 1020 |
| aatgacggac gtcaccgtgt cactaaaatg gactaccgtt tcttgaacac acttgataca | 1080 |
| atcggaaatg ctccagaacc aaacttgaca gtcctttggg attctaaact tccttactca | 1140 |
| ttcaaacgtt attcaatgtc tatgagccac aagcattctt ctattcaata tgaaggtgtt | 1200 |
| gaaacaatgg ctaaagatgg atatggcgaa atgtcatgta tctcttgttg tgtctcacca | 1260 |
| cttgatccag aaaatgaaga aggacgtcat aacctccaat actttggtgc gcgtgtaaac | 1320 |
| gtcttgaaag caatgttgac tggtttgaac ggtggttatg atgacgttca taaagattat | 1380 |
| aaagtattcg acatcgaacc tgttcgtgac gaaattcttg actatgatac agttatggaa | 1440 |
| aactttgaca atctctcga ctggttgact gatacttatg ttgatgcaat gaatatcatt | 1500 |
| cattacatga ctgataaata taactatgaa gcagttcaaa tggccttctt gcctactaaa | 1560 |
| gttcgtgcta acatgggatt tggtatctgt ggattcgcaa atacagttga ttcactttca | 1620 |
| gcaattaaat atgctaaagt taaaacattg cgtgatgaaa atggctatat ctacgattac | 1680 |
| gaagtagaag gtgatttccc tcgttatggt gaagatgatg atcgtgctga tgatattgct | 1740 |
| aaacttgtca tgaaaatgta ccatgaaaaa ttagcttcac acaaactta caaaaatgct | 1800 |
| gaagctactg tttcactttt gacaattaca tctaacgttg cttactctaa acaaactggt | 1860 |
| aattctccag tacataaagg agtattcctc aatgaagatg gtacagtaaa taaatctaaa | 1920 |
| cttgaattct tctcaccagg tgctaaccca tctaataaag ctaagggtgg ttggttgcaa | 1980 |
| aatcttcgct cattggctaa gttggaattc aaagatgcaa atgatggtat ttcattgact | 2040 |
| actcaagttt cacctcgtgc acttggtaaa actcgtgatg aacaagtgga taacttggtt | 2100 |
| caaattcttg atggatactt cacaccaggt gctttgatta tggtactga atttgcaggt | 2160 |
| caacacgtta acttgaacgt aatggaccct aaagatgttt acgataaaat catgcgtggt | 2220 |
| gaagatgtta tcgttcgtat ctctggttac tgtgtcaata ctaaatacct cacaccagaa | 2280 |
| caaaaacaag aattaactga acgtgtcttc catgaagttc tttcaaacga tgatgaagaa | 2340 |
| gtaatgcata cttcaaacat ctaa | 2364 |

<210> SEQ ID NO 76
<211> LENGTH: 2325
<212> TYPE: DNA
<213> ORGANISM: Streptococcus equinus

<400> SEQUENCE: 76

| | |
|---|---|
| atggcgactg ttaaaacaaa tgcagatgtt tttgaaaaag cctgggaagg ctttaaaggt | 60 |
| actgactgga agaaaaagc cagcgtttct cgcttcgttc aagctaacta cacaccatat | 120 |
| gatggtgatg aaagcttctt agcaccagct actgaacgct ctcttaaaat caagaaaatc | 180 |
| attgaagaca ctaaagctga atacgaagca actcgtttcc caatggacac tcgtccaaca | 240 |
| tcaatcgcag atattcctgc cggctatatt caaaaagacg atgaattaat ctacggtatt | 300 |
| caaaatgatg agttgttcaa attgaatttc atgccaaaag gtggtatccg tatggcagaa | 360 |
| acagcactta agaacatgg ttatgaacca gatcctgctg ttcatgaaat tttcacaaaa | 420 |
| tacactacta cagtaaatga cggaattttc cgcgcttata catctaatat ccgccgtgcc | 480 |
| cgtcacgctc acacagtaac tggtcttcca gatgcttact cacgcggacg tatcatcggt | 540 |
| gtttatgctc gtcttgctct ttatggtgca gactacttga tgcaagaaaa agttaacgac | 600 |

```
tggaacgcta tcacagaaat cgacgaagaa tctattcgtc ttcgcgaaga agttaacatg    660
caataccaag ctcttggtga agttgttaaa cttggtgacc tttacggact tgatgtccgt    720
aaaccagcca tgaacgttaa agaagctatc caatgggtaa acatcgcctt catggccgta    780
tgtcgtgtta tcaacggtgc tgctacttct cttggacgtg tgccaatcgt tcttgatatc    840
tttgctgaac gtgaccttgc tcgtggtact ttcacagaat cagaaatcca agaatttgtc    900
gatgactttg tcttgaaact tcgtactgta aaatttgctc gtactaaagc ttacgacgaa    960
ctttactctg gtgacccaac attcatcact acatctatgg ctggtatggg tgctgacggt   1020
cgtcaccgtg ttactaaaat ggactaccgt ttcttgcaca cacttgataa tatcggtaac   1080
gctccagaac caaacttgac agttctttgg actgataaat tgccatattc attccgtcgc   1140
tactgtatga aaatgtcaca caaacactcg tcaatccaat acgaaggtgt gacaacaatg   1200
gctaaagatg gttacggtga atgtcatgt atctcatgtt gtgtatcacc acttgaccca   1260
gaaaacgaag aacaacgtca caacatccaa tactttggtg ctcgtgtaaa cgtccttaaa   1320
gctcttctta ctggttttgaa cggtggttat gacgacgtcc acaaagacta caaagtattt   1380
gatatcgaac cagttcgtga tgaaatcctt gatttcgaaa cggttaaagc taatttcgaa   1440
aaatctcttg attggttgac ttcaacttac gtagatgccc ttaacatcat tcactacatg   1500
actgataaat acaactacga agctgttcaa atggcattct tgccaactaa caacgtgcc   1560 aacatgggat tcggtatctg tggtttcgct aataccgttg atactttatc agcaatcaaa   1620
tacgctactg ttaaaccaat ccgtgacgaa gatggttaca tctacgacta cgaaacaact   1680
ggtgacttcc ctcgttgggg tgaagatgac cctcgttcta acgaacttgc tgaatggttg   1740
gtagaagctt acactactcg tcttcgtagc cacaaacttt acaagaacgc tgaagctact   1800
gtatcacttc ttacaatcac ttcaaacgtt gcttattcta aacaaactgg taactctcca   1860
gttcacaaag gtgtttacct taacgaagat ggtactgtaa acctttctaa acttgaattc   1920
ttctcaccag gtgccaaccc atctaacaaa gctcgtggtg gttggttgca aaacttgaac   1980
tctcttgcaa gccttgactt ctcatatgct gcagatggta tctcacttac aactcaagtt   2040
tctccacgcg ctcttggtaa gacatttgat gaacaagttg ataacttggt aactatcctt   2100
gatggttact tcgaaaacgg tggacaacac gttaacttga acgtcatgga ccttaaagat   2160
gtttatgaca agattatgaa tggtgaagat gttatcgttc gtatatcagg ttactgtgtc   2220
aacactaaat accttactaa agaacaaaag acagaattga cacaacgcgt cttccacgaa   2280
gttctttcaa tggatgatgt tgctgaaact gttgctgcta aataa                   2325
```

<210> SEQ ID NO 77
<211> LENGTH: 789
<212> TYPE: DNA
<213> ORGANISM: Streptococcus equinus

<400> SEQUENCE: 77

```
atgactgaaa tagattacgg aaaagtgaca ggaatgattc attcaacaga agtttttggt     60
tctgtggatg ggcctggtgt tcgctttgtc atttttatgc aaggctgcaa gatgcgttgc    120
caatattgtc acaatccaga tacttgggca ttagagacaa ataattctcg tgaacgcact    180
gttgatgatg tttttagcaga agcttttgcgt tatcgacatt tctggggtga aatggtggg    240 attaccgttt caggtggtga agccatgttg caaattgagt ttgtaacagc ccttttttacc    300 aaggctaaag aattaggaat tcattgcacg cttgatacgt gtggttttac gttccgagat    360
```

| | |
|---|---|
| acgcctgaat atcacgaaat tgtggataag ttactagctg tgacggattt agttcttta | 420 |
| gatttaaaag aaatcaatcc taaacaacac attgttgtaa cacgtcaacc caatactaat | 480 |
| attctagctt ttgctcgtta tttgtctgat aagggtgttc cagtctggat tcgtcatgtc | 540 |
| ttggttccag gattgaccga ttttgatgaa gacttaattg agctagggaa atttgttgaa | 600 |
| acgttaaaaa acgtggataa atttgaaatt ttgccttatc ataccttggg tgaattcaag | 660 |
| tggcgtgaat tgggaattcc ttatacccct gaaggggtta accaccgac tagagaacgt | 720 |
| gtccaaaatg ctaaaaagct tatgcataca gagtcttaca cagactacat gaaacgcatt | 780 |
| catcactag | 789 |

<210> SEQ ID NO 78
<211> LENGTH: 717
<212> TYPE: DNA
<213> ORGANISM: Clostridium thermocellum

<400> SEQUENCE: 78

| | |
|---|---|
| atgacattaa agggcaggat acactcattt gaatcttttg ggacactgga cggaccgggt | 60 |
| ataagatttg tggttttcat gcagggctgt cccttgcgtt gtatatattg ccacaacagg | 120 |
| gatacctggg atgttaatgc ggggagtgag tacactcccc ggcaagtaat tgatgaaatg | 180 |
| atgaaataca tagactatat aaaggtctcc ggaggcggaa taactgttac cggcggggag | 240 |
| cctgttctcc aggccgattt tgtggccgag gtgttcagac ttgcaaaaga gcagggagtg | 300 |
| catacggcgc tggataccaa tggatttgct gacatagaga aggttgaaag gcttataaaa | 360 |
| tacaccgatc ttgtattgct ggatataaag catgcccggg aggataaaca taagataatt | 420 |
| accggtgtgt ccaacgaaaa aatcaagcgt tttgcgctgt atctttcgga ccagggagtg | 480 |
| cctatctgga taagatatgt ccttgtcccc ggatataccg acgatgaaga tgaccttaaa | 540 |
| atggcggctg atttcataaa aaagcttaaa acggtggaaa aaatcgaagt tcttccttat | 600 |
| cacaacatgg gagcatacaa atgggaaaaa cttggtcaga aatacatgct tgaaggagta | 660 |
| aaggggccga gtgcgcaaga ggtggaaaaa gcaaagagga ttctgtcagg caaataa | 717 |

<210> SEQ ID NO 79
<211> LENGTH: 1269
<212> TYPE: DNA
<213> ORGANISM: Jeotgalicoccus sp; ATCC8456

<400> SEQUENCE: 79

| | |
|---|---|
| atggcaacac ttaagaggga taagggctta gataatactt tgaaagtatt aaagcaaggt | 60 |
| tatctttaca caacaaatca gagaaatcgt ctaaacacat cagttttcca aactaaagca | 120 |
| ctcggtggta aaccattcgt agttgtgact ggtaaggaag gcgctgaaat gttctacaac | 180 |
| aatgatgttg ttcaacgtga aggcatgtta ccaaaacgta tcgttaatac gcttttggt | 240 |
| aaaggtgcaa tccatacggt agatggtaaa aaacacgtag acagaaaagc attgttcatg | 300 |
| agcttgatga ctgaaggtaa cttgaattat gtacgagaat taacgcgtac attatggcat | 360 |
| gcgaacacac aacgtatgga agtatggat gaggtaaata tttaccgtga atctatcgta | 420 |
| ctacttacaa aagtaggaac acgttgggca ggcgttcaag caccacctga agatatcgaa | 480 |
| agaatcgcaa cagacatgga catcatgatc gattcatta gagcacttgg tggtgccttt | 540 |
| aaaggttaca aggcatcaaa agaagcacgt cgtcgtgttg aagattggtt agaagaacaa | 600 |
| attattgaga ctcgtaaagg gaatattcat ccaccagaag gtacagcact ttacgaattt | 660 |
| gcacattggg aagactactt aggtaaccca atggactcaa gaacttgtgc gattgactta | 720 |

```
atgaacacat tccgcccatt aatcgcaatc aacagattcg tttcattcgg tttacacgcg      780
atgaacgaaa acccaatcac acgtgaaaaa attaaatcag aacctgacta tgcatataaa      840
ttcgctcaag aagttcgtcg ttactatcca ttcgttccat tccttccagg taaagcgaaa      900
gtagacatcg acttccaagg cgttacaatt cctgcaggtg taggtcttgc attagatgtt      960
tatggtacaa cgcatgatga atcactttgg gacgatccaa atgaattccg cccagaaaga     1020
ttcgaaactt gggacggatc accatttgac cttattccac aaggtggtgg agattactgg     1080
acaaatcacc gttgtgcagg tgaatggatc acagtaatca tcatggaaga acaatgaaa      1140 tactttgcag aaaaaataac ttatgatgtt ccagaacaag atttagaagt ggacttaaac     1200
agtatcccag gatacgttaa gagtggcttt gtaatcaaaa atgttcgcga agttgtagac     1260
agaacataa                                                             1269

<210> SEQ ID NO 80
<211> LENGTH: 684
<212> TYPE: DNA
<213> ORGANISM: Aspergillus niger

<400> SEQUENCE: 80
atgttcaact cacttctatc cggtactact acaccaaact ccggccgtgc atctcctccc       60
gccagcgaaa tgcccatcga taatgatcac gtggccgttg cccgtccagc tccccgccgc      120
cgccgcattg tagtagccat gacgggtgcc actggagcca tgctcggcat caaagtccta      180
attgctctgc gccgtctaaa tgtggagaca cacctggtga tgagtaaatg gcgcggaggct     240 acgatcaaat acgagactga ctaccatccc tcaaacgtgc gagcgctggc cgactacgtg      300
cacaacatca tgacatggcc cgccccagta tccagcggct cattccgcgc ggacggaatg      360
attgtggtac cgtgcagcat gaaaacattg gctgctatcc actcgggctt tgcgacgat      420 ctcatttcaa ggacagcaga tgtgatgctc aaggagcgca ggcggttggt gctagtagcg      480
cgggagacgc cattgagcga gatccatctg cgaaacatgt tggaggttac acgcgctggg      540
gcagtcatct ccccccagt accggcgttc tacatcaagg ccggaagtat cgaggacctc      600
atcgaccaga gtgttggacg aatgttggat ttatttgacc tcgacacggg ggattttgaa      660
cgttggaatg gatgggaaaa ataa                                            684

<210> SEQ ID NO 81
<211> LENGTH: 1555
<212> TYPE: DNA
<213> ORGANISM: Aspergillus niger

<400> SEQUENCE: 81
atgtctgcgc aacctgctca cctgtgtttc cgctccttcg tcgaagccct caaggtcgac       60
aacgaccttg ttgaaatcaa taccccaatt gaccccaatc tcgaagctgc tgctattacc      120
cgccgagtat gtgagaccaa cgacaaggct ccttttattca acaacctcat cggcatgaaa      180
aatggcctct tccgtatact tggggctcct ggctctctca ggaagtcgtc tgctgatcgc      240
tacggccgcc ttgctcgtca cctagccctc ccacctacgg cctcaatgcg tgagattctc      300
gataagatgc tctccgccag cgtatatgcct cccatccctc cgaccattgt tcccaccggg     360
ccatgcaagg agaacagctt agatgactct gaattcgacc ttaccgaact ccccgttcct      420
cttattcaca aatcggatgg tggtaaatac atccaaaccct atggcatgca cattgtgcag     480
tctccggatg gaacctggac caactggtct attgcccgtg cgatggtcca tgacaagaac      540
```

-continued

```
catctgaccg gcctggttat tccccctcag cacatctggc agattcacca gatgtggaag      600
aaggaaggcc gcagtgacgt tccctgggct ttggcctttg gtgtcccacc cgctgccatt      660
atggcctcta gcatgcctat tcccgatggt gtcaccgaag ctgggtacgt gggagctatg      720
acgggatcct ccctggagct tgttaaatgt gatacgaacg atctatatgt ccccgctacc      780
tcagaaatcg ttctcgaggg cacactctct atcagcgaga caggcccaga gggaccttc      840 ggtgagatgc atggttacat cttccccggg gatactcacc tcggcgccaa atacaaggtt      900
aaccggatca cctaccgcaa caacgccatc atgcccatgt cttcttgtgg ccgcttgacg      960
gatgaaacgg taagtttagt ccctgtcctg ccatttatag ccaaggacta acacggtcta     1020
gcacaccatg atcggctctc tggctgcggc ggagatccgt aagctctgcc agcagaatga     1080
cctccctatc actgatgcct cgctcctttt cgagtctcaa gttacctggg ttgctctgcg     1140
ggtcgatact gagaagctac gtgccatgaa acaacgtct gagggattcc gcaagagagt     1200
gggagacgtc gtcttcaacc acaaggccgg atacaccatt catcgtctgg tgttggtcgg     1260
tgacgacatt gatgtctatg aaggaaagga tgtgctctgg gcgttctcca cccgttgccg     1320
tcctggtatg gacgagactt tgtttgagga tgttcgtggg ttccccttga ttccgtatat     1380
gggacacggg aatgggcccg cccaccgcgg cggaaaggtt gtgtccgacg ctcttatgcc     1440
gactgagtac accactggtc gcaactggga ggctgctgac ttcaaccaat cttatcccga     1500
ggatctgaag cagaaggtgt tggacaactg gacgaagatg ggtttcagca actaa         1555
```

<210> SEQ ID NO 82
<211> LENGTH: 2224
<212> TYPE: DNA
<213> ORGANISM: Aspergillus niger

<400> SEQUENCE: 82

```
atgggcaccc cgataaatcg tgaagagatt gaccgcgtgc tgcgaatgaa acgcaatcag       60
cgcgaggctc gagcgtgtta tccttgccgc cagcgcaagg tgaaatgcga cagcactcag      120
ccgtgtcgaa catgtcgccg acgaggccat ccccaaatat gtgtgtatga ccaagattcg      180
tctgggtcta aaaaggctcg tagcaccggc caaagacgtt cctctgctgc ttctcgtgga      240
acaaatcaga caccaaccgc cgagcaggca ttcgatgccg aaccacaatc tctgccctca      300
gcgcgcagtt taccagaagt ccagccaaaa acaagacagt actatagtac tcgaatcccg      360
tcttccgatg gccccgataa tgatcttatc tactcgggcg acaactcggt attgtcttat      420
ttgcgcaacc ggacgcaaga taccaatggc tccatgaccc gtgaggtggg ctctgttcta      480
ggcctgcaaa atacctacgg cagttatcca tttatggact ttcggacacc ccaggaccgg      540
tggaaggagc ttctacgtat tattccgcag cgagcggaac tgttgaagta agcacatctt      600
attgttgttt ttgataacct ctaacggata gcaggttctt ccatttctac agaatatcag      660
cttacccttt caatccgatc atacttgaca ttgagagatt tgagcaagat gtgtgttcat      720
acctcaatga tcttgcagca ggagagctgc agaacacttc aaagatttgc gaacgttggg      780
ccactgatcg gtctgtcggg ctgatcagcc tgctacttgc ggccttggct tccggtgcgc      840
attattctga cctggattac atgcaaagaa cagagctatg ccaggatttt ggtacgtaac      900
cagtatcttt acctatgcat gtttgactaa acaggagaag caaaacgatc ctttcaagct      960
cttcgactag ccaattttct tttccgtccg acgatggata taatacaagc acttctaatc     1020
ataggaaaca ctctgcaaaa caatggccag tctgatgcag catgggtttt gttagggaca     1080
acagtccgtc tcgcgcagac attaggtctt cacacagaaa agagtgtagc acgcctaccg     1140
```

```
gatcatgtca aatacaaagc acgaaagcta tggtacataa accatgctac aggtaacgac   1200
acaagctgac gcggctacag gtacactgtc gtttggcaag attgcctgct ctgtttatgt   1260
tacgaccggc ctcgcgtagt ctctatgacc gggtgggctc cagattattc aatcctctcg   1320
agcagcgaac tatcttttcac agaagctatg tattttctat gccaaactgc cttaaatatg   1380
atcacaacag acggaccgga gatatcggaa aatgcgcgac agcttgacat tttggccacg   1440
attgatagcc tcaaccaacg cactcagcca tatctgcgtg accgccagga atgcaaaacc   1500
ctccaacaca atctggagca cctggcgtta cgaatgcaca tgtctctagt tatttccgtc   1560
ctgacacgtc cagcactgaa gcgcactgta atgcaagacg cgtcctatga catcttgcgc   1620
acccgcgcca aattgagcct gatcgacgcc tctagggcct ttttggattt tcaggctctg   1680
agtgtggtac ccctccgaag ctggtcaatg gtgcacacgg tgcttagttc cactttactt   1740
ctctgcattt gggaggagac ccgaaacgat cccgagtgtc gtgatttaca gcaaaaggtg   1800
attgaggtct tttctgccgc tggcacagtg ggcacagtgg agaacacagc atcggagaat   1860
gggcaatggc tatcggaacg gcatatacga gcgctaatca cactgcgcaa ttcggtccga   1920
acggcagtcg aacgtgaaaa gggggaggca agcgttggga cagaacgcgc ggagcagccc   1980
cagccttttt ttcctgtcta tgggtatgtg cacccgctat tgtctgataa gtggagctgt   2040
gcgatggatg ctgattttgc agtatgccga acgggatccc ggatgacttc ggtcaagact   2100
tctcaccagc aagctatctt gactccatta tgaacggtat gctgaggctc ccgactattt   2160
atcgatcgaa ctaaccgtcg tagtacccat gtttgactta tcccaagagc tgggttttct   2220
ttga                                                                2224

<210> SEQ ID NO 83
<211> LENGTH: 723
<212> TYPE: DNA
<213> ORGANISM: Aspergillis oryzae

<400> SEQUENCE: 83
atgctctcct ccttccttcc ttccggcacc aacacatcaa actccggtca tcacagcccc    60
gacaatgcat ccgaaacaca atcaaccaca cagtccgcac cactcgagca catatccacc   120
gcaatgccac cagtcccaac caaaggtcga cgcaaacgaa tcgtcgtagc catgaccgga   180
gccaccggct caatcctggg aatcaaagtc ctcatcgccc ttcgccgcct caacatcgaa   240
acccacctcg taatcagcaa atgggccgaa gcaaccataa aatacgaaac agactatcac   300
ccgcggaatg ttcgtgccct agccgactac gtccacaaca taaacgacat ggcggcaccc   360
atatccagcg ggtccttcaa gaccgacggc atgatcgtcg tcccatgttc catgaaaaca   420
ctcgccgcta tcaactccgg gttctgtgaa gatctcatct cccggactgc agacgtcatg   480
ctcaaggagc gcaggaagct ggttcttgtt gctagggaaa cgcctcttag tgatattcat   540
cttcgcaata tgctttctgt gtctcaggct ggggctatta tcttcccgcc tgtgccggcg   600
tactatatca aggcggcgtc tgtggatgaa cttgtggatc agagtgttgg gcgcatgttg   660
gatctgtttg atctggatac ggctgatttt gctagatggg agggttggaa gaaggataac   720
tga                                                                 723

<210> SEQ ID NO 84
<211> LENGTH: 1512
<212> TYPE: DNA
<213> ORGANISM: Aspergillis oryzae
```

<400> SEQUENCE: 84

```
atggccgcga ttaacgaagt cgatcattcc ttccgcgcct tgtcgaagc cctcaaggcc      60
gacgatgact tggtcgagat caacaccgag atcgactcta acctggaagc cgccgcgatc    120
actcgtcttg tctgcgagac cgatgacaaa gcccccctct tcaataacct caaaggcatg    180
ggaaagaatg gcctcttccg tatcctgggc gctccgggct ctctcagaaa gtccaaacgt    240
gaccgctacg gccggctcgc ccgccacctg gcgctgcctc ctactgccag catgaaggaa    300
atccttgaca agatgctctc cgcctctcag ctacctccca ttgaccctaa gattgtagag    360
actggtcctg tgaaggacaa ttcccttgaa ggcgacgaaa tcgacctcac tgcgctccca    420
gtgcccatgg tgcacaagtc tgacggcggc aaatatctac aaacatacgg aatgcatgtc    480
gtgcagtctc ctgatggaaa gtggacgaac tggtctatcg cccgtgcgat ggtcaaggac    540
aagaaccatt tgacaggcct ggttattgag ccccagcata tttggcaaat ccaccagatg    600
tggaaaaagg agggaaagga tgtcccgtgg gctctatgct tcggagttcc tcctgccgct    660
atcatggcat catcgatgcc catcccggat ggtgtaactg aggctggcta cgttggtgcc    720
atgactggtc gcgccttgga gctcgtcaag tgcgacacca accatctcta cgtccctgcc    780
aatgcggaga ttgtcctcga gggtaccctc tccatcactg aaaccgccga tgaaggcccc    840
ttcggtgaga tgcacggcta cgtcttcccc ggcgatagcc acaagtgtcc cgtttacaaa    900
gttaacaaga tcacctaccg caccgatgct atcctgccca tgtccgcctg cggtcgtctt    960
accgacgaga cccatactat gattggctcg ttggctgccg ctgagattcg taaaatttgc   1020
caactggccg gcctccccat caccgacacc ttttctcccct tcgaggcaca ggttacctgg   1080
gtggctctca agttgacac cgcaaagctt cgtcaaatga agctagcccc taaagagctt   1140
cagaaatggg tcggagacgt ggtctttaac cacaaggctg gtacactat ccaccgcctg    1200
gtcctggttg gcgatgatat tgacccgtat gagtggaagg atgtcatgtg ggctttcgca   1260
acacggtgtc gacccaatgc tgatgaaatg ttctttgaag acgtccgtgg tttcccccctt   1320
atcccgtata tgggtcacgg cacggggtcg cccaccaagg gtggtaaggt ggtttccgac   1380
gctctgatgc ccacagagta taccacaggt gctgattggg aagctgctga cttttgagcac   1440
tcctatccgg aggagatcaa ggccaaggtg agggccaact gggaggcttt gggattcaga   1500
aaacaggatt aa                                                       1512
```

<210> SEQ ID NO 85
<211> LENGTH: 723
<212> TYPE: DNA
<213> ORGANISM: Aspergillis oryzae

<400> SEQUENCE: 85

```
atgctctcct ccttccttcc ttccggcacc aacacatcaa actccggtca tcacagcccc      60
gacaatgcat ccgaaacaca atcaaccaca cagtccgcac cactcgagca catatccacc    120
gcaatgccac cagtcccaac caaaggtcga cgcaaacgaa tcgtcgtagc catgaccgga    180
gccaccggct caatcctggg aatcaaagtc ctcatcgccc ttcgccgcct caacatcgaa    240
acccacctcg taatcagcaa atgggccgaa gcaaccataa aatacgaaac agactatcac    300
ccgcggaatg ttcgtgccct agccgactac gtccacaaca taaacgacat ggcggcaccc    360
atatccagcg gtccttcaa gaccgacggc atgatcgtcg tcccatgttc catgaaaaca    420
ctcgccgcta tcaactccgg gttctgtgaa gatctcatct cccggactgc agacgtcatg    480
ctcaaggagc gcaggaagct ggttcttgtt gctagggaaa cgcctcttag tgatattcat    540
```

```
cttcgcaata tgctttctgt gtctcaggct ggggctatta tcttcccgcc tgtgccggcg      600
tactatatca aggcggcgtc tgtggatgaa cttgtggatc agagtgttgg gcgcatgttg      660
gatctgtttg atctggatac ggctgatttt gctagatggg agggttggaa gaaggataac      720
tga                                                                    723
```

<210> SEQ ID NO 86
<211> LENGTH: 1050
<212> TYPE: DNA
<213> ORGANISM: Picrophilus torridus

<400> SEQUENCE: 86

```
ttgaatgatc ttaatgttta tggtgaaaaa ataagaaata tgcttcttga acttggcatt      60
tataataaat cagatgatta ttcacctgat attaaataca ataaaacgtt ccacgcaaat     120
ggatacccaa taacaggtct ttataaattc cttggatact atgatagggga taataacata     180 gccaactttc catcgatatc gttcacaacg aacttttcat catgtgatgt tacatgcagg     240
gtattaagat caggcaatga caggatcata ttcaacggga aaaacaatga aaagtattac     300
aaaagggctg aaaaggccct gtcatttctc aggaaaaaat atagaataga tgcagcattt     360
gagtttaaca tcaggataaa tagaagatac agggatgcca aaggccttgg agaatcggca     420
gccgtggcat cggcaaccgc cagggccgtt gccgcagcag tctttggcat ggatgctgca     480
aaagacaggg ttttgtatc ataccctggcc aggcatgtct ctggctccgg taccagatct     540
gcggcaggaa cctttcaat gtggctttca tatcctggaa tagacgattt atcttcaatt     600
ggcttcgaaa taagaaaaga cgatttattc catttctatg ccataccaat gagatcaaga     660
atagagacat taaatgcaca tgattatgca tcctcatcaa ttttttataa tgcatgggtc     720
aaatcaaaat ttttttgatat aatagacatc attgaaaaca aattcaatac aaggatgatg     780
cttgaatact ccatgaagga tatgtacagg ctgcaggcgc ttttaatatc ctctggatat     840
atcatatatg aaaagcatta tttagacatt ataagaaaat taagatcatc attaaataac     900
tacaaaaacg tttatttcac atctgataca ggaacaagca ttgttgttat gtcaacatca     960
atgaatgagc tttcaaggtt cgttaacgat cttgatcttg atggtataag cggcaattttt    1020 ccagagaaga tcattataga ggaactatga                                       1050
```

<210> SEQ ID NO 87
<211> LENGTH: 975
<212> TYPE: DNA
<213> ORGANISM: Picrophilus torridus

<400> SEQUENCE: 87

```
atggaaaatt acaatgttaa dacaagggcg ttcccaacaa taggcataat actgcttggt      60
gggatctcgg ataaaaagaa caggataccg ctgcatacaa cggcaggcat agcatatact     120
ggtataaaca tgatgtttta cactgagaca aagctttatg tatcaaaaga tgaaaaatgc     180
tatattgatg gaaaggaaat tgatttaaat tcagatagat caccatcgaa ggttattgat     240
aaattcaagc atgaaatact tatgagagta atcttgatg atgaaaataa cctttcaatt     300
gattcaagga actttaatat attaagtggc agctcagatt ctggggccgc tgcactggga     360
gagtgcatag aatcaatttt tgaatacaat ataaatatat ttacatttga aaacgatctt     420
cagaggatat cagaaagtgt tggaagaagc ctttacggtg gtttaacagt aaactatgcc     480
aatggcaggg aatcattaac agagccatta cttgagcctg aggcatttaa taactttaca     540
```

```
ataattggtg cacattttaa cattgataga aaccatcaa atgagattca tgaaaatatc    600
ataaaacatg aaaattacag ggaaagaata aaaagtgctg agagaaaggc gaaaaaactt    660
gaggagctat caaggaatgc aaacataaag ggtatctttg aacttgcaga atccgataca    720
gtggaatacc ataaaatgct ccatgatgtt ggcgttgaca taataaatga tagaatggag    780
aacctcattg aaagggtaaa agaaatgaaa ataacttct ggaattcata catagttacc    840
ggcggcccga acgttttgt aataacagag aaaaaggacg ttgataaggc aatggaagga    900
ttaaatgatc tgtgcgatga tataagatta ttaaaagttg caggaaagcc acaggtcatt    960
tcaaaaaact tttaa                                                    975
```

```
<210> SEQ ID NO 88
<211> LENGTH: 1191
<212> TYPE: DNA
<213> ORGANISM: Saccharomyces cerevisiae

<400> SEQUENCE: 88
atgaccgttt acacagcatc cgttaccgca cccgtcaaca tcgcaacccct taagtattgg     60 gggaaaaggg acacgaagtt gaatctgccc accaattcgt ccatatcagt gactttatcg    120
caagatgacc tcagaacgtt gacctctgcg gctactgcac ctgagtttga acgcgacact    180
ttgtggttaa atggagaacc acacagcatc gacaatgaaa gaactcaaaa ttgtctgcgc    240
gacctacgcc aattaagaaa ggaaatggaa tcgaaggacg cctcattgcc acattatct    300 caatggaaac tccacattgt ctccgaaaat aactttccta cagcagctgg tttagcttcc    360
tccgctgctg gctttgctgc attggtctct gcaattgcta agttatacca attaccacag    420
tcaacttcag aaatatctag aatagcaaga aaggggtctg gttcagcttg tagatcgttg    480
tttggcggat acgtggcctg ggaaatggga aaagctgaag atggtcatga ttccatggca    540
gtacaaatcg cagacagctc tgactggcct cagatgaaag cttgtgtcct agttgtcagc    600
gatattaaaa aggatgtgag ttccactcag ggtatgcaat tgaccgtggc aacctccgaa    660
ctatttaaag aaagaattga acatgtcgta ccaaagagat ttgaagtcat gcgtaaagcc    720
attgttgaaa aagatttcgc caccctttgca aaggaaacaa tgatggattc caactctttc    780
catgccacat gtttggactc tttccctcca atattctaca tgaatgacac ttccaagcgt    840
atcatcagtt ggtgccacac cattaatcag ttttacggag aaacaatcgt tgcatacacg    900
tttgatgcag gtccaaatgc tgtgttgtac tacttagctg aaaatgagtc gaaactcttt    960
gcatttatct ataaattgtt tggctctgtt cctggatggg acaagaaatt tactactgag   1020
cagcttgagg cttttcaacca tcaatttgaa tcatctaact ttactgcacg tgaattggat   1080
cttgagttgc aaaaggatgt tgccagagtg attttaactc aagtcggttc aggcccacaa   1140
gaaacaaacg aatctttgat tgacgcaaag actggtctac caaggaata a             1191
```

```
<210> SEQ ID NO 89
<211> LENGTH: 1182
<212> TYPE: DNA
<213> ORGANISM: Schizosaccharomyces pombe

<400> SEQUENCE: 89
atggacaaaa aggtttatca atgcaccgtt agtgcgcctg ttaatattgc agtaattaaa     60
tactggggaa agagagatgt ggcattgaac ttgcctacca atagctcgat cagtgtgacc    120
ctttctcaag atgacttacg tactgttact acagctagtt gtagcgagaa gtttgagaat    180
gatacactgt ggttaaatgg aaacgctgag gaaatctttg ccaataaacg acttcgtgtc    240
```

```
tgtgtagagg aactgcgtaa agctagatta gatctcgaag aggaaaatga tgatcttgac      300
aagattggtg cattgaagct tcatgtcgtt tcagaaaaca acttccctac tgctgctggt      360
ttggcatctt cagctgctgg ttatgctgct ttttgtgaag caatcgctag attgtacgat      420
ttaccatgga cacccactca attatctcgc attgctagac aggggtctgg aagtgcttgt      480
cgtagcttgt ttgggggcta tgtagcctgg gagatgggcg agcttcatag cggtgctgat      540
agtgtagcag ttcaagttga acctgttgaa aattggcccg aaatacgtgt tgctgtttta      600
gtagcgtccg ctgccaaaaa agggggtttcc tcaacagctg gcatgcaagc tacagttgca      660
tcttctacct tgttccaaca tcgtattcaa aacatcgttc cacaacgtat ccaagaaatg      720
aagaccgcca ttcgtgagcg tgattttgag acttttgcga agcttaccat gactgattcc      780
aatcaattcc atgcgtgctg ccttgatact tttccccccta tcttttactt gaacgatact      840
tcacgtgcgg ttatccgagt tgttgagaat ataaatgcta ctgctggaaa gaccattgct      900
gcctatacat ttgatgctgg cccaaatgct gttatttact tcttggaaga aaactccgag      960
attgtattaa atacactttta tgctgttact aaaaatgctg aaggatggag caagcagtat     1020
ggctcttccc ccgttactgt tgattctgct gcagccaata ttgtatcatc tggtataagc     1080
cgagttatct taactcgagt gggtaatggg cctcgagttt tgacgattga cgaatctttg     1140
atcgatgcat ctggcaaccc taaatttata ggaagtcatt aa                        1182

<210> SEQ ID NO 90
<211> LENGTH: 972
<212> TYPE: DNA
<213> ORGANISM: Halorhabdus utahensis

<400> SEQUENCE: 90
atgaaagcga cagcgacggc ccacccgatc caggggctgg tgaagtacca cgggatacgc       60
gaccccgaac tccggacgcc gtatcacgat tcgatcagcc tctgcactgc gccgagtaac      120
tccacgacga cggtcgcctt cgaacccgag cgtcccgagg acgagtacgt catcgacggc      180
gaacacatcg acgggcgcgg ggccgagcgc atccggaccg tcgtcgataa cgttcgcgaa      240
cgggccgatc tcgacgagcg cgtccgcgtc gcaagtgaga acaacttccc gtcgaacgtc      300
ggctttggct cctcggcgtc gggattcgcg gcgctggcga ctgctctcgt tgaggccgct      360
ggcctggacc tctcacgccc ggagatctcg acgattgccc gccgcggctc gacctcggcg      420
gcgcgggcgg tcacgggtgg cttttcggat ctgcgggcgg gcagtaacga cgccgactgc      480
cgttcgaagc gactcgacgt ccccttggag gatgacgttc gcatcgtcgg cgcagtgatt      540
cctgcataca aagagaccga ggcggcccac gaggaggccg ccgagagcca catgttcgag      600
ggccgactcg cccacgtcca cgagcaactc gcggacatgc gcgacgcgct cggtcgcggg      660
gacttcgagc ggtccttcga gatcgccgaa cacgacacac tctcgctggc ggcgacgacg      720
atgaccggac cgagcggctg ggtctactgg caacccgaga gcctcgaagt cttcgagacg      780
gttcgggacc ttcgcgacga cggggttccc gtctacttct ccggggatac cggcgcaagc      840
atctacgtca acaccacggc cgagtacgtc gaccgcgtcg aatcggcgat cgaaaccctc      900
gggatcgaga cgctcacctg cgcgtcggt ggccccgcgc cgtccgtga tcccgagaag      960 gcactgttct ga                                                         972

<210> SEQ ID NO 91
<211> LENGTH: 984
<212> TYPE: DNA
```

<213> ORGANISM: Haloterrigena turkmenica

<400> SEQUENCE: 91

| | | | | | |
|---|---|---|---|---|---|
| atgaaagcga | ccgccatggc | ccacccgatt | caggggctgg | tcaagtatca | cgggatgcga | 60 |
| gacgagatcg | agcgcctgcc | gtatcacgac | agtatcagtc | tctgtacggc | ccgagccac | 120 |
| actcgcacga | ccgtggagtt | ctcgatggac | tacgaggagg | acacgttcgt | cgtcgacggc | 180 |
| gaggaactcg | acgccgggc | ctacgagcgc | gtcgaagccg | tcgtcgagaa | ggctcgttcg | 240 |
| aagtccgacg | cggcccacac | cgtctatccg | gttcgcctcg | agagcgagaa | cagtttcccg | 300 |
| tcgaacgtcg | ggctgggctc | ctcttcctcg | ggcttcgccg | ccgccgcgat | ggcgctggcc | 360 |
| gaggccgccg | aactcgacgc | ctcccgccag | gagatttcga | cgatcgctcg | cgtcggctcg | 420 |
| gcgtcggccg | cccgcgcggt | caccggcgcg | ttttcgcaac | tgcacacggg | tctgaacgac | 480 |
| gaggattgtc | gctcgcggcg | catcccgagt | gaccttcacg | aggacctgaa | gatcgtcgtc | 540 |
| ggcctcgtcc | cctaccacaa | ggagaccgag | gacgcccacc | gcgaggccgc | cgacagccac | 600 |
| atgttccagg | cccgcaacgc | ccacatccac | ggccagatcg | ccgagatgcg | cgacgccctg | 660 |
| cggaacaacg | agttcgaccg | cgccttcgaa | ctcgccgagc | aggactccct | ctcgctggcc | 720 |
| gcgacgacga | tgaccggccc | ctccgggtgg | gtctactggc | agcccgctac | cctgaagatc | 780 |
| ttcaataccgg | tgcgggaact | ccgcgaggag | gaggacatcc | ccgtctactt | ctcgacggac | 840 |
| accggcgcca | gcgtctacgt | caacaccacc | gaggaacacg | tcgacgaggt | cgaggaggcg | 900 |
| gtctcggatt | gcggcgtctc | caccaccgtc | tgggacgtcg | gcggccctgc | gaagctgcta | 960 |
| gacgaggaaa | agcacctgtt | ctag | | | | 984 |

<210> SEQ ID NO 92
<211> LENGTH: 951
<212> TYPE: DNA
<213> ORGANISM: Leuconostoc kimchii

<400> SEQUENCE: 92

| | | | | | |
|---|---|---|---|---|---|
| atgcctacaa | cagccacagc | acatactaat | attgcattta | ttaaatattg | gggtaaaaaa | 60 |
| gatgcgcgct | taaatttacc | gacaaccagt | tctttatccc | taacactctc | acaattttat | 120 |
| acaacaacaa | cagtcacaca | aaacaccgac | aaagatcaac | ttgttttaaa | cggtgagcta | 180 |
| gccgacccta | ctagaataca | tcattttta | aatacaatac | gtgatatcct | tggtgatttt | 240 |
| cctgctgtga | cagtcacttc | agaaaaccat | gtgccaacca | gtgcaggtct | agcctcttcg | 300 |
| gcttcatctt | tcgctgcgct | aacaggtgca | gtaacaagag | aaatgggatt | tgatttgtct | 360 |
| aatcaatcct | tatctcggtt | agcacgccgt | ggatctggtt | ccgcctcacg | atcgttttac | 420 |
| agtcactttg | ctatctggca | tgctggtatg | gatgatgcct | catcttttgc | tgaaagttta | 480 |
| aatgcccctg | acatgccgat | tgcccttgtc | gttgccgaag | tgtccacttc | agcaaagaaa | 540 |
| gtgagctcaa | gtgatggcat | gcaacgtgca | atcacttcac | caaactacga | tgattggctc | 600 |
| aaccgcagcg | cgacacaatt | tatggatatg | cagtctgcca | ttcaacaatc | agacatcgaa | 660 |
| aaaattggta | cgcttgctga | agaaaacgct | ttagctatgc | atgcgcttaa | tctcactgca | 720 |
| cgccataaac | cattcaccta | tttcacgcaa | gaaacccaac | aaatacttgc | cctagtatca | 780 |
| gatttacgac | gacaagggat | cctagccttc | gcaacaatgg | atgctggtcc | aaacgtcaaa | 840 |
| attataacga | ctttaaatga | tgcaccaaaa | attgttacag | cactacattc | tgctttacca | 900 |
| tatatccatc | tcgaaactgc | tacaagcgga | tcaggtatta | cctatgacta | a | 951 |

<210> SEQ ID NO 93
<211> LENGTH: 1005
<212> TYPE: DNA
<213> ORGANISM: Halobacterium salinarum

<400> SEQUENCE: 93

| | | | | | |
|---|---|---|---|---|---|
| atgcgcgcga | cacccccgca | tcgacgtatg | aaagcaaccg | cgcgcgcaca | ccccatccag | 60 |
| ggcctcgtga | ataccacgg | gatgcgcgac | gagtcgcttc | gcatgccgta | ccacgactcc | 120 |
| atcagcgtct | gcaccgcgcc | cagcaacacc | acgacgaccg | tcgagttcga | tcccgaccgc | 180 |
| gacgccgacc | agtacgtcgt | cgacggcgac | acggtcaccg | gtcacggcgc | ggaccgcatc | 240 |
| cgcagtgtgg | tcgatgcggt | ccgcgaccgc | gccgggttcg | accaccgcgt | gcgcctggag | 300 |
| agccagaaca | gcttccccac | gaacatcggc | ctggggtcgt | cgtcgtcggg | gttcgcggcg | 360 |
| gccgcgctgg | cgtgcgtccg | cgccgccggc | ctggatctgg | acctcccgac | ggtgtcgacg | 420 |
| gtcgcgcgcc | gcggatcggc | gtcggcggcc | cgcgccgtca | cgggcgggtt | ctcggatctg | 480 |
| cacgcgggat | tgaacgacgc | cgactgccgc | agcaacgcc | tcgacgcccc | cgcggagttc | 540 |
| gcgtccgatc | tgcgcatcgt | cgtgggcgaa | gtgcccgcgt | acaaggagac | ggagtctgcc | 600 |
| cacgccgagg | ccgccgacag | ccacatgttc | gacgcgcggc | tggcacacgt | ccagggccaa | 660 |
| ctcgcggaga | tgcgtgacgc | cgtccgcgcg | ggcgacttcc | agcgcgtctt | cgagaccgcc | 720 |
| gaacacgact | cgctgtcgct | cgcggcgacg | acgatgacgg | ggccgtccgg | gtgggtgtac | 780 |
| tggaagcccg | agacgctctc | gatattcgag | accgtgcggg | agctccgggc | ggacggcgtg | 840 |
| ccgacgtact | tctcgacgga | taccggcgcg | acagtgtacg | tgaacaccac | tgcgagtcac | 900 |
| gccgacgagg | tcgaggctgc | ggtcgccgac | tgcggcgtcg | acaccgccgt | ctgggaggtc | 960 |
| ggcgggcctg | cccacgaact | cgacgagcgc | gacgcgatct | tctga | | 1005 |

<210> SEQ ID NO 94
<211> LENGTH: 1300
<212> TYPE: DNA
<213> ORGANISM: Aspergillus clavatus

<400> SEQUENCE: 94

| | | | | | |
|---|---|---|---|---|---|
| atggcggctg | cggactcttc | ggtctatagg | gccaccacta | ctgcccctgt | caatattgct | 60 |
| gtcatcaagt | aagttgactg | ccccccccc | ctaaataaac | caaccgcctc | cttttcttct | 120 |
| atcattaaat | ttgtactaac | gctgggactt | ctctagatac | tggggaaaac | gggacgcaac | 180 |
| tctgaacctg | cccaccaatt | cttccctctc | tgtgaccctt | tcccagcgtt | cgctccgcac | 240 |
| cctcaccacc | gctcctgtt | ctgctatcta | ccccaccgca | gatgagctta | tcctcaatgg | 300 |
| caagcctcaa | gatatccaat | cctccaagcg | tacgctcgcc | tgtctctcca | gcctgcgctc | 360 |
| tcttcgccag | gcgctggaat | ctacagactc | atcgttgccg | aaattatcta | cacttccctt | 420 |
| gcggattgtt | tccgagaaca | atttccccac | ggccgctggt | cttgctagct | cagctgctgg | 480 |
| gtttgcagcc | ctcgttcgtg | ctgtagcgaa | cctctaccaa | cttccgcaat | cacctcggga | 540 |
| gctcagccgt | atcgctcgtc | agggatctgg | ctctgcttgc | cggtctctga | tgggcggcta | 600 |
| cgtggcttgg | cgcgctggag | agttggagga | cggcagcgat | agtcttgctg | aggaggttgc | 660 |
| acctgcctca | cactggcctg | agatgcgtgc | cattgtcctg | gtggtcagcg | ccgagaagaa | 720 |
| ggatgtcccc | agtaccgagg | gcatgcagac | gacggtcgct | acctcgagtc | tcttcgctac | 780 |
| cagagcgaca | tctgttgttc | ccgagcggat | ggctgccatt | gagacagcaa | tcctgaacaa | 840 |
| ggactttcct | gccttcgccg | aactcaccat | gcgcgactct | aacggcttcc | acgccacctg | 900 |

```
ccttgactcc tggcccccaa ttttctatat gaacgacgtt tcccgggctg ctgtcagaat    960
tgtccacgat atcaaccgtg ctattggccg aactgtgtgt gcgtacacct ttgatgctgg   1020
accgaatgct gttatctatt atctggaaaa ggattcggag ctggtcgcag aactgtcaa    1080
ggcaatcttg accaccaaca ctgacggctg aatggtcct ttctacgata ttctgaagga    1140
cgtcactgcc ccgggtgttt ctttggataa gattgactct agagccgttg aagttctcaa   1200
ggagggagtc agccgcgtga ttctgaccgg tgttggtgag ggtcctgtca gtgtagaaga   1260
ccacctggtc agcgcaactg gagatgttct ttcgcactaa                         1300

<210> SEQ ID NO 95
<211> LENGTH: 1283
<212> TYPE: DNA
<213> ORGANISM: Neosartorya fischeri

<400> SEQUENCE: 95
atggcggcta cttctgatca taccgtctat cgtgctacca ctaccgcccc ggtcaatatt    60
gctgttatta agtgagttga ctatcgcccc ctaatccgtc ctgtggtgat tcttgtttcc   120
tcctaacagg gtcctctagg tattggggta aaagagatgc gtctctgaat ctgccaacca   180
attcctccct ctctgttacc ctctctcagc gctcccctcg aacctcact accgcctcct    240
gctcagctat ctaccccgcc gcagacgagc tcatcttgaa cggcaagcca caggatattc   300
agtcctccaa acgcacactc gcttgtctct ccaacctacg ttccctccgt caggctctcg   360
aaaatgccga cccctcattg cctaaactgt ctgctctccc attgcgaatt gtttccgaga   420
acaacttccc caccgctgct ggtctcgcga gctcagctgc tggtttcgca gcccttgtcc   480
gtgctatagc agatctttat cagcttccac aatctcctct ggagctcagc cgtattgccc   540
gtcagggttc cggctctgct tgtcggtctc tgatgggcgg ttatgttgcc tggcgtgctg   600
gcgagcggga agatggtagc gacagtctgg ctgaggaagt cgctcccgca tctcattggc   660
ctgagatgcg tgcaattatc ctggtggtta gtgccgagaa gaaagacgtc cccagtacag   720
agggtatgca gactacagtt gctacctcga gtctctttgc tacccgggcc gcatctgttg   780
tccctgagcg gatggccgcc attgagacgg caatccagaa caaggacttc gctacctttg   840
cggaaatcac catgcgtgac tctaacagtt tccacgcaac ttgcctcgac tcctggcctc   900
cgatcttcta catgaacgac gtctccagag ctgccgtgag actcgtccac gacatcaacc   960
gtgctgttgg ccggactgtg tgtgcttaca cattcgacgc tggcccgaat gccgttatct   1020
actaccttga gaaagactcg gaggtggtcg caggaaccgt caaggctatt tgggccccca  1080
acaccgaagg gttcgacggc ccattctatg atatcttgaa gaatgtcact gcttcagtcg  1140
tgcctctgga gaatgttgac tctagagctg tagaagtctt gaagaacggc atcagccgcg  1200
tcattctgac tggtgtcggg gagggtccta tcagcgtgga ggatcacctt gtgagcgcga  1260
cgggtgatat cctcgcttct tga                                          1283

<210> SEQ ID NO 96
<211> LENGTH: 954
<212> TYPE: DNA
<213> ORGANISM: Streptococcus pseudopneumoniae

<400> SEQUENCE: 96
atggatagag agcctgtaac agtacgttcc tacgcaaata ttgctattat caaatattgg    60
ggaaagaaaa aagaaaaaga gatagtgcct gctactagca gtatttctct aactttggaa   120
aatatgtata cagagacgac cttgtcgcct ttaccagcca atgtaacagc tgacgaattt   180
```

```
tacatcaatg ctcagctaca aaatgaggtc gagcatgcca agatgagtaa gattattgac      240
cgttatcgtc cagctggtga gggctttgtc cgtatcgata ctcaaaataa tatgcctacg      300
gcagcgggcc tgtcctcaag ttctagtggt ttgtccgccc tggtcaaggc ttgtaatgct      360
tatttccagc ttggtttgtc tcggagtcag ttggcacagg aggctaagtt tgcctcaggt      420
tcttcttctc ggagttttta tggaccacta ggtgcctggg acaaggatag tgggggaatt      480
taccctgtag agacaaactt gaaactagct atgatcatgt tggtgctaga ggacaagaaa      540
aaaccaatct ctagccgtga cgggatgaaa ctttgtgtgg agacttcgac gacttttgac      600
gactgggttc gtcagtctga gaaggactat caggatatgc tgatttatct caaggaaaat      660
gactttgcca agattggaga attaacggag aaaaatgctc ttgctatgca cgctacgaca      720
aaaacagcat caccagcctt ttcttatctg accgattcat cttatgaagc gatggacttt      780
gttcgtcaac ttcgcgagca aggagaggcc tgctacttta ctatggatgc cggtcctaat      840
gtcaaagttc tttgtcaaga gaaagacttg gagcatttat caaaaatctt cggtcaacgt      900
taccgcttga ttgtgtcaaa aacaaaggat ttgagtcaag atgattgctg ttaa            954

<210> SEQ ID NO 97
<211> LENGTH: 1005
<212> TYPE: DNA
<213> ORGANISM: Lactobacillus rhamnosus

<400> SEQUENCE: 97
atgacaactt atgcacgtgc gcacactaac attgcattga tcaaatattg gggcaaagca       60
aataagcaac tgatgctgcc ggcaaccagc agtatttcgc ttaccttgaa tgacttttac      120
acggacacgg cggtaacttt tgaccctgca ctcgatcagg atcaattcac gttaaatcac      180
caaatgcagt cgcctactgc tgtcagccgc tttttggatc atgttcggca cctggcccaa      240
attgatacac gcgctcgggt caactcgttg aatcatgtac cgactgctgc cggtttggcc      300
agttcggctt ctgcgtttgc ggcactggca ctggctacaa gtcgcgcggc tggcctaaat      360
ttaaccccta ccgctttgtc acggttggca cgtcgcggct cagggtcggc caccgttca      420 atctttggcg gagcggtaat ttggcaccgt ggcagcgatg atcaatcctc gtttgccgaa      480
cccttaacca ttcagccaac tctgccgctg cggatgttgg tcgtcacggt ttccgatcag      540
aaaaaggcag tcagctcccg caccggcatg gccaacacgg ttgcgaccag cccttattac      600
caggcatggg tacaatcgaa tgaagcgtta atttcaccta tgatcacggc attggccgaa      660
aatgatctga cgacgattgg tgcactcacc gaattatcga gtatgcgcat gcacgctgcc      720
attatggctg aggagccgcc gttcacctac tttttgccgg aaactttacg cgcctggcaa      780
ttggtgcaag aacaacgggc actcggcatt ccggcgtttg ccacgatgga tgccggaccc      840
aacgtcaaga tcctcacaac cgcaccgtac gtggatgttc tcatgaccgc cttgcagcct      900
gtttttggcg accggatttt gagcacccgc ctcggcccgg acgcgcaagt gattacaaag      960
gagcaattta atgacacaga gtcagcaatc acatcgcaag gatga                   1005

<210> SEQ ID NO 98
<211> LENGTH: 939
<212> TYPE: DNA
<213> ORGANISM: Borrelia afzelii

<400> SEQUENCE: 98
atgaaagtaa agtgta

| | |
|---|---|
| gatgtttttt taaacattcc agcgacttct agtcttgctg ttagtgttga taaattttat | 120 |
| tcaataagtg agcttgaact ttcagatcga gatgaaataa ttttaaattc aaagccagtt | 180 |
| atattgcaaa atagagaaaa ggtgttttt gattatgcaa gaaaaattct tagtgaaccg | 240 |
| aatgttagat ttaaaattaa aagtgaaaac aattttccaa cagcagcagg ccttgcaagt | 300 |
| tcaagttcag gatttgcttc tattgctgct tgtattttga atatttttga taaatattct | 360 |
| tttaatagtg catctaatct tgcaagagta ggatcagctt ctgcagcaag ggctatttac | 420 |
| ggagggttta ctattttgaa agaaggttca aaagaatctt ttcaattaag agatgaatct | 480 |
| tattttaatg atttgcgcat aatatttgcc ataattgata gtagtgaaaa agaattgtcc | 540 |
| tcaagagccg caatgaatat ttgcaaacac catggatttt attatgatgc ttggattgct | 600 |
| tctagtaaaa agattttaa agatgcttta tatttttt taaaaaaaga ttttgtgcat | 660 |
| tttggagcaa ctattgtaaa aagttatcag aatatgtttg ctttaatgtt tgcatcttct | 720 |
| attttttatt ttaaaaatag cacaatagat ttaattaaat atgccgctta tttaagaaat | 780 |
| aaaggaattt tggtatttga gacaatggat gcgggccccc aagtgaagtt tctttgtttg | 840 |
| gagaaaaatt taaatactat tttaaaagga cttaagcaga attttactga cattgagttt | 900 |
| attgtttcaa aggttggatg tgacttagaa tggatttga | 939 |

<210> SEQ ID NO 99
<211> LENGTH: 549
<212> TYPE: DNA
<213> ORGANISM: Escherichia coli

<400> SEQUENCE: 99

| | |
|---|---|
| atgcaaacgg aacacgtcat tttattgaat gcacagggag ttcccacggg tacgctggaa | 60 |
| aagtatgccg cacacacggc agacacccgc ttacatctcg cgttctccag ttggctgttt | 120 |
| aatgccaaag gacaattatt agttacccgc cgcgcactga gcaaaaaagc atggcctggc | 180 |
| gtgtggacta actcggtttg tgggcaccca caactgggag aaagcaacga agacgcagtg | 240 |
| atccgccgtt gccgttatga gcttggcgtg gaaattacgc ctcctgaatc tatctatcct | 300 |
| gactttcgct accgcgccac cgatccgagt ggcattgtgg aaaatgaagt gtgtccggta | 360 |
| tttgccgcac gcaccactag tgcgttacag atcaatgatg atgaagtgat ggattatcaa | 420 |
| tggtgtgatt tagcagatgt attcacggt attgatgcca cgccgtgggc gttcagtccg | 480 |
| tggatggtga tgcaggcgac aaatcgcgaa gccagaaaac gattatctgc atttacccag | 540 |
| cttaaataa | 549 |

<210> SEQ ID NO 100
<211> LENGTH: 867
<212> TYPE: DNA
<213> ORGANISM: Saccharomyces cerevisiae

<400> SEQUENCE: 100

| | |
|---|---|
| atgactgccg acaacaatag tatgccccat ggtgcagtat ctagttacgc caaattagtg | 60 |
| caaaaccaaa cacctgaaga cattttggaa gagtttcctg aaattattcc attacaacaa | 120 |
| agacctaata cccgatctag tgagacgtca atgacgaaaa gcggagaaac atgtttttct | 180 |
| ggtcatgatg aggagcaaat taagttaatg aatgaaaatt gtattgtttt ggattgggac | 240 |
| gataatgcta ttggtgccgg taccaagaaa gtttgtcatt taatggaaaa tattgaaaag | 300 |
| ggtttactac atcgtgcatt ctccgtcttt atttcaatg aacaaggtga attacttta | 360 |
| caacaaagag ccactgaaaa aataactttc cctgatcttt ggactaacac atgctgctct | 420 |

```
catccactat gtattgatga cgaattaggt ttgaagggta agctagacga taagattaag    480
ggcgctatta ctgcggcggt gagaaaacta gatcatgaat taggtattcc agaagatgaa    540
actaagacaa ggggtaagtt tcactttta acagaatcc attacatggc accaagcaat     600
gaaccatggg gtgaacatga aattgattac atcctatttt ataagatcaa cgctaaagaa    660
aacttgactg tcaacccaaa cgtcaatgaa gttagagact tcaaatgggt ttcaccaaat    720 gattttgaaaa ctatgtttgc tgacccaagt tacaagttta cgccttggtt taagattatt   780
tgcgagaatt acttattcaa ctggtgggag caattagatg acctttctga agtggaaaat   840
gacaggcaaa ttcatagaat gctataa                                        867

<210> SEQ ID NO 101
<211> LENGTH: 996
<212> TYPE: DNA
<213> ORGANISM: Streptococcus mutans

<400> SEQUENCE: 101
atgacaaata gaaaagatga tcatataaaa tatgccttag actatcgttc gccatataat     60
agtttcgatg acatagaact cattcatcat tctttaccag attatgattt agccgagatt   120
gatttgtcta cacattttgc tggtcaggat tttgattttc cttttatat caacgctatg    180 acaggcggaa gccaaaaagg gaaagaagtt aatgaaaaat tagctcaggt agcggacacc   240
tgtggtcttc tttttgtaac aggttcttac agcacagctc ttaaaaatcc agacgatact   300
tcttatcagg taaaaaaatc cagacctcat ttattactag caaccaatat cggccttgac   360
aaaccttatc aggctggctt acaggcagtt agggatttac agcctttatt tcttcaagtt   420
catattaatc ttatgcaaga gctccttatg ccagaggggg aacgcgaatt taggtcttgg   480
aagaaacatt tatctgacta tgcgaagaaa ctacaacttc cttttatttt aaaagaagtt   540
ggttttggta tggacgttaa aacaatccaa actgctattg acctagggggt aaaactgtc   600 gatatttctg gccgaggcgg aactagtttt gcttatatcg aaaatagacg tggcggaaat   660
cgttcttatc ttaatcaatg gggacaaaacc acagcgcaag ttctattaaa tgctcagccg   720
cttatggata aggtagaaat cctggctagc ggcgggattc gtcatccatt ggacataata   780
aaagctttgg tccttggagc caaagcggtc ggtttatctc gaacgatgtt agaattagtt    840
gaacagcatt ctgttcatga agtcattgct attgtaaatg gttggaaaga agatttgcgc   900
ctgatcatgt gcgcccttaa ctgtcaaacg attgcagaac ttcgaaatgt tgactatctt   960
ttatatgggc gcttaagaga aggacagaga caataa                              996

<210> SEQ ID NO 102
<211> LENGTH: 1050
<212> TYPE: DNA
<213> ORGANISM: Bacillus subtilis

<400> SEQUENCE: 102
gtgactcgag cagaacgaaa aagacaacac atcaatcatg ccttgtccat cggccagaag     60
cgggaaacag gtcttgatga tattacgttt gttcacgtca gtctgcccga tcttgcatta   120
gaacaagtag atatttccac aaaaatcggc gaactttcaa gcagttcgcc gattttatc   180 aatgcaatga ctggcggcgg cggaaaactt acatatgaga ttaataaatc gcttgcgcga   240
gcggcttctc aggctggaat tccccttgct gtgggatcgc aaatgtcagc attaaaagat   300
ccatcagagc gtcttttccta tgaaattgtt cgaaaggaaa acccaaacgg gctgattttt   360
```

```
gccaacctgg gaagcgaggc aacggctgct caggcaaagg aagccgttga gatgattgga    420
gcaaacgcac tgcagatcca cctcaatgtg attcaggaaa ttgtgatgcc tgaagggggac   480 agaagcttta gcggcgcatt gaaacgcatt gaacaaattt gcagccgggt cagtgtaccg    540
gtcattgtga agaagtcgg cttcggtatg agcaaagcat cagcaggaaa gctgtatgaa     600
gctggtgctg cagctgttga cattggcggt tacgggggaa caaatttctc gaaaatcgaa    660
aatctccgaa gacagcggca aatctccttt tttaattcgt ggggcatttc gacagctgca    720
agtttggcgg aaatccgctc tgagtttcct gcaagcacca tgatcgcctc tggcggtctg    780
caagatgcgc ttgacgtggc aaaggcaatt gcgctggggg cctcttgcac cggaatggca    840
gggcattttt taaaagcgct gactgacagc ggtgaggaag actgcttga ggagattcag     900 ctgatccttg aggaattaaa gttgattatg accgtgctgg gtgccagaac aattgccgat    960
ttacaaaagg cgccccttgt gatcaaaggt gaaacccatc attggctcac agagagaggg   1020
gtcaatacat caagctatag tgtgcgataa                                    1050
```

<210> SEQ ID NO 103
<211> LENGTH: 939
<212> TYPE: DNA
<213> ORGANISM: Escherichia coli

<400> SEQUENCE: 103

```
atgaaagtcg cagtcctcgg cgctgctggc ggtattggcc aggcgcttgc actactgtta     60
aaaacccaac tgccttcagg ttcagaactc tctctgtatg atatcgctcc agtgactccc    120
ggtgtggctg tcgatctgag ccatatccct actgctgtga aaatcaaagg tttttctggt    180
gaagatgcga ctccggcgct ggaaggcgca gatgtcgttc ttatctctgc aggcgtagcg    240
cgtaaaccgg gtatggatcg ttccgacctg tttaacgtta acgccggcat cgtgaaaaac    300
ctggtacagc aagttgcgaa aacctgcccg aaagcgtgca ttggtattat cactaacccg    360
gttaacacca cagttgcaat tgctgctgaa gtgctgaaaa agccggtgt ttatgacaaa     420 aacaaactgt tcggcgttac cacgctggat atcattcgtt ccaacaccct tgttgcggaa    480
ctgaaaggca acagccagg cgaagttgaa gtgccggtta ttggcggtca ctctggtgtt    540
accattctgc cgctgctgtc acaggttcct ggcgttagtt ttaccgagca ggaagtggct    600
gatctgacca aacgcatcca gaacgcgggt actgaagtgg ttgaagcgaa ggccggtggc    660
gggtctgcaa ccctgtctat gggccaggca gctgcacgtt ttggtctgtc tctggttcgt    720
gcactgcagg gcgaacaagg cgttgtcgaa tgtgcctacg ttgaaggcga cggtcagtac    780
gcccgttcct ctctctcaacc gctgctgctg ggtaaaaacg gcgtggaaga gcgtaaatct    840
atcggtaccc tgagcgcatt tgaacagaac gcgctggaag gtatgctgga tacgctgaag    900
aaagatatcg ccctgggcga agagttcgtt aataagtaa                           939
```

<210> SEQ ID NO 104
<211> LENGTH: 990
<212> TYPE: DNA
<213> ORGANISM: Escherichia coli

<400> SEQUENCE: 104

```
atgaaactcg ccgtttatag cacaaaacag tacgacaaga agtacctgca acaggtgaac     60
gagtcctttg gctttgagct ggaattttttt gactttctgc tgacggaaaa aaccgctaaa    120
actgccaatg gctgcgaagc ggtatgtatt ttcgtaaacg atgacggcag ccgcccggtg    180
ctggaagagc tgaaaaagca cggcgttaaa tatatcgccc tgcgctgtgc cggtttcaat    240
```

```
aacgtcgacc ttgacgcggc aaaagaactg gggctgaaag tagtccgtgt tccagcctat      300
gatccagagg ccgttgctga acacgccatc ggtatgatga tgacgctgaa ccgccgtatt      360
caccgcgcgt atcagcgtac ccgtgacgct aacttctctc tggaaggtct gaccggcttt      420
actatgtatg gcaaaacggc aggcgttatc ggtaccggta aaatcggtgt ggcgatgctg      480
cgcattctga aaggttttgg tatgcgtctg ctggcgttcg atccgtatcc aagtgcagcg      540
gcgctggaac tcggtgtgga gtatgtcgat ctgccaaccc tgttctctga atcagacgtt      600
atctctctgc actgcccgct gacaccggaa aactaccatc tgttgaacga agccgccttc      660
gatcagatga aaaatggcgt gatgatcgtc aataccagtc gcggtgcatt gattgattct      720
caggcagcaa ttgaagcgct gaaaaatcag aaaattggtt cgttgggtat ggacgtgtat      780
gagaacgaac gcgatctgtt ctttgaagat aaatccaacg acgtgatcca ggatgacgta      840
ttccgtcgcc tgtctgcctg ccacaacgtg ctgtttaccg gcaccaggc attcctgaca      900 gcagaagctc tgaccagtat ttctcagact acgctgcaaa acttaagcaa tctggaaaaa      960
ggcgaaacct gcccgaacga actggtttaa                                      990
```

<210> SEQ ID NO 105
<211> LENGTH: 1050
<212> TYPE: DNA
<213> ORGANISM: Ralstonia eutropha

<400> SEQUENCE: 105

```
atgaagatct ccctcaccag cgcccgccag cttgcccgcg acatcctcgc cgcgcagcag       60
gtgcccgccg acatcgctga cgacgtggcc gagcacctgg tcgaatccga ccgctgcggc      120
tatatcagcc acggcctgtc gatcctgccc aactaccgca ccgccctcga cggccacagc      180
gtcaacccgc aaggccgcgc caaatgcgtg ctggaccagg gcacgctgat ggtgttcgac      240
ggcgacggcg gcttcggcca gcacgtgggc aagtccgtga tgcaagcagc gatcgagcgc      300
gtgcgccagc atgccactg catcgtcact ctgcccgct cgcaccatct cggccgcatg      360
ggccactacg gcgagatggc ggccgccgcc ggctttgtgc tgctgagctt caccaacgtg      420
atcaaccgcg cgccggtggt ggcgccgttc ggcggccgcg tggcgcggct caccaccaac      480
ccgctgtgtt cgccggccc gatgcccaac gggcggccgc ctctggtggt ggacatcgcc      540
accagcgcga ttgccatcaa caaggcccgt gtgctggccg agaaaggcga gccggcgccc      600
gaaggcagca tcatcggcgc cgacggcaac cccaccaccg acgcgtcaac catgttcggc      660
gaacaccccg cgcgctgct gcccttggc ggccacaagg gctacgcact gggcgttgtg      720
gccgagctgc tggcgggcgt gctgtccggc ggcggtacca tccagccaga caatccgcgc      780
ggcggcgtgg ccaccaacaa cctgttcgcg gtgctgctca tcccgcgct ggacctgggc      840 ctggactggc agagcgccga ggtcgaggcg ttcgtgcgct acctgcacga cacaccgccg      900
gcgccgggcg tcgaccgcgt gcagtacccc ggcgagtacg aggccgccaa ccgggcgcag      960
gccagcgaca cgctaaacat caacccggcc atctggcgca atcttgagcg cctggcgcag     1020
tcgctcaacg tggccgtccc cacggcctga                                      1050
```

<210> SEQ ID NO 106
<211> LENGTH: 1056
<212> TYPE: DNA
<213> ORGANISM: Clostridium beijerinckii

<400> SEQUENCE: 106

-continued

| | |
|---|---|
| atgaaaggtt ttgcaatgct aggtattaat aagttaggat ggatcgaaaa agaaaggcca | 60 |
| gttgcgggtt catatgatgc tattgtacgc ccattagcag tatctccgtg tacatcagat | 120 |
| atacatactg tttttgaggg agctcttgga gataggaaga atatgatttt agggcatgaa | 180 |
| gctgtaggta agttgttga agtaggaagt gaagtgaagg attttaaacc tggtgacaga | 240 |
| gttatagttc cttgtacaac tccagattgg agatctttgg aagttcaagc tggttttcaa | 300 |
| cagcactcaa acggtatgct cgcaggatgg aaatttttcaa atttcaagga tggagttttt | 360 |
| ggtgaatatt ttcatgtaaa tgatgcggat atgaatcttg cgattctacc taaagacatg | 420 |
| ccattagaaa atgctgttat gataacagat atgatgacta ctggatttca tggagcagaa | 480 |
| cttgcagata ttcaaatggg ttcaagtgtt gtggtaattg cattggagc tgttggctta | 540 |
| atgggaatag caggtgctaa attcgtggga gcaggtagaa taattggagt ggggagcagg | 600 |
| ccgatttgtg ttgaggctgc aaaattttat ggagcaacag atattctaaa ttataaaaat | 660 |
| ggtcatatag ttgatcaagt tatgaaatta acgaatggaa aaggcgttga ccgcgtaatt | 720 |
| atggcaggcg gtggttctga acattatcc caagcagtat ctatggttaa accaggagga | 780 |
| ataatttcta atataaatta tcatggaagt ggagatgctt tactaatacc acgtgtagaa | 840 |
| tggggatgtg aatggctca aagactata aaggagggtc tttgtcctgg gggacgtttg | 900 |
| agagcagaaa tgttaagaga tatggtagta tataatcgtg ttgatctaag taaattagtt | 960 |
| acacatgtat atcatggatt tgatcacata gaagaagcac tgttattaat gaaagacaag | 1020 |
| ccaaaagact taattaaagc agtagttata ttataa | 1056 |

<210> SEQ ID NO 107
<211> LENGTH: 1059
<212> TYPE: DNA
<213> ORGANISM: Thermoanaerobacter brockii

<400> SEQUENCE: 107

| | |
|---|---|
| atgaaaggtt ttgcaatgct cagtatcggt aaagttggct ggattgagaa ggaaaagcct | 60 |
| gctcctggcc catttgatgc tattgtaaga cctctagctg tggccccttg cacttcggac | 120 |
| attcataccg tttttgaagg cgccattggc gaaagacata acatgatact cggtcacgaa | 180 |
| gctgtaggtg aagtagttga agtaggtagt gaggtaaaag attttaaacc tggtgatcgc | 240 |
| gttgttgtgc cagctattac ccctgattgg cggacctctg aagtacaaag aggatatcac | 300 |
| cagcactccg gtggaatgct ggcaggctgg aaattttcga atgtaaaaga tggtgttttt | 360 |
| ggtgaatttt ttcatgtgaa tgatgctgat atgaatttag cacatctgcc taaagaaatt | 420 |
| ccattggaag ctgcagttat gattcccgat atgatgacca ctggttttca cggagctgaa | 480 |
| ctggcagata tagaattagg tgcgacggta gcagttttgg gtattggccc agtaggtctt | 540 |
| atggcagtcg ctggtgccaa attgcgtgga gccggaagaa ttattgccgt aggcagtaga | 600 |
| ccagtttgtg tagatgctgc aaaatactat ggagctactg atattgtaaa ctataaagat | 660 |
| ggtcctatcg aaagtcagat tatgaatcta actgaaggca aggtgtcga tgctgccatc | 720 |
| atcgctggag gaaatgctga cattatggct acagcagtta agattgttaa acctggtggc | 780 |
| accatcgcta atgtaaatta ttttggcgaa ggagaggttt gcctgttcc tcgtcttgaa | 840 |
| tggggttgcg gcatggctca taaaactata aaggcgggc tatgccccgg tggacgtcta | 900 |
| agaatgaaaa gactgattga ccttgttttt tataagcgtg tcgatccttc taagctcgtc | 960 |
| actcacgttt tccggggatt tgacaatatt gaaaagcct ttatgttgat gaaagacaaa | 1020 |
| ccaaaagacc taatcaaacc tgttgtaata ttagcataa | 1059 |

<210> SEQ ID NO 108
<211> LENGTH: 2537
<212> TYPE: DNA
<213> ORGANISM: Rhodococcus ruber

<400> SEQUENCE: 108

| | | | | | |
|---|---|---|---|---|---|
| ctgcagggct | tcaccctcgg | ccactacacc | cacgtcttcc | ccgagttcgc ggcgaagatg | 60 |
| gggccgtggc | tcgcggccgg | cgacgtggtg | ttcgacgaga | cgatcgtcga cggcatcggc | 120 |
| aactcggtcg | atgccttcct | cgacctcatg | cgcgggcgca | acgtcggcaa gatgctcgtc | 180 |
| cgaaccgcct | gacgtccgga | gccggaacgg | ccggcgtcgt | gcagcggaag attcgctcca | 240 |
| gtgccgggcg | gcgcaccttc | ccggccgta | gagtcgggcg | catgaaagcc ctccagtaca | 300 |
| ccgagatcgg | ctccgagccg | gtcgtcgtcg | acgtccccac | cccggcgccc gggccgggtg | 360 |
| agatcctgct | gaaggtcacc | gcggccggct | tgtgccactc | ggacatcttc gtgatggaca | 420 |
| tgccggcaga | gcagtacatc | tacggtcttc | ccctcaccct | cggccacgag ggcgtcggca | 480 |
| ccgtcgccga | actcggcgcc | ggcgtcaccg | gattcgagac | ggggggacgcc gtcgccgtgt | 540 |
| acgggccgtg | ggggtgcggt | gcgtgccacg | cgtgcgcgcg | cggccgggag aactactgca | 600 |
| cccgcgccgc | cgagctgggc | atcaccccgc | ccggtctcgg | ctcgcccggg tcgatggccg | 660 |
| agtacatgat | cgtcgactcg | gcgcgccacc | tcgtcccgat | cggggacctc gaccccgtcg | 720 |
| cggcggttcc | gctcaccgac | gcgggcctga | cgccgtacca | cgcgatctcg cgggtcctgc | 780 |
| ccctgctggg | acccgctcg | accgcggtcg | tcatcggggt | cggcggactc gggcacgtcg | 840 |
| gcatccagat | cctgcgcgcc | gtcagcgcgg | cccgcgtgat | cgccgtcgat ctcgacgacg | 900 |
| accgactcgc | gctcgcccgc | gaggtcggcg | ccgacgcggc | ggtgaagtcg ggcgccgggg | 960 |
| cggcggacgc | gatccgggag | ctgaccggcg | gtgagggcgc | gacggcggtg ttcgacttcg | 1020 |
| tcggcgccca | gtcgacgatc | gacacggcgc | agcaggtggt | cgcgatcgac gggcacatct | 1080 |
| cggtggtcgg | catccatgcc | ggcgcccacg | ccaaggtcgg | cttcttcatg atcccgttcg | 1140 |
| gcgcgtccgt | cgtgacgccg | tactgggca | cgcggtccga | gctgatggac gtcgtggacc | 1200 |
| tggcccgtgc | cggccggctc | gacatccaca | ccgagacgtt | caccctcgac gagggaccca | 1260 |
| cggcctaccg | gcggctacgc | gagggcagca | tccgcggccg | cggggtggtc gtcccgggct | 1320 |
| gacacgacga | cgaaggctcc | gcactcggat | cgagtgcgga | gccttcgtcg ggtacgggga | 1380 |
| tcagcgagcg | aacagcagcg | cgcgcttgac | ctcctggatc | gccttcgtca cctggatgcc | 1440 |
| gcgcgggcac | gcgtcggtgc | agttgaaggt | ggtgcggcag | cgccacacgc cctcgacgtc | 1500 |
| gttgaggatg | tcgagacgct | cggcggcgcc | ctcgtcacgg | ctgtcgaaga tgaaccggtg | 1560 |
| cgcgttgacg | atggcggcgg | gaccgaagta | gctgccgtcg | ttccagtaca ccgggcacga | 1620 |
| ggtggtgcag | cacgcgcaca | ggatgcactt | ggtggtgtcg | tcgaaccggg cacggtcggc | 1680 |
| ctgcgactgg | atccgctcgc | gggtgggctc | gttgcccgtg | gcgatgagga acggcttcac | 1740 |
| ggcgcggaac | gcgtcgaaga | agggctccat | gtcgacgacg | aggtccttct cgaccggcag | 1800 |
| gccgcggatc | ggctcgacgg | tgatggtcac | cggcttgccg | tccttgggca gcatgtcctt | 1860 |
| catcaggatc | ttgcaggcca | ggcggttgac | gccgttgatc | cgcatggcgt ccgagccgca | 1920 |
| caccccgtgc | gcgcagctgc | ggcggaacgt | gagggtgccg | tcgaggtagc ccttcacgta | 1980 |
| gagcagcagg | ttgagcatgc | ggtccgacgg | cagcgccgga | acctgaaagc tgtcccagtg | 2040 |
| ctgacccttg | ccgtcctcgg | ggttgaaccg | cgcgatcttg | agggtgacca tcgtggcgcc | 2100 |

| | |
|---|---|
| ctcgggcacg gtggcaggt tcgagacgtc ggcttcgttc ttctcgaggg ttgtcatcaa | 2160 |
| gtacttccgc tccatcggct cgtagcgggt ctgcaccacc ggcttgtagt ccaggcggat | 2220 |
| gggggagatc agctccgtcc cctccttgta ggccatggtg tgcttgagga acttctcgtc | 2280 |
| gtcgcgcttc gggaagtcct cgcgggcgtg accgccgcgc gattccttcc ggttgagcgc | 2340 |
| accggcgacg gtgacctcgg ccatctcgag caggaagccc agctcgacgg cctcgagcag | 2400 |
| gtcgctgttg tagcgcttgc ccttgtcctg gacggtgatg ttcttgtacc gctccttcag | 2460 |
| cgcgtggatg tcctcgagcg ccttggtgag cgtctcctcg gtgcggaaca ccgaggcgtt | 2520 |
| gttgtccatg gactgca | 2537 |

<210> SEQ ID NO 109
<211> LENGTH: 1173
<212> TYPE: DNA
<213> ORGANISM: Pyrococcus furiosus

<400> SEQUENCE: 109

| | |
|---|---|
| atgtttgaga tatcaattta tcttcccaca gaaatagttt ttggtcctgg gaagcttgaa | 60 |
| atgcttccta aactagtgaa gaagcatggg ctttctggga aggccctaat agtaactgga | 120 |
| aggagaagca caaaggaaac tggagttctt tatagagttc aagaactact taagcaagct | 180 |
| ggggtagaga gcatagtttt tgacaaaatt attccaaatc caatatctac tcatgtggat | 240 |
| gaaggggcag agatagcgag aaaagaaaat gttagctttg ttgttggctt gggtggtgga | 300 |
| agtgcgatag atagtgcaaa agctatagca atgactgccg ccagtggagg taaatattgg | 360 |
| gactatgttc cagctgtggg aggaggaaag aagcctactg gagcgcttcc aatagttgca | 420 |
| attccaacaa cccacgggac tggaacggag gctgatcctt atgctgttat aactaatcct | 480 |
| gaaacaaagg agaagcaggg aattggatat gatgttctct tccccaaatt ctctatagtt | 540 |
| gatccagaac ttatgcttac tcttccaaaa gatcaaacag tgtacacttc aatggatgct | 600 |
| ttctaccact ccattgaggc ctttcttaat gttagagcaa atccatattc ggatgttctg | 660 |
| gctctcgact caatgaggcg cattgttaca taccttccat tggcctacga aacttgaga | 720 |
| aatcttgaag caagaacgca acttgcctgg gcaagtactg aggctggaat aacggaaacg | 780 |
| gtaacgggag ttgtggcaaa tcatgcactt gagcatggtc taagtggatt ctatcctgaa | 840 |
| gtgcctcatg gtctgggcct ctgcattcta ggaccctacc tctttgaata cattctcgac | 900 |
| tatgcctatg aaaagttggc gatagtcgga agagaggtat ttggagttta cgagccaaat | 960 |
| gacagaaagg cagcagagct agctattaag aagctacgtg acttccagag cctcttttga | 1020 |
| gtaaacaaga agctcagaga attaggggtt aaagaggaag acattccaga gatggctagg | 1080 |
| actgcttata gaatgatgaa acctgttata gaggcaacac cgggagattt gaaagttgaa | 1140 |
| gacttggaag agatctatag aagagcatac taa | 1173 |

<210> SEQ ID NO 110
<211> LENGTH: 2676
<212> TYPE: DNA
<213> ORGANISM: Escherichia coli

<400> SEQUENCE: 110

| | |
|---|---|
| atggctgtta ctaatgtcgc tgaacttaac gcactcgtag agcgtgtaaa aaaagcccag | 60 |
| cgtgaatatg ccagtttcac tcaagagcaa gtagacaaaa tcttccgcgc cgccgctctg | 120 |
| gctgctgcag atgctcgaat cccactcgcg aaaatggccg ttgccgaatc cggcatgggt | 180 |
| atcgtcgaag ataaagtgat caaaaaccac tttgcttctg aatatatcta caacgcctat | 240 |

```
aaagatgaaa aaacctgtgg tgttctgtct gaagacgaca cttttggtac catcactatc    300
gctgaaccaa tcggtattat ttgcggtatc gttccgacca ctaacccgac ttcaactgct    360
atcttcaaat cgctgatcag tctgaagacc cgtaacgcca ttatcttctc cccgcacccg    420
cgtgcaaaag atgccaccaa caaagcggct gatatcgttc tgcaggctgc tatcgctgcc    480
ggtgctccga agatctgat cggctggatc gatcaacctt ctgttgaact gtctaacgca    540
ctgatgcacc acccagacat caacctgatc ctcgcgactg tggtccgggg catggttaaa    600
gccgcataca gctccggtaa accagctatc ggtgtaggcg cgggcaacac tccagttgtt    660
atcgatgaaa ctgctgatat caaacgtgca gttgcatctg tactgatgtc caaaaccttc    720
gacaacggcg taatctgtgc ttctgaacag tctgttgttg ttgttgactc tgtttatgac    780
gctgtacgtg aacgttttgc aacccacggc ggctatctgt tgcagggtaa agagctgaaa    840
gctgttcagg atgttatcct gaaaaacggt gcgctgaacg cggctatcgt tggtcagcca    900
gcctataaaa ttgctgaact ggcaggcttc tctgtaccag aaaacaccaa gattctgatc    960
ggtgaagtga ccgttgttga tgaaagcgaa ccgttcgcac atgaaaaact gtccccgact   1020
ctggcaatgt accgcgctaa agatttcgaa gacgcgtag aaaaagcaga gaaactggtt   1080
gctatgggcg gtatcggtca tacctcttgc ctgtacactg accaggataa ccaaccggct   1140
cgcgtttctt acttcggtca gaaaatgaaa acggcgcgta tcctgattaa cacccccagcg   1200 tctcagggtg gtatcggtga cctgtataac ttcaaactcg caccttccct gactctgggt   1260
tgtggttctt ggggtggtaa ctccatctct gaaaacgttg gtccgaaaca cctgatcaac   1320
aagaaaaccg ttgctaagcg agctgaaaac atgttgtggc acaaacttcc gaaatctatc   1380
tacttccgcc gtggctccct gccaatcgcg ctggatgaag tgattactga tggccacaaa   1440
cgtgcgctca tcgtgactga ccgcttcctg ttcaacaatg gttatgctga tcagatcact   1500
tccgtactga aagcagcagg cgttgaaact gaagtcttct tcgaagtaga agcggacccg   1560 acctgagca tcgttcgtaa aggtgcagaa ctggcaaact ccttcaaacc agacgtgatt   1620
atcgcgctgg gtggtggttc cccgatggac gccgcgaaga tcatgtgggt tatgtacgaa   1680
catccggaaa ctcacttcga agagctggcg ctgcgcttta tggatatccg taaacgtatc   1740
tacaagttcc cgaaaatggg cgtgaaagcg aaaatgatcg ctgtcaccac cacttctggt   1800
acaggttctg aagtcactcc gtttgcggtt gtaactgacg acgctactgg tcagaaatat   1860
ccgctggcag actatgcgct gactccggat atggcgattg tcgacgccaa cctggttatg   1920
gacatgccga gtccctgtg tgctttcggt ggtctggacg cagtaactca cgccatggaa   1980
gcttatgttt ctgtactggc atctgagttc tctgatggtc aggctctgca ggcactgaaa   2040
ctgctgaaag aatatctgcc agcgtcctac cacgaagggt ctaaaaatcc ggtagcgcgt   2100
gaacgtgttc acagtgcagc gactatcgcg ggtatcgcgt ttgcgaacgc cttcctgggt   2160
gtatgtcact caatggcgca caaactgggt tcccagttcc atattccgca cggtctggca   2220
aacgccctgc tgatttgtaa cgttattcgc tacaatgcga acgacaaccc gaccaagcag   2280
actgcattca gccagtatga ccgtccgcag gctcgccgtc gttatgctga aattgccgac   2340
cacttgggtc tgagcgcacc gggcgaccgt actgctgcta agatcgagaa actgctggca   2400
tggctggaaa cgctgaaagc tgaactgggt attccgaaat ctatccgtga agctggcgtt   2460
caggaagcag acttcctggc gaacgtggat aaactgtctg aagatgcatt cgatgaccag   2520
tgcaccggcg ctaacccgcg ttacccgctg atctccgagc tgaaacagat tctgctggat   2580
```

```
acctactacg gtcgtgatta tgtagaaggt gaaactgcag cgaagaaaga agctgctccg    2640
gctaaagctg agaaaaaagc gaaaaaatcc gcttaa                              2676

<210> SEQ ID NO 111
<211> LENGTH: 3015
<212> TYPE: DNA
<213> ORGANISM: Clostridium acetobutylicum

<400> SEQUENCE: 111
attttacttt attctaataa tacgtaatac acccacttat aactagtatt tggcaataaa      60
aatagttata atcattaatt attgttaaat gtttgacaat ctttaattac tgttatataa     120
taatattata gaaataaaaa tgactgcata atttttactat agaaatacaa gcgttaaata    180
tgtacatatc aacggtttat cacattagaa gtaaataatg taaggaaacc acactctata    240
atttataagg catcaaagtg tgttatataa tacaataagt tttatttgca atagtttgtt    300
aaatatcaaa ctaataataa attttataaa ggagtgtata taaatgaaag ttacaaatca    360
aaaagaacta aaacaaaagc taatgaatt gagagaagcg caaagaagt ttgcaaccta      420 tactcaagag caagttgata aaatttttaa acaatgtgcc atagccgcag ctaaagaaag    480
aataaactta gctaaattag cagtagaaga aacaggaata ggtcttgtag aagataaaat    540
tataaaaaat cattttgcag cagaatatat atacaataaa tataaaaatg aaaaaacttg    600
tggcataata gaccatgacg attctttagg cataacaaag gttgctgaac caattggaat    660
tgttgcagcc atagttccta ctactaatcc aacttccaca gcaattttca aatcattaat    720
ttctttaaaa acaagaaacg caatattctt ttcaccacat ccacgtgcaa aaaaatctac    780
aattgctgca gcaaaattaa ttttagatgc agctgttaaa gcaggagcac ctaaaaatat    840
aataggctgg atagatgagc catcaataga acttctcaa gattttgatga gtgaagctga    900 tataatatta gcaacaggag gtccttcaat ggttaaagcg gcctattcat ctggaaaacc    960
tgcaattggt gttggagcag gaaatacacc agcaataata gatgagagtg cagatataga    1020
tatggcagta agctccataa ttttatcaaa gacttatgac aatggagtaa tatgcgcttc    1080
tgaacaatca atattagtta tgaattcaat atacgaaaaa gttaagagg aatttgtaaa    1140 acgaggatca tatatactca atcaaaatga aatagctaaa ataaagaaa ctatgtttaa    1200 aaatggagct attaatgctg acatagttgg aaaatctgct tatataattg ctaaaatggc    1260
aggaattgaa gttcctcaaa ctacaaagat acttataggc gaagtacaat ctgttgaaaa    1320
aagcgagctg ttctcacatg aaaaactatc accagtactt gcaatgtata agttaagga    1380 ttttgatgaa gctctaaaaa aggcacaaag gctaatagaa ttaggtggaa gtggacacac    1440
gtcatcttta tatatagatt cacaaaacaa taaggataaa gttaagaat ttggattagc    1500 aatgaaaact tcaaggacat ttattaacat gcccttcttca cagggagcaa gcggagattt    1560
atacaatttt gcgatagcac catcatttac tcttggatgc ggcacttggg gaggaaactc    1620
tgtatcgcaa aatgtagagc ctaaacattt attaaatatt aaaagtgttg ctgaaagaag    1680
ggaaaatatg ctttggttta aagtgccaca aaaaatatat tttaaatatg gatgtcttag    1740
atttgcatta aaagaattaa aagatatgaa taagaaaga gccttatag taacagataa    1800 agatcttttt aaacttggat atgttaataa aataacaaag gtactagatg agatagatat    1860
taaatacagt atatttacag atattaaatc tgatccaact attgattcag taaaaaaagg    1920
tgctaaagaa atgcttaact ttgaacctga tactataatc tctattggtg gtggatcgcc    1980
aatggatgca gcaaaggtta tgcacttgtt atatgaatat ccagaagcag aaattgaaaa    2040
```

-continued

```
tctagctata aactttatgg atataagaaa gagaatatgc aatttcccta aattaggtac    2100
aaaggcgatt tcagtagcta ttcctacaac tgctggtacc ggttcagagg caacacctttc   2160
tgcagttata actaatgatg aaacaggaat gaaatacccct ttaacttctt atgaattgac   2220
cccaaacatg gcaataatag atactgaatt aatgttaaat atgcctagaa aattaacagc    2280
agcaactgga atagatgcat tagttcatgc tatagaagca tatgtttcgg ttatggctac    2340
ggattatact gatgaattag ccttaagagc aataaaaatg atatttaaat atttgcctag    2400
agcctataaa aatgggacta acgacattga agcaagagaa aaaatggcac atgcctctaa    2460
tattgcgggg atggcatttg caaatgcttt cttaggtgta tgccattcaa tggctcataa    2520
acttggggca atgcatcacg ttccacatgg aattgcttgt gctgtattaa tagaagaagt    2580
tattaaatat aacgctacag actgtccaac aaagcaaaca gcattccctc aatataaatc    2640
tcctaatgct aagagaaaat atgctgaaat tgcagagtat ttgaatttaa agggtactag    2700
cgataccgaa aaggtaacag ccttaataga agctatttca aagttaaaga tagatttgag    2760
tattccacaa aatataagtg ccgctggaat aaataaaaaa gattttttata atacgctaga   2820
taaaatgtca gagcttgctt ttgatgacca atgtacaaca gctaatccta ggtatccact    2880
tataagtgaa cttaaggata tctatataaa atcattttaa aaaataaaga atgtaaaata    2940
gtctttgctt cattatatta gcttcatgaa gcacatagac tattttacat tttactcttg    3000
tttttttatct ttcaa                                                    3015
```

<210> SEQ ID NO 112
<211> LENGTH: 2685
<212> TYPE: DNA
<213> ORGANISM: Leuconostoc mesenteroides
<400> SEQUENCE: 112

```
atgagcaagt aaaggagcaa agattatggc agaagcaatt gcaaagaaac ccgcaaaaaa     60
ggttttgacc cctgaagaaa aagcggaatt acaaacacaa gctgagaaga tgactgttgt    120
attgattgaa aaatcacaaa aggcattgtc tgaattttca acattttcgc aagaacaagt    180
tgataaaatt gttgcagcta tggccttggc aggttctgag aattcacttc tgttagccca    240
tgctgctcac gacgagactg gacgtggggt tgtggaagat aaggatacga aaaatcgttt    300
cgcctcagaa tcagtttata acgctattaa gtttgataag actgtgggtg ttattagtga    360
agacaagatt caaggtaagg tagaattagc agccccactt ggtattttgg ctggaatcgc    420
tccaacgaca aatccaacgt cgacaactat tttcaaatca atgttgacag caaagacacg    480
taacacaatt atctttgctt tccatcccca gcctcaaaaa gcatcggttc ttgctgcaaa    540
aattgtttat gatgctgctg ttaaagcagg cgcaccggaa aactttatcc aatggattga    600
aaagccttca ctttatgcaa caagtgcgct gatacaaaat cctcacattg cttcaattct    660
agctactggt gggccatcaa tggttaatgc agctttgaag tcaggaaatc catccatggg    720
tgtcggtgct ggaaacggtg cagtttatat tgatgcaact gttgacacag atcgtgccgt    780
gtctgatttg ttgttatcaa agcgtttcga taatggcatg atttgtgcca cagaaaactc    840
agccgttatt caagcaccaa tctatgacga aattttaact aagttacaag aacaaggtgc    900
atacctttgtt cctaagaaag actacaagaa aattgctgat tatgtcttta gcctaacgc     960
agagggattg gtattgctg gtcctgttgc tggtatgtca ggacgttgga ttgctgagca   1020
agcaggcgta aagattcctg atggtaaaga tgtacttttg ttcgaattag atcagaagaa   1080
```

-continued

| | |
|---|---|
| cataggtgaa gcgttatctt ctgaaaagtt atcgccatta ctttcaattt ataaagttga | 1140 |
| gaagcgtgaa gaagctattg agactgttca atccttgtta aactatcaag gcgcagggca | 1200 |
| caacgcagca attcaaattg gttcacaaga tgatccattc attaaagagt atgctgacgc | 1260 |
| tattggtgca tcacgtattt tggttaacca acctgactca atcggtggcg ttggggatat | 1320 |
| ttatacagat gctatgcgtc catcgttgac acttggtacc ggatcatggg ggaagaattc | 1380 |
| attgtctcat aacttatcaa catacgactt acttaatatt aagaccgtgg ctcgccgccg | 1440 |
| taatcgtcct caatgggttc gtttacctaa ggaagtttac tacgaaacca atgccattac | 1500 |
| ttacttacaa gacttgccta ctataaaccg tgcatttatt gtcgctgatc ctggtatggt | 1560 |
| tcagttcgga tttgttggca gagtactagg tcaacttaag ttacgtcaag aacaggttga | 1620 |
| aacaaatatc tatggttcag ttaagcctga cccaactttg tcacaagctg ttgaaattgc | 1680 |
| tcgccaaatg gcagacttca aaccagatac agttatttta cttggcggtg gttcggcact | 1740 |
| tgacgctggt aaaattggtc ggttcttgta cgaatactcg acacgccatg aaggaatttt | 1800 |
| agaagatgac gaggcgatta agagctatt cttagaacta caacaaaagt ttatggatat | 1860 |
| tcgtaagcga atcgttaagt tttaccacgc acgtttgaca caaatggttg cgattccaac | 1920 |
| aacttcaggt actggatcag aagtcacacc atttgccgtt attacagatg atgaaacaca | 1980 |
| tgtaaagtat ccactagccg attatgaatt gacaccggaa gttgctattg ttgatccaga | 2040 |
| atttgttatg accgtaccac aacacacggt atcttggtca ggattagatg ctttgtcaca | 2100 |
| tgctttggaa tcgtatgtct cagtgatggc ttctgaattc tcacgtcctt gggcattaca | 2160 |
| agctattaag ttgattttg ataacttaac aaattcatac aattatgatc ctaaacaccc | 2220 |
| aactaaggaa ggtcagaatg cacgcacaaa gatgcactat gcgtcaacat ggctggtat | 2280 |
| gtcatttgcg aatgccttct tgggacttaa ccactcacta gcacacaaaa ctggtggaga | 2340 |
| attcggacta cctcacggta tggcaatcgc tattgcaatg ccacatgtga ttaagtttaa | 2400 |
| tgcggtaaca ggaaatgtaa agcgcacacc atacccacga tacgaaacct atacagcaca | 2460 |
| aaaagattat gctgatattg cacgttactt aggtttgaaa ggtgaaacag atgctgaatt | 2520 |
| ggtcgatgta ttgattgcag aaatcaagaa gttggctgca tcagtgggtg tcaatcaaac | 2580 |
| actatctggc aacggtgttt caaagcatga ctttgataca aagttagaaa agatgattga | 2640 |
| cttagtttac aatgaccaat gcacgccggg aaaccctcgc caacc | 2685 |

<210> SEQ ID NO 113
<211> LENGTH: 3164
<212> TYPE: DNA
<213> ORGANISM: Saccharomyces cerevisiae

<400> SEQUENCE: 113

| | |
|---|---|
| atgccgccgc tattcaaggg actgaaacag atggcaaagc caattgccta tgtttcaaga | 60 |
| ttttcggcga aacgaccaat tcatataata ctttttttctc taatcatatc cgcattcgct | 120 |
| tatctatccg tcattcagta ttacttcaat ggttggcaac tagattcaaa tagtgttttt | 180 |
| gaaactgctc caaataaaga ctccaacact ctatttcaag aatgttccca ttactacaga | 240 |
| gattcctctc tagatggttg ggtatcaatc accgcgcatg aagctagtga gttaccagcc | 300 |
| ccacaccatt actatctatt aaacctgaac ttcaatagtc ctaatgaaac tgactccatt | 360 |
| ccagaactag ctaacacggt ttttgagaaa gataatacaa aatatattct gcaagaagat | 420 |
| ctcagtgttt ccaaagaaat ttcttctact gatggaacga aatggaggtt aagaagtgac | 480 |
| agaaaaagtc ttttcgacgt aaagacgtta gcatattctc tctacgatgt attttcagaa | 540 |

```
aatgtaaccc aagcagaccc gtttgacgtc cttattatgg ttactgccta cctaatgatg    600
ttctacacca tattcggcct cttcaatgac atgaggaaga ccgggtcaaa ttttttggttg   660 agcgcctcta cagtggtcaa ttctgcatca tcactttttct tagcattgta tgtcacccaa   720
tgtattctag gcaaagaagt ttccgcatta actctttttg aaggtttgcc tttcattgta    780
gttgttgttg gtttcaagca caaaatcaag attgcccagt atgccctgga gaaatttgaa    840
agagtcggtt tatctaaaag gattactacc gatgaaatcg tttttgaatc cgtgagcgaa    900
gagggtggtc gtttgattca agaccatttg ctttgtatt ttgcctttat cggatgctct     960
atgtatgctc accaattgaa gactttgaca aacttctgca tattatcagc atttatccta   1020 attttttgaat tgattttaac tcctacattt tattctgcta tcttagcgct tagactggaa   1080
atgaatgtta tccacagatc tactattatc aagcaaacat tagaagaaga cggtgttgtt   1140
ccatctacag caagaatcat tttaaagcag aaaagaaatc cgtatcttct ttcttaaatc   1200
tcagtgtggt tgtcattatc atgaaactct ctgtcatact gttgtttgtc ttcatcaact   1260
tttataactt tggtgcaaat tgggtcaatg atgccttcaa ttcattgtac ttcgataagg   1320
aacgtgtttc tctaccagat tttattacct cgaatgcctc tgaaaacttt aaagagcaag   1380
ctattgttag tgtcaccca ttattatatt acaaacccat taagtcctac caacgcattg    1440
aggatatggt tcttctattg cttcgtaatg tcagtgttgc cattcgtgat aggttcgtca   1500
gtaaattagt tctttccgcc ttagtatgca gtgctgtcat caatgtgtat ttattgaatg   1560
ctgctagaat tcataccagt tatactgcag accaattggt gaaaactgaa gtcaccaaga   1620
agtcttttac tgctcctgta caaaaggctt ctacaccagt tttaaccaat aaaacagtca   1680
tttctggatc gaaagtcaaa agtttatcat ctgcgcaatc gagctcatca ggaccttcat   1740 catcagtga ggaagatgat tcccgcgata ttgaaagctt ggataagaaa atacgtcctt    1800
tagaagaatt agaagcatta ttaagtagtg gaaatacaaa acaattgaag aacaaagagg   1860
tcgctgcctt ggttattcac ggtaagttac ctttgtacgc tttggagaaa aaattaggtg   1920
atactacgag agcggttgcg gtacgtagga aggctcttc aatttttggca gaagctcctg    1980 tattagcatc tgatcgttta ccatataaaa attatgacta cgaccgcgta tttggcgctt   2040
gttgtgaaaa tgtttataggt tacatgcctt gcccgttgg tgttataggc cccttggtta   2100
tcgatggtac atcttatcat ataccaatgg caactacaga gggttgtttg gtagcttctg   2160
ccatgcgtgg ctgtaaggca atcaatgctg gcggtggtgc aacaactgtt ttaactaagg   2220
atggtatgac aagaggccca gtagtccgtt tcccaacttt gaaaagatct ggtgcctgta   2280
agatatggtt agactcagaa gagggacaaa acgcaattaa aaaagctttt aactctacat   2340
caagatttgc acgtctgcaa catattcaaa cttgtctagc aggagattta ctcttcatga   2400
gatttagaac aactactggt gacgcaatgg gtatgaatat gatttctaaa ggtgtcgaat   2460
actcattaaa gcaaatggta gaagagtatg gctgggaaga tatggaggtt gtctccgttt   2520
ctggtaacta ctgtaccgac aaaaaaccag ctgccatcaa ctggatcgaa ggtcgtggta   2580
agagtgtcgt cgcagaagct actattcctg gtgatgttgt cagaaaagtg ttaaaaagtg   2640
atgtttccgc attggttgag ttgaacattg ctaagaattt ggttggatct gcaatggctg   2700
ggtctgttgg tggatttaac gcacatgcag ctaatttagt gacagctgtt ttcttggcat   2760
taggacaaga tcctgcacaa aatgttgaaa gttccaactg tataacattg atgaaagaag   2820
tggacggtga tttgagaatt tccgtatcca tgccatccat cgaagtaggt accatcggtg   2880
```

```
gtggtactgt tctagaacca caaggtgcca tgttggactt attaggtgta agaggcccgc   2940
atgctaccgc tcctggtacc aacgcacgtc aattagcaag aatagttgcc tgtgccgtct   3000
tggcaggtga attatcctta tgtgctgccc tagcagccgg ccatttggtt caaagtcata   3060
tgacccacaa caggaaacct gctgaaccaa caaaacctaa caatttggac gccactgata   3120
taaatcgttt gaaagatggg tccgtcacct gcattaaatc ctaa                     3164
```

<210> SEQ ID NO 114
<211> LENGTH: 1290
<212> TYPE: DNA
<213> ORGANISM: Comamonas testosteroni

<400> SEQUENCE: 114

```
atggccgtcg attcgcgtct tcccaatttc cgagctctca ccccgcaca gcgctgggag      60 catgtcgcca ccgcatgcaa tctcagcgcc gaagaacgca atctactgac ccaggcgggc    120
gccctgcccg ccaccttggc tgacggcatg atcgaaaatg tggtgggcac gttcgagcta    180
cccatgggca tcgcaggcaa cttccgcatc aacggtcgcg atgtgctgat tccgctcgca    240
gtggaagagc cctccatcat cgctgctgct tcgtatatgg ccaagctggc ccgtgaagac    300
ggaggctttg aaacgtcgag caccttgccg ctgatgcgtg cgcaggtgca aatcgtcggc    360
atcagcgacc cctatggtgc aagactggcg ttgttcaagg cccgcgatga gatcctcgcg    420
caagccaata gccgagacaa ggtgctgatc agcctgggcg tggctgcaa ggacatcgaa    480 atccacgtct tcccagattc tccgcgcggc cctatggtcg tgatgcactt gatcgtggac    540
gtgcgcgatg ccatgggtgc caacaccgtg aacaccatgg ccgaatcagt ctcgccactg    600
gtggaaaaga ttaccggtgg ttcggtgcgc ctgcgcattc tctcgaacct ggcagacctg    660
cgcctggccc gtgctcgtgt acgcctgaca ccgcaaacct ggccaccaa agagcgcagc    720 ggcgaagcaa ttattgaagg cgtgctcgac gcctacactt tcgccgccat tgacccctac    780
cgcgccgcta cccacaacaa gggcatcatg aacggtatcg accccgtcat cgtcgctaca    840
ggcaacgatt ggcgcgcggt cgaagccggt gcccatgcct atgccagccg caacggccaa    900
tacacctcgc tgacgcactg ggaaaaagac aatgccggcg ccttggtggg aacgatcgag    960
ctacccatgc ccgtgggctt ggtgggcggt gccaccaaga cccatccgct ggcgcgcctg   1020
gcgctcaaga tcatggaggt gaagtctgcc caggaactgg gcgagattgc cgccgcagtg   1080
ggtctggccc agaacctggg tgctttgcgc gcgctggcca ccgaaggcat tcagcgcggc   1140
catatggcac ttcatgctcg caatattgcg caggtcgcag gagccgtggg tgaagaagta   1200
gagatcgtcg ccaagcgcct ggctaccgag catgacgtgc gcaccgatcg cgcactggaa   1260
gtgctgcaag aaattcgcgc ccagcgctaa                                     1290
```

<210> SEQ ID NO 115
<211> LENGTH: 1284
<212> TYPE: DNA
<213> ORGANISM: Desulfurococcus kamchatkensis

<400> SEQUENCE: 115

```
atggagaaga caagccgtat acagggcttc tacaagcttc cccttgaaga agacggagg      60 atagtctgcg agtgggctgg gctaacagag gaagagtgca ggacactgag cgaattcggt    120
aatctaccag ttaagatagg ggacagcatg attgagaacg ttataggcgc gatgagctat    180
cccttgcgag tagcgacaaa cttcctgatc aatggggagg attaccttgt cccaatggtt    240
atagaggaga caagcgtcgt agcggctgca agcaatgcgg ccaggatgct taggcatggg    300
```

```
aaagggatac ttgcaaatgc tgagagacag gagatgatca gccaaataca cctggttaaa      360
gtaaactccc cacgctttaa agccatgaag attatcgagg ccaagaagga gctactggac      420
tacgcggcac agcaggatcc aaccctgcta agtacggcg ggggtcccag ggacctcgag      480
gtaagagcaa tggagcaccc tgctttaggc ggggtcataa tagtccacct agtagtagac      540
gtcagagacg ccatgggtgc taacactgtt aacacgatgg ctgaagcgat agccccgctt      600
ctagagaaga taacgggtgg ggaagcaagg ctcagaatag tttcaaacca cgcagtatac      660
agggttacac gggcatgggc tgcgacacct gtcgaagaag tgggaggcct tgaagtagcc      720
aggaggataa tggaggcatc tatactcgcc gagatagatc cctatagggc ggtaacccat      780
aacaagggca taatgaatgg agtaatagca gtagccctcg cgacgggaca ggatcaccgc      840
gccatagagc tggagcccca tgcatacgcc tctagaacgg gggtctacaa gcccctcagc      900
tactgggagg taacaagcga taactatctt gcgggaagcc ttgagatacc tctccaaata      960
ggcgttgttg gaggagcagt caaggtacac cctgtggcaa agatagcatt gaagatccta     1020
ggggtaaaca cggctaggga gctcgccgag gtaatggctg cggtagggct agcccagaac     1080
ctagccgctc taagagccct cgtgacagag ggtattcaga aaggccatat gaggctccac     1140
gccagaaacc tcgctataat ggctggtgca tcaggagatc taatagataa gatagccgag     1200
aaaatgatca gggacggtag aataagatac gactacgcta acaactagt agagaaagca     1260 ctacagggcg agccattaga ctag                                             1284

<210> SEQ ID NO 116
<211> LENGTH: 1281
<212> TYPE: DNA
<213> ORGANISM: Staphylococcus aureus

<400> SEQUENCE: 116
atgcaaaatt tagataagaa ttttcgacat ttatctcgta aagaaaagtt acaacaattg       60
gttgataagc aatggttatc agaagaacaa ttcgacattt tactgaatca tccattaatc      120
gatgaagaag tagccaatag tttaattgaa aatgtcatcg cgcaaggtgc attacccgtt      180
ggattattac cgaatatcat tgtggacgat aaggcatatg ttgtacctat gatggtggaa      240
gagccttcag ttgtcgctgc agctagttat ggtgcaaagc tagtgaatca gactggcgga      300
tttaaaacgg tatcttctga acgtattatg ataggtcaaa tcgtctttga tggcgttgac      360
gatactgaaa aattatcagc agacattaaa gctttagaaa agcaaattca taaaattgcg      420
gatgaggcat atccttctat taagcgcgt ggtggtggtt accaacgtat agcgattgat      480
acatttcctg agcaacagtt actatcttta aaagtatttg ttgatacgaa agatgctatg      540
ggcgctaata tgcttaatac gatttttagag gccataactg cattttttaaa aaatgaattt      600 ccgcaaagcg acattttaat gagtattta tccaatcatg caacagcgtc cgttgttaaa      660
gttcaaggcg aaattgatgt taaagattta gcaggggcg agagaactgg agaagaggtt      720
gccaaacgaa tggaacgtgc ttctgtattg gcacaagtag atattcatcg tgcagcaaca      780
cataataaag gtgttatgaa tggcatacat gctgttgttt tagcaacagg aaatgatacg      840
cgtggtgcag aagcaagtgc gcatgcatac gcaagtcgtg acggacagta tcgtggtatt      900
gctacatggc gttacgatca agatcgtcaa cgattgattg gtacaattga agtgcctatg      960
acattggcaa ttgttggggg tggtacgaaa gtattaccaa tagctaaagc ttcattagag     1020
ctactaaatg tagagtcagc acaagaatta ggtcatgtag ttgctgccgt tggtttagcg     1080
```

| | |
|---|---|
| caaaactttg cagcatgtcg cgcgcttgtg tcagaaggta ttcaacaagg tcatatgagt | 1140 |
| ttacaatata aatcattagc tattgttgta ggagcaaaag gtgatgaaat tgctaaagta | 1200 |
| gctgaagctt tgaaaaaaga accccgtgca aatacacaag cagcggaacg tattttacaa | 1260 |
| gatttaagaa gccaacaata g | 1281 |

<210> SEQ ID NO 117
<211> LENGTH: 1236
<212> TYPE: DNA
<213> ORGANISM: Lactobacillus johnsonii

<400> SEQUENCE: 117

| | |
|---|---|
| atgaaattag aagaatcatc taaaagaaa ttttatcaat ggttaccaga ggaagaaga | 60 |
| gtcttttaa ctgaaaaagg aattaaacta agtgagattg agtctgaaac tttggaaaga | 120 |
| ctagataaac ttagtgaaaa tgtaattggt caagtccgtc ttcctcttgg tgtgcttcct | 180 |
| aagttaatag ttaacgggaa agattatcaa gtaccaatgg ccgtagaaga accatcggtt | 240 |
| gttgcagcag caaccatgc agctaaaatt tttaatcaaa atggtggagc agtagctgat | 300 |
| agtagacgaa atggaatata tggtcaaatt gttttagagg taactgataa ttttgattta | 360 |
| actaagttta ctactgaatt tcctcaatta attagcttag ctaataaaaa attcgttagc | 420 |
| ttagtcaagc atggtggagg agttcgtaaa attgaagctt ctcaaaaaga aaatttagtt | 480 |
| tttcttagag ttttggttga cccagcagaa gctatgggag ctaataaaac aaatgctatt | 540 |
| ttagaatttt taggaaatga attagagaag cagccagata ttgaacaaac tctgtatgca | 600 |
| attttgtcta attatcctac gcaattgact agtgctaaag taagtctttc aattgacagt | 660 |
| gtaggaggat taaagttgc taaaaagata gctttattga gtaaaatagg acaaactgat | 720 |
| atttaccggg cagtgactaa taataaagga attatgaatg gtattgatag tgtattggtt | 780 |
| gcaactggta atgattatcg tggagttgaa gcagcaactg ctgtttgggc taataaaaat | 840 |
| ggtgcctata catctttgag taagtggaaa attgaagaag atagactagt ggggactgta | 900 |
| acagttccct tagcaatcgg tgtagtaggt ggctcaatta aggctcgtcg agacgttcaa | 960 |
| caaagcttta gttttattagg taatatatct gccaagcaac tagcagaagt tattgcgaca | 1020 |
| actggcttag caaataactt ttcagctctt ttagcaattt ctactaaggg aattcaagct | 1080 |
| gggcatatga aattgcaggc gagaaattta gtagcaaccct taaaagctag tgaaggtgaa | 1140 |
| aaagcaatag ttttaaaaaa attgcaggaa agtaaaaaat atactcaaga agcagctttt | 1200 |
| gaattttaa gcgaaataag aaaggatcaa aaataa | 1236 |

<210> SEQ ID NO 118
<211> LENGTH: 912
<212> TYPE: DNA
<213> ORGANISM: Acinetobacter sp. ADP1

<400> SEQUENCE: 118

| | |
|---|---|
| ttgatatcaa tcagggaaaa acgcgtgaac aaaaaacttg aagctctctt ccgagagaat | 60 |
| gtaaaaggta agtggctttt gatcactggt gcatctagtg gaatcggttt gacgattgca | 120 |
| aaaagaattg ctgcggcagg tgctcatgta ttattggttg cccgaaccca agaaacactg | 180 |
| gaagaagtga aagctgcaat tgaacagcaa ggggacagg cctctatttt tccttgtgac | 240 |
| ctgactgaca tgaatgcgat tgaccagtta tcacaacaaa ttatggccag tgtcgatcat | 300 |
| gtcgatttcc tgatcaataa tgcagggcgt tcgattcgcc gtgccgtaca cgagtcgttt | 360 |
| gatcgcttcc atgattttga acgcaccatg cagctgaatt actttggtgc ggtacgttta | 420 |

```
gtgttaaatt tactgccaca tatgattaag cgtaaaaatg ccagatcat caatatcagc      480 tctattggtg tattggccaa tgcgacccgt ttttctgctt atgtcgcgtc taaagctgcg      540
ctggatgcct tcagtcgctg tctttcagcc gaggtactca agcataaaat ctcaattacc      600
tcgatttata tgccattggt gcgtacccca atgatcgcac ccaccaaaat ttataaatac      660
gtgcccacgc tttccccaga agaagccgca gatctcattg tctacgccat tgtgaaacgt      720
ccaaaacgta ttgcgacgca cttgggtcgt ctggcgtcaa ttacctatgc catcgcacca      780
gacatcaata atattctgat gtcgattgga tttaacctat cccaagctc aacggctgca       840 ctgggtgaac aggaaaaatt gaatctgcta acgtgcct atgcccgctt gttcccaggc        900
gaacactggt aa                                                         912
```

<210> SEQ ID NO 119
<211> LENGTH: 1670
<212> TYPE: DNA
<213> ORGANISM: Acinetobacter baylyi

<400> SEQUENCE: 119

```
cagaagatat ggttcggtta tcggttggga ttgaacatat tgatgatttg attgcagatc       60
tggaacaagc attggccaca gtttgagcgt aaattttata aaaaacctct gcaatttcag      120
aggttttttt atatttgctt tattatcgta tgatgtcat aattgatcta gcaaataata       180
aaaattagag caattactct aaaaacattt gtaatttcag atacttaaca ctagattttt      240
taaccaaatc actttagatt aactttagtt ctggaaattt tatttccctt taaccgtctt      300
caatccaaat acaataatga cagcctttac agtttgatat caatcaggga aaaacgcgtg      360
aacaaaaaac ttgaagctct cttccgagag aatgtaaaag gtaaagtggc tttgatcact      420
ggtgcatcta gtggaatcgg tttgacgatt gcaaaaagaa ttgctgcggc aggtgctcat      480
gtattattgg ttgcccgaac ccaagaaaca ctggaagaag tgaaagctgc aattgaacag      540 caaggggggac aggcctctat ttttccttgt gacctgactg acatgaatgc gattgaccag      600
ttatcacaac aaattatggc cagtgtcgat catgtcgatt tcctgatcaa taatgcaggg      660
cgttcgattc gccgtgccgt acacgagtcg tttgatcgct tccatgattt tgaacgcacc      720
atgcagctga attactttgg tgcggtacgt ttagtgttaa atttactgcc acatatgatt      780
aagcgtaaaa atggccagat catcaatatc agctctattg gtgtattggc caatgcgacc      840 cgttttctg cttatgtcgc gtctaaagct gcgctggatg ccttcagtcg ctgtctttca      900
gccgaggtac tcaagcataa aatctcaatt acctcgattt atatgccatt ggtgcgtacc      960
ccaatgatcg cacccaccaa aatttataaa tacgtgccca cgctttcccc agaagaagcc     1020
gcagatctca ttgtctacgc cattgtgaaa cgtccaacac gtattgcgac gcacttgggt     1080
cgtctggcgt caattaccta tgccatcgca ccagacatca ataatattct gatgtcgatt     1140
ggatttaacc tattcccaag ctcaacggct gcactgggtg aacaggaaaa attgaatctg     1200
ctacaacgtg cctatgcccg cttgttccca ggcgaacact ggtaaaattt ataaagaag      1260 cctctcatac cgagaggctt ttttatggtt acgaccatca gccagattta gaggaaattg     1320 actttttcctg ttttacatc ataaatcgca ccaacaatat caatttcttt gcgatccagc     1380
atatctttaa gtacagaact atgctgaata atgtattgaa tattatagtg aacattcata     1440
gcagtcacct gatcaataaa tgctttgctt aattcacgcg gttgcataat atcaaataca     1500
ctgccaaccg aatgcatgag tggcccaagc acgtattgga tgtgtggcat ttcctgaata     1560
```

| | |
|---|---|
| tcggaaatct gcttatgttg caatcttaac tggcatgcgc tggtgaccgc accacagtcg | 1620 |
| gtatgtccca aaaccagaat cactttggaa cctttggctt gacaggcaaa | 1670 |

<210> SEQ ID NO 120
<211> LENGTH: 1362
<212> TYPE: DNA
<213> ORGANISM: Clostridium kluyveri

<400> SEQUENCE: 120

| | |
|---|---|
| atgagtaatg aagtatctat aaaagaatta attgaaaagg caaggtggc acaaaaaaaa | 60 |
| ttggaagcct atagtcaaga acaagttgat gtactagtaa aagcactagg aaaagtggtt | 120 |
| tatgataatg cagaaatgtt tgcaaaagaa gcagttgaag aaacagaaat gggtgtttat | 180 |
| gaagataaag tagctaaatg tcatttgaaa tcaggagcta tttggaatca tataaaagac | 240 |
| aagaaaactg taggcataat aaaagaagaa cctgaaaggg cacttgttta tgttgctaag | 300 |
| ccaaagggag ttgtggcagc tactacgcct ataactaatc cagtggtaac tcctatgtgt | 360 |
| aatgcaatgg ctgctataaa gggcagaaat acaataatag tagcaccaca tcctaaagca | 420 |
| aagaaagttt cagctcatac tgtagaactt atgaatgctg agcttaaaaa attgggagca | 480 |
| ccagaaaata tcatacagat agtagaagca ccatcaagaa aagctgctaa ggaacttatg | 540 |
| gaaagtgctg atgtagttat tgctacaggc ggtgctggaa gagttaaagc tgcttactcc | 600 |
| agtggaagac cagcttatgg cgttggacct ggaaattcac aggtaatagt tgataaggga | 660 |
| tacgattata caaagctgc acaggatata ataacaggaa gaaaatatga caatggaatt | 720 |
| atatgttctt cagagcaatc agtttatagct cctgctgaag attatgataa ggtaatagca | 780 |
| gcttttgtag aaaatggggc attctatgta gaagatgagg aaacagtaga aaagtttaga | 840 |
| tcaactttat ttaagatgg aaaaataaac agcaagatta taggtaaatc cgtccaaatt | 900 |
| attgcggatc ttgcaggagt aaaagtacca gaaggtacta aggttatagt acttaagggt | 960 |
| aaaggtgcag agaaaaaga tgtactttgt aaagaaaaaa tgtgtccagt tttagtagca | 1020 |
| ttgaaatatg atacttttga agaagcagtt gaaatagcta tggctaatta tatgtatgaa | 1080 |
| ggagctggtc atacagcagg catacattct gacaatgacg agaacataag atatgcagga | 1140 |
| actgtattac ctataagcag attagttgta atcagcctg caactactgc tggaggaagt | 1200 |
| ttcaataatg gatttaaccc tactactaca ctaggctgcg gatcatgggg cagaaacagt | 1260 |
| atttcagaaa atcttactta cgagcatctt ataaatgttt caagaatagg gtatttcaat | 1320 |
| aaagaagcaa aagttcctag ctatgaggaa atatgggat aa | 1362 |

<210> SEQ ID NO 121
<211> LENGTH: 1356
<212> TYPE: DNA
<213> ORGANISM: Porphyromonas gingivalis

<400> SEQUENCE: 121

| | |
|---|---|
| atggaaatca agaaatggt gagccttgca cgcaaggctc agaaggagta tcaagctacc | 60 |
| cataaccaag aagcagttga caacatttgc cgagctgcag caaaagttat ttatgaaaat | 120 |
| gcagctattc tggctcgcga agcagtagac gaaaccggca tgggcgttta cgaacacaaa | 180 |
| gtggccaaga atcaaggcaa atccaaaggt gtttggtaca acctccacaa taaaaaatcg | 240 |
| attggtatcc tcaatataga cgagcgtacc ggtatgatcg agattgcaaa gcctatcgga | 300 |
| gttgtaggag ccgtaacgcc gacgaccaac ccgatcgtta ctcgatgag caatatcatc | 360 |
| tttgctctta agacctgcaa tgccatcatt attgccccc accccagatc caaaaaatgc | 420 |

```
tctgcacacg cagttcgtct gatcaaagaa gctatcgctc cgttcaacgt accggaaggt    480
atggttcaga tcatcgaaga acccagcatc gagaagacgc aggaactcat gggcgccgta    540
gacgtagtag ttgctacggg tggtatgggc atggtgaagt ctgcatattc ttcaggaaag    600
ccttctttcg gtgttggagc cggtaacgtt caggtgatcg tggatagcaa catcgatttc    660
gaagctgctg cagaaaaaat catcaccggt cgtgctttcg acaacggtat catctgctca    720
ggcgaacaga gcatcatcta caacgaggct gacaaggaag cagttttcac agcattccgc    780
aaccacggtg catatttctg tgacgaagcc gaaggagatc gggctcgtgc agctatcttc    840
gaaaatggag ccatcgcgaa agatgtagta ggtcagagcg ttgccttcat tgccaagaaa    900
gcaaacatca atatccccga gggtacccgt attctcgttg ttgaagctcg cggcgtagga    960
gcagaagacg ttatctgtaa ggaaaagatg tgtcccgtaa tgtgcgccct cagctacaag   1020
cacttcgaag aaggtgtaga atcgcacgt acgaacctcg ccaacgaagg taacggccac   1080
acctgtgcta tccactccaa caatcaggca cacatcatcc tcgcaggatc agagctgacg   1140
gtatctcgta tcgtagtgaa tgctccgagt gccactacag caggcggtca catccaaaac   1200
ggtcttgccg taaccaatac gctcggatgc ggatcatggg gtaataactc tatctccgag   1260
aacttcactt acaagcacct cctcaacatt tcacgcatcg caccgttgaa ttcaagcatt   1320
cacatccccg atgacaaaga aatctgggaa ctctaa                             1356
```

<210> SEQ ID NO 122
<211> LENGTH: 1407
<212> TYPE: DNA
<213> ORGANISM: Clostridium saccharoperbutylacetonicum

<400> SEQUENCE: 122

```
atgattaaag acacgctagt ttctataaca aaagatttaa aattaaaaac aaatgttgaa     60
aatgccaatc taaagaacta caaggatgat tcttcatgtt tcggagtttt cgaaaatgtt    120
gaaaatgcta taagcaatgc cgtacacgca caaaagatat tatcccttca ttatacaaaa    180
gaacaaagag aaaaaatcat aactgagata agaaaggccg cattagaaaa taagagatt    240 ctagctacaa tgattcttga agaaacacat atgggaagat atgaagataa atattaaag    300 catgaattag tagctaaata cactcctggg acagaagatt taactactac tgcttggtca    360
ggagataacg gcttacagt tgtagaaatg tctccatatg gcgttatagg tgcaataact    420
ccttctacga atccaactga aactgtaata tgtaatagta taggcatgat agctgctgga    480
aatactgtgg tatttaacgg acatccaggc gctaaaaaat gtgttgcttt tgctgtcgaa    540
atgataaata aagctattat ttcatgtggt ggtcctgaga atttagtaac aactataaaa    600
aatccaacta tggactctct agatgcaatt attaagcacc cttcaataaa actactttgc    660
ggaactggag ggccaggaat ggtaaaaacc ctcttaaatt ctggtaagaa agctataggt    720
gctggtgctg gaaatccacc agttattgta gatgatactg ctgatataga aaaggctggt    780
aagagtatca ttgaaggctg ttctttgat aataatttac cttgtattgc agaaaaagaa    840
gtatttgttt ttgagaacgt tgcagatgat ttaatatcta acatgctaaa aaataatgct    900
gtaattataa atgaagatca agtatcaaag ttaatagatt tagtattaca aaaaataat    960 gaaactcaag aatactctat aaataagaaa tgggtcggaa aagatgcaaa attattctta   1020 gatgaaaatag atgttgagtc tccttcaagt gttaaatgca taatctgcga agtaagtgca   1080
aggcatccat ttgttatgac agaactcatg atgccaatat taccaattgt aagagttaaa   1140
```

| gatatagatg aagctattga atatgcaaaa atagcagaac aaaatagaaa acatagtgcc | 1200 |
| tatatttatt caaaaaatat agacaaccta aataggtttg aaagagaaat cgatactact | 1260 |
| atctttgtaa agaatgctaa atcttttgcc ggtgttggtt atgaagcaga aggctttaca | 1320 |
| actttcacta ttgctggatc cactggtgaa ggaataactt ctgcaagaaa ttttacaaga | 1380 |
| caaagaagat gtgtactcgc cggttaa | 1407 |

<210> SEQ ID NO 123
<211> LENGTH: 1407
<212> TYPE: DNA
<213> ORGANISM: Clostridium beijerinckii

<400> SEQUENCE: 123

| atgaataaag acacactaat acctacaact aaagatttaa agtaaaaac aaatggtgaa | 60 |
| aacattaatt taagaactaa caaggataat tcttcatgtt tcggagtatt cgaaaatgtt | 120 |
| gaaaatgcta taagcagcgc tgtacacgca caaaagatat tatcccttca ttatacaaaa | 180 |
| gagcaaagag aaaaaatcat aactgagata agaaaggccg cattacaaaa taagagggtc | 240 |
| ttggctacaa tgattctaga agaaacacat atgggaagat atgaggataa aatattaaaa | 300 |
| catgaattgg tagctaaata tactcctggt acagaagatt taactactac tgcttggtca | 360 |
| ggtgataatg gtcttacagt tgtagaaatg tctccatatg gtgttatagg tgcaataact | 420 |
| ccttctacga atccaactga aactgtaata tgtaatagca taggcatgat agctgctgga | 480 |
| aatgctgtag tatttaacgg acacccatgc gctaaaaaat gtgttgcctt gctgtgttgaa | 540 |
| atgataaata aggcaattat ttcatgtggc ggtcctgaaa atctagtaac aactataaaa | 600 |
| aatccaacta tggagtctct agatgcaatt attaagcatc cttcaataaa acttctttgc | 660 |
| ggaactgggg gtccaggaat ggtaaaaacc ctcttaaatt ctggtaagaa agctataggt | 720 |
| gctggtgctg gaaatccacc agttattgta gatgatactg ctgatataga aaaggctggt | 780 |
| aggagcatca ttgaaggctg ttctttttgat aataatttac cttgtattgc agaaaaagaa | 840 |
| gtatttgttt ttgagaatgt tgcagatgat ttaatatcta acatgctaaa aaataatgct | 900 |
| gtaattataa atgaagatca agtatcaaaa ttaatagatt tagtattaca aaaaaataat | 960 |
| gaaactcaag aatactttat aaacaaaaaa tgggtaggaa aagatgcaaa attattctta | 1020 |
| gatgaaaatag atgttgagtc tccttcaaat gttaaatgca taatctgcga agtaaatgca | 1080 |
| aatcatccat ttgttatgac agaactcatg atgccaatat tgccaattgt aagagttaaa | 1140 |
| gatatagatg aagctattaa atatgcaaag atagcagaac aaaatagaaa acatagtgcc | 1200 |
| tatatttatt ctaaaaatat agacaaccta aatagatttg aaagagaaat agatactact | 1260 |
| attttttgtaa agaatgctaa atcttttgct ggtgttggtt atgaagcaga aggatttaca | 1320 |
| actttcacta ttgctggatc tactggtgag ggaataaccct ctgcaaggaa ttttacaaga | 1380 |
| caaagaagat gtgtacttgc cggctaa | 1407 |

<210> SEQ ID NO 124
<211> LENGTH: 999
<212> TYPE: DNA
<213> ORGANISM: Metallosphaera sedula

<400> SEQUENCE: 124

| atgaaagctg tcgtagtgaa aggacataaa cagggttatg aggtcaggga agttcaggac | 60 |
| ccgaaacctg cttcaggaga agtaatcatc aaggtcagga gagcagccct gtgttatagg | 120 |
| gaccttctcc agctacaggg gttctaccct agaatgaagt accctgtggt tctaggacat | 180 |

```
gaggttgttg gggagatact ggaggtaggt gagggagtga ccggtttctc tccaggagac      240
agagtaattt cactcctcta tgcgcctgac ggaacctgcc actactgcag acagggtgaa      300
gaggcctact gccactctag gttaggatac tctgaggaac tagatggttt cttctctgag      360
atggccaagg tgaaggtaac cagtctcgta aaggttccaa cgagagcttc agatgaggga      420
gccgttatgg ttccctgcgt cacaggcatg tgtacagag ggttgagaag gccaatcta       480 agagagggtg aaactgtgtt agttacggga gcaagcggtg gagttggaat acatgccctg      540
caagtggcaa aggccatggg agccagggta gtgggtgtca cgacgtcgga ggagaaggca      600
tccatcgttg gaaagtatgc tgatagggtc atagttggat cgaagttctc ggaggaggca      660
aagaaagagg acattaacgt ggtaatagac accgtgggaa cgccaacctt cgatgaaagc      720
ctaaagtcgc tctggatggg aggtaggata gtccaaatag gaaacgtgga cccaacccaa      780
tcctatcagc tgaggttagg ttacaccatt ctaaaggata tagccataat tgggcacgcg      840
tcagccacaa ggagggatgc agagggagca ctaaagctga ctgctgaggg gaagataaga      900
ccagtggttg cgggaactgt tcacctggag gagatagaca agggatatga aatgcttaag      960
gataagcaca aagtggggaa agtactcctt accacgtaa                            999

<210> SEQ ID NO 125
<211> LENGTH: 1005
<212> TYPE: DNA
<213> ORGANISM: Sulfolobus tokodaii

<400> SEQUENCE: 125
atgaaagcaa ttgtagttcc aggacctaag caagggtata aacttgaaga ggtacctgat       60
cctaagccgg gaaaagatga agtaataatt agggtagata gagctgctct ttgttataga      120
gatttgcttc aactacaagg atattatcca agaatgaaat acccagttat actagggcat      180
gaagttgtag gaaccataga agaagtcgga gaaaatataa agggatttga agtaggtgat      240
aaagtaattt ctttattata tgcaccagat ggtacatgcg aatattgcca aataggtgag      300
gaagcatatt gtcatcatag gttaggctac tcagaagagc tagacggatt ttttgcagag      360
aaagctaaaa ttaaagtaac tagcttagta aaggttccaa aaggtacccc agatgaggga      420
gcagtacttg taccttgtgt aaccggaatg atatatagag gtattagaag ggctggtggt      480
atacgtaaag gggagctagt gttagttact ggtgccagtg gtggagtagg aatacatgca      540
attcaagttg ctaaggcctt aggtgctaaa gttataggg taacaacatc agaagaaaaa       600
gcaaagataa ttaagcagta tgcggattat gtcatcgttg gtacaaagtt ttctgaagaa      660
gcaaagaaga taggtgatgt tactttagtt attgatactg tgggtactcc tactttcgat      720
gaaagcttaa agtcattgtg gatgggcgga aggattgttc aaatagggaa tgtcgaccct      780
tctcaaatct ataatttaag attgggctac ataatattaa aagatttaaa gatagttggt      840
catgcctcag ctaccaaaaa agatgctgaa gatacactaa aattaacaca gagggaaaa       900 attaaaccag ttattgcagg aacagtcagt cttgaaaata ttgatgaagg ttataaaatg      960
ataaaggata agaataaagt aggcaaagtc ttagtaaaac cataa                     1005

<210> SEQ ID NO 126
<211> LENGTH: 999
<212> TYPE: DNA
<213> ORGANISM: Metallosphaera cuprina

<400> SEQUENCE: 126
```

```
atgaaagctg ttatcgttaa gggagccaaa caaggttatg aagtcagaga cgttcaagat    60
ccgaaacctc aacctgatga ggtagtaata aaggttaaca gagctgccct atgttacaga   120
gatctccttc aacttcaggg gttttacccc aggatgaaat acccagtggt tctgggacac   180
gaagtgatag gcgaaatcgt tgacgtaggt agagacgtga aggggttcgc catagggat    240
agagtcatat ccttacttta cgctcctgac ggtagctgtc actactgtaa aaggggagag   300
gaggcatact gtcactctag actgggctat tctgaggagc ttgatggatt cttcgcggag   360
atggcaaggg ttaaagtaag tagcctcgtt aaggtacctc ctggagtttc cgatgagggg   420
ggagtcatgg taccttgcgt aaccgggatg atatatagag gtttaagaag agctaactta   480
agcgaagggg agaccgtttt agtgacaggg gccagtggag gagtcggaat acacgccctg   540
caagtcgcga aaggaatggg ggccagagtg attggggtga cgacttcaga ggagaagagt   600
tcgattatag cgaagtactc tgacagggta atagtaggtt ccaagttctc ggaagaggcc   660
aagaaagagg acgtcaacgt gatcattgat accgttggaa ctcctacgtt tgaggaaagc   720
ctcagatcgt tatggatggg aggtagaata gtccagattg gtaacgtaga tcctacacag   780
gcttaccaat tgagattagg ctacacgatt ctcaaagata ttgccataat tgggcatgcc   840
tcagctacca aacgcgatgc tgaagccgct ttaaaactaa cttcagaagg caaggtaagg   900
ccgatagtag ctggaaccgt cagcttagag gagatagata agggttacga aatcctcaag   960
gacaaacaca aagtagggaa ggtattgcta aagcccttag                         999

<210> SEQ ID NO 127
<211> LENGTH: 1788
<212> TYPE: DNA
<213> ORGANISM: Streptomyces clavuligerus

<400> SEQUENCE: 127
atgggacagt acgctgcacc gttgcgcgac atgcaattcg tcttgcacga attgctgaac    60
gtcgaagccg aactgaagca actgcctaag cacgcggatc tggatgccga tacgatcaat   120
gcggtgctgc aggaggcggg caagttctgc tccgaggtcc tgtttccgtt gaaccaggtt   180
ggcgaccagc agggttgtac gtatgtcggc gacggcgtgg tgaccacgcc cgagggcttc   240
aagcaagcgt accagcagta tatcgaggcc ggctggccgg cgttgggctg cgatccggcc   300
tatgccggcc agggcttgcc cgcgttcgtg aacaacgcgc tgtacgagat gctcaattcg   360
gcgaaccagg catggaccat gtatcctggc ctgtcgcacg gcgcgtacga atgcctgcac   420
gcgcacggca cgccggagct tcaacagcgg tatctaccga agctggtatc cggtcagtgg   480
accggcacga tgtgcttgac cgagccgcat tgcggcaccg accttgggat cttgcgcacg   540
cgggccgagc ccaacggcga cggctcgtac tcgattaccg gcacgaagat ctttatttcg   600
agcggcgagc acgacctcgc cgacaacatc gtccacctgg tgctcgcgcg gttgccggac   660
gcgccggcgg ggaccaaggg catttcattg ttcatcgtgc ccaagttcat cccgacgac    720
aacgcgagc ctgggcagcg caacggcgtc aagtgtggct cgatcgagca aagatgggc    780
atccatggca atgcgacgtg cgtaatcaat ctggatgatg ccaggggctg gctggtcggc   840
gagccgaaca agggcttgaa tgcgatgttc gtgatgatga atgcgcgcg gctcggcgtg    900
ggcatgcaag gcctggggct gaccgaagtc gcgtaccaga actcgctcgc ctacgcgagg   960
cagcggctgc agatgcgctc gcttagcggt cctaaggcgc cggacaaggc ggccgacccg   1020
atcatcgtgc acccggatgt gcgacgcatg ttgttgacgc agaaggccta cgtcgaggcg   1080
gggcgcgcgt tcacgtactg ggcggctctg cagatcgaca aggaactgtc gcacgaggac  1140
```

```
gaggcggtgc gccgggatgc ggccgacctg gttgcgttgc tcacaccggt catcaaggcg    1200
ttcctgaccg acaacgcgtt cgaggcgacc aacaacgcca tgcaggtgtt gggcggccat    1260
ggctatatcg ctgagtgggg catcgagcaa tatgtgcgtg atgcgcgcat caacatgatt    1320
tacgaaggca ctaacacgat tcagtcgctg gacctgctgg ggcgcaaggt gctcggcgac    1380
atgggcgcga agctgaagaa gtttggcaag ctcgtgcagg attttgtcca ggccgagggc    1440
atcaaccccg acatgcagga gttcgtcaat ccgctggcgg acatcggcga aaaggtacag    1500
aagctgacga tggaaatcgg catgaaggcg atgcagagcc cggacgaagt tggcgccgcg    1560
gcggtaccgt acctgcgcac ggtcgggcat ttagtgttct cgtacttttg ggcgcgcatg    1620
gcccgtctgg cgctggacaa gcaaggtagc ggcgacccat tctaccggtc caagctcgcg    1680
accgcgcggt tctactttgc gaagctgtta cccgagacgg ccttcacgat ccgcgccgcg    1740
cgtgccggag ccaagccgct gaccgagatc gacgaagcgc tgtttttaa               1788

<210> SEQ ID NO 128
<211> LENGTH: 981
<212> TYPE: DNA
<213> ORGANISM: Rhodobacter sphaeroides

<400> SEQUENCE: 128
gtgagagccg ttctgataga gaaatccgac gatacgcagt ccgtttcggt gacggagctt      60
gccgaggacc agctgcccga gggcgacgtt ctggtcgacg tcgcctattc gaccttgaac     120
tacaaggacg cgctggcgat caccggcaag gcgccggtcg tgcggcgctt ccccatggtg     180
ccgggcatcg acttcacggg cacggtggca caaagcagcc atgccgattt caagcccggc     240
gaccgggtca tcctgaatgg ctggggcgtg ggggaaaaac actggggcgg gctggccgaa     300
cgggcacggg tccgcggcga ctggctggtt ccgctgccgg cgcccctcga cttgcggcag     360
gcggcgatga tcggcacggc gggctatacg gccatgctct gcgttctggc gctcgagcgg     420
cacggggtcg tgcccggcaa tggcgagatc gtcgtgagcg gcgccgctgg cggtgtcggc     480
agcgttgcga cgacacttct tgccgcgaag ggctacgaag ttgctgcggt caccggccgt     540
gcctccgagg cggagtatct gcgcggtctg ggcgccgcgt cggtgatcga ccgcaacgaa     600
ctgaccggca aggtccgtcc gctggggcag gagcgttggg ccggcggcat cgatgttgcg     660
ggcagcacgg tgctggcgaa catgctctcg atgatgaaat accggggcgt cgtcgcggcc     720
tgcggtcttg ccgcgggaat ggatctgccc gcgtcggtgg cgcccttcat cctgcgcggt     780
atgaccctgg ccggggtcga cagcgtcatg tgcccgaaaa ccgaccgcct tgcggcctgg     840
gctcggctcg ccagcgatct cgatccggca aagctcgagg agatgacgac cgaactgccc     900
ttctccgagg tcatcgagac cgccccgaag ttccttgacg ggaccgtccg aggacgcatc     960
gtcattccgg tcaccccctg a                                              981

<210> SEQ ID NO 129
<211> LENGTH: 1104
<212> TYPE: DNA
<213> ORGANISM: Clostridium propionicum

<400> SEQUENCE: 129
atggctttta acagtgctga tataaattcg tttcgagata tttgggtatt ttgcgaacag      60
agagaaggca agcttattaa tacagatttt gagctgattt cagaaggaag aaagctcgct     120
gatgagcggg gctcaaaatt ggttggtatt ttattaggac atgaggtaga agagattgca     180
```

```
aaagagctag gtggatatgg tgcagataaa gtgattgttt gcgaccatcc cgaattaaaa    240
ttttatacca cagatgctta tgccaaggta ctttgtgatg tggttatgga ggagaaaccc    300
gaggttattt tgattggtgc aacaaatatt ggccgtgatt taggccccag atgtgcagca    360
cgcttacata cgggtttaac agcagattgt acccatttgg atattgatat gaacaaatat    420
gtggactttc tttccacctc ctcaacattg gatatatcat ccatgacctt tcctatggag    480
gacacaaatt taaaaatgac ccgtcctgcc tttggcggac atttgatggc aactatcatt    540
tgccctagat tccgcccttg tatgtctact gtaagacccg gggttatgaa aaaagcagag    600
tttagccagg aaatggctca ggcttgtcag gttgttacac gccatgtaaa tttatctgat    660
gaggacttaa agacgaaagt aatcaatatt gtgaaagaaa ctaaaaaaat tgttgattta    720
atcggcgccg aaattattgt ttctgttgga cgtggaatca gcaaggatgt gcaagggggc    780
attgccctag cagaaaagct tgccgatgcg tttgggaatg gtgttgttgg cggttctcgt    840
gcggttattg attccggttg gctccctgcg gatcatcagg ttgggcagac gggaaaaacc    900
gtgcatccta aggtatatgt tgcccttggt atttccggcg ccattcagca taaggcaggt    960
atgcaggatt cagagttgat tattgcggta aataagacg agactgctcc tattttcgat   1020
tgtgctgatt atggtataac aggggatttg tttaaaattg taccaatgat gattgatgca   1080
attaaggaag gtaaaaatgc ttga                                          1104

<210> SEQ ID NO 130
<211> LENGTH: 804
<212> TYPE: DNA
<213> ORGANISM: Clostridium propionicum

<400> SEQUENCE: 130
atgagaattt atgtttgtgt aaaacaagtt ccggatacat cgggaaaggt tgctgtaaac     60
cccgatggaa ccttaaaccg tgcatctatg gcggctatta ttaatcccga tgatatgagt    120
gccattgagc aggcccttaa gttgaaggat gaaacaggct gtcaagttac agcccttacc    180
atggggccac ctcctgcgga gggaatgttg cgggaaatta tcgcaatggg cgcagatgat    240
ggcgttttaa tttccgccag agagttcggt ggttccgata ccttcgcaac ctctcaaatt    300
atatcggcgg cgatacataa attagggctt tccaatgagg atatgatttt tgcggtagg    360 caggcaattg atggagatac agcacaggta ggaccgcaaa ttgcagaaaa attaagcatt    420
cctcaggtga cttatggggc agggattaaa aaaagcggag atttggtttt ggtaaagcgc    480
atgctggaag atggatatat gatgatagag gtggaaacac cctgcttgat tacttgcatt    540
caggataagg ctgtaaaacc acgctatatg actttgaatg gaattatgga atgctatagc    600
aagcctcttt tggtattaga ttatgaagcc cttaaggatg aacccctaat cgaattggat    660
acgatcggtc tgaaaggttc tcctacaaat atatttaaat cctttacgcc gccacaaaag    720
ggtgtaggcg ttatgcttca aggaacagac aaagaaaaag ttgaagattt ggtggacaaa    780
ttgatgcaga agcatgtcat ttaa                                          804

<210> SEQ ID NO 131
<211> LENGTH: 1562
<212> TYPE: DNA
<213> ORGANISM: Candida boidinii

<400> SEQUENCE: 131
ttcaactaaa aattgaacta tttaaacact atgatttcct tcaattatat taaaatcaat     60
ttcatatttc cttacttctt tttgctttat tatacatcaa taactcaatt aactcattga    120
```

```
ttatttgaaa aaaaaaaaca tttattaact taactccccg attatatatt atattattga      180
ctttacaaaa tgaagatcgt tttagtctta tatgatgctg gtaagcacgc tgctgatgaa      240
gaaaaattat atggttgtac tgaaaataaa ttaggtattg ctaattggtt aaaagatcaa      300
ggtcatgaac taattactac ttctgataaa gaaggtgaaa caagtgaatt ggataaacat      360
atcccagatg ctgatattat catcaccact cctttccatc ctgcttatat cactaaggaa      420
agacttgaca aggctaagaa cttaaaatta gtcgttgtcg ctggtgttgg ttctgatcac      480
attgatttag attatattaa tcaaacaggt aagaaaatct cagtcttgga agttacaggt      540
tctaatgttg tctctgttgc tgaacacgtt gtcatgacca tgcttgtctt ggttagaaat      600
ttcgttccag cacatgaaca aattattaac cacgattggg aggttgctgc tatcgctaag      660
gatgcttacg atatcgaagg taaaactatt gctaccattg gtgctggtag aattggttac      720
agagtcttgg aaagattact ccctttaat ccaaaagaat tattatacta cgattatcaa      780
gctttaccaa aagaagctga agaaaaagtt ggtgctagaa gagttgaaaa tattgaagaa      840
ttagttgctc aagctgatat cgttacagtt aatgctccat acacgcagg tacaaaaggt       900
ttaattaata aggaattatt atctaaattt aaaaaaggtg cttggttagt caataccgca      960
agaggtgcta tttgtgttgc tgaagatgtt gcagcagctt tagaatctgg tcaattaaga     1020
ggttacggtg tgatgtttg gttcccacaa ccagctccaa aggatcaccc atggagagat     1080
atgagaaata aatatggtgc tggtaatgcc atgactcctc actactctgg tactactta     1140
gatgctcaaa caagatacgc tgaaggtact aaaaatatct tggaatcatt ctttactggt     1200
aaatttgatt acagaccaca agatattatc ttattaaatg gtgaatacgt tactaaagct     1260
tacggtaaac acgataagaa ataaattttc ttaacttgaa aactataatt gctataacaa     1320
ttcttcaatt tctctttttc ttccttttt tgaagaattt ttaacaatca aaattttgac     1380
tctttgattt cccgcaatct ctgagctcag catactcatt attatttat tattattat     1440
attattactt ttattattat tatattttty cttctttaac gatatcgttt gtgttttatc     1500
ttttatgatt taaattttat acgaatttat gaatacaaca aaatatttaa gtttacacaa     1560
tg                                                                    1562
```

<210> SEQ ID NO 132
<211> LENGTH: 1131
<212> TYPE: DNA
<213> ORGANISM: Saccharomyces cerevisiae

<400> SEQUENCE: 132

```
atgtcgaagg gaaaggtttt gctggttctt tacgaaggtg gtaagcatgc tgaagagcag      60
gaaaagttat ggggtgtat tgaaaatgaa cttggtatca gaaatttcat tgaagaacag      120
ggatacgagt tggttactac cattgacaag gaccctgagc caacctcaac ggtagacagg     180
gagttgaaag acgctgaaat tgtcattact acgcccttt tccccgccta catctctgaga      240
aacaggattg cagaagctcc taacctgaag ctctgtgtaa ccgctggcgt cggttcagac      300
catgtcgatt tagaagctgc aaatgaacgg aaaatcacgg tcaccgaagt tactggttct      360
aacgtcgttt ctgtcgcaga gcacgttatg ccacaattt tggttttgat aagaaactat      420
aatggtggtc atcaacaagc aattaatggt gagtgggata ttgccggcgt ggctaaaaat      480
gagtatgatc tggaagacaa aataatttca acggtaggtg ccggtagaat tggatatagg     540
gttctggaaa gattggtcgc atttaatccg aagaagttac tgtactacga ctaccaggaa     600
```

| | |
|---|---|
| ctacctgcgg aagcaatcaa tagattgaac gaggccagca agcttttcaa tggcagaggt | 660 |
| gatattgttc agagagtaga gaaattggag gatatggttg ctcagtcaga tgttgttacc | 720 |
| atcaactgtc cattgcacaa ggactcaagg ggtttattca ataaaaagct tatttcccac | 780 |
| atgaaagatg gtgcatactt ggtgaatacc gctagaggtg ctatttgtgt cgcagaagat | 840 |
| gttgccgagg cagtcaagtc tggtaaattg gctggctatg gtggtgatgt ctgggataag | 900 |
| caaccagcac caaaagacca tccctggagg actatggaca ataaggacca cgtgggaaac | 960 |
| gcaatgactg ttcatatcag tggcacatct ctggatgctc aaaagaggta cgctcaggga | 1020 |
| gtaaagaaca tcctaaatag ttactttcc aaaaagtttg attaccgtcc acaggatatt | 1080 |
| attgtgcaga atggttctta tgccaccaga gcttatggac agaagaaata a | 1131 |

<210> SEQ ID NO 133
<211> LENGTH: 438
<212> TYPE: DNA
<213> ORGANISM: Saccharomyces cerevisiae

<400> SEQUENCE: 133

| | |
|---|---|
| atgtcgaagg gaaaggtttt gctggttctt tatgaaggtg gtaagcatgc tgaagagcag | 60 |
| gaaaagttat tggggtgtat tgaaaatgaa cttggtatca gaaatttcat tgaagaacag | 120 |
| ggatacgagt tggttactac cattgacaag gaccctgagc caacctcaac ggtagacagg | 180 |
| gagttgaaaa acgctgaaat tgtcattact acgcccttt tccccgccta catctcgaga | 240 |
| aacaggattg cagaagctcc taacctgaag ctctgtgtaa ccgctggcgt cggttcagac | 300 |
| catgtcgatt tagaagctgc aaatgaacgg aaaatcacgg tcaccgaagt tactggttct | 360 |
| aacgtcgttt ctgtcgcaga gcacgttatg gccacaattt tggttttgat aagaaactat | 420 |
| aatggtggtc atcaataa | 438 |

<210> SEQ ID NO 134
<211> LENGTH: 867
<212> TYPE: DNA
<213> ORGANISM: Cupriavidus necator

<400> SEQUENCE: 134

| | |
|---|---|
| atgatgcgct gcatgcagtc accggaggtg catccggccg cggccggaga cgccgagccg | 60 |
| cccactcaca gcaccttcgc cgtcagccgc tggcgccgcg cgagctgat gctgagcccc | 120 |
| gatgaagtgg ccgaggaagt gccggtcgcg ctggtgtaca acggcatctc gcacgcggtg | 180 |
| atgctggcga cgccggccga cctggaggac ttcgcactcg gcttcagcct gagcgaaggc | 240 |
| atcgttaccc gtgccagcga cgtctatgac atcgagatcg acacgcgcga gcacggcatc | 300 |
| gccgtgcagc tggagatcgc atcggaagcc ttcatgcggc tcaaggaccg ccgccgctcg | 360 |
| ctggccgggc gcaccggctg cgggctgtgc ggcaccgaat cgctggaaca ggtgatgcgc | 420 |
| ctgccggcac cggtgcgcag cgatgccagc ttccataccg acgtgatcca ggccgcgttc | 480 |
| gtgcaactgc aactgcggca ggaactgcag caacacacgg gtgcgacgca cgctgccgca | 540 |
| tggctgcgtg ccgatggcca tgtatcactg gtgcgtgaag acgtgggccg ccacaacgcg | 600 |
| ctggacaagc tggcgggcgc gctcgccagc agcggcgagg acatctccag cggcgcggtg | 660 |
| ctggtgacca gccgcgccag ctatgaaatg gtgctgaaga ccgccgccat cggcgccggc | 720 |
| gtgctcgccg cagtgtccgc accgacggcg ctggccgtgc ggcttgccga acaagccagc | 780 |
| atcacccctgg ccggcttcgt gcgcgccggc gcgcacgtgg tctatgccca tccccaacgc | 840 |
| ctgcagcacg aagcgagcct ggcatga | 867 |

<210> SEQ ID NO 135
<211> LENGTH: 2880
<212> TYPE: DNA
<213> ORGANISM: Cupriavidus necator

<400> SEQUENCE: 135

| | | | | | |
|---|---|---|---|---|---|
| atgaacgccc | gcaacgagat | cgatttcggc | acgcccgcca | gcccatccac | cgaactggtc | 60 |
| accctggagg | tcgatggcgt | cagcgtcacc | gtgcccgccg | gcacctcggt | gatgcgcgcc | 120 |
| gcgatggaag | cgcagatcgc | cgtccccaag | ctgtgcgcca | ccgacagcct | cgaagccttc | 180 |
| ggctcgtgcc | ggctgtgcct | ggtcgagatc | gaagggcgcc | gcggctatcc | ggcatcgtgc | 240 |
| accacgccgg | tcgaagccgg | catgaaggtc | aagacccaga | gcgacaagct | ggccgacctg | 300 |
| cgccgcggcg | tgatggagct | gtatatctcc | gaccacccgc | tcgattgcct | gacctgcccg | 360 |
| accaacggca | actgcgagct | gcaggacatg | gccggcgtgg | tcggcctgcg | tgaagtgcgc | 420 |
| tacaacgacg | gcgccccgga | agctgcgccc | atcgcgaccc | acacgcagat | gaagaaggac | 480 |
| gaatccaatc | cttacttcac | ctacgacccc | tccaagtgca | tcgtctgcaa | ccgctgcgtg | 540 |
| cgcgcctgcg | aggaaacgca | gggcaccttc | gccctgacca | tcagcggccg | cggcttcgat | 600 |
| tcccgcgtct | cgcccggaac | cagccagtcg | ttcatggaat | cggactgcgt | ctcgtgcggc | 660 |
| gcctgcgtgc | aggcgtgccc | gaccgcgacg | ctgaccgaga | cctcggtgat | caagttcggc | 720 |
| cagccctcgc | acagcaccgt | gaccacctgt | gcctattgcg | gcgtgggctg | ttcgttcaag | 780 |
| gccgagatga | agggcaatga | agtggtcgcg | atggtgccgt | acaaggacgg | caaggccaat | 840 |
| gaaggccacg | cctgcgtcaa | gggccgcttt | gcctggggct | acgccacgca | aaggaccgc | 900 |
| atcctcaagc | cgatgatccg | cgccaagatc | accgatccgt | ggcgcgaggt | gtcgtgggaa | 960 |
| gaggcgatcg | actatgccgc | gtcgcagttc | aagcgtatcc | aggccgagca | cggcaaggac | 1020 |
| tccatcggcg | gcatcgtgtc | gtcgcgctgc | accaatgaag | agggctacct | ggtgcagaag | 1080 |
| ctggtgcgcg | cagccttcgg | caacaacaac | gtcgacacct | gcgcgcgcgt | gtgccattcg | 1140 |
| ccgaccggct | acggcctgaa | gcagaccctg | ggcgaatcgg | ccggcacgca | gaccttcaag | 1200 |
| tcggtggaga | aggccgacgt | gatcatggtg | atcggtgcca | cccgaccga | cggccacccg | 1260 |
| gtctttgcgt | cgcgcatgaa | gaagcgcctg | cgcgccggcg | ccaggctgat | cgtggtcgat | 1320 |
| ccgcgccgca | tcgacctggt | cgactccccg | catatccgtg | ccgactatca | cctgcaactg | 1380 |
| cgcccgggca | ccaacgtggc | gctggtgacc | tcgctggccc | acgtgatcgt | caccgaaggc | 1440 |
| ctgctcaacg | aagctttcat | cgccgagcgc | tgcgaggacc | gcgccttcca | gcaatggcgc | 1500 |
| gatttcgtct | cgctgccgga | gaactcgccg | gaggcgatgg | aaagcgtgac | cggcattccg | 1560 |
| gcggaacagc | tgcgcggtgc | cgcacgcctg | tatgccaccg | gcggcaacgc | tgcgatctac | 1620 |
| tacggcctgg | gcgtgaccga | gcatgcgcaa | ggctcaacca | ccgtgatggg | cattgccaac | 1680 |
| ctcgccatgg | ccaccggcaa | tatcggccgc | gaaggcgtgg | gtgtgaaccc | gctgcgcggg | 1740 |
| cagaacaatg | tgcagggctc | gtgcgacatc | ggttcgttcc | gcatgagct | gccgggctat | 1800 |
| cgccacgtgt | cggactcgac | cacgcgcggt | ctgttcgaag | ccgcgtggaa | tgtcgagatc | 1860 |
| agccccgagc | cgggcctgcg | catccccaat | atgtttgaag | ccgcgctggc | cggcagcttc | 1920 |
| aagggcctct | actgccaggg | cgaggacatt | gtccagtccg | acccgaacac | gcagcacgtg | 1980 |
| tccgaggcgc | tgtcatcgat | ggaatgcatc | gtggtgcagg | acatcttcct | gaacgagacc | 2040 |
| gccaagtacg | cgcacgtgtt | cctgccgggc | tcgtccttcc | tggaaaagga | cggcaccttc | 2100 |

| | |
|---|---|
| accaacgccg agcgccgcat ctcgcgcgtg cgcaaggtga tgccgcccaa ggcgcgctat | 2160 |
| gccgactggg aagccaccat cctgctggcc aatgcgctgg gctacccgat ggactacaag | 2220 |
| catccgtcgg agatcatgga cgagatcgcg cgcctgacgc cgaccttcgc cggtgtcagc | 2280 |
| tacaagcgcc tggaccagct cggcagcatc cagtggccgt gcaacgccga cgcgccggaa | 2340 |
| ggcacgccga ccatgcatat cgacaccttc gtgcgcggca agggcaagtt catcatcacc | 2400 |
| aagtacgtgc ccaccaccga aagatcacg cgcgccttcc cgctgatcct gaccaccggc | 2460 |
| cgcatcctgt cgcaatacaa cgtcggcgcg cagacgcgcc gtaccgacaa cgtctactgg | 2520 |
| catgccgagg accggctcga gatccatccg cacgatgccg aggagcgcgg catcaaggac | 2580 |
| ggcgactggg tcggggtgca gagccgtgcc ggcgacacgg tgctgcgcgc gatcgtcagc | 2640 |
| gagcgcatgc agccgggcgt ggtctacacc accttccact ccccggaatc cggcgccaac | 2700 |
| gtgatcacca ccgacaactc cgactgggcc accaactgcc cggagtacaa ggtgaccgcg | 2760 |
| gtgcaggtgc tgccggtggc gcagccgtcg gcgtggcagc gggagtacca ggagttcaac | 2820 |
| gcccagcagc tgcaactgct ggaagccgcc agcgccgacc cggcgcaggc cgtacgctga | 2880 |

<210> SEQ ID NO 136
<211> LENGTH: 1563
<212> TYPE: DNA
<213> ORGANISM: Cupriavidus necator

<400> SEQUENCE: 136

| | |
|---|---|
| atgatcacga tcaccaccat cttcgtgccg cgcgattcca ccgcgctggc actgggcgcc | 60 |
| gacgacgtcg cccgcgccat cgcgcgtgaa gccgcggcgc gcaacgagca cgtgcgcatt | 120 |
| gtgcgcaatg gctcgcgcgg catgttctgg ctggagccgc tggtcgaggt gcagaccgga | 180 |
| gccgccgcg tggcctatgg cccggtcagc gccgcagacg tgccggggct gttcgacgcc | 240 |
| ggcttgctgc aaggcggcga gcacgcgctg tcgcagggcg tcaccgaaga gatccccttc | 300 |
| ctgaagcagc aggagcgcct gaccttcgcc gcgtcggca tcaccgatcc gctgtcgctg | 360 |
| gacgactacc gcgcgcatga gggctttgcc ggcctggagc gcgcgctggc gatgcagccc | 420 |
| gccgagatcg tgcaggaggt caccgactcc ggcctgcgcg gccgcggcgg cgggcgttc | 480 |
| ccgaccggca tcaagtggaa gaccgtgctg ggcgcgcagt ccgcggtcaa gtacatcgtc | 540 |
| tgcaatgccg acgagggcga ctcgggcacg ttctccgatc gcatggtgat ggaagacgac | 600 |
| ccgttcatgc tgatcgaagg catgaccatt gccgcgcttg cggtgggtgc ggagcagggc | 660 |
| tacatctact gccgttccga ataccccgac gcgattgccg tgctggaaag cgcgattggt | 720 |
| atcgccaacg ccgccggctg gctcggcgac gacatccgcg gcagcggcaa gcgcttccac | 780 |
| ctcgaagtgc gcaagggcgc cggcgcctat gtctgcggcg aggaaaccgc gctgctggaa | 840 |
| agcctggaag gacggcgcgg cgtggtgcgc gccaagccgc gctgccggc gctgcagggg | 900 |
| ctgttcggca gcccacggt gatcaacaac gtgatctcgc tggccaccgt gccggtgatc | 960 |
| ctggcgcgcg cgcgcagta ctaccgcgac tacggcatgg ccgttcgcg cggcacgctg | 1020 |
| ccgttccagc ttgccggcaa catcaagcag ggcggactgg tggaaaaggc gttcggcgtg | 1080 |
| acgctgcgcg agctgctggt cgactacggc ggcggcacgc gcagcggccg cgccatccgc | 1140 |
| gcggtgcagg tgggcgggcc gctgggcgcc tacctgcccg agtcgcgctt cgacgtgccg | 1200 |
| ctggactatg aagcctatgc cgcgttcggc ggcgtggtcg gccacggcgg catcgtggtg | 1260 |
| ttcgatgaaa ccgtcgacat ggcaaagcag gcccgctacg cgatggagtt ctgcgcgatc | 1320 |
| gaatcgtgcg gcaagtgcac cccgtgccgg atcggctcga cccgcggcgt cgaagtgatg | 1380 |

```
gaccgcatca tcgccggcga gcagccggtc aagcacgtcg ccctggtgcg cgacctgtgc    1440
gacaccatgc tcaacggctc gctgtgcgcg atgggcggca tgaccccgta cccggtgctg    1500
tccgcgctga tgaattcccc gaggacttcg gcctcgcct ccaacccagc caaggccgcc     1560
tga                                                                  1563
```

<210> SEQ ID NO 137
<211> LENGTH: 225
<212> TYPE: DNA
<213> ORGANISM: Cupriavidus necator

<400> SEQUENCE: 137

```
atgaagatcg acaacctcat caccatggcc aaccagatcg gcagcttctt cgaggccatg     60
ccggatcggg aagaggccgt ctctgatatt gcagggcata tcaagcggtt ttgggagccg    120
cgcatgcgca aggccttgct ggggcatgtg gatgccgagg cagggagcgg gctgctggac    180
atcgtgcgcg aggcgctggg gcggcatcgg gcgatgctgg agtag                   225
```

<210> SEQ ID NO 138
<211> LENGTH: 531
<212> TYPE: DNA
<213> ORGANISM: Cupriavidus necator

<400> SEQUENCE: 138

```
atgccagaaa tttcccccca cgcaccggca tccgccgatg ccacgcgcat cgccgccatc     60
gtggccgcgc gccaggacat accgggcgcc ttgctgccga tcctgcatga gatccaggac    120
acacagggct atatccccga cgccgccgtg cccgtcattg cccgcgcgct gaacctgtcg    180
cgcgccgagg tgcacggcgt gatcaccttc taccaccatt tccgccagca gccggccggg    240
cgccacgtgg tgcaggtctg ccgcgccgaa gcctgccagt cggtcggcgc cgaagcgctg    300
gccgagcatg cgcagcgcgc acttggctgt ggctttcatg aaaccaccgc ggacgggcag    360
gtgacgctgg agccggtttta ttgcctgggc cagtgcgcct gcggccccgc cgtgatggtc    420
ggcgagcagc tgcacggcta tgtcgatgcc aggcgcttcg acgcgctggt gcgctcgctg    480
cgcgagtcgt ccgcggaaaa gaccacggaa gccgcggagg cacaggcatg a             531
```

<210> SEQ ID NO 139
<211> LENGTH: 1095
<212> TYPE: DNA
<213> ORGANISM: Cupriavidus necator

<400> SEQUENCE: 139

```
atgattcgca tctcgatcca cccgcacctg cagatccggg acgacgccag ccccggtggc     60
gaggccctgg acgtgtcccg cctggtggcc ctgctcggcc atatcgagga atccggcagc    120
atcagccact cggcgcaggc ggtatcgctg tcctaccgct acgcctgggg catcctgcgc    180
gatgccgagg cgctgttcgg cggcccgctg atcgacaaga cccgcgggcg cggcagcgcg    240
ctgacgccgc tggcgcagca gttggtgtgg gccagcaagc ggatcggcgc gcggctgtcg    300
ccgacgctgg acagcctggc gtccgagctg gagatcgagt tgaagaagct gatggaccag    360
cccgaagcca cggcgcggct gcatgccagc cacggcttcg cggtggcggc gctgcgcgac    420
ttcctcgacg agcagcaggt gcggcacgac ctgaagtact gcgcagcgt cgaggccgtg    480 gcggcactgg ccgaaggcgc ctgcgatatc gccggcttcc atgtgccggt gggcgagttc    540
gagcacggca tgtggcggca tttcaccacc tggctcaagc cggacaccca ctgcctggtg    600
```

-continued

```
cacctggcgg tgcgcagcca gggactgttc gtgcggccgg acaacccgct tggcatccac    660
acgctggaag acctgacccg gcgcgaggtg cgcttcgtca accgccaggt gggctcgggc    720
acgcgcctgc tgctggacct gatgctggcc gcgcgcggca tcgacacggc ccgcatcgag    780
ggctacagca acggtgaatt cacccacgcc gcggtggccg cgtatatcgg cagcggcatg    840
gccgacgtgg gctttggcgt ggaaaccgcg gcgcggcgct tcgggctggc gttcgtgccg    900
gtgatcaagg agcgctactt ctttgcgatc gagcgcgcca agctgcgcag cgcggcactg    960
gccggcgcgg tggacgcgct taccagcgaa gccttccgcc agcgcgtcaa tgcactgccc   1020
ggctacgacg gcacgctgac cggcaccgtg ctgacgctgg aagaagcgtt cccggattac   1080
gctgaggcgc gctag                                                    1095
```

MODIFIED MICROORGANISMS AND METHODS OF MAKING BUTADIENE USING SAME

CROSS-REFERENCE TO RELATED APPLICATIONS

This application claims the benefit of U.S. Provisional Application No. 61/576,788, filed Dec. 16, 2011, and U.S. Provisional Application No. 61/606,035, filed on Mar. 2, 2012, the disclosures of which are incorporated by reference herein in their entirety.

BACKGROUND

Butadiene (1,3-butadiene, $CH_2=CH-CH=CH_2$, CAS 106-99-0) is a linear, conjugated 4-carbon hydrocarbon typically manufactured (along with other 4-carbon molecules) by steam cracking petroleum-based hydrocarbons. This process involves harsh conditions and high temperatures (at least about 850° C.). Other method of butadiene production involve toxic and/or expensive catalysts, highly flammable and/or gaseous carbon sources, and high temperatures. Globally, several million tons of butadiene-containing polymers are produced annually. Butadiene can be polymerized to form polybutadiene, or reacted with hydrogen cyanide (prussic acid) in the presence of a nickel catalyst to form adiponitrile, a precursor to nylon. More commonly, however, butadiene is polymerized with other olefins to form copolymers such as acrylonitrile-butadiene-styrene (ABS), acrylonitrile-butadiene (ABR), or styrene-butadiene (SBR) copolymers.

SUMMARY

The present disclosure generally relates to microorganisms (e.g., non-naturally occurring microorganisms, also referred to herein as modified microorganisms) that comprise one or more polynucleotides coding for enzymes in one or more pathways that catalyze a conversion of a carbon source to butadiene and the uses of such microorganisms in industrial processes including, for use in the production of butadiene and products derived therefrom.

The present disclosure provides methods of producing butadiene from a fermentable carbon source, comprising: providing a fermentable carbon source; contacting the fermentable carbon source with a microorganism comprising one or more polynucleotides coding for enzymes in a pathway that catalyzes a conversion of the fermentable carbon source to one or more intermediates in a pathway for the production of butadiene, and one or more polynucleotides coding for enzymes in a pathway that catalyze a conversion of the one or more intermediates to butadiene in a fermentation media; and expressing the one or more polynucleotides coding for the enzymes in the pathway that catalyzes a conversion of the fermentable carbon source to one or more intermediates in a pathway for the production of butadiene and the one or more polynucleotides coding for enzymes in a pathway that catalyze a conversion of the one or more intermediates to butadiene in the microorganism to produce butadiene.

In some embodiments which may be combined with any of the above or below mentioned embodiments, the enzymes that catalyze the conversion of the fermentable carbon source to one or more intermediates in the pathway for the production of butadiene are set forth in any one of Tables 1-3.

In some embodiments which may be combined with any of the above or below mentioned embodiments, the enzymes that catalyze the conversion of the one or more intermediates to butadiene are set forth in any one of Tables 1-3.

In some embodiments which may be combined with any of the above or below mentioned embodiments, butadiene is produced via an acetyl-CoA and propionyl-CoA intermediate; a crotonyl-CoA intermediate; and/or a formic acid intermediate.

In some embodiments which may be combined with any of the above or below mentioned embodiments, the one or more polynucleotides coding for enzymes in a pathway that catalyze a conversion of acetyl-CoA and propionyl-CoA to ketovaleryl-CoA code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of ketovaleryl-CoA to (R) or (S) 3-hydroxyaleryl-CoA code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of (R) or (S) hydroxyaleryl-CoA to 2-pentenoyl-CoA code for a dehydratase including, for example, a dehydratase encoded by a polynucleotide as set forth in any one of SEQ ID NOs: 37-55.

In some embodiments which may be combined with any of the above or below mentioned embodiments, the one or more polynucleotides coding for enzymes in a pathway that catalyze a conversion of 2-pentenoyl-CoA to 2-pentenoic acid code for a transferase or a hydrolase including, for example, a transferase or a hydrolase encoded by a polynucleotide as set forth in any one of SEQ ID NOs: 1-28 or 29-33, respectively.

In some embodiments which may be combined with any of the above or below mentioned embodiments, the one or more polynucleotides coding for enzymes in a pathway that catalyze a conversion of 2-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the one or more polynucleotides coding for enzymes in a pathway that catalyze a conversion of 2-pentenoic acid to 4-pentenoic acid code for an isomerase including, for example, and isomerase encoded by a polynucleotide as set forth in any one of SEQ ID NOs: 99-102.

In some embodiments which may be combined with any of the above or below mentioned embodiments, the one or more polynucleotides coding for enzymes in a pathway that catalyze a conversion of 4-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the one or more polynucleotides coding for enzymes in a pathway that catalyze a conversion of 2-pentenoyl-CoA to pent-2,4-dienoyl-CoA code for a dehydrogenase including, for example, a dehydrogenase encoded by a polynucleotide as set forth in any one of SEQ ID NOs: 124-139.

In some embodiments which may be combined with any of the above or below mentioned embodiments, the one or more polynucleotides coding for enzymes in a pathway that catalyze a conversion of pent-2,4-dienoyl-CoA to pent-2,4-dienoic code for a transferase or a hydrolase including, for example, a transferase or a hydrolase encoded by a polynucleotide as set forth in any one of SEQ ID NOs: 1-28 or 29-33, respectively.

In some embodiments which may be combined with any of the above or below mentioned embodiments, the one or more polynucleotides coding for enzymes in a pathway that catalyze a conversion of 2,4-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the one or more polynucleotides coding for enzymes in a pathway that catalyze a conversion of crotonyl-CoA to crotonyl alcohol code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of crotonyl-CoA to crotonaldehyde code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of crotonaldehyde to crotonyl alcohol code for an oxidoreductase or CoA synthetase including, for example, an oxidoreductase or synthetase encoded by a polynucleotide as set forth in any one of SEQ ID NOs: 103-123 or SEQ ID NOs: 34-36, respectively.

In some embodiments which may be combined with any of the above or below mentioned embodiments, the one or more polynucleotides coding for enzymes in a pathway that catalyze a conversion of crotonyl alcohol to butadiene code for a dehydratase including, for example, a dehydratase encoded by a polynucleotide as set forth in any one of SEQ ID NOs: 37-55.

In some embodiments which may be combined with any of the above or below mentioned embodiments, the one or more polynucleotides coding for enzymes in a pathway that catalyze a conversion of $CO_2$ to formic acid code for a dehydrogenase including, for example, a dehydrogenase encoded by a polynucleotide as set forth in any one of SEQ ID NOs: 124-139.

In some embodiments which may be combined with any of the above or below mentioned embodiments, the one or more polynucleotides coding for enzymes in a pathway that catalyze a conversion of pyruvate and CoA to acetyl-CoA and formic acid code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of formic acid to formyl-CoA code for a transferase or a CoA synthetase including, for example, a transferase or a CoA synthetase encoded by a polynucleotide as set forth in any one of SEQ ID NOs: 1-28 or 34-36, respectively.

In some embodiments which may be combined with any of the above or below mentioned embodiments, the one or more polynucleotides coding for enzymes in a pathway that catalyze a conversion of 2 acetyl-CoA to acetoacetyl-CoA code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of acetoacetyl-CoA and formyl-CoA to 3,5-ketovaleryl-CoA code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of 3,5-ketovaleryl-CoA to (R) or (S)-5-hydroxy-3-ketovaleryl-CoA code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of (R) or (S)-5-hydroxy-3-ketovaleryl-CoA to (R) or (S)-3,5-dihydroxyaleryl-CoA code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of (R) or (S)-3,5-dihydroxyaleryl-CoA to (R) or (S) 3-hydroxy-4-pentenoyl-CoA code for a dehydratase including, for example, a dehydratase encoded by a polynucleotide as set forth in any one of SEQ ID NOs: 37-55.

In some embodiments which may be combined with any of the above or below mentioned embodiments, the one or more polynucleotides coding for enzymes in a pathway that catalyze a conversion of (R) or (S)-3-hydroxy-4-pentenoyl-CoA to 3-hydroxy-4-pentenoic acid code for a transferase or a hydrolase including, for example, a transferase or a hydrolase encoded by a polynucleotide as set forth in any one of SEQ ID NOs: 1-28 or 29-33, respectively.

In some embodiments which may be combined with any of the above or below mentioned embodiments, the one or more polynucleotides coding for enzymes in a pathway that catalyze a conversion of 3-hydroxy-4-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the microorganism is a bacterium is selected from the genera consisting of: *Burkholderia, Propionibacterium, Propionispira, Clostridium, Bacillus, Escherichia, Pelobacter*, or *Lactobacillus*.

In some embodiments which may be combined with any of the above or below mentioned embodiments, the microorganism is a eukaryote is a yeast, filamentous fungi, protozoa, or algae.

In some embodiments which may be combined with any of the above or below mentioned embodiments, the yeast is *Saccharomyces cerevisiae, Zymomonas mobilis*, or *Pichia pastoris*.

In some embodiments which may be combined with any of the above or below mentioned embodiments, the carbon source is sugarcane juice, sugarcane molasses, hydrolyzed starch, hydrolyzed lignocellulosic materials, glucose, sucrose, fructose, lactate, lactose, xylose, pyruvate, or glycerol in any form or mixture thereof.

In some embodiments which may be combined with any of the above or below mentioned embodiments, the carbon source is a monosaccharide, oligosaccharide, or polysaccharide.

In some embodiments which may be combined with any of the above or below mentioned embodiments, the butadiene is secreted by the microorganism into the fermentation media.

In some embodiments which may be combined with any of the above or below mentioned embodiments, the methods may further comprise recovering the butadiene from the fermentation media.

In some embodiments which may be combined with any of the above or below mentioned embodiments, the microorganism has been genetically modified to express the one or more polynucleotides coding for enzymes in a pathway that catalyzes a conversion of the fermentable carbon source to one or more intermediates in the pathway for the production of butadiene and the one or more polynucleotides coding for enzymes in a pathway that catalyze a conversion of one or more intermediates to butadiene.

In some embodiments which may be combined with any of the above or below mentioned embodiments, the conversion of the fermentable carbon source to butadiene is ATP positive (e.g., generates a net of ATP per mol of butadiene produced) and may be additionally combined with a NADH consuming pathway to provide an anaerobic process for butadiene production.

The present disclosure also provides microorganisms comprising one or more polynucleotides coding for enzymes in a pathway that catalyzes a conversion of a fermentable carbon source to one or more intermediates in a pathway for the production of butadiene and one or more polynucleotides coding for enzymes in a pathway that catalyze a conversion of the one or more intermediates to butadiene.

In some embodiments which may be combined with any of the above or below mentioned embodiments, the enzymes that catalyze the conversion of the fermentable carbon source to one or more intermediates in the pathway for the production of butadiene are set forth in any one of Tables 1-3.

In some embodiments which may be combined with any of the above or below mentioned embodiments, the enzymes that catalyze the conversion of the one or more intermediates to butadiene are set forth in any one of Tables 1-3.

In some embodiments which may be combined with any of the above or below mentioned embodiments, butadiene is produced via an acetyl-CoA and propionyl-CoA intermediate; a crotonyl-CoA intermediate; and/or a formic acid intermediate.

In some embodiments which may be combined with any of the above or below mentioned embodiments, the microorganism is a bacterium is selected from the genera consisting of: *Burkholderia, Propionibacterium, Propionispira, Clostridium, Bacillus, Escherichia, Pelobacter,* or *Lactobacillus*.

In some embodiments which may be combined with any of the above or below mentioned embodiments, the microorganism is a eukaryote is a yeast, filamentous fungi, protozoa, or algae.

In some embodiments which may be combined with any of the above or below mentioned embodiments, the yeast is *Saccharomyces cerevisiae, Zymomonas mobilis,* or *Pichia pastoris*.

In some embodiments which may be combined with any of the above or below mentioned embodiments, the microorganism has been genetically modified to express the one or more polynucleotides coding for enzymes in a pathway that catalyzes a conversion of the fermentable carbon source to one or more intermediates in the pathway for the production of butadiene and the one or more polynucleotides coding for enzymes in a pathway that catalyze a conversion of one or more intermediates to butadiene.

These and other embodiments of the present disclosure will be disclosed in further detail herein below.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

Figure 1:
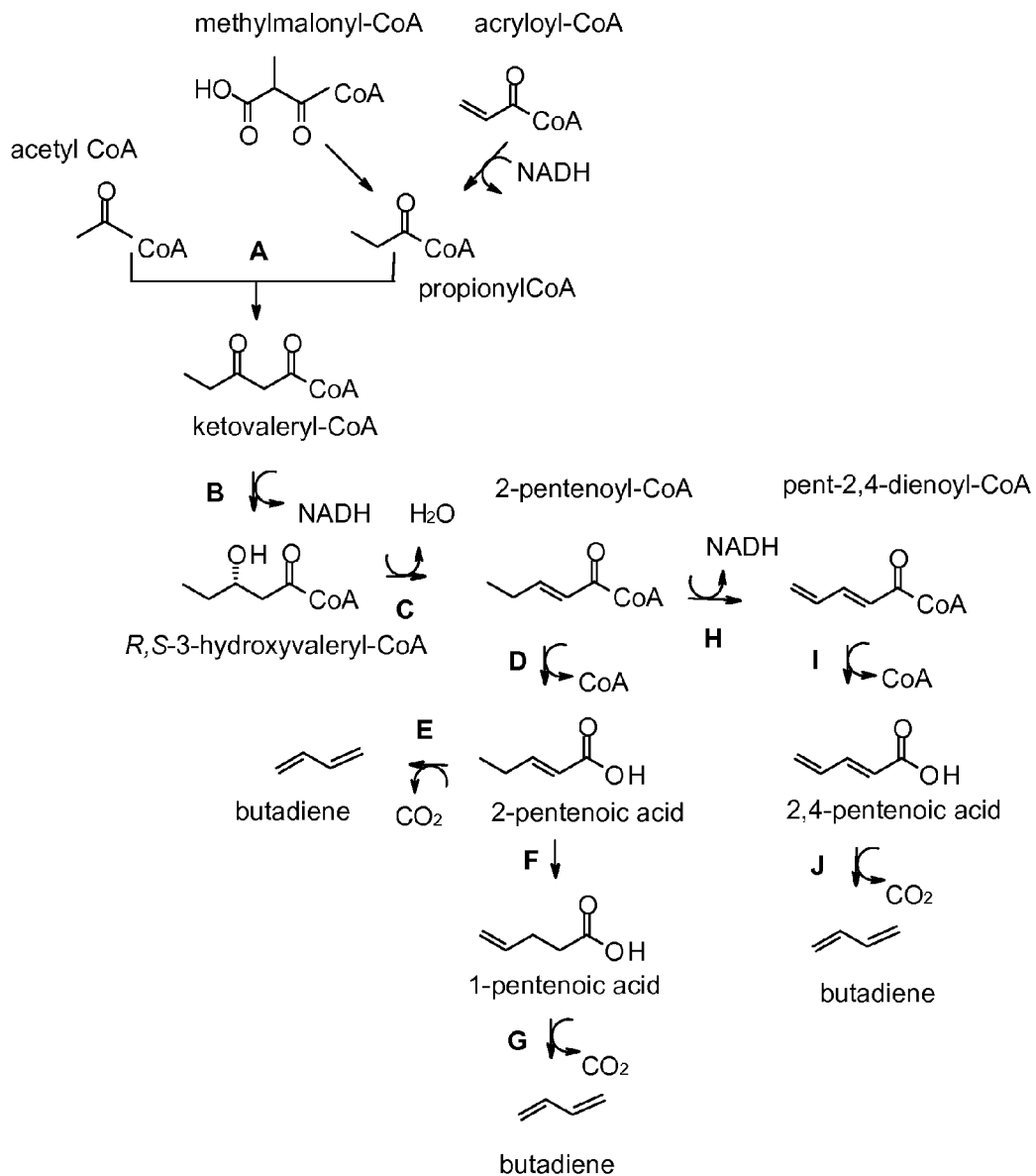
FIG. 1 depicts an exemplary pathway for the production of butadiene from a fermentable carbon source via an acetyl-CoA and propionyl-CoA intermediate.
Figure 2:
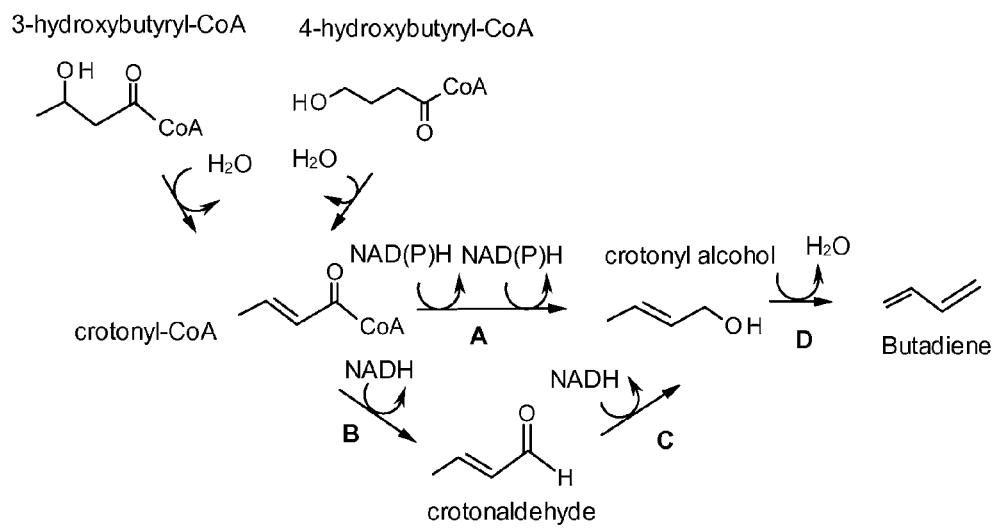
FIG. 2 depicts an exemplary pathway for the production of butadiene from a fermentable carbon source via a crotonyl-CoA intermediate.
Figure 3:
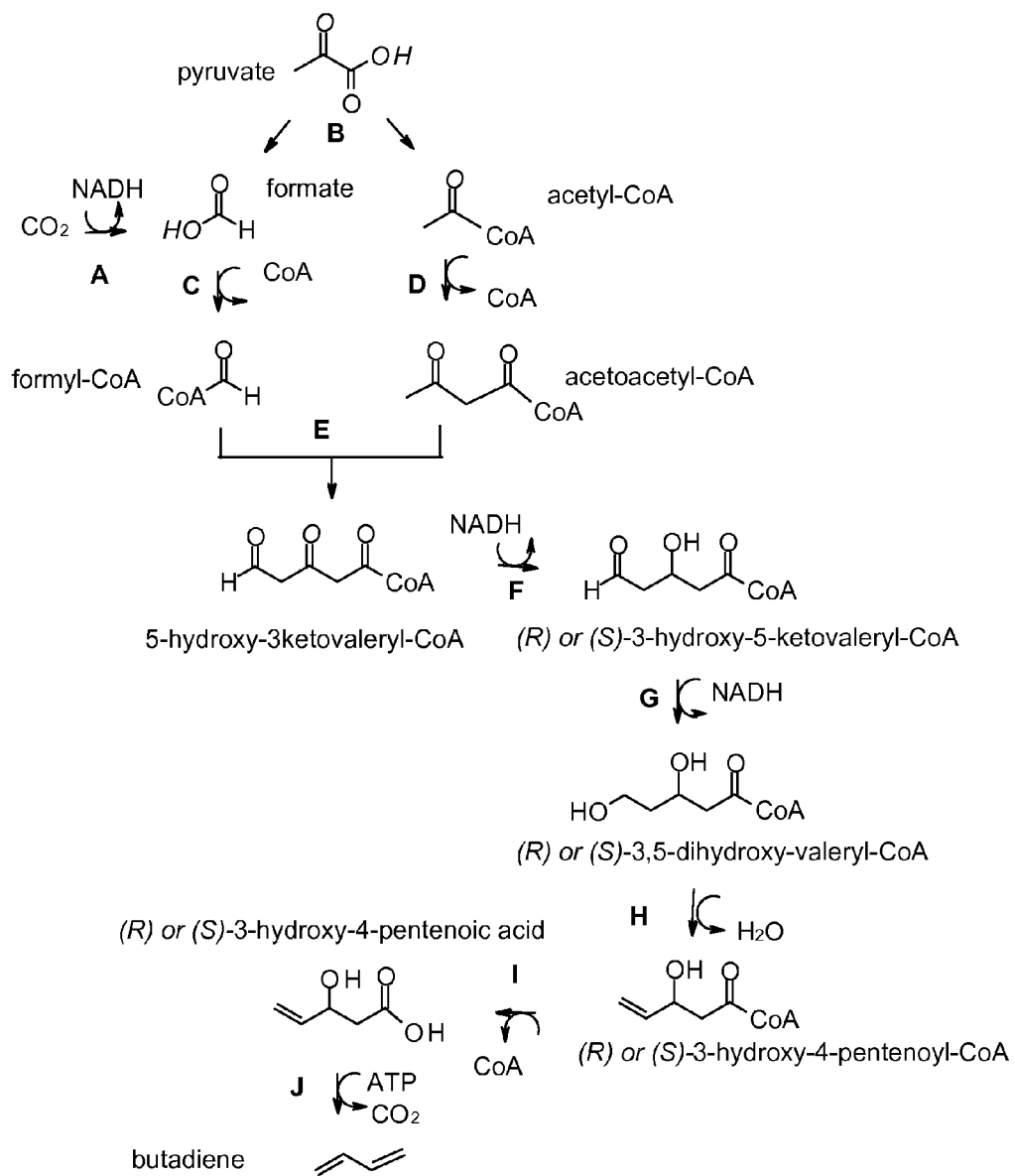
FIG. 3 depicts an exemplary pathway for the production of butadiene from a fermentable carbon source via a formic acid intermediate.

The present disclosure generally relates to microorganisms (e.g., non-naturally occurring microorganisms; modified microorganisms) that comprise a genetically modified pathway and uses of the microorganisms for the conversion of a fermentable carbon source to butadiene (see, FIGS. 1-3). Such microorganisms comprise one or more polynucleotides coding for enzymes that catalyze a conversion of a fermentable carbon source to butadiene via novel enzymatic pathways. Optionally, the produced butadiene may subsequently be converted to polybutadiene or any number of other butadiene-containing polymers.

This disclosure provides, in part, the discovery of novel enzymatic pathways including, for example, novel combinations of enzymatic pathways, for the production of butadiene from a carbon source (e.g., a fermentable carbon source). The enzymatic pathways disclosed herein permit the enzymatic production of butadiene via: an acetyl-CoA and propionyl-CoA intermediate; a crotonyl-CoA intermediate; and/or a formic acid intermediate.

The methods provided herein provide end-results similar to those of sterilization without the high capital expenditure and continuing higher management costs that are typically required to establish and maintain sterility throughout a production process. In this regard, most industrial-scale butadiene production processes are operated in the presence of measurable numbers of bacterial contaminants due to the aerobic nature of their processes. It is believed that bacterial contamination of a butadiene production processes causes a reduction in product yield and an inhibition of growth of the microorganism producing butadiene. Such drawbacks of prior methods are avoided by the presently disclosed methods as the toxic nature of the produced butadiene reduces contaminants in the production process.

The enzymatic pathways disclosed herein are advantageous over prior known enzymatic pathways for the production of butadiene in that the enzymatic pathways disclosed herein are ATP positive and when combined with a NADH consuming pathway it can provide an anaerobic pathway for butadiene. While it is possible to use aerobic processes to produce butadiene, anaerobic processes are preferred due to the risk incurred when olefins (which are by nature are explosive) are mixed with oxygen during the fermentation process, especially for butadiene fermentation. Moreover, the supplementation of oxygen and nitrogen in a fermenter requires an additional investment for air compressor, fermenters (bubble column or air-lift fermenter), temperature control and nitrogen. The presence of oxygen can also catalyze the polymerization of butadiene and can promote the growth of aerobic contaminants in the fermenter broth. Additionally, aerobic fermentation processes for the production of butadiene present several drawbacks at industrial scale (where it is technically challenging to maintain aseptic conditions) such as the fact that: (i) greater biomass is obtained reducing overall yields on carbon for the desired products; (ii) the presence and oxygen favors the growth of contaminants (Weusthuis et al., 2011, *Trends in Biotechnology*, 2011, Vol. 29, No. 4, 153-158) and (iii) the mixture of oxygen and gaseous compounds such as butadiene, poses serious risks of explosion, (iv) the oxygen can catalyze the unwanted reaction of polymerization of the olefin and, finally, (v) higher costs of fermentation and purification in aerobic conditions. Additionally, the butadiene produced by the processes disclosed herein is not diluted by $O_2$ and $N_2$ thus preventing both costly and time-consuming purification of the produced butadiene.

It will be understood that the steps involved in any and all of the methods described herein may be performed in any order and are not to be limited or restricted to the order in which they are particularly recited. For example, the present disclosure provides methods of producing butadiene from a fermentable carbon source, comprising: providing a fermentable carbon source; contacting the fermentable carbon source with a microorganism comprising one or more polynucleotides coding for enzymes in a pathway that catalyzes a conversion of the fermentable carbon source to one or more intermediates in a pathway for the production of butadiene, and one or more polynucleotides coding for enzymes in a pathway that catalyze a conversion of the one or more intermediates to butadiene in a fermentation media; and expressing the one or more polynucleotides coding for the enzymes in the pathway that catalyzes a conversion of the fermentable carbon source to one or more intermediates in a pathway for the production of butadiene and one or more polynucleotides coding for enzymes in a pathway that catalyze a conversion of the one or more intermediates to butadiene in the microorganism to produce butadiene. As such, expression of the one or more polynucleotides coding for the enzymes in the pathway that catalyzes a conversion of the fermentable carbon source to one or more intermediates in a pathway for the production of butadiene and one or more polynucleotides coding for enzymes in a pathway that catalyze a conversion of the one or more intermediates to butadiene in the microorganism to produce butadiene may be performed prior to or after contacting the fermentable carbon source with a microorganism comprising one or more polynucleotides coding for enzymes in a pathway that catalyzes a conversion of the fermentable carbon source to one or more intermediates in a pathway for the production of butadiene, and one or more polynucleotides coding for enzymes in a pathway that catalyze a conversion of the one or more intermediates to butadiene in a fermentation media.

It will also be understood that the microorganisms disclosed herein may comprise the entire pathway disclosed in any of FIGS. 1-3 including, comprising all of the polynucleotides that code for enzymes that catalyze a conversion of a fermentable carbon source to butadiene. Alternatively, it will also be understood that the microorganisms disclosed herein may comprises one or more of the polynucleotides coding for enzymes that catalyze a conversion of a fermentable carbon source to butadiene in any of FIGS. 1-3 (e.g., a microorganism may comprise 2, 3, 4, 5, 6, 7, 8, 9, 10 or more polynucleotides that code for enzymes that catalyze a conversion of a fermentable carbon source to butadiene as disclosed in any of FIGS. 1-3.

In some embodiments, the ratio of grams of the produced butadiene to grams of the fermentable carbon source is 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, or 1.00.

In some embodiments, a number of moles of carbon in the produced butadiene comprises 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of a number of moles of carbon in the fermentable carbon source.

As used herein, "butadiene" is intended to mean buta-1,3-diene or 1,3-butadiene (CAS 106-99-0), with a general formula $CH_2=CH-CH=CH_2$, and a molecular mass of 54.09 g/mol.

As used herein, the term "biological activity" or "functional activity," when referring to a protein, polypeptide or peptide, may mean that the protein, polypeptide or peptide exhibits a functionality or property that is useful as relating to some biological process, pathway or reaction. Biological or functional activity can refer to, for example, an ability to interact or associate with (e.g., bind to) another polypeptide or molecule, or it can refer to an ability to catalyze or regulate the interaction of other proteins or molecules (e.g., enzymatic reactions).

As used herein, the term "culturing" may refer to growing a population of cells, e.g., microbial cells, under suitable conditions for growth, in a liquid or on solid medium.

As used herein, the term "derived from" may encompass the terms originated from, obtained from, obtainable from, isolated from, and created from, and generally indicates that one specified material finds its origin in another specified material or has features that can be described with reference to the another specified material.

As used herein, the term "an expression vector" may refer to a DNA construct containing a polynucleotide or nucleic acid sequence encoding a polypeptide or protein, such as a DNA coding sequence (e.g., gene sequence) that is operably linked to one or more suitable control sequence(s) capable of affecting expression of the coding sequence in a host. Such control sequences include a promoter to affect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome (e.g., independent vector or plasmid), or may, in some instances, integrate into the genome itself (e.g., integrated vector). The plasmid is the most commonly used form of expression vector. However, the disclosure is intended to include such other forms of expression vectors that serve equivalent functions and which are, or become, known in the art.

As used herein, the term "expression" may refer to the process by which a polypeptide is produced based on a nucleic acid sequence encoding the polypeptides (e.g., a gene). The process includes both transcription and translation.

As used herein, the term "gene" may refer to a DNA segment that is involved in producing a polypeptide or protein (e.g., fusion protein) and includes regions preceding and following the coding regions as well as intervening sequences (introns) between individual coding segments (exons).

As used herein, the term "heterologous," with reference to a nucleic acid, polynucleotide, protein or peptide, may refer to a nucleic acid, polynucleotide, protein or peptide that does not naturally occur in a specified cell, e.g., a host cell. It is intended that the term encompass proteins that are encoded by naturally occurring genes, mutated genes, and/or synthetic genes. In contrast, the term homologous, with reference to a nucleic acid, polynucleotide, protein or peptide, refers to a nucleic acid, polynucleotide, protein or peptide that occurs naturally in the cell.

As used herein, the term a "host cell" may refer to a cell or cell line, including a cell such as a microorganism which a recombinant expression vector may be transfected for expression of a polypeptide or protein (e.g., fusion protein). Host cells include progeny of a single host cell, and the progeny may not necessarily be completely identical (in morphology or in total genomic DNA complement) to the original parent cell due to natural, accidental, or deliberate mutation. A host cell may include cells transfected or transformed in vivo with an expression vector.

As used herein, the term "introduced," in the context of inserting a nucleic acid sequence or a polynucleotide sequence into a cell, may include transfection, transformation, or transduction and refers to the incorporation of a nucleic acid sequence or polynucleotide sequence into a eukaryotic or prokaryotic cell wherein the nucleic acid sequence or polynucleotide sequence may be incorporated into the genome of the cell (e.g., chromosome, plasmid, plastid, or mitochondrial DNA), converted into an autonomous replicon, or transiently expressed.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Non-naturally occurring microbial organisms of the disclosure can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely. Those skilled in the art will understand that the genetic alterations, including metabolic modifications exemplified herein, are described with reference to a suitable host organism such as $E.$ $coli$ and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the $E.$ $coli$ metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

As used herein, "butadiene" is intended to mean a conjugated linear diene with the molecular formula C4H6, a general formula of $CH_2$=CH—CH=$CH_2$ and a molecular mass of 54.09 g/mol. Butadiene is also known in the art as 1,3-butadiene, but-1,3-diene, biethylene, erythrene, divinyl, and vinylethylene.

As used herein, the term "operably linked" may refer to a juxtaposition or arrangement of specified elements that allows them to perform in concert to bring about an effect. For example, a promoter may be operably linked to a coding sequence if it controls the transcription of the coding sequence.

As used herein, the term "a promoter" may refer to a regulatory sequence that is involved in binding RNA polymerase to initiate transcription of a gene. A promoter may be an inducible promoter or a constitutive promoter. An inducible promoter is a promoter that is active under environmental or developmental regulatory conditions.

As used herein, the term "a polynucleotide" or "nucleic acid sequence" may refer to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Such polynucleotides or nucleic acid sequences may encode amino acids (e.g., polypeptides or proteins such as fusion proteins). Because the genetic code is degenerate, more than one codon may be used to encode a particular amino acid, and the present disclosure encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.).

Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms polynucleotide, nucleic acid, and oligonucleotide are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S (thioate), P(S)S (dithioate), (O)NR$_2$ (amidate), P(O)R, P(O)OR', COCH$_2$ (formacetal), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, the term a "protein" or "polypeptide" may refer to a composition comprised of amino acids and recognized as a protein by those of skill in the art. The conventional one-letter or three-letter code for amino acid residues is used herein. The terms protein and polypeptide are used interchangeably herein to refer to polymers of amino acids of any length, including those comprising linked (e.g., fused) peptides/polypeptides (e.g., fusion proteins). The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, related proteins, polypeptides or peptides may encompass variant proteins, polypeptides or peptides. Variant proteins, polypeptides or peptides differ from a parent protein, polypeptide or peptide and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence.

As used herein, the term "recovered," "isolated," "purified," and "separated" may refer to a material (e.g., a protein, peptide, nucleic acid, polynucleotide or cell) that is removed from at least one component with which it is naturally associated. For example, these terms may refer to a material which is substantially or essentially free from components which normally accompany it as found in its native state, such as, for example, an intact biological system.

As used herein, the term "recombinant" may refer to nucleic acid sequences or polynucleotides, polypeptides or proteins, and cells based thereon, that have been manipulated by man such that they are not the same as nucleic acids, polypeptides, and cells as found in nature. Recombinant may also refer to genetic material (e.g., nucleic acid sequences or polynucleotides, the polypeptides or proteins they encode, and vectors and cells comprising such nucleic acid sequences or polynucleotides) that has been modified to alter its sequence or expression characteristics, such as by mutating the coding sequence to produce an altered polypeptide, fusing the coding sequence to that of another coding sequence or gene, placing a gene under the control of a different promoter, expressing a gene in a heterologous organism, expressing a gene at decreased or elevated levels, expressing a gene conditionally or constitutively in manners different from its natural expression profile, and the like.

As used herein, the term "selective marker" or "selectable marker" may refer to a gene capable of expression in a host cell that allows for ease of selection of those hosts containing an introduced nucleic acid sequence, polynucleotide or vector. Examples of selectable markers include but are not limited to antimicrobial substances (e.g., hygromycin, bleomycin, or chloramphenicol) and/or genes that confer a metabolic advantage, such as a nutritional advantage, on the host cell.

As used herein, the term "substantially similar" and "substantially identical" in the context of at least two nucleic acids, polynucleotides, proteins or polypeptides may mean that a nucleic acid, polynucleotide, protein or polypeptide comprises a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) nucleic acid, polynucleotide, protein or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:10915; Karin et al. (1993) Proc. Natl. Acad. Sci. 90:5873; and Higgins et al. (1988) Gene 73:237). Software for performing BLAST analyses is publicly available through the National Center for Biotechnology Information. Also, databases may be searched using FASTA (Person et al. (1988) Proc. Natl. Acad. Sci. 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

As used herein, the term "transfection" or "transformation" may refer to the insertion of an exogenous nucleic acid or polynucleotide into a host cell. The exogenous nucleic acid or polynucleotide may be maintained as a non-integrated vector, for example, a plasmid, or alternatively, may be integrated into the host cell genome. The term transfecting or transfection is intended to encompass all conventional techniques for introducing nucleic acid or polynucleotide into host cells. Examples of transfection techniques include, but are not limited to, calcium phosphate precipitation, DEAE-dextran-mediated transfection, lipofection, electroporation, and microinjection.

As used herein, the term "transformed," "stably transformed," and "transgenic" may refer to a cell that has a non-native (e.g., heterologous) nucleic acid sequence or polynucleotide sequence integrated into its genome or as an episomal plasmid that is maintained through multiple generations.

As used herein, the term "vector" may refer to a polynucleotide sequence designed to introduce nucleic acids into one or more cell types. Vectors include cloning vectors, expression vectors, shuttle vectors, plasmids, phage particles, single and double stranded cassettes and the like.

As used herein, the term "wild-type," "native," or "naturally-occurring" proteins may refer to those proteins found in nature. The terms wild-type sequence refers to an amino acid or nucleic acid sequence that is found in nature or naturally occurring. In some embodiments, a wild-type sequence is the starting point of a protein engineering project, for example, production of variant proteins.

Unless defined otherwise herein, all technical and scientific terms used herein have the same meaning as commonly understood by one of ordinary skill in the art to which this disclosure belongs. Singleton, et al., Dictionary of Microbiology and Molecular Biology, second ed., John Wiley and Sons, New York (1994), and Hale & Markham, The Harper Collins Dictionary of Biology, Harper Perennial, NY (1991) provide one of skill with a general dictionary of many of the terms used in this disclosure. Further, it will be understood that any of the substrates disclosed in any of the pathways herein may alternatively include the anion or the cation of the substrate.

Numeric ranges provided herein are inclusive of the numbers defining the range.

Unless otherwise indicated, nucleic acids sequences are written left to right in 5' to 3' orientation; amino acid sequences are written left to right in amino to carboxyl orientation, respectively.

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

Modification of Microorganism

A microorganism may be modified (e.g., genetically engineered) by any method known in the art to comprise and/or express (e.g., including over express) one or more polynucleotides (e.g., heterologous polynucleotides and/or non-heterologous polynucleotides) coding for enzymes in one or more pathways that are capable of converting a fermentable carbon source to butadiene. The microorganism may naturally express all of the enzymes in one or more pathways needed to convert a fermentable carbon source to butadiene or may be modified to express including, for example, over express, one or more enzymes in the one or more pathways. In some embodiments, the microorganism may comprise fewer than all of the enzymes in such pathway and polynucleotides coding for the missing enzymes may be genetically introduced into the microorganism. For example, the modified microorganism may be modified to comprise one or more polynucleotides coding for enzymes that catalyze a conversion of a fermentable carbon source (e.g., glucose) to one or more intermediates (e.g., acetyl-CoA and propionyl-CoA; crotonyl-CoA; and/or formic acid) in a pathway for the production of butadiene. Additionally or alternatively, the modified microorganism may be modified to comprise one or more polynucleotides coding for enzymes that catalyze a conversion of the one or more intermediates (e.g., acetyl-CoA and propionyl-CoA; crotonyl-CoA; and/or formic acid) to butadiene. In some embodiments, a polynucleotide may code for an enzyme that catalyzes a conversion of one or more intermediates in a pathway for the production of butadiene. In some embodiments, polynucleotides may be modified (e.g., genetically engineered) to modulate (e.g., increase or decrease) the substrate specificity of the encode enzyme, or the polynucleotides may be modified to change the substrate specificity of the encoded enzyme (e.g., a polynucleotide that codes for an enzyme with specificity for a substrate may be modified such that the enzyme has specificity for another substrate). Preferred microorganisms may comprise polynucleotides coding for one or more of the enzymes as set forth in any one of Tables 1-3 and FIG. 1-3.

A microorganism may comprise one or more polynucleotides coding for enzymes in a pathway that catalyze a conversion of acetyl-CoA and propionyl-CoA to butadiene. In some embodiments, the one or more polynucleotides coding for enzymes in a pathway that catalyze a conversion of acetyl-CoA and propionyl-CoA to butadiene may include, but are not limited to:

one or more polynucleotides coding for enzymes in a pathway that catalyze a conversion of acetyl-CoA and propionyl-CoA to ketovaleryl-CoA (e.g., a thiolase);

one or more polynucleotides coding for enzymes in a pathway that catalyze a conversion of ketovaleryl-CoA to (R) or (S) 3-hydroxyaleryl-CoA (e.g., a hydroxyvaleryl-CoA dehydrogenase);

one or more polynucleotides coding for enzymes in a pathway that catalyze a conversion of (R) or (S) hydroxyaleryl-CoA to 2-pentenoyl-CoA (e.g., a hydroxyvaleryl-CoA dehydratase);

one or more polynucleotides coding for enzymes in a pathway that catalyze a conversion of 2-pentenoyl-CoA to 2-pentenoic acid (e.g., a pentenoyl-CoA hydrolase or transferase);

one or more polynucleotides coding for enzymes in a pathway that catalyze a conversion of 2-pentenoic acid to butadiene (e.g., a 2-pentenoic acid decarboxylase);

one or more polynucleotides coding for enzymes in a pathway that catalyze a conversion of 2-pentenoic acid to 4-pentenoic acid (e.g., a transposing C=C bonds isomerase);

one or more polynucleotides coding for enzymes in a pathway that catalyze a conversion of 4-pentenoic acid to butadiene (e.g., a 4-pentenoic acid decarboxylase);

one or more polynucleotides coding for enzymes in a pathway that catalyze a conversion of 2-pentenoyl-CoA to pent-2,4-dienoyl-CoA (e.g., a pentenoyl-CoA dehydrogenase);

one or more polynucleotides coding for enzymes in a pathway that catalyze a conversion of pent-2,4-dienoyl-CoA to pent-2,4-dienoic (e.g., a pent-2,4-dienoyl-CoA hydrolase, or transferase); and/or one or more polynucleotides coding for enzymes in a pathway that catalyze a conversion of 2,4-pentenoic acid to butadiene (e.g., a pent,2,4-dienoic acid decarboxylase).

In some embodiments, the microorganism further comprises one or more polynucleotides coding for enzymes in a pathway that catalyze a conversion of a fermentable carbon source (e.g., glucose) to methylmalonyl-CoA and/or acryloyl-CoA.

In some embodiments, a microorganism is provided that comprises one or more of the above polynucleotides including, all, of the polynucleotides above.

Exemplary enzymes which convert acetyl-CoA and propionyl-CoA to butadiene are presented in Table 1 below, as well as, the substrates that they act upon and product that they produce. The enzyme number represented in Table 1 correlates with the enzyme numbering used in FIG. 1 which schematically represents the enzymatic conversion of a fermentable carbon source to butadiene through an acetyl-CoA and propionyl-CoA intermediate.

TABLE 1

Production of butadiene via acetyl-CoA and propionyl-CoA intermediates.

| Enzyme No. | Enzyme Name | E.C. number | Mediated Conversion |
| --- | --- | --- | --- |
| A | thiolase | 2.3.1. | acetyl-CoA + propionyl-CoA → ketovaleryl-CoA |
| B | hydroxyvaleryl-CoA dehydrogenase | 1.1.1. 1.1.1. | ketovaleryl-CoA + NADH→ (R) or (S) 3-hydroxyaleryl-CoA |
| C | hydroxyvaleryl-CoA dehydratase | 4.2.1. | (R) or (S) hydroxyaleryl-CoA→ 2-pentenoyl-CoA |
| D | pentenoyl-CoA hydrolase or transferase | 3.1.2, 2.8.3 or 2.3.3 | 2-pentenoyl-CoA → 2-pentenoic acid |
| E | 2-pentenoic acid decarboxylase | 4.1.1. | 2-pentenoic acid → butadiene |
| F | transposing C=C bonds isomerase | 5.3.3 | 2-pentenoic acid → 4-pentenoic acid |
| G | 4-pentenoic acid decarboxylase | 4.1.1.33 | 4-pentenoic acid → butadiene |
| H | pentenoyl-CoA dehydrogenase | 1.3.1. | 2-pentenoyl-CoA → pent-2,4-dienoyl-CoA |
| I | pent-2,4-dienoyl-CoA hydrolase, or transferase | 3.1.2, 2.8.3 or 2.3.3 | pent-2,4-dienoyl-CoA → pent-2,4-dienoic |
| J | pent,2,4-dienoic acid decarboxylase | 4.1.1. | 2,4-pentenoic acid → butadiene |

A microorganism may comprise one or more polynucleotides coding for enzymes in a pathway that catalyze a conversion of crotonyl-CoA to butadiene. In some embodiments, the one or more polynucleotides coding for enzymes in a pathway that catalyze a conversion of crotonyl-CoA to butadiene may include, but are not limited to:

one or more polynucleotides coding for enzymes in a pathway that catalyze a conversion of crotonyl-CoA to crotonyl alcohol (e.g., a crotonyl-CoA reductase (bifunctional));

one or more polynucleotides coding for enzymes in a pathway that catalyze a conversion of crotonyl-CoA to crotonaldehyde (e.g., a crotonaldehyde dehydrogenase);

one or more polynucleotides coding for enzymes in a pathway that catalyze a conversion of crotonaldehyde to crotonyl alcohol (e.g., a crotonyl alcohol dehydrogenase); and/or one or more polynucleotides coding for enzymes in a pathway that catalyze a conversion of crotonyl alcohol to butadiene (e.g., a crotonyl alcohol dehydratase).

In some embodiments, a microorganism is provided that comprises one or more of the above polynucleotides including, all, of the polynucleotides above.

In preferred embodiments, the microorganism further comprises one or more polynucleotides coding for enzymes in a pathway that catalyze a conversion of a fermentable carbon source (e.g., glucose) to crotonyl-CoA.

In some embodiments, the microorganism may further comprise one or more polynucleotides coding for enzymes in a pathway that catalyze a conversion of a fermentable carbon source (e.g., glucose) to 3-hydroxybutyryl-CoA and/or 4-hydroxybutyryl-CoA. In such embodiments, the microorganism further comprises one or more polynucleotides coding for enzymes in a pathway that catalyze a conversion of 3-hydroxybutyryl-CoA to crotonyl-CoA and/or one or more polynucleotides coding for enzymes in a pathway that catalyze a conversion of 4-hydroxybutyryl-CoA to crotonyl-CoA.

Exemplary enzymes which convert crotonyl-CoA to butadiene are presented in Table 1 below, as well as, the substrates that they act upon and product that they produce. The enzyme number represented in Table 1 correlates with the enzyme numbering used in FIG. 1 which schematically represents the enzymatic conversion of a fermentable carbon source to butadiene through a crotonyl-CoA intermediate.

TABLE 2

Production of butadiene via a crotonyl-CoA intermediate.

| Enzyme No. | Enzyme Name | E.C. number | Mediated Conversion |
| --- | --- | --- | --- |
| A | crotonyl-CoA reductase (bifuncional) | 1.1.1 | crotonyl-CoA → crotonyl alcohol |
| B | crotonaldehyde dehydrogenase | 1.2.1 | crotonyl-CoA → crotonaldehyde |
| C | crotonyl alcohol dehydrogenase | 1.1.1 1.1.1.1 | crotonaldehyde → crotonyl alcohol |
| D | crotonyl alcohol dehydratase | 4.2.1 4.2.1. | crotonyl alcohol → butadiene |

A microorganism may comprise one or more polynucleotides coding for enzymes in a pathway that catalyze a conversion of formic acid to butadiene. In some embodiments, the one or more polynucleotides coding for enzymes in a pathway that catalyze a conversion of formic acid to butadiene may include, but are not limited to:

one or more polynucleotides coding for enzymes in a pathway that catalyze a conversion of $CO_2$ to formic acid (e.g., a formate dehydrogenase);

one or more polynucleotides coding for enzymes in a pathway that catalyze a conversion of pyruvate and CoA to acetyl-CoA and formic acid (e.g., an acetyl-CoA:formate C-acetyltransferase);

one or more polynucleotides coding for enzymes in a pathway that catalyze a conversion of formic acid to formyl-CoA (e.g., a formyl-CoA transferase or synthase);

one or more polynucleotides coding for enzymes in a pathway that catalyze a conversion of 2 acetyl-CoA to acetoacetyl-CoA (e.g., an acetoacetyl-CoA thiolase);

one or more polynucleotides coding for enzymes in a pathway that catalyze a conversion of acetoacetyl-CoA and formyl-CoA to 3,5-ketovaleryl-CoA (e.g., a 3,5-ketovaleryl-CoA thiolase);

one or more polynucleotides coding for enzymes in a pathway that catalyze a conversion of 3,5-ketovaleryl-CoA to (R) or (S)-5-hydroxy-3-ketovaleryl-CoA (e.g., a 3,5-ketovaleryl-CoA dehydrogenase);

one or more polynucleotides coding for enzymes in a pathway that catalyze a conversion of (R) or (S)-5-hydroxy-3-ketovaleryl-CoA to (R) or (S)-3,5-dihydroxyaleryl-CoA (e.g., a 5-hydroxy-3-ketovaleryl-CoA dehydrogenase);

one or more polynucleotides coding for enzymes in a pathway that catalyze a conversion of (R) or (S)-3,5-dihydroxyaleryl-CoA to (R) or (S) 3-hydroxy-4-pentenoyl-CoA (e.g., a 3,5-hydroxyvaleryl-CoA dehydratase);

one or more polynucleotides coding for enzymes in a pathway that catalyze a conversion of (R) or (S)-3-hydroxy-4-pentenoyl-CoA to 3-hydroxy-4-pentenoic acid (e.g., a 3-hydroxy-4-pentenoyl-CoA hydrolase, transferase or synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase).

In some embodiments, the microorganism further comprises one or more polynucleotides coding for enzymes in a pathway that catalyze a conversion of a fermentable carbon source (e.g., glucose) to pyruvate.

In some embodiments, a microorganism is provided that comprises one or more of the above polynucleotides including, all, of the polynucleotides above.

Exemplary enzymes which convert formic acid to butadiene are presented in Table 3 below, as well as, the substrates that they act upon and product that they produce. The enzyme number represented in Table 3 correlates with the enzyme numbering used in FIG. 3 which schematically represents the enzymatic conversion of a fermentable carbon source to butadiene through a formic acid intermediate.

TABLE 3

Production of butadiene via a formic acid intermediate.

| Enzyme No. | Enzyme Name | E.C. number | Mediated Conversion |
|---|---|---|---|
| A | formate dehydrogenase | 1.2.1.2 | $CO_2$ → Formate |
| B | acetyl-CoA:formate C-acetyltransferase | 2.3.1.54 | pyruvate + CoA → acetyl-CoA + formic acid |
| C | formyl-CoA transferase or synthase | 2.8.3.16 6.2.1 | formic acid → formyl-CoA |
| D | acetoacetyl-CoA thiolase | 2.3.1.16 | 2 acetyl-CoA → acetoacetyl-CoA |
| E | 3,5-ketovaleryl-CoA thiolase | 2.3.1. 2.3.1.16 | acetoacetyl-CoA + formyl-CoA → 3,5-ketovaleryl-CoA |
| F | 3,5-ketovaleryl-CoA dehydrogenase | | 3,5-ketovaleryl-CoA → (R) or 5-(S)-hydroxy-3-Ketovaleryl-CoA |
| G | 5-hydroxy-3-ketovaleryl-CoA dehydrogenase | 1.1.1.35 1.1.1.36 | (R) or (S)-5-hydroxy-3-ketovaleryl-CoA → (R) or (S)-3,5-dihydroxyaleryl-CoA |
| H | 3,5-hydroxyvaleryl-CoA dehydratase | 4.2.1.17 4.2.1.54 | (R) or (S)-3,5-dihydroxyaleryl-CoA→ (R) or (S) 3-hydroxy-4-pentenoyl-CoA |

TABLE 3-continued

Production of butadiene via a formic acid intermediate.

| Enzyme No. | Enzyme Name | E.C. number | Mediated Conversion |
|---|---|---|---|
| I | 3-hydroxy-4-pentenoyl-CoA hydrolase, transferase or synthase | 3.1.2, 2.8.3 or 2.3.3 | (R) or (S)-3-hydroxy-4-pentenoyl-CoA → 3-hydroxy-4-pentenoic acid |
| J | 3-hydroxy-4-pentenoic acid decarboxylase | 4.1.1.33 | 3-hydroxy-4-pentenoic acid → butadiene |

A microorganism is also provided that comprises one or more polynucleotides coding for enzymes in a pathway that catalyze a conversion of a fermentable carbon source to acetyl-CoA and propionyl-CoA and one or more polynucleotides coding for enzymes in a pathway that catalyze a conversion of acetyl-CoA and propionyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to methylmalonyl-CoA; one or more polynucleotides coding for enzymes in a pathway that catalyze a conversion of methylmalonyl-CoA to propionyl-CoA; one or more polynucleotides coding for enzymes in a pathway that catalyze a conversion of pyruvate to acryloyl-CoA; one or more polynucleotides coding for enzymes in a pathway that catalyze a conversion of acryloyl-CoA to propionyl-CoA; one or more polynucleotides coding for enzymes in a pathway that catalyze a conversion of acetyl-CoA and propionyl-CoA to ketovaleryl-CoA (e.g., a thiolase); one or more polynucleotides coding for enzymes in a pathway that catalyze a conversion of ketovaleryl-CoA to (R) or (S) 3-hydroxyvaleryl-CoA (e.g., a hydroxyvaleryl-CoA dehydrogenase); one or more polynucleotides coding for enzymes in a pathway that catalyze a conversion of (R) or (S) 3-hydroxyvaleryl-CoA to 2-pentenoyl-CoA (e.g., a hydroxyvaleryl-CoA dehydratase); one or more polynucleotides coding for enzymes in a pathway that catalyze a conversion of 2-pentenoyl-CoA to 2-pentenoic acid (e.g., a pentenoyl-CoA hydrolase, a pentenoyl-CoA transferase or a pentenoyl-CoA synthase); one or more polynucleotides coding for enzymes in a pathway that catalyze a conversion of 2-pentenoic acid to 4-pentenoic acid (e.g., a transposing bonds C=C isomerase); and/or one or more polynucleotides coding for enzymes in a pathway that catalyze a conversion of 4-pentenoic acid to butadiene (e.g., a 4-pentenoic fatty acid decarboxylase or a 2-petenoic acid decarboxylase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source to ethyl-malonyl-CoA and one or more polynucleotides coding for enzymes in a pathway that catalyze a conversion of ethyl-malonyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyzes a conversion of pyruvate to acetyl-CoA; one or more polynucleotides coding for enzymes in a pathway that catalyzes a conversion of acetyl-CoA to acetoacetyl-CoA (e.g., an acetoacetyl-CoA thiolase); one or more polynucleotides coding for enzymes in a pathway that catalyzes a conversion of acetoacetyl-CoA to 3-hydroxybutyryl-CoA (e.g., a 3-hydroxybutyryl-CoA dehydrogenase); one or more polynucleotides coding for enzymes in a pathway that catalyzes a conversion of 3-hydroxybutyryl-CoA to crotonyl-CoA (e.g., a crotonase); one or more polynucleotides coding for enzymes in a pathway that catalyzes a conversion of crotonyl-CoA to ethyl-malonyl-CoA (e.g., a crotonyl-CoA carboxylase/reductase); one or more polynucleotides coding for enzymes in a pathway that catalyzes a conversion of crotonyl-CoA to butyric acid (e.g., butyryl-CoA dehydrogenase); one or more polynucleotides coding for enzymes in a pathway that catalyzes a conversion of butyric acid to ethyl-malonyl-CoA (e.g., a butanoyl-CoA:carbon-dioxide ligase); one or more polynucleotides coding for enzymes in a pathway that catalyze a conversion of ethyl-malonyl-CoA to 2-(formol)butanoic acid (e.g., an ethyl-malonyl-CoA reductase (aldehyde forming)); one or more polynucleotides coding for enzymes in a pathway that catalyze a conversion of 2-(formol)butanoic acid to 2-(hydroxymethyl)butanoic acid (e.g., a 2-(formyl)butanoic acid reducatase (alcohol forming)); one or more polynucleotides coding for enzymes in a pathway that catalyze a conversion of ethyl malonyl-CoA to 2-(hydroxymethyl)butanoic acid (e.g., an ethyl-malonyl-CoA reductase (alcohol forming)); one or more polynucleotides coding for enzymes in a pathway that catalyze a conversion of 2-(hydroxymethyl)butanoic acid to 2-(phosphanyloxymethyl)butanoic acid (e.g., a 2-(hydroxymethyl)butanoc acid kinase); one or more polynucleotides coding for enzymes in a pathway that catalyze a conversion of 2-(phosphanyloxymethyl)butanoic acid to 2-(diphosphanyloxymethyl)butanoic acid (e.g., a 2-(phosphanyloxymethyl)butanoic acid kinase); one or more polynucleotides coding for enzymes in a pathway that catalyze a conversion of 2-(diphosphanyloxymethyl)butanoic acid to [(E)-but-2-enoxy]-phosphanyl-phosphane (e.g., 2-(diphosphanyloxymethyl)butanoic acid decarboxylase); and/or one or more polynucleotides coding for enzymes in a pathway that catalyze a conversion of [(E)-but-2-enoxy]-phosphanyl-phosphane to butadiene (e.g., butadiene synthetase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source to 4-hydroxybutyryl-CoA and 3-hydroxybutyryl-CoA and one or more polynucleotides coding for enzymes in a pathway that catalyze a conversion of 4-hydroxybutyryl-CoA and 3-hydroxybutyryl-CoA to butadiene including, but not limited to: one or more polynucleotides coding for enzymes in a pathway that catalyze a conversion of a fermentable carbon source (e.g., glucose) to PEP; one or more polynucleotides coding for enzymes in a pathway that catalyze a conversion of PEP to oxaloacetate (e.g., a PEP carboxykinase or PEP carboxylase); one or more polynucleotides coding for enzymes in a pathway that catalyze a conversion of PEP to pyruvate; one or more polynucleotides coding for enzymes in a pathway that catalyze a conversion of pyruvate to acetyl-CoA (e.g., a pyruvate dehydrogenase or a pyruvate ferrodoxin oxirreductase) or oxaloacetate (e.g., a PEP carboxykinase or PEP carboxylase); one or more polynucleotides coding for enzymes in a pathway that catalyze a conversion of acetyl-CoA to acetoacetyl-CoA (e.g., an acetoacetyl-CoA thiolase); one or more polynucleotides coding for enzymes in a pathway that catalyze a conversion of acetoacetyl-CoA to 3-hydroxybutyryl-CoA (e.g., 3-hydroxybutyryl-CoA dehydrogenase); one or more polynucleotides coding for enzymes in a pathway that catalyze a conversion of oxaloacetate to malate (e.g., a malate dehydrogenase); one or more polynucleotides coding for enzymes in a pathway that catalyze a conversion of malate to fumarate (e.g., a fumarase); one or more polynucleotides coding for enzymes in a pathway that catalyze a conversion of fumarate to succinate (e.g., a fumarate reductase); one or more polynucleotides coding for enzymes in a pathway that catalyze a conversion of succinate to succinyl-CoA (e.g., a succinyl-CoA transferase or a succinyl-CoA synthase); one or more polynucleotides coding for enzymes in a pathway that catalyze a conversion of succinyl-CoA to succinyl semialdehyde (e.g., a succinyl-CoA reductase); one or more polynucleotides coding for enzymes in a pathway that catalyze a conversion of succinyl semialdehyde to 4-hydroxybutyrate (e.g., a 4-hydroxybutyrate dehydrogenase); one or more polynucleotides coding for enzymes in a pathway that catalyze a conversion of succinate to 4-hydroxybutyrate (e.g., a succinate reductase, phosphopantatheinylase or 4-hydroxybutyrate dehydrogenase); one or more polynucleotides coding for enzymes in a pathway that catalyze a conversion of 4-hydroxybutyrate to 4-hydroxybutyryl-CoA (e.g., a 4-hydroxybutyryl-CoA transferase or a 4-hydroxybutyryl-CoA synthase); one or more polynucleotides coding for enzymes in a pathway that catalyze a conversion of 4-hydroxybutyryl-CoA to crotonyl-CoA (e.g., a 4-hydroxybutyryl-CoA dehydratase); one or more polynucleotides coding for enzymes in a pathway that catalyze a conversion of 3-hydroxybutyryl-CoA to crotonyl-CoA (e.g., a crotonase); one or more polynucleotides coding for enzymes in a pathway that catalyze a conversion of crotonyl-CoA to crotonaldehyde (e.g., a crotonaldehyde dehydrogenase); one or more polynucleotides coding for enzymes in a pathway that catalyze a conversion of crotonaldehyde to crotonyl alcohol (e.g., an alcohol dehydrogenase); one or more polynucleotides coding for enzymes in a pathway that catalyze a conversion of crotonyl-CoA to crotonyl alcohol (e.g., a crotonyl-CoA reductase (bifunctional); and/or one or more polynucleotides coding for enzymes in a pathway that catalyze a conversion of crotonyl alcohol to butadiene (e.g., a crotonyl alcohol dehydratase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source to acryloyl-CoA and acetyl-CoA and one or more polynucleotides coding for enzymes in a pathway that catalyze a conversion of acryloyl-CoA and acetyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to lactate (e.g., a lactate dehydrogenase); one or more polynucleotides coding for enzymes in a pathway that catalyze a conversion of lactate to lactoyl-CoA (e.g., a lactoyl-CoA transferase or synthase); one or more polynucleotides coding for enzymes in a pathway that catalyze a conversion of lactoyl-CoA to acryloyl-CoA; one or more polynucleotides coding for enzymes in a pathway that catalyze a conversion of pyruvate to acetyl-CoA; one or more polynucleotides coding for enzymes in a pathway that catalyze a conversion of acryloyl-CoA and acetyl-CoA to 3-keto-4-pentenoyl-CoA (e.g., a thiolase); one or more polynucleotides coding for enzymes in a pathway that catalyze a conversion of 3-keto-4-pentenoyl-CoA to (R) or (S) 3-hydroxy-4-pentenoyl-CoA (e.g., a 3-keto-4-pentenoyl-CoA dehydrogenase); one or more polynucleotides coding for enzymes in a pathway that catalyze a conversion of (R) or (S) 3-hydroxy-4-pentenoyl-CoA to 3-hydroxy-4-pentenoic acid (e.g., a 3-hydroxy-4-pentenoyl-CoA transferase, a hydrolase, or a synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to acetyl-CoA and 3-hydroxypropionyl-CoA and one or more polynucleotides coding for enzymes in a pathway that catalyze a conversion of acetyl-CoA and 3-hydroxypropionyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to lactate; one or more polynucleotides coding for enzymes in a pathway that catalyze a conversion of lactate to lactoyl-CoA (e.g., lactoyl-CoA transferase or synthase); one or more polynucleotides coding for enzymes in a pathway that catalyze a conversion of lactoyl-CoA to acryloyl-CoA (e.g., lactoyl-CoA dehydratase); one or more polynucleotides coding for enzymes in a pathway that catalyze a conversion of acryloyl-CoA to 3-hydroxypropionyl-CoA (e.g., acryloyl-CoA hydratase); one or more polynucleotides coding for enzymes in a pathway that catalyze a conversion of pyruvate to 3-hydroxypropionate; one or more polynucleotides coding for enzymes in a pathway that catalyze a conversion of 3-hydroxypropionate to 3-hydroxypropionyl-CoA; one or more polynucleotides coding for enzymes in a pathway that catalyze a conversion of acetyl-CoA and 3-hydroxypropionyl-CoA to 5-hydroxy-3-ketovaleryl-CoA (e.g., a thiolase); one or more polynucleotides coding for enzymes in a pathway that catalyze a conversion of 5-hydroxy-3-ketovaleryl-CoA to (R) or (S) 3,5-dihydroxy-valeryl-CoA (e.g., a 5-hydroxy-3-ketovaleryl-CoA dehydrogenase); one or more polynucleotides coding for enzymes in a pathway that catalyze a conversion of (R) or (S) 3,5-dihydroxy-valeryl-CoA to (R) or (S) 3-hydroxy-4-pentenoyl-CoA (e.g., a 3,5-hydroxyvaleryl-CoA dehydratase); one or more polynucleotides coding for enzymes in a pathway that catalyze a conversion of (R) or (S) 3-hydroxy-4-pentenoyl-CoA to 3-hydroxy-4-pentenoic acid (e.g., a 3-hydroxy-4-pentenoyl-CoA hydrolase, transferase, or synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to acetoacetyl-CoA and formyl-CoA and one or more polynucleotides coding for enzymes in a pathway that catalyze a conversion acetoacetyl-CoA and formyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to acetyl-CoA and formate (e.g., a pyruvate formate-lyase); one or more polynucleotides coding for enzymes in a pathway that catalyze a conversion of acetyl-CoA to acetoacetyl-CoA (e.g., thiolase); one or more polynucleotides coding for enzymes in a pathway that catalyze a conversion of $CO_2$ to formate (e.g., formate dehydrogenase); one or more polynucleotides coding for enzymes in a pathway that catalyze a conversion of formate to formyl-CoA (e.g., a formyl-CoA transferase, or formyl-CoA synthase); one or more polynucleotides coding for enzymes in a pathway that catalyze a conversion of formyl-CoA and acetoacetyl-CoA to 3,5-ketovaleryl-CoA (e.g., a thiolase); one or more polynucleotides coding for enzymes in a pathway that catalyze a conversion of 3,5-ketovaleryl-CoA to 5-hydroxy-3-ketovaleryl-CoA; one or more polynucleotides coding for enzymes in a pathway that catalyze a conversion of 5-hydroxy-3-ketovaleryl-CoA to (R) or (S) 3,5-dihydroxy-valeryl-CoA (e.g., a 5-hydroxy-3-Ketovaleryl-CoA dehydrogenase); one or more polynucleotides coding for enzymes in a pathway that catalyze a conversion of (R) or (S) 3,5-dihydroxy-valeryl-CoA to (R) or (S) 3-hydroxy-4-pentenoyl-CoA (e.g., a 3,5-hydroxyvaleryl-CoA dehydratase); one or more polynucleotides coding for enzymes in a pathway that catalyze a conversion of (R) or (S) 3-hydroxy-4-pentenoyl-CoA to 3-hydroxy-4-pentenoic acid (e.g., a 3-hydroxy-4-pentenoyl-CoA hydrolase, transferase, or synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to acetyl-CoA and 3-hydroxypropionyl-CoA and one or more polynucleotides coding for enzymes in a pathway that catalyze a conversion of acetyl-CoA and 3-hydroxypropionyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to acryloyl-CoA; one or more polynucleotides coding for enzymes in a pathway that catalyze a conversion of acryloyl-CoA to 3-hydroxypropionyl-CoA; one or more polynucleotides coding for enzymes in a pathway that catalyze a conversion of pyruvate to 3-hydroxypropionate; one or more polynucleotides coding for enzymes in a pathway that catalyze a conversion of 3-hydroxypropionate to 3-hydroxypropionyl-CoA; one or more polynucleotides coding for enzymes in a pathway that catalyze a conversion of acetyl-CoA and 3-hydroxypropionyl-CoA to 5-hydroxy-3-ketovaleryl-CoA (e.g., a thiolase); one or of more polynucleotides coding for enzymes in a pathway that catalyze a conversion of 5-hydroxy-3-ketovaleryl-CoA to (R) or (S) 3,5-dihydroxy-valeryl-CoA (e.g., a 5-hydroxy-3-ketovaleryl-CoA dehydrogenase); one or more polynucleotides coding for enzymes in a pathway that catalyze a conversion of (R) or (S) 3,5-dihydroxy-valeryl-CoA to 3,5-hydroxypentanoic acid (e.g., a 3,5-hydroxypentanoic acid kinase); one or more polynucleotides coding for enzymes in a pathway that catalyze a conversion of 3,5-hydroxypentanoic acid to 3,5-hydroxypentanoic acid phosphate (e.g., a 3,5-hydroxypentanoic acid kinase); one or more polynucleotides coding for enzymes in a pathway that catalyze a conversion of 3,5-hydroxypentanoic acid phosphate to 3,5-hydroxypentanoic acid diphosphate (e.g., a 3,5-hydroxypentanoic acid phosphate kinase); one or more polynucleotides coding for enzymes in a pathway that catalyze a conversion of 3,5-hydroxypentanoic acid diphosphate to 1-butenyl-4-diphosphate (e.g., a hydroxypentanoic acid diphosphate decarboxylase); and/or one or more polynucleotides coding for enzymes in a pathway that catalyze a conversion of 1-butenyl-4-diphosphate to butadiene (e.g., a butadiene synthase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to ethyl-malonyl-CoA and one or more polynucleotides coding for enzymes in a pathway that catalyze a conversion of ethyl-malonyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyzes a conversion of pyruvate to acetyl-CoA; one or more polynucleotides coding for enzymes in a pathway that catalyzes a conversion of acetyl-CoA to acetoacetyl-CoA (e.g., an acetoacetyl-CoA thiolase); one or more polynucleotides coding for enzymes in a pathway that catalyzes a conversion of acetoacetyl-CoA to 3-hydroxybutyryl-CoA (e.g., a 3-hydroxybutyryl-CoA dehydrogenase); one or more polynucleotides coding for enzymes in a pathway that catalyzes a conversion of 3-hydroxybutyryl-CoA to crotonyl-CoA (e.g., a crotonase); one or more polynucleotides coding for enzymes in a pathway that catalyzes a conversion of crotonyl-CoA to ethyl-malonyl-CoA (e.g., a crotonyl-CoA carboxylase/reductase); one or more polynucleotides coding for enzymes in a pathway that catalyzes a conversion of crotonyl-CoA to butyric acid (e.g., butyryl-CoA dehydrogenase); one or more polynucleotides coding for enzymes in a pathway that catalyzes a conversion of butyric acid to ethyl-malonyl-CoA (e.g., a butanoyl-CoA:carbon-dioxide ligase); one or more polynucleotides coding for enzymes in a pathway that catalyze a conversion of ethyl-malonyl-CoA to 2-hydroxymethyl-butanoic acid (e.g., an ethyl-malonyl-CoA reductase, an alcohol dehydrogenase, or a aldehyde dehydrogenase); one or more polynucleotides coding for enzymes in a pathway that catalyze a conversion of 2-hydroxymethyl-butanoic acid to 2-butenyl 4-diphosphate (e.g., a 2-hydroxymethyl-butanoate kinase, a hydroxymethyl butanoate-phosphate kinase, or a 2-hydroxymethyl butanoate-diphosphate decarboxylase); one or more polynucleotides coding for enzymes in a pathway that catalyze a conversion of 2-hydroxymethyl-butanoic acid to 2-butenyl 4-phosphate; one or more polynucleotides coding for enzymes in a pathway that catalyze a conversion of 2-butenyl 4-phosphate to butadiene, and/or one or more polynucleotides coding for enzymes in a pathway that catalyze a conversion of 2-butenyl 4-diphosphate to butadiene (e.g., butadiene synthetase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to lactate and acetyl-CoA and oxalacetate and one or more polynucleotides coding for enzymes in a pathway that catalyze a conversion of lactate and acetyl-CoA and oxalacetate to butadiene including, but are not limited to: one or more polynucleotides coding for enzymes in a pathway that catalyze a conversion of a fermentable carbon source (e.g., glucose) to PEP; one or more polynucleotides coding for enzymes in a pathway that catalyze a conversion of PEP to pyruvate; one or more polynucleotides coding for enzymes in a pathway that catalyze a conversion of pyruvate to acetyl-CoA; one or more polynucleotides coding for enzymes in a pathway that catalyze a conversion of lactate to lactoyl-CoA (e.g., a lactate CoA-transferase); one or more polynucleotides coding for enzymes in a pathway that catalyze a conversion of lactoyl-CoA to acryloyl-CoA (e.g., a lactoyl-CoA dehydratase); one or more polynucleotides coding for enzymes in a pathway that catalyze a conversion of acryloyl-CoA to propionyl-CoA (e.g., an acryloyl-CoA oxidoreductase); one or more polynucleotides coding for enzymes in a pathway that catalyze a conversion of propionyl-CoA to ketovaleryl-CoA (e.g., a thiolase); one or more polynucleotides coding for enzymes in a pathway that catalyze a conversion of ketovaleryl-CoA to 2-pentenoyl-CoA (e.g., a ketovaleryl-CoA dehydratase); one or more polynucleotides coding for enzymes in a pathway that catalyze a conversion of 2-pentenoyl-CoA to 2-pentenoic acid (e.g., a pentenoyl-CoA hydrolase, transferase, or synthase); one or more polynucleotides coding for enzymes in a pathway that catalyze a conversion of 2 pentenoic acid to butadiene (e.g., a 4-pentenoic acid decarboxylase); one or more polynucleotides coding for enzymes in a pathway that catalyze a conversion of 2-pentenoic acid to 4-pentenoic acid (e.g., a transposing C=C bonds isomerase); one or more polynucleotides coding for enzymes in a pathway that catalyze a conversion of 4-pentenoic acid to butadiene (e.g., a 4-pentenoic acid decarboxylase); one or more polynucleotides coding for enzymes in a pathway that catalyze a conversion of oxalacetate to malate (e.g., a malate dehydrogenase); one or more polynucleotides coding for enzymes in a pathway that catalyze a conversion of malate to fumarate (e.g., a fumarase); one or more polynucleotides coding for enzymes in a pathway that catalyze a conversion of fumarate to succinate (e.g., a fumarate reductase); one or more polynucleotides coding for enzymes in a pathway that catalyze a conversion of succinate to succynil-CoA (e.g., a succinyl-CoA transferase synthase); one or more polynucleotides coding for enzymes in a pathway that catalyze a conversion of succynil-CoA to succinate semialdehyde (e.g., a succinyl-CoA reducatase); one or more polynucleotides coding for enzymes in a pathway that catalyze a conversion of succinate semialdehyde to 4-hydroxybutyrate (e.g., a 4 hydroxybutyrate dehydrogenase); one or more polynucleotides coding for enzymes in a pathway that catalyze a conversion of 4-hydroxybutyrate to 4-hydroxybutyril-CoA (e.g., a 4-hydroxybutyryl-CoA transferase, or a 4-hydroxybutyryl-CoA synthase); one or more polynucleotides coding for enzymes in a pathway that catalyze a conversion of 4-hydroxybutyril-CoA to crotonyl-CoA (e.g., a 4-hydroxybutyryl-CoA dehydratase); one or more polynucleotides coding for enzymes in a pathway that catalyze a conversion of crotonyl-CoA to crotonaldehyde (e.g., a crotonaldehyde dehydrogenase); one or more polynucleotides coding for enzymes in a pathway that catalyze a conversion of crotonyl-CoA to crotonyl-alcohol (e.g., a crotonyl-CoA reductase or a bifunctional alcohol dehydrogenase); one or more polynucleotides coding for enzymes in a pathway that catalyze a conversion of crotonaldehyde to crotonyl-alcohol (e.g., an alcohol dehydrogenase); and/or one or more polynucleotides coding for enzymes in a pathway that catalyze a conversion of crotonyl-alcohol to butadiene (e.g., a crotonyl alcohol dehydratase).

Any of the microorganisms provided herein may optionally comprise one or more polynucleotides coding for enzymes that permit for a redox balanced conversion of a fermentable carbon source to butadiene.

The microorganism may be an archea, bacteria, or eukaryote. In some embodiments, the bacteria is a *Propionibacterium, Propionispira, Clostridium, Bacillus, Escherichia, Pelobacter*, or *Lactobacillus* including, for example, *Pelobacter propionicus, Clostridium propionicum, Clostridium acetobutylicum, Lactobacillus, Propionibacterium acidipropionici* or *Propionibacterium freudenreichii*. In some embodiments, the eukaryote is a yeast, filamentous fungi, protozoa, or algae. In some embodiments, the yeast is *Saccharomyces cerevisiae, Zymomonas mobilis*, or *Pichia pastoris*.

In some embodiments, the disclosure contemplates the modification (e.g., engineering) of one or more of the enzymes provided herein. Such modification may be performed to redesign the substrate specificity of the enzyme and/or to modify (e.g., reduce) its activity against others substrates in order to increase its selectivity for a given substrate. Additionally or alternatively, one or more enzymes as provided herein may be engineered to alter (e.g., enhance including, for example, increase its catalytic activity or its substrate specificity) one or more of its properties.

Any of the enzymes (e.g., the polynucleotide coding for the enzyme) may be modified (e.g., mutagenized or diversified) to expand or alter its substrate specificity (e.g., change the substrate specificity of an enzyme from one substrate to another substrate) by any method known in the art. Such methods include, but are not limited to EpPCR Pritchard et al., J. Theor. Biol. 234:497-509 (2005)); Error-prone Rolling Circle Amplification (epRCA) Fujii et al., Nucleic Acids Res. 32:e145 (2004); and Fujii et al., Nat. Protoc. 1:2493-2497 (2006)); DNA or Family Shuffling Stemmer, Proc. Natl. Acad. Sci. U.S.A. 91:10747-10751 (1994); and Stemmer, Nature 370:389-391 (1994)); Staggered Extension (StEP) Zhao et al., Nat. Biotechnol. 16:258-261 (1998)); and/or Random Priming Recombination (RPR) Shao et al., Nucleic Acids Res 26:681-683 (1998)).

Additional exemplary methods for mutagenesis of a polynucleotide include Heteroduplex Recombination (Volkov et al., Nucleic Acids Res. 27:e18 (1999); and Volkov et al., Methods Enzymol. 328:456-463 (2000)); Random Chimeragenesis on Transient Templates (RACHITT) (Coco et al., Nat. Biotechnol. 19:354-359 (2001)); Recombined Extension on Truncated templates (RETT) (Lee et al., J. Molec. Catalysis 26:119-129 (2003)); Degenerate Oligonucleotide Gene Shuffling (DOGS) (Bergquist and Gibbs, Methods Mol. Biol. 352:191-204 (2007); Bergquist et al., Biomol. Eng. 22:63-72 (2005); Gibbs et al., *Gene* 271:13-20 (2001)); Incremental Truncation for the Creation of Hybrid Enzymes (ITCHY) (Ostermeier et al., Proc. Natl. Acad. Sci. U.S.A. 96:3562-3567 (1999); and Ostermeier et al., Nat. Biotechnol. 17:1205-1209 (1999)); Thio-Incremental Truncation for the Creation of Hybrid Enzymes (THIO-ITCHY) (Lutz et al., Nucleic Acids Res. 29:E16 (2001)); SCRATCHY (Lutz et al., Proc. Natl. Acad. Sci U.S.A. 98:11248-11253 (2001)); Random Drift Mutagenesis (RNDM) (Bergquist et al., Biomol. Eng. 22:63-72 (2005)); Sequence Saturation Mutagenesis (SeSaM) (Wong et al., Biotechnol. J. 3:74-82 (2008); Wong et al., Nucleic Acids Res. 32:e26 (2004); and Wong et al., Anal. Biochem. 341:187-189 (2005)); Synthetic Shuffling (Ness et al., Nat. Biotechnol. 20:1251-1255 (2002)); Nucleotide Exchange and Excision Technology NexT (Muller et al., Nucleic Acids Res. 33:e117 (2005)). Additional exemplary methods include Sequence Homology-Independent Protein Recombination (SHIPREC) (Sieber et al., Nat. Biotechnol. 19:456-460 (2001)); Gene Site Saturation Mutagenesis™ (GSSM™) (Kretz et al., Methods Enymol. 388:3-11 (2004)); Combinatorial Cassette Mutagenesis (CCM) (Reidhaar-Olson et al. Methods Enzymol. 208:564-586 (1991); and Reidhaar-Olson et al. Science 241:53-57 (1988)); Combinatorial Multiple Cassette Mutagenesis (CMCM) (Reetz et al., Angew. Chem. Int. Ed Engl. 40:3589-3591 (2001)); and the Mutator Strains technique (Selifonova et al., Appl. Environ. Microbiol. 67:3645-3649 (2001); Low et al., J. Mol. Biol. 260:359-3680 (1996)). Further exemplary methods include Look-Through Mutagenesis (LTM) (Rajpal et al., Proc. Natl. Acad. Sci. U.S.A. 102:8466-8471 (2005)); Gene Reassembly (Tunable GeneReassembly™ (TGR™) Technology supplied by Verenium Corporaiton), in Silico Protein Design Automation (PDA) (Hayes et al., Proc. Natl. Acad. Sci. U.S.A. 99:15926-15931 (2002)); and Iterative Saturation Mutagenesis (ISM) (Reetz et al., Nat. Protoc. 2:891-903 (2007); and Reetz et al., Angew. Chem. Int. Ed Engl. 45:7745-7751 (2006)).

In some embodiments, sequence alignment and comparative modeling of proteins may be used to alter one or more of the enzymes disclosed herein. Homology modeling or comparative modeling refers to building an atomic-resolution model of the desired protein from its primary amino acid sequence and an experimental three-dimensional structure of a similar protein. This model may allow for the enzyme substrate binding site to be defined, and the identification of specific amino acid positions that may be replaced to other natural amino acid in order to redesign its substrate specificity.

Variants or sequences having substantial identity or homology with the polynucleotides encoding enzymes as disclosed herein may be utilized in the practice of the disclosure. Such sequences can be referred to as variants or modified sequences. That is, a polynucleotide sequence may be modified yet still retain the ability to encode a polypeptide exhibiting the desired activity. Such variants or modified sequences are thus equivalents. Generally, the variant or modified sequence may comprise at least about 40%-60%, preferably about 60%-80%, more preferably about 80%-90%, and even more preferably about 90%-95% sequence identity with the native sequence.

In some embodiments, a microorganism may be modified to express including, for example, over express, one or more enzymes as provided herein. The microorganism may be modified by genetic engineering techniques (i.e., recombinant technology), classical microbiological techniques, or a combination of such techniques and can also include naturally occurring genetic variants to produce a genetically modified microorganism. Some of such techniques are generally disclosed, for example, in Sambrook et al., 1989, Molecular Cloning: A Laboratory Manual, Cold Spring Harbor Labs Press.

A microorganism may include a microorganism in which a polynucleotide has been inserted, deleted or modified (i.e., mutated; e.g., by insertion, deletion, substitution, and/or inversion of nucleotides), in such a manner that such modifications provide the desired effect of expression (e.g., over-expression) of one or more enzymes as provided herein within the microorganism. Genetic modifications which result in an increase in gene expression or function can be referred to as amplification, overproduction, over expression, activation, enhancement, addition, or up-regulation of a gene. Addition of cloned genes to increase gene expression can include maintaining the cloned gene(s) on replicating plasmids or integrating the cloned gene(s) into the genome of the production organism. Furthermore, increasing the expression of desired cloned genes can include operatively linking the cloned gene(s) to native or heterologous transcriptional control elements.

Where desired, the expression of one or more of the enzymes provided herein are under the control of a regulatory sequence that controls directly or indirectly the expression of the enzyme in a time-dependent fashion during a fermentation reaction.

In some embodiments, a microorganism is transformed or transfected with a genetic vehicle such as, an expression vector comprising an exogenous polynucleotide sequence coding for the enzymes provided herein.

Polynucleotide constructs prepared for introduction into a prokaryotic or eukaryotic host may typically, but not always, comprise a replication system (i.e. vector) recognized by the host, including the intended polynucleotide fragment encoding the desired polypeptide, and may preferably, but not necessarily, also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, mRNA stabilizing sequences, nucleotide sequences homologous to host chromosomal DNA, and/or a multiple cloning site. Signal peptides may also be included where appropriate, preferably from secreted polypeptides of the same or related species, which allow the protein to cross and/or lodge in cell membranes or be secreted from the cell.

The vectors can be constructed using standard methods (see, e.g., Sambrook et al., Molecular Biology: A Laboratory Manual, Cold Spring Harbor, N. Y. 1989; and Ausubel, et al., Current Protocols in Molecular Biology, Greene Publishing, Co. N.Y, 1995).

The manipulation of polynucleotides of the present disclosure including polynucleotides coding for one or more of the enzymes disclosed herein is typically carried out in recombinant vectors. Numerous vectors are publicly available, including bacterial plasmids, bacteriophage, artificial chromosomes, episomal vectors and gene expression vectors, which can all be employed. A vector of use according to the disclosure may be selected to accommodate a protein coding sequence of a desired size. A suitable host cell is transformed with the vector after in vitro cloning manipulations. Host cells may be prokaryotic, such as any of a number of bacterial strains, or may be eukaryotic, such as yeast or other fungal cells, insect or amphibian cells, or mammalian cells including, for example, rodent, simian or human cells. Each vector contains various functional components, which generally include a cloning site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a polypeptide repertoire member according to the disclosure.

Vectors, including cloning and expression vectors, may contain nucleic acid sequences that enable the vector to replicate in one or more selected host cells. For example, the sequence may be one that enables the vector to replicate independently of the host chromosomal DNA and may include origins of replication or autonomously replicating sequences. Such sequences are well known for a variety of bacteria, yeast and viruses. For example, the origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

A cloning or expression vector may contain a selection gene also referred to as a selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors may be performed in $E.$ $coli$ (e.g., strain TB1 or TG1, DH5α, DH10β, JM110). An $E.$ $coli$-selectable marker, for example, the β-lactamase gene that confers resistance to the antibiotic ampicillin, may be of use. These selectable markers can be obtained from $E.$ $coli$ plasmids, such as pBR322 or a pUC plasmid such as pUC18 or pUC19, or pUC119.

Expression vectors may contain a promoter that is recognized by the host organism. The promoter may be operably linked to a coding sequence of interest. Such a promoter may be inducible or constitutive. Polynucleotides are operably linked when the polynucleotides are in a relationship permitting them to function in their intended manner.

Promoters suitable for use with prokaryotic hosts may include, for example, the α-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Moreover, host constitutive or inducible promoters may be used. Promoters for use in bacterial systems will also generally contain a Shine-Dalgarno sequence operably linked to the coding sequence.

Viral promoters obtained from the genomes of viruses include promoters from polyoma virus, fowlpox virus, adenovirus (e.g., Adenovirus 2 or 5), herpes simplex virus (thymidine kinase promoter), bovine papilloma virus, avian sarcoma virus, cytomegalovirus, a retrovirus (e.g., MoMLV, or RSV LTR), Hepatitis-B virus, Myeloproliferative sarcoma virus promoter (MPSV), VISNA, and Simian Virus 40 (SV40). Heterologous mammalian promoters include, e.g., the actin promoter, immunoglobulin promoter, heat-shock protein promoters.

The early and late promoters of the SV40 virus are conveniently obtained as a restriction fragment that also contains the SV40 viral origin of replication (see, e.g., Fiers et al., Nature, 273:113 (1978); Mulligan and Berg, Science, 209:1422-1427 (1980); and Pavlakis et al., Proc. Natl. Acad. Sci. USA, 78:7398-7402 (1981)). The immediate early promoter of the human cytomegalovirus (CMV) is conveniently obtained as a Hind III E restriction fragment (see, e.g., Greenaway et al., Gene, 18:355-360 (1982)). A broad host range promoter, such as the SV40 early promoter or the Rous sarcoma virus LTR, is suitable for use in the present expression vectors.

Generally, a strong promoter may be employed to provide for high level transcription and expression of the desired product. Among the eukaryotic promoters that have been identified as strong promoters for high-level expression are the SV40 early promoter, adenovirus major late promoter, mouse metallothionein-I promoter, Rous sarcoma virus long terminal repeat, and human cytomegalovirus immediate early promoter (CMV or CMV IE). In an embodiment, the promoter is a SV40 or a CMV early promoter.

The promoters employed may be constitutive or regulatable, e.g., inducible. Exemplary inducible promoters include jun, fos and metallothionein and heat shock promoters. One or both promoters of the transcription units can be an inducible promoter. In an embodiment, the GFP is expressed from a constitutive promoter while an inducible promoter drives transcription of the gene coding for one or more enzymes as disclosed herein and/or the amplifiable selectable marker.

The transcriptional regulatory region in higher eukaryotes may comprise an enhancer sequence. Many enhancer sequences are known from mammalian genes e.g., from globin, elastase, albumin, α-fetoprotein and insulin genes. A suitable enhancer is an enhancer from a eukaryotic cell virus. Examples include the SV40 enhancer on the late side of the replication origin (bp 100-270), the enhancer of the cytomegalovirus immediate early promoter (Boshart et al. Cell 41:521 (1985)), the polyoma enhancer on the late side of the replication origin, and adenovirus enhancers (see also, e.g., Yaniv, Nature, 297:17-18 (1982) on enhancing elements for activation of eukaryotic promoters). The enhancer sequences may be introduced into the vector at a position 5' or 3' to the gene of interest, but is preferably located at a site 5' to the promoter.

Yeast and mammalian expression vectors may contain prokaryotic sequences that facilitate the propagation of the vector in bacteria. Therefore, the vector may have other components such as an origin of replication (e.g., a nucleic acid sequence that enables the vector to replicate in one or more selected host cells), antibiotic resistance genes for selection in bacteria, and/or an amber stop codon which can permit translation to read through the codon. Additional eukaryotic selectable gene(s) may be incorporated. Generally, in cloning vectors the origin of replication is one that enables the vector to replicate independently of the host chromosomal DNA, and includes origins of replication or autonomously replicating sequences. Such sequences are well known, e.g., the ColE1 origin of replication in bacteria. Various viral origins (e.g., SV40, polyoma, adenovirus, VSV or BPV) are useful for cloning vectors in mammalian cells. Generally, a eukaryotic replicon is not needed for expression in mammalian cells unless extrachromosomal (episomal) replication is intended (e.g., the SV40 origin may typically be used only because it contains the early promoter).

To facilitate insertion and expression of different genes coding for the enzymes as disclosed herein from the constructs and expression vectors, the constructs may be designed with at least one cloning site for insertion of any gene coding for any enzyme disclosed herein. The cloning site may be a multiple cloning site, e.g., containing multiple restriction sites.

The plasmids may be propagated in bacterial host cells to prepare DNA stocks for subcloning steps or for introduction into eukaryotic host cells. Transfection of eukaryotic host cells can be any performed by any method well known in the art. Transfection methods include lipofection, electroporation, calcium phosphate co-precipitation, rubidium chloride or polycation mediated transfection, protoplast fusion and microinjection. Preferably, the transfection is a stable transfection. The transfection method that provides optimal transfection frequency and expression of the construct in the particular host cell line and type, is favored. Suitable methods can be determined by routine procedures. For stable transfectants, the constructs are integrated so as to be stably maintained within the host chromosome.

Vectors may be introduced to selected host cells by any of a number of suitable methods known to those skilled in the art. For example, vector constructs may be introduced to appropriate cells by any of a number of transformation methods for plasmid vectors. For example, standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation and conjugation may also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods may be used (e.g., Rose et al., 1990, Methods in Yeast Genetics, Cold Spring Harbor Laboratory Press, Cold Spring Harbor, N.Y.). Transformed cells may be isolated on selective media appropriate to the selectable marker used. Alternatively, or in addition, plates or filters lifted from plates may be scanned for GFP fluorescence to identify transformed clones.

For the introduction of vectors comprising differentially expressed sequences to mammalian cells, the method used may depend upon the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or Lipo-Taxi™ (Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

The host cell may be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation. Immortalized host cell cultures amenable to transfection and in vitro cell culture and of the kind typically employed in genetic engineering are preferred. Examples of useful mammalian host cell lines are monkey kidney CV1 line transformed by SV40 (COS-7, ATCC CRL 1651); human embryonic kidney line (293 or 293 derivatives adapted for growth in suspension culture, Graham et al., J. Gen Virol., 36:59 (1977); baby hamster kidney cells (BHK, ATCC CCL 10); DHFR-Chinese hamster ovary cells (ATCC CRL-9096);

dp12.CHO cells, a derivative of CHO/DHFR-(EP 307,247 published 15 Mar. 1989); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); PEER human acute lymphoblastic cell line (Ravid et al. Int. J. Cancer 25:705-710 (1980)); MRC 5 cells; FS4 cells; human hepatoma line (Hep G2), human HT1080 cells, KB cells, JW-2 cells, Detroit 6 cells, NIH-3T3 cells, hybridoma and myeloma cells. Embryonic cells used for generating transgenic animals are also suitable (e.g., zygotes and embryonic stem cells).

Suitable host cells for cloning or expressing polynucleotides (e.g., DNA) in vectors may include, for example, prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), *E. coli* JM110 (ATCC 47,013) and *E. coli* W3110 (ATCC 27,325) are suitable.

In addition to prokaryotes, eukaryotic microbes such as filamentous fungi or yeast may be suitable cloning or expression hosts for vectors comprising polynucleotides coding for one or more enzymes. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastors* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

When the enzyme is glycosylated, suitable host cells for expression may be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk moth) have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, petunia, tomato, tobacco, lemna, and other plant cells can also be utilized as host cells.

Examples of useful mammalian host cells are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, (Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for production of one or more enzymes as disclosed herein or with polynucleotides coding for one or more enzymes as disclosed herein and cultured in conventional nutrient media modified as appropriate for inducing promoters, selecting transformants, or amplifying the genes encoding the desired sequences.

Host cells containing desired nucleic acid sequences coding for the disclosed enzymes may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44, (1979); Barnes et al., Anal. Biochem. 102: 255 (1980); U.S. Pat. No. 4,767,704; 4,657, 866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adeNOSine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Polynucleotides and Encoded Enzymes

Any known polynucleotide (e.g., gene) that codes for an enzyme or variant thereof that is capable of catalyzing an enzymatic conversion including, for example, an enzyme as set forth in any one of Tables 1-3 or FIGS. 1-3, is contemplated for use by the present disclosure. Such polynucleotides may be modified (e.g., genetically engineered) to modulate (e.g., increase or decrease) the substrate specificity of an encoded enzyme, or the polynucleotides may be modified to change the substrate specificity of the encoded enzyme (e.g., a polynucleotide that codes for an enzyme with specificity for a substrate may be modified such that the enzyme has specificity for an alternative substrate). Preferred microorganisms may comprise polynucleotides coding for one or more of the enzymes as set forth in any one of Tables 1-3 and FIG. 1-3.

In some embodiments, the microorganism may comprise an oxidoreductase such as a hydroxyvaleryl-CoA dehydrogenase, a crotonyl-CoA reductase (bifunctional), a crotonaldehyde dehydrogenase, a crotonyl alcohol dehydrogenase, a 3,5-ketovaleryl-CoA dehydrogenase, or an oxidoreductase as set forth in SEQ ID NOs: 103-123. In some embodiments, the microorganism may comprise a transferase such as a pentenoyl-CoA transferase, a pent-2,4-dienoyl-CoA transferase, a formyl-CoA transferase, a 3-hydroxy-4-pentenoyl-CoA transferase, or a transferase as set forth in SEQ ID NOs: 1-28. In some embodiments, the microorganism may comprise a hydrolase such as a pentenoyl-CoA hydrolase, a pent-2,4-dienoyl-CoA hydrolase, a 3-hydroxy-4-pentenoyl-CoA hydrolase, or a hydrolase as set forth in SEQ ID NOs: 29-33. In some embodiments, the microorganism may comprise a CoA synthase such as a formyl-CoA synthase or a CoA synthase as set forth in SEQ ID NOs: 34-36. In some embodiments, the microorganism may comprise a ketothiolase such as a thiolase, an acetyl-CoA:formate C-acetyltransferase, an acetoacetyl-CoA thiolase, a 3,5-ketovaleryl-CoA thiolase, or a ketothiolase as set forth in SEQ ID NOs: 58-78. In some embodiments, the microorganism may comprise a dehydrogenase such as a pentenoyl-CoA dehydrogenase, a formate dehydrogenase, or a dehydrogenase as set forth in SEQ ID NOs: 124-139. In some embodiments, the microorganism may comprise a dehydratase such as a hydroxyvaleryl CoA dehydratase, a crotonyl alcohol dehydratase, a 3,5-hydroxyvaleryl-CoA dehydratase, or a dehydratase as set forth in SEQ ID NOs: 37-55. In some embodiments, the microorganism may comprise an isomerase such as a transposing C=C bonds isomerase, or an isomerase as set forth in SEQ ID NOs: 99-102. In some embodiments, the microorganism may comprise a decarboxylase such as a 2-pentenoic acid decarboxylase, a 4-pentenoic acid decarboxylase, a pent,2,4-dienoic acid decarboxylase, a 3-hydroxy-4-pentenoic acid decarboxylase, or a decarboxylase as set forth in SEQ ID NOs: 79-98.

Enzymes for catalyzing the conversions in FIGS. 1-3 are categorized in Table 4 by Enzyme Commission (EC) number, function, and the step in FIGS. 1-3 in which they catalyze a conversion (Table 4).

TABLE 4

EC number for employed enzymes

| EC Number | Function | FIG. (Number) and Step (Letter) |
|---|---|---|
| 1.1.1. | Oxidoreductase | 1B, 2A, 2B, 2C, 3F, 3G |
| 2.8.3. | Transferase | 1D, 1I, 3C, 3I |
| 3.1.2. | Hydrolase | 1D, 1I, 3I |
| 6.2.1 | CoA Synthetase | 3C |
| 2.3.1. | Ketothiolase | 1A, 3B, 3D, 3E |
| 1.3.1. or 1.2.99 | Dehydrogenase | 1H, 3A |
| 4.2.1. | Dehydratase | 1C, 2D, 3H |
| 5.3.3. | Isomerase | 1F |
| 4.1.1. | Decarboxylase | 1E, 1G, 1J, 3J |

Steps D and I of FIG. 1, and steps C and I in FIG. 3 can be catalyzed by transferases in EC 2.8.3 including, for example, a transferase that catalyzes the reversible transfer of a CoA moiety from one molecule to another. Any known polynucleotide coding for a CoA transferase enzyme including, for example, those polynucleotides set forth in Table 5 below, is contemplated for use by the present disclosure.

TABLE 5

Exemplary genes coding for enzymes in EC 2.8.3

| Gene | Gene ID | Organism | SEQ ID NO: |
|---|---|---|---|
| atoA | 2492994 | Escherichia coli K12 | 1 |
| atoD | 2492990 | Escherichia coli K12 | 2 |
| actA | 62391407 | Corynebacterium glutamicum ATCC 13032 | 3 |
| Cg0592 | 62289399 | Corynebacterium glutamicum ATCC 13032 | 4 |
| ctfA | 15004866 | Clostridium acetobutylicum | 5 |
| ctfB | 15004867 | Clostridium acetobutylicum | 6 |
| Ach1 | 60396828 | Roseburia sp. A2-183 | 7 |
| Pct | 7242549 | Clostridium propionicum | 8 |
| Cbei_4543 | 150019354 | Clostridium beijerinchii | 9 |
| pcaI | 50084858 | Acinetobacter sp. ADP1 | 10 |
| PcaJ | 141776 | Acinetobacter sp. ADP1 | 11 |
| pcaI | 24985644 | Pseudomonas putida | 12 |
| pcaJ | 141776 | Pseudomonas putida | 13 |
| ScoA | 16080950 | Bacillus subtilis | 14 |
| ScoB | 16080949 | Bacillus subtilis | 15 |
| Cat1 | 729048 | Clostridium kluyveri | 16 |
| Cat2 | 172046066 | Clostridium kluyveri | 17 |
| Cat3 | 146349050 | Clostridium kluyveri | 18 |
| gctA | 559392 | Acidaminococcus fermentans | 19 |
| gctB | 559393 | Acidaminococcus fermentans | 20 |
| frc | 12931869 | Escherichia coli | 21 |
| BBta_3113 | 5149017 | Bradyrhizobium sp. | 22 |
| RPA1945 | 2688995 | Rhodopseudomonas palustris | 23 |
| SDY_2572 | 3797090 | Shigella dysenteriae | 24 |
| RPB_3427 | 3911229 | Rhodopseudomonas palustris | 25 |
| frc | 8191935 | Methylobacterium extorquens | 26 |
| H16_B1711 | 4455693 | Ralstonia eutropha H16 | 27 |
| Bxe_B2760 | 4006524 | Burkholderia xenovorans | 28 |

Steps D and I of FIG. 1, and step I of FIG. 3 can be catalyzed by hydrolases in EC 3.1.2 including, for example, hydrolases with broad substrate ranges capable of hydrolyzing 2-petentenoyl-CoA, 2,4-pentenoyl-CoA, and 3-hydroxypentenoyl-CoA to their corresponding acids. Any known polynucleotide coding for a hydrolase including, for example, those polynucleotides set forth in Table 6 below, is contemplated for use by the present disclosure.

TABLE 6

Exemplary genes coding for enzymes in EC 3.1.2.

| Gene | Gene ID | Organism | SEQ ID NO: |
|---|---|---|---|
| Orf1 | 23664428 | Azoarcus evansii | 29 |
| COG0824 | 46200680 | Magnetospirillum magnetotacticum | 30 |
| Jann_0674 | 89052491 | Jannaschia sp. CCS1 | 31 |
| SSE37_24444 | 126729407 | Sagittula stellata | 32 |
| entH | 1786813 | Escherichia coli | 33 |

Step C in FIG. 3 may be catalyzed by a CoA synthetase in EC 6.2.1., including, for example, a CoA synthetase with a broad substrate range capable of activating formic acid to formyl-CoA. Any known polynucleotide coding for a CoA synthetase including, for example, those polynucleotides set forth in Table 7 below, is contemplated for use by the present disclosure.

TABLE 7

Exemplary genes coding for enzymes in EC 6.2.1.

| Gene | Gene ID (GI) | Organism | SEQ ID NO: |
|---|---|---|---|
| acs | 8434601 | Acetobacter pasteurianus | 34 |
| Avin_10660 | 7760010 | Azotobacter vinelandii | 35 |
| acs | 8657923 | Dehalococcoides sp. | 36 |

The hydration of a double bond can be catalyzed by hydratase enzymes in EC 4.2.1 and the removal of water to form a double bond can be catalyzed by dehydratase enzymes in EC 4.2.1. Hydratase enzymes are sometimes reversible and may also catalyze dehydration. Likewise, dehydratase enzymes are sometimes reversible and may also catalyze hydration. The addition or removal of 7 water from a given substrate is required by step C in FIG. 1, step D in FIG. 2, and step H in FIG. 3. Any known polynucleotide coding for a hydratase or dehydratase including, for example, those polynucleotides set forth in Table 8 below, is contemplated for use by the present disclosure.

For example, the linalool dehydratase-isomerase from *Castellaniella defragrans* strain 65Phen (E.C. 4.2.1.127; SEQ ID NO: 55) catalyzes the stereospecific hydration of beta-myrcene to (3S)-linalool, the isomerization of (3S)-linalool to geraniol, and is involved in the initial steps of the anaerobic degradation of the monoterpene beta-myrcene. Additionally, this linalool dehydratase-isomerase catalyzes the reverse reactions, i.e. the isomerization of geraniol to linalool and the dehydration of linalool to myrcene. In this direction, the formation of myrcene from geraniol may be seen as a detoxification process for the monoterpene alcohol. Thus, linalool dehydratase represents a suitable candidate for step D in FIG. 2 below.

TABLE 8

Exemplary genes coding for enzymes in EC 4.2.1.

| Gene | Gene ID | Organism | SEQ ID NO: |
|---|---|---|---|
| mhpD | 87081722 | Escherichia coli | 37 |
| ctmF | 1263188 | Pseudomonas putida | 38 |
| todG | 1263188 | Pseudomonas putida | 39 |
| hpaH | 7150958100 | Klebsiella pneumoniae | 40 |
| hpaH | 8178258 | Escherichia coli | 41 |
| cnbE | 6386628 | Comamonas testosteroni | 42 |
| leuD | 2122345 | Methanocaldococcus jannaschii | 43 |
| dmdA | 9884634 | Eubacterium limosum | 44 |
| dmdB | 9884633 | Eubacterium limosum | 45 |
| Olhyd_maccj | 7390838 | Macrococcus caseolyticus | 46 |
| ech | 1047000 | Pseudomonas putida | 47 |
| crt | 1118895 | Clostridium acetobutylicum | 48 |
| phaB | 1046931 | Pseudomonas putida | 49 |
| fadA | 12934462 | Escherechia coli | 50 |
| fadB | 12934454 | Escherechia coli | 51 |
| fadI | 12933009 | Escherechia coli | 52 |
| fadJ | 12931539 | Escherechia coli | 53 |
| fadR | 12931108 | Escherechia coli | 54 |
| ldi | 302064203 | Castellaniella defragrans | 55 |

In some embodiments, a dehydratase-isomerase including, 4-hydroxybutyryl-CoA dehydratase/vinylacetyl-CoA-Delta-isomerasemay be engineered by standard methods to accept crotonyl-alcohol as a substrate or increase its selectivity for crotonyl-alcohol. Exemplary genes that can be engineered to accept crotonyl alcohol or increase its selectivity for crotonyl-alcohol are set forth in Table 9 below and represent a suitable candidate for step D in FIG. 2 below:

TABLE 9

Exemplary genes that can be engineered to accept crotonyl alcohol or increase its selectivity for crotonyl-alcohol.

| Gene | Gene ID | Organism | SEQ ID NO: |
|---|---|---|---|
| ldi | 302064203 | Castellaniella defragrans | 56 |
| abdD | 1453964 | Sulfolobus solfataricus | 57 |

Step A of FIG. 1, and steps C, D and E of FIG. 3 require condensation of either acetyl-CoA or acetoacetyl-CoA with formyl-CoA or propionyl-CoA. Such a condensation can be catalyzed with a ketothiolase set forth in EC 2.3.1. However, any known polynucleotide coding for a ketothiolase including, for example, those polynucleotides set forth in Table 10 below, is contemplated for use by the present disclosure.

TABLE 10

Exemplary genes coding for enzymes in EC 2.3.1.

| Gene | Gene ID | Organism | SEQ ID NO: |
|---|---|---|---|
| paaJ | 12934018 | Escherichia coli | 58 |
| phaD | 1046928 | Pseudomonas putida | 59 |
| pcaF | 10441755 | Pseudomonas putida | 60 |
| pcaF | 11639550 | Acinetobacter calcoaceticus | 61 |
| fadA | 4490319 | Aeromonas hydrophila | 62 |
| AtoB | 4997503 | Aeromonas salmonicida | 63 |
| pcaF | 4383639 | Pseudomonas aeroginosa | 64 |
| bktB | 428815 | Ralstonia eutropha | 65 |
| pimB | 2692199 | Rhodopseudomonas palustris | 66 |
| syn_02642 | 3882984 | Syntrophus aciditrophicus | 67 |
| phaA | 10921806 | Cupriavidus necator | 68 |
| atoB | 12934272 | Escherichia coli | 69 |
| thlA | 1119056 | Clostridium acetobutylicum | 70 |
| thlB | 1116083 | Clostridium acetobutylicum | 71 |
| ERG10 | 856079 | Saccharomyces cerevisiae | 72 |
| pflB | 12931841 | Escherichia coli | 73 |
| pflA | 12930359 | Escherichia coli | 74 |
| pfl | 15671982 | Lactococcus lactis | 75 |
| pfl | 3168596 | Streptococcus equinus | 76 |
| act | 14141682 | Streptococcus equinus | 77 |
| Clo1313_1716 | 12421448 | Clostridium thermocellum | 78 |

Steps E, G, and J in FIG. 1, and step J in FIG. 2 can be catalyzed by a decarboxylase enzyme as set forth in EC class 4.1.1 Numerous decarboxylases have been characterized and shown to decarboxylate structurally similar substrates to 2-pentenoic acid, 2,4-pentedienoic acid (FIG. 1) and 3-hydroxypentenoic acid (FIG. 3). Exemplary enzymes for step J of FIG. 1 include sorbic acid decarboxylase and aconitate decarboxylase as set forth in EC 4.1.1.16. Exemplary enzymes for steps G and E of FIG. 1 may include p450 fatty acid decarboxylase from *Jeotgalicoccus*. Exemplary enzymes for step J of FIG. 3 may include those enzymes as set forth in EC 4.1.1.33 such as diphosphomevalonate decarboxylase. However, any known polynucleotide coding for a decarboxylase including, for example, those polynucleotides set forth in Table 11 below, is contemplated for use by the present disclosure.

TABLE 11

Exemplary genes coding for enzymes in EC 4.1.1.

| Gene | Gene ID | Organism | SEQ ID NO: |
|---|---|---|---|
| OleT$_{JE}$ | 320526717 XXX | Jeotgalicoccus sp; ATCC8456 | 79 |
| PadA1 | 145235767 | Aspergillus niger | 80 |
| ohbA1 | 145235771 | Aspergillus niger | 81 |

TABLE 11-continued

Exemplary genes coding for enzymes in EC 4.1.1.

| Gene | Gene ID | Organism | SEQ ID NO: |
|---|---|---|---|
| sdrA | 145235769 | Aspergillus niger | 82 |
| padA1 | 169786362 | Aspergillis oryzae | 83 |
| ohbA1 | 169768360 | Aspergillis oryzae | 84 |
| sdrA | 169768362 | Aspergillis oryzae | 85 |
| Mvd | 2845318 | Picrophilus torridus | 86 |
| mvd | 2845209 | Picrophilus torridus | 87 |
| mvd | 855779 | Saccharomyces cerevisiae | 88 |
| mvd | 162312575 | Schizosaccharomyces pombe | 89 |
| mvd | 257051090 | Halorhabdus utahensis | 90 |
| mvd | 8741675 | Haloterrigena turkmenica | 91 |
| mvd | 9132821 | Leuconostoc kimchii | 92 |
| dvd | 1447408 | Halobacterium salinarum | 93 |
| dfd | 121708954 | Aspergillus clavatus | 94 |
|  | 4593483 | Neosartorya fischeri | 95 |
| mvaD | 11027973 | Streptococcus pseudopneumoniae | 96 |
| mvaD | 8433456 | Lactobacillus rhamnosus | 97 |
| mvaD | 12158799 | Borrelia afzelii | 98 |

Step F of FIG. 1 involves an isomerase enzyme as set forth in EC 5.3.3. Exemplary enzymes for the step include the isopentenyl-diphosphate delta-isomerase. However, any known polynucleotide coding for an isomerase including, for example, those polynucleotides set forth in Table 12 below, is contemplated for use by the present disclosure.

TABLE 12

Exemplary genes coding for enzymes in EC 5.3.3.

| Gene | Gene ID | Organism | SEQ ID NO: |
|---|---|---|---|
| Idi | 12930440 | Escherichia coli | 99 |
| Idi1 | 855986 | Saccharomyces cerevisiae | 100 |
| fni | 1028286 | Streptococcus mutans | 101 |
| fni | 938985 | Bacillus subtilis | 102 |

Step B of FIG. 1, steps A, B and C of FIG. 2, and steps F and G of FIG. 3 involve the reduction of a ketone to an alcohol and can be catalyzed by oxidoreductase enzymes in EC class 1.1.1. However, any known polynucleotide coding for an oxidoreductase including, for example, those polynucleotides set forth in Table 13 below, is contemplated for use by the present disclosure.

TABLE 13

Exemplary genes coding for enzymes in EC 1.1.1.

| Gene | Gene ID | Organism | SEQ ID NO: |
|---|---|---|---|
| mdh | 6059112 | Escherichia coli | 103 |
| idhA | 5591397 | Escherichia coli | 104 |
| idh | 113866693 | Ralstonia eutropha | 105 |
| adh | 60592974 | Clostridium beijerinckii | 106 |
| Adh | 113443 | Thermoanaerobacter brockii | 107 |
| Sadh | 21615552 | Rhodococcus ruber | 108 |
| adhA | 3288810 | Pyrococcus furiosus | 109 |
| adhE | 12930611 | Escherichia coli | 110 |
| adhE2 | 12958626 | Clostridium acetobutylicum | 111 |
| adhE | 55818563 | Leuconostoc mesenteroides | 112 |
| HMG1 | 854900 | Saccharomyces cerevisiae | 113 |
| CtCNB1_3119 | 8560791 | Comamonas testosteroni | 114 |
| DKAM_0720 | 7170894 | Desulfurococcus kamchatkensis | 115 |
| mvaA | 1004602 | Staphylococcus aureus | 116 |
| LJ1608 | 2742117 | Lactobacillus johnsonii | 117 |
| acr1 | 2879608 | Acinetobacter sp. ADP1 | 118 |
| acr1 | 1684885 | Acinetobacter baylyi | 119 |
| sucD | 5394466 | Clostridium kluyveri | 120 |
| sucD | 2551522 | Porphyromonas gingivalis | 121 |

TABLE 13-continued

Exemplary genes coding for enzymes in EC 1.1.1.

| Gene | Gene ID | Organism | SEQ ID NO: |
|---|---|---|---|
| bld | 31075383 | Clostridium saccharoperbutylacetonicum | 122 |
| Cbei_3832 | 5294993 | Clostridium beijerinckii | 123 |

Step I of FIG. 1, and step A of FIG. 3 involve a dehydrogenase as set forth in EC 1.3.1 or 1.2.99. However, any known polynucleotide coding for a dehydrogenase including, for example, those polynucleotides set forth in Table 14 below, is contemplated for use by the present disclosure.

TABLE 14

Exemplary genes coding for enzymes in EC 1.3.1 or 1.2.99.

| Gene | Gene ID | Organism | SEQ ID NO: |
|---|---|---|---|
| Msed_1426 | 5104797 | Metallosphaera sedula | 124 |
| ST0480 | 1458422 | Sulfolobus tokodaii | 125 |
| Mcup_0809 | 10493000 | Metallosphaera cuprina | 126 |
| RBRH_02090 | 9986550 | Streptomyces clavuligerus | 127 |
| RSP_1434 | 3718801 | Rhodobacter sphaeroides | 128 |
| acrA | JN244654.1 | Clostridium propionicum | 129 |
| acrB | JN244655 | Clostridium propionicum | 130 |
| Fdh1 | 2276464 | Candida boidinii | 131 |
| Fdh1 | 854570 | Saccharomyces cerevisiae | 132 |
| Fdh2 | 1370568 | Saccharomyces cerevisiae | 133 |
| fdsC | 4248880 | Cupriavidus necator | 134 |
| fdsA | 4248878 | Cupriavidus necator | 135 |
| fdsB | 4248879 | Cupriavidus necator | 136 |
| fdsD | 4248881 | Cupriavidus necator | 137 |
| fdsG | 4248882 | Cupriavidus necator | 138 |
| fdsR | 4248883 | Cupriavidus necator | 139 |

Methods for the Production of Butadiene

Butadiene (e.g., fermentation product) may be produced by contacting one or more genetically modified microorganisms provided herein with a fermentable carbon source. Such methods may preferably comprise contacting a fermentable carbon source with a microorganism comprising one or more polynucleotides coding for enzymes in a pathway that catalyzes a conversion of the fermentable carbon source to any of the intermediates provided in Tables 1-3 or FIGS. 1-3 and one or more polynucleotides coding for enzymes in a pathway that catalyze a conversion of the one or more intermediates provided in Tables 1-3 or FIGS. 1-3 to butadiene in a fermentation media including, under sufficient conditions and for a suitable period of time; and expressing the one or more polynucleotides coding for the enzymes in the pathway that catalyzes a conversion of the fermentable carbon source to the one or more intermediates provided in Tables 1-3 or FIGS. 1-3 and one or more polynucleotides coding for enzymes in a pathway that catalyze a conversion of the one or more intermediates provided in Tables 1-3 or FIGS. 1-3 to butadiene in the microorganism to produce butadiene. In some embodiments, the conversion of the fermentable carbon source to butadiene is ATP positive (e.g., generates a net of ATP per mol of butadiene produced; produces ATP as a byproduct) and when combined with a NADH consuming pathway it can provide an anaerobic process for butadiene production. For example, the conversion of a fermentable carbon source such as glucose or fructose to butadiene may produce a net of 1 mol of ATP per mol of butadiene produced.

Exemplary fermentable carbon sources may include, but are not limited to, sugarcane juice, sugarcane molasses, hydrolyzed starch, hydrolyzed lignocellulosic materials, glucose, sucrose, fructose, lactate, lactose, xylose, pyruvate, or glycerol in any form or mixture thereof. In some embodiments, the carbon source is a monosaccharide, oligosaccharide, or polysaccharide.

Metabolic pathways that lead to the production of industrially important compounds such as butadiene involve oxidation-reduction (redox) reactions. For example, during fermentation, glucose is oxidized in a series of enzymatic reactions into smaller molecules with the concomitant release of energy. The electrons released are transferred from one reaction to another through universal electron carriers, such Nicotinamide Adenine Dinucleotide (NAD) and Nicotinamide Adenine Dinucleotide Phosphate (NAD(P)), which act as cofactors for oxidoreductase enzymes. In microbial catabolism, glucose is oxidized by enzymes using the oxidized form of the cofactors (NAD(P)+ and/or NAD+) as cofactor thus generating reducing equivalents in the form of the reduced cofactor (NAD(P)H and NADH). In order for fermentation to continue, redox-balanced metabolism is required, i.e., the cofactors must be regenerated by the reduction of microbial cell metabolic compounds. In some embodiment, the novel pathways disclosed herein are advantageous in that they provide for the conversion of a fermentable carbon source to butadiene through a pathway that redistributes the end products to achieve a redox balance.

Some key parameters for efficient fermentation of a fermentable carbon source by one or more modified microorganisms as disclosed herein include: the ability to grow microorganisms to a greater cell density, increased yield of desired products, increased amount of volumetric productivity, removal of unwanted co-metabolites, improved utilization of inexpensive carbon and nitrogen sources, adaptation to varying fermenter conditions, increased production of a primary metabolite, increased production of a secondary metabolite, increased tolerance to acidic conditions, increased tolerance to basic conditions, increased tolerance to organic solvents, increased tolerance to high salt conditions and increased tolerance to high or low temperatures. Inefficiencies in any of these parameters can result in high manufacturing costs, inability to capture or maintain market share, and/or failure to bring fermented end-products to market.

The methods of the present disclosure can be adapted to conventional fermentation bioreactors (e.g., batch, fed-batch, cell recycle, and continuous fermentation). In some embodiments, a microorganism (e.g., a genetically modified microorganism) as provided herein is cultivated in liquid fermentation media (i.e., a submerged culture) which leads to excretion of the fermented product(s) into the fermentation media. Fermentation may occur in a bioreactor configured as a stirred tank, a bubble column, an airlift reactor or any other suitable configuration known in the art. In one embodiment, the fermented end product(s) can be isolated from the fermentation media using any suitable method known in the art.

In some embodiments, formation of the fermented product may occur during an initial, fast growth period of the microorganism. In one embodiment, formation of the fermented product may occur during a second period in which the culture is maintained in a slow-growing or non-growing state. In one embodiment, formation of the fermented product may occur during more than one growth period of the microorganism. In such embodiments, the amount of fermented product formed per unit of time is generally a function of the metabolic activity of the microorganism, the physiological culture conditions (e.g., pH, temperature, medium composition), and the amount of microorganisms present in the fermentation process.

In some embodiments, the fermentation product is recovered from the periplasm or culture medium as a secreted metabolite. In one embodiment, the fermentation product is extracted from the microorganism, for example when the microorganism lacks a secretory signal corresponding to the fermentation product. In one embodiment, the microorganisms are ruptured and the culture medium or lysate is centrifuged to remove particulate cell debris. The membrane and soluble protein fractions may then be separated if necessary. The fermentation product of interest may then be purified from the remaining supernatant solution or suspension by, for example, distillation, fractionation, chromatography, precipitation, filtration, and the like. In one embodiment, fermentation products are extracted by one or more of: distillation, reactive distillation, azeotropic distillation and extractive distillation.

The methods of the present disclosure are preferably preformed under anaerobic conditions. Both the degree of reduction of a product as well as the ATP requirement of its synthesis determines whether a production process is able to proceed aerobically or anaerobically. To produce butadiene via anaerobic microbial conversion, or at least by using a process with reduced oxygen consumption, redox imbalances should be avoided. Several types of metabolic conversion steps involve redox reactions including some of the conversions as set forth in Table 1-3 or FIGS. 1-3. Such redox reactions involve electron transfer mediated by the participation of redox cofactors such as NADH, NADPH and ferredoxin. Since the amounts of redox cofactors in the cell are limited to permit the continuation of metabolic processes, the cofactors have to be regenerated. In order to avoid such redox imbalances, alternative ways of cofactor regeneration may be engineered, and in some cases additional sources of ATP generation may be provided. Alternatively, oxidation and reduction processes may be separated spatially in bioelectrochemical systems (Rabaey and. Rozendal, 2010, *Nature reviews, Microbiology*, vol 8: 706-716).

In some embodiment, redox imbalances may be avoided by using substrates (e.g., fermentable carbon sources) that are more oxidized or more reduced. for example, if the utilization of a substrate results in a deficit or surplus of electrons, a requirement for oxygen can be circumvented by using substrates that are more reduced or oxidized, respectively. For example, glycerol which is a major byproduct of biodiesel production is more reduced than sugars, and is therefore more suitable for the synthesis of compounds whose production from sugar results in cofactor oxidation, such as succinic acid. In some embodiments, if the conversion of a substrate to a product results in an electron deficit, co-substrates can be added that function as electron donors (Babel 2009, Eng. Life Sci. 9, 285-290). An important criterion for the anaerobic use of co-substrates is that their redox potential is higher than that of NADH (Geertman et al., 2006, *FEMS Yeast Res.* 6, 1193-1203). If the conversion of substrate to produce results in an electron surplus, co-substrates can be added that function as electron acceptors.

Methods for the Production of Polybutadiene and Other Compounds from Butadiene

Butadiene is gaseous at room temperature or in fermentative conditions (20-45° C.), and their production from a fermentation process results in a gas that could accumulate in the headspace of a fermentation tank, and be siphoned and concentrated. Butadiene may be purified from fermentation of gases, including gaseous alcohol, $CO_2$ and other compound by solvent extraction, cryogenic processes, distillation, fractionation, chromatography, precipitation, filtration, and the like.

Butadiene produced via any of the processes or methods disclosed herein may be converted to polybutadiene. Alternatively, butadiene produced via methods disclosed herein may be polymerized with other olefins to form copolymers such as acrylonitrile-butadiene-styrene (ABS), acrylonitrile-butadiene (ABR), or styrene-butadiene (SBR) copolymers, BR butyl rubber (RB), poly butadiene rubber (PBR), nitrile rubber and polychloroprene (Neoprene). Those synthetic rubbers or plastic elastomers applications include productions of tires, plastic materials, sole, shoe hills, technical goods, home appliance, neoprene, paper coatings, gloves, gaskets and seals.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Modification of Microorganism for Production of Butadiene

A microorganism such as a bacterium may be genetically modified to produce butadiene from a fermentable carbon source including, for example, glucose.

In an exemplary method, a microorganism may be genetically engineered by any methods known in the art to comprise: i.) one or more polynucleotides coding for enzymes in a pathway that catalyze a conversion of the fermentable carbon source to acetyl-CoA and propionyl-CoA, and/or one or more polynucleotides coding for enzymes in a pathway that catalyze a conversion of acetyl-CoA and propionyl-CoA to butadiene; ii.) one or more polynucleotides coding for enzymes in a pathway that catalyze a conversion of the fermentable carbon source to crotonyl-CoA, and/or one or more polynucleotides coding for enzymes in a pathway that catalyze a conversion of crotonyl-CoA to butadiene; or iii.) one or more polynucleotides coding for enzymes in a pathway that catalyze a conversion of the fermentable carbon source to formic acid, and/or one or more polynucleotides coding for enzymes in a pathway that catalyze a conversion of formic acid to butadiene.

Alternatively, a microorganism that lacks one or more enzymes (e.g., one or more functional enzymes that are catalytically active) for the conversion of a fermentable carbon source to butadiene may be genetically modified to comprise one or more polynucleotides coding for enzymes (e.g., functional enzymes including, for example any enzyme disclosed herein) in a pathway that the microorganism lacks to catalyze a conversion of the fermentable carbon source to butadiene.

Example 2

Fermentation of a Carbon Source by a Genetically Modified Microorganism to Produce Butadiene A genetically modified microorganism, as produced in Example 1 above, may be used to ferment a carbon source, to produce butadiene.

In an exemplary method, a previously-sterilized culture medium comprising a fermentable carbon source (e.g., 9 g/L glucose, 1 g/L $KH_2PO_4$, 2 g/L $(NH_4)_2HPO_4$, 5 mg/L $FeSO_4.7H_2O$, 10 mg/L $MgSO_4.7H_2O$, 2.5 mg/L $MnSO_4.H_2O$, 10 mg/L $CaCl_2.6H_2O$, 10 mg/L $CoCl_2.6H_2O$, and 10 g/L yeast extract) is charged in a bioreactor.

During fermentation, anaerobic conditions are maintained by, for example, sparging nitrogen through the culture medium. A suitable temperature for fermentation (e.g., about 30° C.) is maintained using any method known in the art. A near physiological pH (e.g., about 6.5) is maintained by, for example, automatic addition of sodium hydroxide. The bioreactor is agitated at, for example, about 50 rpm. Fermentation is allowed to run to completion.

The produced butadiene is then recovered from the culture medium using conventional methods. When the fermentation products are recovered by distillation, the butadiene fraction may be optionally polymerized to form polybutadiene. Distillation fractions containing other intermediates along the butadiene pathway (if any) may be subjected to a subsequent fermentation in a bioreactor to produce additional butadiene.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A method of producing butadiene from a fermentable carbon source, the method comprising:
   a.) providing a fermentable carbon source;
   b.) contacting the fermentable carbon source with a microorganism comprising one or more polynucleotides coding for enzymes in a pathway that catalyzes a conversion of the fermentable carbon source to one or more intermediates in a pathway for the production of butadiene, and one or more polynucleotides coding for enzymes in a pathway that catalyze a conversion of the one or more intermediates to butadiene in a fermentation media; and
   c.) expressing the one or more polynucleotides coding for the enzymes in the pathway that catalyzes a conversion of the fermentable carbon source to one or more intermediates in a pathway for the production of butadiene and the one or more polynucleotides coding for enzymes in a pathway that catalyze a conversion of the one or more intermediates to butadiene in the microorganism to produce butadiene,
   wherein the one or more intermediates in the pathway for the production of butadiene is crotonyl-CoA, and
   wherein all of the enzymes are required from either (i) crotonyl-CoA reductase (bifunctional) (E.C. 1.1.1), and crotonyl alcohol dehydratase (E.C. 4.2.1, 4.2.1.127) or (ii) crotonaldehyde dehydrogenase (E.C. 1.2.1), crotonyl alchol dehydrogenase (E.C. 1.1.1, 1.1.1.1), and crotonyl alcohol dehydratase (E.C. 4.2.1, 4.2.1.127).

2. The method of claim 1, wherein the microorganism is a bacterium is selected from the genera consisting of: *Burkholderia, Propionibacterium, Propionispira, Clostridium, Bacillus, Escherichia, Pelobacter*, or *Lactobacillus*.

3. The method of claim 1, wherein the microorganism is a eukaryote is a yeast, filamentous fungi, protozoa, or algae.

4. The method of claim 3, wherein the yeast is *Saccharomyces cerevisiae, Zymomonas mobilis*, or *Pichia pastoris*.

5. The method of claim 1, wherein the carbon source is sugarcane juice, sugarcane molasses, hydrolyzed starch, hydrolyzed lignocellulosic materials, glucose, sucrose, fructose, lactate, lactose, xylose, pyruvate, or glycerol in any form or mixture thereof.

6. The method of claim 1, wherein the carbon source is a monosaccharide, oligosaccharide, or polysaccharide.

7. The method of claim 1, wherein the butadiene is secreted by the microorganism into the fermentation media.

8. The method of claim 7 further comprising recovering the butadiene from the fermentation media.

9. The method of claim 1, wherein the conversion of the fermentable carbon source to butadiene is performed under anaerobic conditions.

10. A genetically modified microorganism comprising one or more polynucleotides coding for enzymes in a pathway that catalyzes a conversion of a fermentable carbon source to one or more intermediates in a pathway for the production of butadiene and one or more polynucleotides coding for enzymes in a pathway that catalyze a conversion of the one or more intermediates to butadiene, wherein the one or more intermediates in the pathway for the production of butadiene is crotonyl-CoA, and wherein all of the enzymes are required from either (i) crotonyl-CoA reductase (bifunctional) (E.C. 1.1.1), and crotonyl alcohol dehydratase (E.C. 4.2.1, 4.2.1.127) or (ii) crotonaldehyde dehydrogenase (E.C. 1.2.1), crotonyl alcohol dehydrogenase (E.C. 1.1.1, 1.1.1.1), and crotonyl alcohol dehydratase (E.C. 4.2.1, 4.2.1.127).

11. The microorganism of claim 10, wherein the microorganism is a bacterium is selected from the genera consisting of: *Burkholderia, Propionibacterium, Propionispira, Clostridium, Bacillus, Escherichia, Pelobacter*, or *Lactobacillus*.

12. The microorganism of claim 10, wherein the microorganism is a eukaryote is a yeast, filamentous fungi, protozoa, or algae.

13. The microorganism of claim 11, wherein the yeast is *Saccharomyces cerevisiae, Zymomonas mobilis*, or *Pichia pastoris*.

14. The method of claim 1, wherein the enzymes are crotonyl-CoA reductase (bifunctional) (E.C. 1.1.1), and crotonyl alcohol dehydratase (E.C. 4.2.1, 4.2.1.127).

15. The method of claim 1, wherein the enzymes are crotonaldehyde dehydrogenase (E.C. 1.2.1), crotonyl alcohol dehydrogenase (E.C. 1.1.1, 1.1.1.1), crotonyl alcohol dehydratase (E.C. 4.2.1, 4.2.1.127).

16. The method of claim 10, wherein the enzymes are crotonyl-CoA reductase (bifuncional) (E.C. 1.1.1), and crotonyl alcohol dehydratase (E.C. 4.2.1, 4.2.1.127).

17. The method of claim 10, wherein the enzymes are crotonaldehyde dehydrogenase (E.C. 1.2.1), crotonyl alcohol dehydrogenase (E.C. 1.1.1, 1.1.1.1), crotonyl alcohol dehydratase (E.C. 4.2.1, 4.2.1.127).

18. The method of claim 1 or claim 10, wherein said crotonyl alcohol dehydratase is a linalool dehydratase (4.2.1.127).

* * * * *